(12) United States Patent
Harper et al.

(10) Patent No.: US 7,692,065 B2
(45) Date of Patent: Apr. 6, 2010

(54) STRESS-REGULATED GENES OF PLANTS, TRANSGENIC PLANTS CONTAINING SAME, AND METHODS OF USE

(75) Inventors: Jeffrey F. Harper, Del Mar, CA (US); Joel Kreps, Carlsbad, CA (US); Xun Wang, San Diego, CA (US); Tong Zhu, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 454 days.

(21) Appl. No.: 11/299,286

(22) Filed: Dec. 9, 2005

(65) Prior Publication Data

US 2006/0183137 A1 Aug. 17, 2006

Related U.S. Application Data

(63) Continuation of application No. 09/938,842, filed on Aug. 24, 2001, now Pat. No. 7,109,033.

(60) Provisional application No. 60/300,111, filed on Jun. 22, 2001, now abandoned, provisional application No. 60/264,647, filed on Jan. 26, 2001, now abandoned, provisional application No. 60/227,866, filed on Aug. 24, 2000, now abandoned.

(51) Int. Cl.
*A01H 5/00* (2006.01)
*C12N 15/11* (2006.01)
*C12N 15/29* (2006.01)

(52) U.S. Cl. .................................. 800/298; 536/24.1

(58) Field of Classification Search ....................... None
See application file for complete search history.

(56) References Cited

U.S. PATENT DOCUMENTS 5,824,875 A * 10/1998 Ranu .......................... 800/311

FOREIGN PATENT DOCUMENTS

EP          1 033 405 A2    9/2000
WO         WO 00/08187      2/2000

OTHER PUBLICATIONS

Seki et al., "Monitoring the Expression Pattern of 1300 Arabidopsis Genes under Drought and Cold Stresses by Using a Full-Length cDNA Microarray," *The Plant Cell*, vol. 13, Jan. 2001, pp. 61-72.

Schenk et al., "Coordinated plant defense responses in *Arabidopsis* revealed by microarray analysis," *PNAS*, vol. 97, No. 21, Oct. 10, 2000, pp. 11655-11660.

Reymond et al., "Differential Gene Expression in Response to Mechanical Wounding and Insect Feeding in *Arabidopsis*," *The Plant Cell*, vol. 12, May 2000, pp. 707-719.

Nuccio et al., "Metabolic engineering of plants for osmotic stress resistance," *Plant Biotechnology*, Apr. 1999, pp. 128-134.

Ruan et al., "Towards *Arabidopsis* genome analysis: monitoring expression profiles of 1400 genes using cDNA microarrays," *The Plant Journal*, vol. 15, (1998), pp. 821-833.

Schena et al., "Quantitative Monitoring of Gene Expression Patterns with a Complementary DNA Mircoarray," Science, vol. 270, Oct. 20, 1995, pp. 467-470.

Jaglo-Ottosen et al., "*Arabidopsis* CBF-1 Overexpression Induces COR Genes and Enhances Freezing Tolerance," *Science*, vol. 280, pp. 104-106, Apr. 3, 1998.

Kasuga et al., "Improving plant drought, salt, and freezing tolerance by gene transfer of a single stress-inducible transcription factor," *Nature Biotechnology*, vol. 17, pp. 287-291, Mar. 1999.

Cubas et al., "The TCP domain: a motif found in proteins regulating plant growth and development," *The Plant Journal*, 18:2, pp. 215-222 (1999).

Kosugi et al., "DNA binding and dimerization specificity and potential targets for the TCP protein family," *The Plant Journal*, 30:3, pp. 337-348 (2002).

* cited by examiner

*Primary Examiner*—James Martinell
(74) *Attorney, Agent, or Firm*—Hugh Wang; Thomas Fitting

(57) ABSTRACT

Clusters of plant genes that are regulated in response to one or more stress conditions are provided, as are isolated plant stress-regulated genes, including portions thereof comprising a coding sequence or a regulatory element, and to consensus sequences comprising a plant stress-regulated regulatory element. In addition, a recombinant polynucleotide, which includes a plant stress-regulated gene, or functional portion thereof, operatively linked to a heterologous nucleotide sequence, is provided, as are transgenic plants, which contain a plant stress-regulated gene or functional portion thereof that was introduced into a progenitor cell of the plant. Also provided are methods of using a plant stress-regulated gene to confer upon a plant a selective advantage to a stress condition, methods of identifying an agent that modulates the activity of a plant stress-regulated regulatory element, and methods of determining whether a plant has been exposed to a stress.

21 Claims, No Drawings

STRESS-REGULATED GENES OF PLANTS, TRANSGENIC PLANTS CONTAINING SAME, AND METHODS OF USE

CROSS REFERENCE TO RELATED APPLICATIONS

This application is a continuation application of U.S. application Ser. No. 09/938,842 filed Aug. 24, 2001, now U.S. Pat. No. 7,109,033; which claims the benefit under 35 USC § 119(e) to U.S. Application Ser. No. 60/300,111 filed Jun. 22, 2001, now abandoned, U.S. Application Ser. No. 60/264,647 filed Jan. 26, 2001, now abandoned, and to U.S. Application Ser. No. 60/227,866 filed Aug. 24, 2000, now abandoned. The disclosure of each of the prior applications is considered part of and is incorporated by reference in the disclosure of this application.

Three CD-R compact discs, labeled "Copy 1", "Copy 2", and "CRF" and having the files listed below, are submitted herewith and are incorporated herein by reference. Copy 1 and Copy 2 each contain two text documents: 1) a file named SCRIP1300-3_SEQUENCE_LISTING, which contains the Sequence Listing, was created on Aug. 20, 2001 (and recorded on the CD-R on Aug. 21, 2001), and is 9,972 KB in size; and 2) a file named SCRIP1300-3_Table__32, which contains Table 32, was created on Aug. 20, 2001 (and recorded on the CD-R on Aug. 21, 2001), and is 1,251 KB in size. The CRF contains a single file named SCRIP1300-3_SEQUENCE_LISTING, which contains the Sequence Listing, was created on Aug. 20, 2001 (and recorded on the CD-R on Aug. 21, 2001), is 9,972 KB in size, and is identical to the files having the same name on Copy 1 and Copy 2.

BACKGROUND OF THE INVENTION

1. Field of the Invention

The present invention relates generally to plant genes, the expression of which are regulated in response to stress, and more specifically to the gene regulatory elements involved in a stress-induced response in plants, to uses of the coding sequences and regulatory elements of such plant stress-regulated genes, and to transgenic plants genetically modified to express such a coding sequence or to express a heterologous polynucleotide from such a regulatory element.

2. Background Information

Microarray technology is a powerful tool that can be used to identify the presence and level of expression of a large number of polynucleotides in a single assay. A microarray is formed by linking a large number of discrete polynucleotide sequences, for example, a population of polynucleotides representative of a genome of an organism, to a solid support such as a microchip, glass slide, or the like, in a defined pattern. By contacting the microarray with a nucleic acid sample obtained from a cell of interest, and detecting those polynucleotides expressed in the cell can hybridize specifically to complementary sequences on the chip, the pattern formed by the hybridizing polynucleotides allows the identification of clusters of genes that are expressed in the cell. Furthermore, where each polynucleotide linked to the solid support is known, the identity of the hybridizing sequences from the nucleic acid sample can be identified.

A strength of microarray technology is that it allows the identification of differential gene expression simply by comparing patterns of hybridization. For example, by comparing the hybridization pattern of nucleic acid molecules obtained from cells of an individual suffering from a disease with the nucleic acids obtained from the corresponding cells of a healthy individual, genes that are differentially expressed can be identified. The identification of such differentially expressed genes provides a means to identify new genes, and can provide insight as to the etiology of a disease.

Microarray technology has been widely used to identify patterns of gene expression associated with particular stages of development or of disease conditions in animal model systems, and is being applied to the identification of specific patterns of gene expression in humans. The recent availability of information for the genomes of plants provides a means to adapt microarray technology to the study of plant gene expression.

Plants and plant products provide the primary sustenance, either directly or indirectly, for all animal life, including humans. For the majority of the world's human population and for many animals, plants and plant products provide the sole source of nutrition. As the world population increases, the best hope to prevent widespread famine is to increase the quantity and improve the quality of food crops, and to make the crops available to the regions of the world most in need of food.

Throughout history, a continual effort has been made to increase the yield and nutritious value of food crops. For centuries, plants having desirable characteristics such as greater resistance to drought conditions or increased size of fruit were crossbred and progeny plants exhibiting the desired characteristics were selected and used to produce seed or cuttings for propagation. Using such classical genetic methods, plants having, for example, greater disease resistance, increased yield, and better flavor have been obtained. The identification of plant genes involved in conferring a selective advantage on the plant to an environmental challenge would facilitate the generation and yield of plants, thereby increasing the available food supply to an increasing world population. The involvement of these genes in a single organism to responses to multiple stress conditions, however, remains unknown. Thus, a need exists to identify plant genes and polynucleotides that are involved in modulating the response of a plant to changing environmental conditions. The present invention satisfies this need and provides additional advantages.

SUMMARY OF THE INVENTION

The present invention relates to clusters of genes that are regulated in response to a stress condition in plants. Such clusters include, for example, plant polynucleotides whose expression is altered in response to two or more different stress conditions; and plant polynucleotides the expression of which are altered in response to one stress condition, but not to others. The identification of such clusters, using microarray technology, has allowed the identification of plant stress-regulated genes in *Arabidopsis thaliana* (see Tables 1 and 2); and homologs and orthologs thereof in other plant species (see Table 32). Thus, the invention provides isolated polynucleotide portions of *Arabidopsis* plant stress-regulated genes, and homologs and orthologs thereof; variants of such sequences, and polynucleotides encoding substantially similar plant stress-regulated polypeptides expressed therefrom. Such sequences include, for example, sequences encoding transcription factors; enzymes, including kinases; and structural proteins, including channel proteins (see Tables 29-31). Accordingly, the present invention also relates to an isolated polynucleotide comprising all or a portion of a plant stress-regulated gene, and to polynucleotide portions thereof, including a coding region (open reading frame), which encodes all or a portion of a stress-regulated polypeptide, for example, as set forth in SEQ ID NOS: 1-2703; and a regulatory element involved in regulating the response of the plant to a stress condition such exposure to an abnormal level of salt, osmotic pressure, temperature or any combination thereof, for example, as set forth in SEQ ID NOS:2704-5379.

The present invention also relates to a recombinant polynucleotide, which contains a nucleotide sequence of a plant stress-regulated gene or functional portion thereof operatively linked to a heterologous nucleotide sequence. In one embodiment, the recombinant polynucleotide comprises a plant stress-regulated gene regulatory element operatively linked to a heterologous nucleotide sequence, which is not regulated by the regulatory element in a naturally occurring plant. The heterologous nucleotide sequence, when expressed from the regulatory element, can confer a desirable phenotype to a plant cell containing the recombinant polynucleotide. In another embodiment, the recombinant polynucleotide comprises a coding region, or portion thereof, of a plant stress-regulated gene operatively linked to a heterologous promoter. The heterologous promoter provides a means to express an encoded stress-regulated polypeptide constitutively, or in a tissue-specific or phase-specific manner.

Accordingly, in one aspect, the present invention provides an isolated polynucleotide comprising a nucleotide sequence of a plant gene that hybridizes under stringent conditions, preferably high stringency conditions, to any one of SEQ ID NOS:1-5379 (see Tables 1 and 2), including to a coding region (SEQ ID NOS: 1-2703) or a regulatory region, which can alter transcription of an operatively linked nucleic acid sequence in response to an abiotic stress (SEQ ID NOS:2704-5379; see Table 2), or to a complement thereof. Additional aspects provide sequences that hybridize under stringent conditions, preferably high stringency conditions, to the complements of SEQ ID NO 1-1261 (cold responsive genes; Tables 3-6), SEQ ID NOS:2227-2427 (saline responsive genes; Tables 7-10), SEQ ID NOS:2428-2585 (osmotic responsive genes; Tables 11-14), SEQ ID NOS:1699-1969 (cold and osmotic responsive genes; Tables 15-17), SEQ ID NOS: 1970-2226 (cold and saline responsive genes; Tables 18-20), SEQ ID NOS:2586-2703 (osmotic and saline responsive genes; Tables 21-23), and SEQ ID NOS:1262-1698(cold, osmotic and saline responsive genes; Tables 24-26), and which can comprise regulatory regions that can alter transcription in response to cold stress, osmotic stress, saline stress, or combinations thereof (SEQ ID NOS:2704-5379; see Table 2). Also provided are nucleotide sequences complementary thereto, and expression cassettes, plants and seeds comprising any of the above isolated sequences.

In another aspect, the present invention provides an isolated polynucleotide comprising a plant nucleotide sequence that hybridizes under stringent conditions, preferably high stringency conditions, to the complement of any one of SEQ ID NOS: 1-2703 (Table 1), including to a coding region thereof (SEQ ID NOS:2704-5379), wherein expression of said coding region is altered in response to an abiotic stress. Additional aspects provide sequences that hybridize under high stringency conditions to the complements of SEQ ID NO 1-1261 (cold responsive genes; Tables 3-6), SEQ ID NOS: 2227-2427 (saline responsive genes; Tables 7-10), SEQ ID NOS:2428-2585 (osmotic responsive genes; Tables 11-14), SEQ ID NOS:1699-1969 (cold and osmotic responsive genes; Tables 15-17), SEQ ID NOS:1970-2226 (cold and saline responsive genes; Tables 18-20), SEQ ID NOS:2586-2703 (osmotic and saline responsive genes; Tables 21-23), and SEQ ID NOS: 1262-1698(cold, osmotic and saline responsive genes; Tables 24-26), and which can comprise a coding region whose transcription is altered in response to cold stress, osmotic stress, saline stress, or a combination thereof. Also provided are nucleotide sequences complementary thereto, and expression cassettes, plants and seeds comprising any of the above sequences.

The invention further relates to a method of producing a transgenic plant, which comprises at least one plant cell that exhibits altered responsiveness to a stress condition. In one embodiment, the method can be performed by introducing a polynucleotide portion of plant stress-regulated gene into a plant cell genome, whereby the polynucleotide portion of the plant stress-regulated gene modulates a response of the plant cell to a stress condition.

The polynucleotide portion of the plant stress-regulated gene can encode a stress-regulated polypeptide or functional peptide portion thereof (see SEQ ID NOS: 1-2703), wherein expression of the stress-regulated polypeptide or functional peptide portion thereof either increases the stress tolerance of the transgenic plant, or decreases the stress tolerance of the transgenic plant. The polynucleotide portion of the plant stress-regulated gene encoding the stress-regulated polypeptide or functional peptide portion thereof can be operatively linked to a heterologous promoter. The polynucleotide portion of the plant stress-regulated gene also can comprise a stress-regulated gene regulatory element (see SEQ ID NOS: 2704-5379). The stress-regulated gene regulatory element can integrate into the plant cell genome in a site-specific manner, whereupon it can be operatively linked to a heterologous nucleotide sequence, which can be expressed in response to a stress condition specific for the regulatory element; or can be a mutant regulatory element, which is not responsive to the stress condition, whereby upon integrating into the plant cell genome, the mutant regulatory element disrupts an endogenous stress-regulated regulatory element of a plant stress-regulated gene, thereby altering the responsiveness of the plant stress-regulated gene to the stress condition.

In one aspect, the invention provides a method for producing a transgenic plant by introducing into at least one plant cell a recombinant nucleic acid construct comprising i) all or a portion of any one of SEQ ID NOS:1-5379; ii) a polynucleotide comprising a coding region that hybridizes under conditions of high stringency to all or a portion of the complement of any one of SEQ ID NOS: 1-2703; iii) a polynucleotide comprising a sequence that alters transcription of an operatively linked coding region in response to abiotic stress, and that hybridizes under conditions of high stringency to the complement of any one of SEQ ID NOS: 2704-5379; iv) a polynucleotide having at least 90% sequence identity with any one of SEQ ID NO: 1-5379; v) a fragment of any one of the sequences of iv), wherein the fragment comprises a coding region; or vi) a fragment of any one of the sequences of iv), wherein the fragment comprises a nucleotide sequence that alters transcription of an operatively linked coding region in response to abiotic stress; and regenerating a plant from the at least one plant cell.

Another aspect provides a method for producing a transgenic plant comprising introducing into at least one plant cell a recombinant nucleic acid construct comprising i) any one of SEQ ID NOS:1-1261 or 2704-3955; ii) a polynucleotide comprising a coding region that hybridizes under conditions of high stringency to the complement of any one of SEQ ID NOS:1-1261; iii) a polynucleotide comprising a sequence that alters transcription of an operatively linked coding region in response to cold stress that hybridizes under conditions of high stringency to the complement of any one of SEQ ID NOS:2704-3955; iv) a polynucleotide that has at least 90% sequence identity with any one of SEQ ID NOS: 1-1261 or 2704-3955; v) a fragment of any one of the sequences of iv), wherein the fragment comprises a coding region; or vi) a fragment of any one of the sequences of iv) wherein the fragment comprises a sequence or region that alters transcription of an operatively linked coding region in response to cold stress; and regenerating a plant from the at least one plant cell.

In another aspect, the invention provides a method for producing a transgenic plant by introducing into at least one plant cell a recombinant nucleic acid construct comprising i) any one of SEQ ID NOS:2428-2585 or 5108-5263; ii) a polynucleotide comprising a coding region that hybridizes under conditions of high stringency to the complement of any one of SEQ ID NOS:2428-2585; iii) a polynucleotide comprising a sequence that alters transcription of an operatively linked coding region in response to osmotic stress that hybridizes under conditions of high stringency to the complement of any one of SEQ ID NOS:5108-5263; iv) a polynucleotide that has at least 90% sequence identity with any one of SEQ ID NOS:2428-2585 or 5108-5263; v) a fragment of any one of the sequences of iv), wherein the fragment comprises a coding region; or vi) a fragment of any one of the sequences of iv), wherein the fragment comprises a sequence or region that alters transcription of an operatively linked coding region in response to osmotic stress; and regenerating a plant from the at least one plant cell.

Still another aspect provides a method for producing a transgenic plant comprising introducing into at least one plant cell a recombinant nucleic acid construct comprising i) any one of SEQ ID NOS:2227-2427 or 4910-5107; ii) a polynucleotide comprising a coding region that hybridizes under conditions of high stringency to the complement of any one of SEQ ID NOS:2227-2427; iii) a polynucleotide comprising a sequence that alters transcription of an operatively linked coding region in response to saline stress that hybridizes under conditions of high stringency to the complement of any one of SEQ ID NOS:2227-2427; iv) a polynucleotide that has at least 90% sequence identity with any one of SEQ ID NOS:4910-5107; v) a fragment of any one of the sequences of iv), wherein the fragment comprises a coding region; or vi) a fragment of any one of the sequences of iv) wherein the fragment comprises a sequence or region that alters transcription of an operatively linked coding region in response to saline stress; and regenerating a plant from the at least one plant cell.

Yet another aspect provides a method for producing a transgenic plant comprising introducing into at least one plant cell a recombinant nucleic acid construct comprising i) any one of SEQ ID NOS: 1699-1969 or 4389-4654; ii) a polynucleotide comprising a coding region that hybridizes under conditions of high stringency to the complement of any one of SEQ ID NOS: 1699-1969; iii) a polynucleotide comprising a sequence that alters transcription of an operatively linked coding region in response to a combination of cold and osmotic stress that hybridizes under conditions of high stringency to the complement of any one of SEQ ID NOS:4389-4654; iv) a polynucleotide that has at least 90% sequence identity with any one of SEQ ID NOS: 1699-1969 or 4389-4654; v) a fragment of any one of the sequences of iv), wherein the fragment comprises a coding region; or vi) a fragment of any one of the sequences of iv), wherein the fragment comprises a sequence or region that alters transcription of an operatively linked coding region in response to a combination of cold and osmotic stress; and regenerating a plant from the at least one plant cell.

Yet another aspect provides a method for producing a transgenic plant comprising introducing into at least one plant cell a recombinant nucleic acid construct comprising i) any one of SEQ ID NOS: 1970-2226 or 4655-4909; ii) a polynucleotide comprising a coding region that hybridizes under conditions of high stringency to the complement of any one of SEQ ID NOS:1970-2226; iii) a polynucleotide comprising a sequence that alters transcription of an operatively linked coding region in response to a combination of cold and saline stress that hybridizes under conditions of high stringency to the complement of any one of SEQ ID NOS:4655-4909; iv) a polynucleotide that has at least 90% sequence identity with array one of SEQ ID NOS: 1970-2226 or 4655-4909; v) a fragment of any one of the sequences of iv), wherein the fragment comprises a coding region; or vi) a fragment of any one of the sequences of iv), wherein the fragment comprises a sequence or region that alters transcription of an operatively linked coding region in response to a combination of cold and saline stress; and regenerating a plant from the at least one plant cell.

A further aspect provides a method for producing a transgenic plant comprising introducing into at least one plant cell a recombinant nucleic acid construct comprising i) any one of SEQ ID NOS:2586-2703 or 5264-5379; ii) a polynucleotide comprising a coding region that hybridizes under conditions of high stringency to the complement of any one of SEQ ID NOS:2586-2703; iii) a polynucleotide comprising a sequence that alters transcription of an operatively linked coding region in response to a combination of osmotic and saline stress that hybridizes under conditions of high stringency to the complement of any one of SEQ ID NOS: 5264-5379; iv) a polynucleotide that has at least 90% sequence identity with any one of SEQ ID NOS:2586-2703 or 5264-5379; v) a fragment of any one of the sequences of iv), wherein the fragment comprises a coding region; or vi) a fragment of any one of the sequences of iv), wherein the fragment comprises a sequence or region that alters transcription of an operatively linked coding region in response to a combination of osmotic and saline stress; and regenerating a plant from the at least one plant cell.

Another aspect provides a method for producing a transgenic plant comprising introducing into at least one plant cell a recombinant nucleic acid construct comprising i) any one of SEQ ID NOS:1262-1698 or 3956-4388; ii) a polynucleotide comprising a coding region that hybridizes under conditions of high stringency to the complement of any one of SEQ ID NOS: 1262-1698; iii) a polynucleotide comprising a sequence that alters transcription of an operatively linked coding region in response to a combination of cold, osmotic and saline stress that hybridizes under conditions of high stringency to the complement of any one of SEQ ID NOS: 3956-4388; iv) a polynucleotide that has at least 90% sequence identity with any one of SEQ ID NOS: 1262-1698 or 3956-4388; v) a fragment of any one of the sequences of iv), wherein the fragment comprises a coding region; or vi) a fragment of any one of the sequences of iv) wherein the fragment comprises a sequence or region that alters transcription of an operatively linked coding region in response to a combination of cold, osmotic and saline stress; and regenerating a plant from the at least one plant cell. Further aspects include plants and uniform populations of plants made by the above methods as well as seeds and progeny from such plants.

In another embodiment, a transgene introduced into a plant cell according to a method of the invention can encode a polypeptide that regulates expression from an endogenous plant stress-regulated gene. Such a polypeptide can be, for example, a recombinantly produced polypeptide comprising a zinc finger domain, which is specific for the regulatory element, and an effector domain, which can be a repressor domain or an activator domain. The polynucleotide encoding the recombinant polypeptide can be operatively linked to and expressed from a constitutively active, inducible or tissue specific or phase specific regulatory element. Expression of the recombinant polypeptide from a plant stress-regulated promoter as disclosed herein can be particularly advantageous in that the polypeptide can be coordinately expressed with the endogenous plant stress-regulated genes upon exposure to a stress condition. The invention also provides transgenic plants produced by a method as disclosed, as well as to a plant cell obtained from such transgenic plant, wherein said plant cell exhibits altered responsiveness to the stress condition; a seed produced by the transgenic plant; and a cDNA or genomic DNA library prepared from the transgenic plant, or from a plant cell from said transgenic plant, wherein said plant cell exhibits altered responsiveness to the stress condition.

In one aspect, the invention provides an isolated nucleic acid molecule comprising a nucleotide sequence substantially similar to a sequence of any one of SEQ ID NOS:2704-5379, which can alter transcription of an operatively linked polynucleotide in a plant cell in response to an abiotic stress. Additional aspects of the invention provide isolated polynucleotides, including, for example, sequences substantially similar to any of SEQ ID NOS:2704-3955, which can alter transcription of an operatively linked polynucleotide in response to a cold stress; isolated polynucleotides substantially similar to a sequence of any o-f SEQ ID NOS:5108-5263, which can alter transcription of an operatively linked polynucleotide in response to an osmotic stress; isolated polynucleotides substantially similar to a sequence of any of SEQ ID NOS:4910-5107, which can alter transcription of an operatively linked polynucleotide in response to a saline stress; isolated polynucleotides substantially similar to a sequence of any of SEQ ID NOS:4389-4654, which can alter transcription of an operatively linked polynucleotide in response to a combination of cold and osmotic stresses; isolated polynucleotides substantially similar to a sequence of any of SEQ ID NOS:4655-4909, which can alter transcription of an operatively linked polynucleotide in response to a combination of cold and saline stresses; isolated polynucleotides substantially similar to a sequence of any of SEQ ID NOS: 5264-5379, which can alter transcription of an operatively linked polynucleotide in response to a combination of osmotic and saline stresses; and isolated polynucleotides substantially similar to a sequence of any of SEQ ID NOS:3956-4388, which can alter transcription of an operatively linked polynucleotide in response to a combination of cold, osmotic and saline stresses.

Related aspects of the invention provide an isolated nucleotide sequences that can alter transcription of an operatively linked polynucleotide in response to an abiotic stress, and that hybridize under stringent conditions, preferably highly stringent conditions, to the complement of any one of SEQ ID NOS:2704-5379. Additional aspects provide an isolated nucleotide sequence that can alter transcription of an operatively linked polynucleotide in response to cold stress, and that hybridizes under stringent conditions, preferably highly stringent conditions, to the complement of any one of SEQ ID NOS:2704-3955; a nucleotide sequence that alters transcription of an operatively linked polynucleotide in response to osmotic stress, and that hybridizes under stringent conditions, preferably highly stringent conditions, to the complement of any one of SEQ ID NOS:5108-5263; a nucleotide sequence that alters transcription of an operatively linked polynucleotide in response to saline stress, and that hybridizes under stringent conditions, preferably highly stringent conditions, to the complement of any one of SEQ ID NOS:4910-5107; a nucleotide sequence that alters transcription of an operatively linked polynucleotide in response to a combination of cold and osmotic stress, and that hybridizes under stringent conditions, preferably highly stringent conditions, to the complement of any one of SEQ ID NOS:4389-4654; a nucleotide sequence that alters transcription of an operatively linked polynucleotide in response to a combination of cold and saline stress, and that hybridizes under stringent conditions, preferably highly stringent conditions, to the complement of any one of SEQ ID NOS:4655-4909; a nucleotide sequence that alters transcription of an operatively linked polynucleotide in response to an combination of osmotic and saline stress, and that hybridizes under stringent conditions, preferably highly stringent conditions, to the complement of any one of SEQ ID NOS:5264-5379; and a nucleotide sequence that alters transcription of an operatively linked polynucleotide in response to a combination of cold, osmotic and saline stress, and that hybridizes under stringent conditions, preferably highly stringent conditions, to the complement of any one of SEQ ID NOS:3956-4388.

Further aspects provide an expression cassette comprising as operatively linked components any of the above isolated nucleic acid sequences that alter transcription, a coding region, and a termination sequence. Also provided are host cells and seeds comprising such expression cassettes, plants containing such host cells and seeds and progeny of plants containing said host cells. In related aspects, the coding region of the expression cassettes comprise sequences encoding marker proteins and sequences involved in gene silencing such as antisense sequences, double stranded RNAi sequences, a triplexing agent, and sequences comprising dominant negative mutations. In additional related aspects, the coding regions comprise sequences encoding polypeptides that alter the response of a plant to an abiotic stress.

The present invention also relates to a method of modulating the responsiveness of a plant cell to a stress condition. Such a method can be performed, for example, by introducing a polynucleotide portion of a plant stress-regulated genes described herein into the plant cell, thereby modulating the responsiveness of the plant cell to a stress condition. Such a method can result in the responsiveness of the plant cell being increased upon exposure to the stress condition, which, in turn, can result in increased or decreased tolerance of the plant cell to a stress condition; or can result in the responsiveness of the plant cell to the stress condition being decreased, which, in turn, can result in increased or decreased tolerance of the plant cell to a stress condition. In one embodiment, the polynucleotide portion of the plant stress-regulated gene can integrate into the genome of the plant cell, thereby modulating the responsiveness of the plant cell to the stress condition. In another embodiment, the polynucleotide portion of the plant stress-regulated gene encodes a stress-regulated polypeptide or functional peptide portion thereof, and can be operatively linked to a heterologous promoter. The polynucleotide portion of the plant stress-regulated gene also can contain a mutation, whereby upon integrating into the plant cell genome, the polynucleotide disrupts (knocks-out) an endogenous plant stress-regulated sequence, thereby modulating the responsiveness of the plant cell to the stress condition. Depending on whether the knocked-out gene encodes an adaptive or a maladaptive stress-regulated polypeptide, the responsiveness of the plant will be modulated accordingly.

The present invention further relates to a method of modulating the activity of a biological pathway in a plant cell, wherein the pathway involves a stress-regulated polypeptide or a non-protein regulatory molecule. Such a method can be performed by introducing a polynucleotide portion of a plant stress-regulated gene, or a polynucleotide derived therefrom, for example a ribozyme derived from a nucleotide sequence as set forth in any of SEQ ID NOS: 1-2703, into the plant cell, thereby modulating the activity of the biological pathway. The method can be performed with respect to a pathway involving any of the stress-regulated polypeptides as disclosed herein or encoded by the polynucleotides disclosed herein, as well as using homologs or orthologs thereof. In one embodiment, the method is performed by introducing a polynucleotide portion of a plant stress-regulated gene into the plant cell, wherein the plant stress-regulated gene comprises a nucleotide sequence as set forth in any of SEQ ID NOS:1-155, 157-228, 230-232, 234-557, 559-572, 574-605, 607-634, 636-786, 788-812, 814-1262, 1264-1386, 1387-1390, 1392-1404, 1406-1444, 1446-1483, 1485-1588, 1590-1608, 1610-1633, 1634-1725, 1727-1865, 1867-1917, 1919-1927, 1929-2855, 2857-2928, 2930-2932, 2934-3256, 3258-3271, 3273-3304, 3306-3323, 3325-3333, 3335-3485, 3487-3511, 3313-3956, 3958-4078, 4080-4097, 4099-4136, 4138-4175, 4177-4279, 4281-4299, 4301-4324, 4326-4414, 4416-4552, 4554-4602, and 4604-5379, thereby modulating the activity of the biological pathway.

The present invention also relates to a method of identifying a polynucleotide that modulates a stress response in a plant cell. In one embodiment the method comprises determining gene expression in a plant exposed to at least one stress to produce an expression profile and identifying sequences whose expression is altered at least two fold compared to plants not exposed to the stress. Such an expression profile can be obtained, for example, by contacting an array of probes representative of a plant cell genome with nucleic acid molecules expressed in a plant cell exposed to the stress; and detecting one or more nucleic acid molecules expressed at a level different from a level of expression in the absence of the stress. The method can further comprise introducing the differentially expressed nucleic acid molecule into a plant cell; and detecting a modulated response of the genetically modified plant cell to a stress, thereby identifying a polynucleotide that modulates a stress response in a plant cell. The stress can be any stress, for example, an abiotic stress such as exposure to an abnormal level of cold, osmotic pressure, and salinity. The contacting is under conditions that allow for selective hybridization of a nucleic acid molecule with probe having sufficient complementarity, for example; under stringent hybridization conditions. Expression of the nucleic acid molecule can increase or decrease the tolerance of the plant cell to the stress, and the nucleic acid molecule can be expressed at a level that is less than or greater than the level of expression in the absence of the stress.

In still another embodiment, the polynucleotide portion of the plant stress-regulated gene can comprise a stress-regulated regulatory element, which can be operatively linked to a heterologous nucleotide sequence, the expression of which can modulate the responsiveness of the plant cell to a stress condition. Such a heterologous nucleotide sequence can encode, for example, a stress-inducible transcription factor such as DREB1A. The heterologous nucleotide sequence also can encode a polynucleotide that is specific for a plant stress-regulated gene, for example, an antisense molecule, an RNAi molecule, a ribozyme, and a triplexing agent, any of which, upon expression in the plant cell, reduces or inhibits expression of a stress-regulated polypeptide encoded by the gene, thereby modulating the responsiveness of the plant cell to a stress condition, for example, an abnormal level of cold, osmotic pressure, and salinity. In another aspect, the method can include introducing a polynucleotide portion of a plant stress-regulated gene into the plant cell, wherein the plant stress-regulated gene includes a nucleotide sequence of a polynucleotide as set forth in any of SEQ ID NOS:1-155, 157-228, 230-232, 234-557, 559-572, 574-605, 607-634, 636-786, 788-812, 814-1262, 1264-1386, 1387-1390, 1392-1404, 1406-1444, 1446-1483, 1485-1588, 1590-1608, 1610-1633, 1634-1725, 1727-1865, 1867-1917, 1919-1927, 1929-2855, 2857-2928, 2930-2932, 2934-3256, 3258-3271, 3273-3304, 3306-3323, 3325-3333, 3335-3485, 3487-3511, 3313-3956, 3958-4078, 4080-4097, 4099-4136, 4138-4175, 4177-4279, 4281-4299, 4301-4324, 4326-4414, 4416-4552, 4554-4602, and 4604-5379, thereby modulating the responsiveness of the plant cell to a stress condition. The invention also relates to a plant cell obtained by any of the methods of modulating the responsiveness of a plant to a stress condition or combination of stress conditions, and to a plant comprising such a plant cell.

The present invention further relates to a method of selecting a plant having an altered resistance to an abiotic stress condition or a combination of abiotic stress conditions, such a method being useful for marker-assisted breeding. Such a method can be performed, for example, by contacting nucleic acid molecules representative of expressed polynucleotides in a plant cell of a plant to be examined for having an altered resistance to an abiotic stress with a nucleic acid probes that selectively hybridizes under stringent conditions to a plant stress-regulated gene comprising a nucleotide sequence as set forth in any of SEQ ID NO: 1-5379; detecting a level of selective hybridization of the nucleic acid probes to a nucleic acid molecule representative of an expressed polynucleotide in the plant cell, wherein the level of selective hybridization corresponds to the level of the expressed polynucleotide in the plant cell, which is indicative of resistance of the plant to an abiotic stress; and selecting a plant having a level of expression of a polynucleotide indicative of altered resistance to an abiotic stress condition. For example, the abiotic stress condition can be cold stress, and the nucleic acid probe can include at least about 15 nucleotides of a nucleotide sequence as set forth in any of SEQ ID NOS:1-1261 and 2704-3955, for example, at least about 15 nucleotides of a nucleotide sequence as set forth in any of SEQ ID NOS:1-155, 157-228, 230-232, 234-557, 559-572, 574-605, 607-634, 636-786, 788-812, 814-1261, 2704-2855, 2857-2928, 2930-2932, 2934-3256, 3258-3271, 3273-3304, 3306-3323, 3325-3333, 3335-3485, 3487-3511, and 3313-3955; or the abiotic stress condition can be saline stress, and the nucleic acid probe can include at least about 15 nucleotides of a nucleotide sequence as set forth in any of SEQ ID NOS:2226-2427 and 4910-5107; or the abiotic stress condition can be osmotic stress, and the nucleic acid probe can include at least about 15 nucleotides of a nucleotide sequence as set forth in any of SEQ ID NOS:2428-2585 and 5108-5263. In addition, a combination of abiotic stress conditions can be a combination of cold stress and osmotic stress, and the nucleic acid probe can include at least about 15 nucleotides of a nucleotide sequence as set forth in any of SEQ ID NOS:1669-1969 and 4389-4654, for example, at least about 15 nucleotides of a nucleotide sequence as set forth in any of SEQ ID NOS: 1699-1725, 1727-1865, 1867-1917, 1919-1927, 1929-1969, 4389-4414, 4416-4552, 4554-4602, 4604-4612, and 4613-4654; or the combination of abiotic stress conditions can be a combination of cold stress and saline stress, and the nucleic acid probe can include at least about 15 nucleotides of a nucleotide sequence as set forth in any of SEQ ID NOS:1970-2226 and 4655-4909; or the combination of abiotic stress conditions can be a combination of osmotic stress and saline stress, and the nucleic acid probe can include at least about 15 nucleotides of a nucleotide sequence as set forth in any of SEQ ID NOS: 2586-2703 and 5264-5379; or the combination of abiotic stress conditions can be a combination of cold stress, osmotic stress and saline stress, and the nucleic acid probe can include at least about 15 nucleotides of a nucleotide sequence as set forth in any of SEQ ID NOS:1262-1698 and 3956-4388, for example, at least about 15 nucleotides of a nucleotide sequence as set forth in any of SEQ ID NOS: 1262, 1264-1386, 1387-1390, 1392-1404, 1406-1444, 1446-1483, 1485-1588, 1590-1608, 1610-1633, 1634-1698, 3956, 3958-4078, 4080-4097, 4099-4136, 4138-4175, 4177-4279, 4281-4299, 4301-4324, and 4326-4388.

The present invention also relates to a method of expressing a heterologous nucleotide sequence in a plant cell. Such a method can be performed, for example, by introducing into the plant cell a plant stress-regulated regulatory element operatively linked to the heterologous nucleotide sequence, whereby, upon exposure of the plant cell to a stress condition, the heterologous nucleotide sequence is expressed in the plant cell. In one embodiment, the stress-regulated gene regulatory element is any of the sequences described herein that are capable of altering transcription of an operatively linked sequence in response to an abiotic stress, for example, SEQ ID NOS:2704-5379. In another embodiment, stress-regulated gene regulatory element comprises a nucleotide sequence as set forth in any of SEQ ID NOS:2704-2855, 2857-2928, 2930-2932, 2934-3256, 3258-3271, 3273-3304, 3306-3323, 3325-3333, 3335-3485, 3487-3511, 3313-3956, 3958-4078, 4080-4097, 4099-4136, 4138-4175, 4177-4279, 4281-4299, 4301-4324, 4326-4414, 4416-4552, 4554-4602, and 4604-5379, whereby, upon exposure of the plant cell to stress condition, the heterologous nucleotide sequence is expressed in the plant cell. The heterologous nucleotide sequence can encode a selectable marker, a diagnostic marker, or a polypeptide that confers a desirable trait upon the plant cell, for example, a polypeptide that improves the nutritional value, digestibility or ornamental value of the plant cell, or a plant comprising the plant cell.

The present invention additionally relates to a method of identifying a stress condition to which a plant cell was exposed by comparing an expression profile from a test plant suspected of having been exposed to at least one stress condition to an expression profile obtained from a reference plant, preferably of the same species, which has been exposed to the suspected stress condition. Such a method can be performed, for example, by contacting nucleic acid molecules representative of expressed polynucleotides in cells of the test plant with at least one nucleic acid probe under conditions suitable for selective hybridization to a complementary nucleotide sequence, wherein the probe comprises at least 15 nucleotides of a plant stress-regulated gene, wherein the stress-regulated gene does not have a nucleotide sequence of a polynucleotide as set forth in any of SEQ ID NOS: 156, 229, 233, 558, 573, 606, 635, 787, 813, 1263, 1386, 1391, 1405, 1445, 1484, 1589, 1609, 1634, 1726, 1866, 1918 or 1928, or a nucleotide sequence complementary thereto, whereby detecting selective hybridization of at least one nucleic acid probe, or detecting a change in a level of selective hybridization as compared to a level of selective hybridization obtained using nucleic acid molecules representative of expressed polynucleotides in cells of a plant known not have been exposed to an abiotic stress, indicates that the test plant has been exposed to an abiotic stress, and whereby an absence of selective hybridization of at least one nucleic acid probe indicates that the test plant has not been exposed to an abiotic stress. For example, the abiotic stress is cold stress, and the probe can include at least 15 nucleotides of a nucleotide sequence as set forth in any of SEQ ID NOS: 1-155, 157-228, 230-232, 234-557, 559-572, 574-605, 607-634, 636-786, 788-812, 814-1261 or a nucleotide sequence complementary thereto; or the abiotic stress can be a saline stress, and the probe can include at least 15 nucleotides of a nucleotide sequence as set forth in any of SEQ ID NOS:2226-2427 or a nucleotide sequence complementary thereto; or the abiotic stress can be an osmotic stress, and the probe can include at least 15 nucleotides of a nucleotide sequence as set forth in two or more of SEQ ID NOS:2428-2585 or a nucleotide sequence complementary thereto.

A method of identifying a stress condition to which a plant cell was exposed also can be performed, for example, by contacting nucleic acid molecules expressed in the test plant cell with an array of probes representative of the plant cell genome; detecting a profile of expressed nucleic acid molecules characteristic of a stress response, and comparing the expression pattern in the test plant to the expression pattern obtained from a reference plant thereby identifying the stress condition to which the plant cell was exposed. The contacting is under conditions that allow for selective hybridization of a nucleic acid molecule with probes having sufficient complementarity, for example, under stringent hybridization conditions. The profile can be characteristic of exposure to a single stress condition, for example, an abnormal level of cold, osmotic pressure, or salinity, or can be characteristic of exposure to more than one stress condition, for example, cold, increased osmotic pressure and increased salinity. In one embodiment, the nucleotide sequence of a gene whose expression is detected is selected from a polynucleotide comprising any of SEQ ID NOS: 1-2703. In further embodiments, the nucleotide sequence of a gene that is expressed in response a particular stress or combination of stresses can comprise a polynucleotide expressed in response to cold stress (SEQ ID NOS:1-1261), osmotic stress (SEQ ID NOS: 2428-2585), saline (salt) stress (SEQ ID NOS:2227-2427), a combination of cold and osmotic stress (SEQ ID NOS:1699-1969), a combination of saline and osmotic stress (SEQ ID NOS:1970-2226), a combination of osmotic and saline stress (SEQ ID NOS:2586-2703), or a combination of cold, osmotic and saline stress (SEQ ID NOS:1262-1698).

In another embodiment, the method can be used for determining whether a test plant has been exposed to a combination of abiotic stress conditions. Such a method can be performed, for example, by contacting nucleic acid molecules representative of expressed polynucleotides in cells of the test plant with at least one nucleic acid probe under conditions suitable for selective hybridization to a complementary nucleotide sequence, whereby detecting selective hybridization of at least one nucleic acid probe, or detecting a change in a level of selective hybridization as compared to a level of selective hybridization obtained using nucleic acid molecules representative of expressed polynucleotides in cells of a plant known not have been exposed to a combination of stress conditions, indicates that the test plant has been exposed to a combination of abiotic stress conditions, and whereby an absence of selective hybridization of at least one nucleic acid probe indicates that the test plant has not been exposed to a combination of abiotic stress conditions. For example, the combination of abiotic stress conditions can be a combination of a cold stress and an osmotic stress, and the probe can include at least 15 nucleotides of a nucleotide sequence as set forth in any of SEQ ID NOS: 1699-1969, or a nucleotide sequence complementary thereto; or the combination of abiotic stress conditions can be a combination of a cold stress and a saline stress, and the probe can include at least 15 nucleotides of a nucleotide sequence as set forth in any of SEQ ID NOS: 1970-2226, or a nucleotide sequence complementary thereto; or the combination of abiotic stress conditions can be a combination of an osmotic stress and a saline stress, and the probe can included at least 15 nucleotides of a nucleotide sequence as set forth in any of SEQ ID NOS:2586-2703, or a nucleotide sequence complementary thereto; or the combination of abiotic stress conditions can be a combination of a cold stress, a saline stress and an osmotic stress, and the probe can include at least 15 nucleotides of a nucleotide sequence as set forth in any of SEQ ID NOS:1262-1698, or a nucleotide sequence complementary thereto.

The present invention also relates to a method for monitoring a population of plants for exposure to a stress condition or combination of stress conditions. Such a method can be performed, for example, by introducing into the population of a plants a sentinel plant, wherein said sentinel plant is a transgenic plant, which contains plant cells containing a stress-regulated regulatory element operatively linked to a polynucleotide encoding a detectable marker; and examining the sentinel plant for expression of the detectable marker, which is indicative of exposure of the population of plants to a stress condition or combination of stress conditions. The stress condition or combination of stress conditions can be any such condition or conditions, particularly an abiotic stress condition or combination of abiotic stress conditions. The detectable marker can be any reporter molecule that is readily or conveniently detectable, particularly a marker that is visibly detectable, for example, a luminescent detectable marker such as luciferin, or a fluorescent detectable marker such as a green fluorescent protein, a yellow fluorescent protein, a cyan fluorescent protein, a red fluorescent protein, or an enhanced or modified form thereof.

The present invention further relates to a transgenic plant, which contains a nucleic acid construct comprising a polynucleotide portion of plant stress-regulated polynucleotide. In one embodiment, the transgenic plant exhibits altered responsiveness to a stress condition as compared to a corresponding reference plant not containing the construct. Such a transgenic plant can contain, for example, a construct that disrupts an endogenous stress-regulated gene in the plant, thereby reducing or inhibiting expression of the gene in response to a stress condition. Such a knock-out can increase or decrease tolerance of the plant to a stress condition. The transgene also can comprise a coding sequence of a plant stress-regulated gene, which can be operatively linked to a heterologous regulatory element such as a constitutively active regulatory element, an regulated regulatory element, a tissues specific or phase specific regulatory element, or the like. In another embodiment, the transgenic plant contains a nucleic acid construct comprising a plant stress-regulated regulatory element, which can be operatively linked to a heterologous nucleotide sequence that can encode a polypeptide. Expression of the heterologous polypeptide can confer a desirable characteristic on the plant, for example, can improve the nutritional or ornamental value of the transgenic plant. In still another embodiment, the transgenic plant contains multiple nucleic acid constructs, which can be multiple copies of the same construct, or can be two or more different constructs.

The present invention also relates to a plant stress-regulated regulatory element, which is obtained from a plant stress-regulated polynucleotide disclosed herein for example any of SEQ ID NOS:2704-5379; a homolog or ortholog thereof. The invention also provides a method of identifying an agent, for example a transcription factor, that specifically binds to or activates a plant stress-regulated regulatory element. Such a method can be performed, for example, by contacting the regulatory element with a plant cell extract, and identifying polypeptides that specifically bind to the regulatory element. Confirmation that the specifically binding polypeptide is a transcription factor can be demonstrated using, for example, the stress-regulated regulatory element operably linked to a reporter gene, and detecting expression of the reporter gene. Control constructs comprising a regulatory element, other than a plant stress-regulated regulatory element, operatively linked to a reporter molecule can be used to confirm that the transcription factor is specific for the plant stress-regulated regulatory element. A polynucleotide encoding such a transcription factor also can be obtained.

The present invention also relates to a method of using a polynucleotide portion of a plant stress-regulated gene to confer a selective advantage on a plant cell. In one embodiment, such a method is performed by introducing a plant stress-regulated regulatory element into a plant cell such as those described herein, wherein, upon exposure of the plant cell to a stress condition to which the regulatory element is responsive, a nucleotide sequence operatively linked to the regulatory element is expressed, thereby conferring a selective advantage to plant cell. The operatively linked nucleotide sequence can be, for example, a transcription factor, the expression of which induces the further expression of polynucleotides involved in a stress response, thereby enhancing the response of a plant to the stress condition. In another embodiment, a coding sequence of a plant stress-regulated gene as disclosed herein is introduced into the cell, thereby providing the plant with a selective advantage in response to a stress condition. In still another embodiment, the method results in the knock-out of a plant stress-regulated gene as disclosed herein in a first population of plants, thereby providing a selective advantage to a stress condition in a second population of plants.

The invention further relates to a method of identifying an agent that modulates the activity of a stress-regulated regulatory element of a plant. In a particular embodiment, is provided a method for identifying an agent that alters the activity of an abiotic stress responsive regulatory element comprising contacting the agent or a composition containing an agent to be tested with at least one abiotic stress responsive regulatory element, preferably selected from the group consisting of SEQ ID NOS:2704-5379 (see Table 2), and determining the effect of the agent on the ability of the regulatory sequence to regulate transcription. In further embodiments, the regulatory elements are associated with particular stresses or combination of stresses such as cold stress (SEQ ID NOS:2704-3955), osmotic stress (SEQ ID NOS:5108-5263), saline stress (SEQ ID NOS:4910-5107), a combination of cold and osmotic stress (SEQ ID NOS:4389-4654), a combination of cold and saline stress (SEQ ID NOS:4655-4909), a combination of osmotic and saline stress (SEQ ID NOS:5264-5379), or a combination of cold, osmotic and saline stress (SEQ ID NOS: 3956-4388). In one embodiment, the regulatory element can be operatively linked to a heterologous polynucleotide encoding a reporter molecule, and an agent that modulates the activity of the stress-regulated regulatory element can be identified by detecting a change in expression of the reporter molecule due to contacting the regulatory element with the agent. Such a method can be performed in vitro in a plant cell-free system, or in a plant cell in culture or in a plant in situ. In another embodiment, the agent is contacted with a transgenic plant containing an introduced plant stress-regulated regulatory element, and an agent that modulates the activity of the regulatory element is identified by detecting a phenotypic change in the transgenic plant. The methods of the invention can be performed in the presence or absence of the stress condition to which the particularly regulatory element is responsive.

Another aspect provides a method for identifying an agent that alters abiotic stress responsive polynucleotide expression in a plant or plant cell comprising contacting a plant or plant cell with a test agent; subjecting the plant cell or plant cell to an abiotic stress or combination of stresses before, during or after contact with the agent to be tested; obtaining an expression profile of the plant or plant cell and comparing the expression profile of the plant or plant cell to an expression profile from a plant or plant cell not exposed to the abiotic stress or combination of stresses. In one embodiment, the expression profile comprises expression data for at least one nucleotide sequence comprising any of SEQ ID NOS: 1-5379 (see Tables 1 and 2). In additional embodiments, the expression profile comprises expression data for at least one, and preferably two or more sequences associated with a particular abiotic stress or combination of stresses such as cold stress (SEQ ID NOS:1-1261 and 2704-3955), osmotic stress (SEQ ID NOS:2428-2585 and 5108-5263), saline stress (SEQ ID NOS:2227-2427 and 4910-5107), a combination of cold and osmotic stress (SEQ ID NOS:1699-1969 and 4389-4654), a combination of cold and saline stress (SEQ ID NOS:1970-2226 and 4655-4909), a combination of osmotic and saline stress (SEQ ID NOS:2586-2703 and 5264-5379), or a combination of cold, osmotic and saline stress (SEQ ID NOS: 1262-1698 and 3956-4388).

Still another aspect provides nucleotide probes useful for detecting an abiotic stress response in plants, the probes comprising a nucleotide sequence of at least 15, 25, 50 or 100 nucleotides that hybridizes under stringent, preferably highly stringent, conditions to at least one sequence comprising any of SEQ ID NOS: 1-2703. Also provided are nucleotide probes comprising at least 15, 25, 50 or 100 nucleotides in length that hybridize under stringent, preferably highly stringent conditions, to at least one gene associated with a particular stress or combination of stresses, for example cold stress, (SEQ ID NOS:1-1261), osmotic stress (SEQ ID NOS:2428-2585), saline stress (SEQ ID NOS:2227-2427), a combination of cold and osmotic stress (SEQ ID NOS: 1699-1969), a combination of cold and saline stress (SEQ ID NOS: 1970-2226), a combination of osmotic and saline stress (SEQ ID NOS: 2586-2703), or a combination of cold, osmotic, and saline stress (SEQ ID NOS:1262-1698).

An additional aspect provides a method for marker-assisted breeding to select plants having an altered resistance to abiotic stress comprising obtaining nucleic acid molecules from the plants to be selected; contacting the nucleic acid molecules with one or more probes that selectively hybridize under stringent, preferably highly stringent, conditions to a nucleic acid sequence selected from the group consisting of SEQ ID NOS:1-2703; detecting the hybridization of the one or more probes to the nucleic acid sequences wherein the presence of the hybridization indicates the presence of a gene associated with altered resistance to abiotic stress; and selecting plants on the basis of the presence or absence of such hybridization. Marker-assisted selection can also be accomplished using one or more probes which selectively hybridize under stringent, preferably highly stringent conditions, to a nucleotide sequence comprising a polynucleotide expressed in response associated with a particular stress, for example, a nucleotide sequence comprising any of SEQ ID NOS:1-1261 (cold stress), SEQ ID NOS:2428-2585 (osmotic stress), SEQ ID NOS:2227-2427 (saline stress), SEQ ID NOS:1699-1969 (cold and osmotic stress), SEQ ID NOS:1970-2226 (cold and saline stress), SEQ ID NOS:2586-2703 (osmotic and saline stress), or SEQ ID NOS:1262-1698 (cold, osmotic and saline stress). In each case marker-assisted selection can be accomplished using a probe or probes to a single sequence or multiple sequences. If multiple sequences are used they can be used simultaneously or sequentially.

A further aspect provides a method for monitoring a population of plants comprising providing at least one sentinel plant containing a recombinant polynucleotide comprising a stress responsive regulatory sequence selected from the group consisting of SEQ ID NOS:2704-5379 which is operatively linked to a nucleotide sequence encoding a detectable marker, for example a fluorescent protein. Additional aspects provide the use of various regulatory sequences including those associated with cold stress (SEQ ID NOS:2704-3955), osmotic stress (SEQ ID NOS:5108-5263), saline stress (SEQ ID NOS: 4910-5107), cold and osmotic stress (SEQ ID NOS:4389-4654), cold and saline stress (SEQ ID NOS:4655-4909), osmotic and saline stress (SEQ ID NOS:5264-5379), and cold, osmotic and saline stress (SEQ ID NOS:3956-4388), or fragments thereof wherein such fragments can alter transcription of an operatively linked nucleotide sequence in response to an abiotic stress.

A further aspect provides a computer readable medium having stored thereon computer executable instructions for performing a method comprising receiving data on gene expression in a test plant of at least one nucleic acid molecule having at least 70%, preferably at least 80%, more preferably at least 90%, and most preferably at least 95% nucleotide sequence identity to one or more polynucleotide sequences as set forth in any of SEQ ID NOS: 1-2703; and comparing expression data from the test plant to expression data for the same polynucleotide sequence or sequences in a plant that has been exposed to at least one abiotic stress.

Yet a further aspect provides a computer readable medium having stored thereon a data structure comprising, sequence data for at least one, and preferably a plurality of nucleic acid molecules having at least 70%, preferably at least 80%, more preferably at least 90%, and most preferably at least 95% nucleotide sequence identity to a polynucleotide comprising any of SEQ ID NOS:1-2703, or the complement thereof; and a module receiving the nucleic acid molecule sequence data which compares the nucleic acid molecule sequence data to at least one other nucleic acid sequence.

DETAILED DESCRIPTION OF THE INVENTION

The present invention relates to clusters of genes that are induced in response to one or a combination of abiotic stress conditions. Abiotic stress conditions, such as a shortage or excess of solar energy, water and nutrients, and salinity, high and low temperature, or pollution (e.g., heavy metals), can have a major impact on plant growth and can significantly reduce the yield, for example, of cultivars. Under conditions of abiotic stress, the growth of plant cells is inhibited by arresting the cell cycle in late G1, before DNA synthesis, or at the G2/M boundary (see Dudits, Plant Cell Division, Portland Press Research, Monograph; Francis, Dudits, and Inze, eds., 1997; chap. 2, page 21; Bergounioux, *Protoplasma* 142:127-136, 1988). The identification of stress-regulated gene clusters, using microarray technology, provides a means to identify plant stress-regulated genes.

As used herein, the term "cluster," when used in reference to stress-regulated genes, refers to nucleotide sequences of genes that have been selected by drawing Venn diagrams, and selecting those genes that are regulated only by a selected stress condition. In general, a cluster of stress-regulated genes includes at least 5, 10, 15, or 20 genes, including polynucleotide portions thereof, each of which is responsive to the same selected stress condition or conditions. The selected stress condition can be a single stress condition, for example, cold, osmotic stress or salinity stress (see Tables 3-14), or can be a selected combination of stress conditions, for example, cold, osmotic stress and salinity stress (see Tables 15-26). In addition, a cluster can be selected based on specifying that all of the genes are coordinately regulated, for example, they all start at a low level and are induced to a higher level. However, a cluster of saline stress-regulated genes, for example, that was selected, or coordinate regulation from low to high, also can be decreased in response to cold or mannitol. By varying the parameters used for selecting a cluster of gene nucleotide sequences, those genes that are expressed in a specific manner following a stress can be identified.

As used herein in reference to a polynucleotide or polynucleotide portion of a gene or nucleic acid molecule, the term "isolated" means a polynucleotide, polynucleotide portion of a gene, or nucleic acid molecule that is free of one or both of the nucleotide sequences that normally flank the polynucleotide in a genome of a naturally-occurring organism from which the polynucleotide is derived. The term includes, for example, a polynucleotide or fragment thereof that is incorporated into a vector or expression cassette; into an autonomously replicating plasmid or virus; into the genomic DNA of a prokaryote or eukaryote; or that exists as a separate molecule independent of other polynucleotides. It also includes a recombinant polynucleotide that is part of a hybrid polynucleotide, for example, one encoding a polypeptide sequence.

The terms "polynucleotide," "oligonucleotide," and "nucleic acid sequence" are used interchangeably herein to refer to a polymeric (2 or more monomers) form of nucleotides of any length, either ribonucleotides or deoxyribonucleotides. Although nucleotides are usually joined by phosphodiester linkages, the term also includes polymers containing neutral amide backbone linkages composed of aminoethyl glycine units. The terms are used only to refer to the primary structure of the molecule. Thus, the term includes double stranded and single stranded DNA molecules, including a sense strand or an antisense strand, and RNA molecules as well as genomic DNA, cDNA, mRNA and the like. It will be recognized that such polynucleotides can be modified, for example, by including a label such as a radioactive, fluorescent or other tag, by methylation, by the inclusion of a cap structure, by containing a substitution of one or more of the naturally occurring nucleotides with a nucleotide analog, by containing an internucleotide modification such as having uncharged linkages (e.g., methyl phosphonates, phosphotriesters, phosphoramidates, carbamates, or the like), by containing a pendant moiety such as a protein (e.g., a nuclease, toxin, antibody, signal peptide, poly-L-lysine, or the like), by containing an intercalator such as acridine or psoralen, by containing a chelator, which can be a metal such as boron, an oxidative metal, or a radioactive metal, by containing an alkylator, or by having a modified linkage (e.g., an alpha anomeric nucleic acid).

The term "recombinant nucleic acid molecule" refers to a polynucleotide produced by human intervention. A recombinant nucleic acid molecule can contain two or more nucleotide sequences that are linked in a manner such that the product is not found in a cell in nature. In particular, the two or more nucleotide sequences can be operatively linked and, for example, can encode a fusion polypeptide, or can comprise a nucleotide sequence and a regulatory element. A recombinant nucleic acid molecule also can be based on, but different, from a naturally occurring polynucleotide, for example, a polynucleotide having one or more nucleotide changes such that a first codon, which normally is found in the polynucleotide, is replaced with a degenerate codon that encodes the same or a conservative amino acid, or such that a sequence of interest is introduced into the polynucleotide, for example, a restriction endonuclease recognition site or a splice site, a promoter, a DNA replication initiation site, or the like.

As used herein, the term "abiotic stress" or "abiotic stress condition" refers to the exposure of a plant, plant cell, or the like, to a non-living ("abiotic") physical or chemical agent or condition that has an adverse effect on metabolism, growth, development, propagation and/or survival of the plant (collectively "growth"). An abiotic stress can be imposed on a plant due, for example, to an environmental factor such as water (e.g., flooding, drought, dehydration), anaerobic conditions (e.g., a low level of oxygen), abnormal osmotic conditions, salinity or temperature (e.g., hot/heat, cold, freezing, frost), a deficiency of nutrients or exposure to pollutants, or by a hormone, second messenger or other molecule. Anaerobic stress, for example, is due to a reduction in oxygen levels (hypoxia or anoxia) sufficient to produce a stress response. A flooding stress can be due to prolonged or transient immersion of a plant, plant part, tissue or isolated cell in a liquid medium such as occurs during monsoon, wet season, flash flooding or excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ or whole plant. Drought stress can be induced by or associated with the deprivation of water or reduced supply of water to a cell, tissue, organ or organism. Saline stress (salt stress) can be associated with or induced by a perturbation in the osmotic potential of the intracellular or extracellular environment of a cell. Osmotic stress also can be associated with or induced by a change, for example, in the concentration of molecules in the intracellular or extracellular environment of a plant cell, particularly where the molecules cannot be partitioned across the plant cell membrane.

As disclosed herein, clusters of plant stress-regulated genes (Example 1; see, also, Tables 1-31) and homologs and orthologs thereof (Table 32) have been identified. Remarkably, several of the stress-regulated genes previously were known to encode polypeptides having defined cellular functions, including roles as transcription factors, enzymes such as kinases, and structural proteins such as channel proteins (see Tables 29-31). The identification of *Arabidopsis* stress-regulated genes provides a means to identify homologous and orthologous genes and gene sequences in other plant species using well known procedures and algorithms based on identity (or homology) to the disclosed sequences. Thus, the invention provides polynucleotide sequences comprising plant stress-regulated genes that are homologs or orthologs, variants, or otherwise substantially similar to the polynucleotides disclosed herein, and having an E value $\leq 1 \times 10^{-8}$, which can be identified, for example, by a BLASTN search using the *Arabidopsis* polynucleotides of Tables 1 and 2 (SEQ ID NOS: 1-5379) as query sequences (see Table 32, on CD).

A polynucleotide sequence of a stress-regulated gene as disclosed herein can be particularly useful for performing the methods of the invention on a variety of plants, including but not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea ultilane*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, duckweed (*Lemna*), barley, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals such as azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum are also included. Additional ornamentals within the scope of the invention include impatiens, Begonia, Pelargonium, Viola, Cyclamen, Verbena, Vinca, Tagetes, Primula, Saint Paulia, Agertum, Amaranthus, Antihirrhinum, Aquilegia, Cineraria, Clover, Cosmo, Cowpea, Dahlia, Datura, Delphinium, Gerbera, Gladiolus, Gloxinia, Hippeastrum, Mesembryanthemum, Salpiglossos, and Zinnia. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga ultilane*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Leguminous plants which may be used in the practice of the present invention include beans and peas. Beans include guar, locust bean, fenugreek, soybean, garden beans, cowpea, mung bean, lima bean, fava bean, lentils, chickpea, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, trifolium, *Phaseolus*, e.g., common bean and lima bean, *Pisum*, e.g., field bean, *Melilotus*, e.g., clover, *Medicago*, e.g., alfalfa, Lotus, e.g., trefoil, lens, e.g., lentil, and false indigo. Preferred forage and turf grass for use in the methods of the invention include alfalfa, orchard grass, tall fescue, perennial ryegrass, creeping bent grass, and redtop.

Other plants within the scope of the invention include *Acacia*, aneth, artichoke, arugula, blackberry, canola, cilantro, clementines, escarole, eucalyptus, fennel, grapefruit, honey dew, jicama, kiwifruit, lemon, lime, mushroom, nut, okra, orange, parsley, persimmon, plantain, pomegranate, poplar, radiata pine, radicchio, Southern pine, sweetgum, tangerine, triticale, vine, yams, apple, pear, quince, cherry, apricot, melon, hemp, buckwheat, grape, raspberry, chenopodium, blueberry, nectarine, peach, plum, strawberry, watermelon, eggplant, pepper, cauliflower, *Brassica*, e.g., broccoli, cabbage, ultilan sprouts, onion, carrot, leek, beet, broad bean, celery, radish, pumpkin, endive, gourd, garlic, snapbean, spinach, squash, turnip, ultilane, chicory, groundnut and zucchini.

As used herein, the term "substantially similar", when used herein with respect to a nucleotide sequence, means a nucleotide sequence corresponding to a reference nucleotide sequence, wherein the corresponding sequence encodes a polypeptide or comprises a regulatory element having substantially the same structure and function as the polypeptide encoded by the reference nucleotide sequence, for example, where only changes in amino acids not affecting the polypeptide function occur. For purposes of the present invention, a reference (or query) sequence is a polynucleotide sequence as set forth in any of SEQ ID NOS: 1-2703 or a polypeptide encoded thereby. Desirably, a substantially similar nucleotide sequence encodes the polypeptide encoded by the reference nucleotide sequence. The percentage of identity between the substantially similar nucleotide sequence and the reference nucleotide sequence desirably is at least 60%, more desirably at least 75%, preferably at least 90%, more preferably at least 95%, still more preferably at least 99% and including 100%. A nucleotide sequence is "substantially similar" to reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C. (stringent conditions), more desirably still in 7% sodium dodecyl sulfate (SDS), 0.5 M NaPO$_4$, 1 mM EDTA at 50° C. with washing in 0.5×SSC, 0.1% SDS at 50° C. (high stringency), preferably in 7% sodium dodecyl sulfate (SDS), 0.5 M NaPO$_4$, 1 mM EDTA at 50° C. with washing in 0.1×SSC, 0.1% SDS at 50° C. (very high stringency), more preferably in 7% sodium dodecyl sulfate (SDS), 0.5 M NaPO$_4$, 1 mM EDTA at 50° C. with washing in 0.1× SSC, 0.1% SDS at 65° C. (extremely high stringency).

In addition, the term "substantially similar," when used in reference to a polypeptide sequence, means that an amino acid sequence relative to a reference (query) sequence shares at least about 65% amino acid sequence identity, particularly at least about 75% amino acid sequence identity, and preferably at least about 85%, more preferably at least about 90%, and most preferably at least about 95% or greater amino acid sequence identity. Generally, sequences having an $E \leq 10^{-8}$ are considered to be substantially similar to a query sequence. Such sequence identity can take into account conservative amino acid changes that do not substantially affect the function of a polypeptide. As such, homologs or orthologs of the *Arabidopsis* stress-regulated nucleotide sequences disclosed herein, variants thereof, and polypeptides substantially similar to the polynucleotide sequence of *Arabidopsis* stress-regulated genes set forth in SEQ ID NOS: 1-5379 are encompassed within the present invention and, therefore, useful for practicing the methods of the invention (see, for example, Table 32, which is on the CD-R filed herewith, and incorporated herein by reference).

Homology or identity is often measured using sequence analysis software such as the Sequence Analysis Software Package of the Genetics Computer Group (University of Wisconsin Biotechnology Center, 1710 University Avenue, Madison, Wis. 53705). Such software matches similar sequences by assigning degrees of homology to various deletions, substitutions and other modifications. The terms "homology" and "identity," when used herein in the context of two or more nucleic acids or polypeptide sequences, refer to two or more sequences or subsequences that are the same or have a specified percentage of amino acid residues or of nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window" is used broadly herein to include reference to a segment of any one of the number of contiguous positions, for example, about 20 to 600 positions, for example, amino acid or nucleotide position, usually about 50 to about 200 positions, more usually about 100 to about 150 positions, in which a sequence may be compared to a reference sequence of the same number of contiguous positions after the two sequences are optimally aligned. Methods of alignment of sequence for comparison are well-known in the art. Optimal alignment of sequences for comparison can be conducted, for example, by the local homology algorithm of Smith and Waterman (*Adv. Appl. Math.* 2:482, 1981), by the homology alignment algorithm of Needleman and Wunsch (*J. Mol. Biol.* 48:443, 1970), by the search for similarity method of Person and Lipman (*Proc. Natl. Acad. Sci., USA* 85:2444, 1988), each of which is incorporated herein by reference; by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences.

A number of genome databases are available for comparison. Several databases containing genomic information annotated with some functional information are maintained by different organizations, and are accessible via the internet, for example, at world wide web addresses (url's) "wwwtigr.org/tdb"; "genetics.wisc.edu"; "genome-www.stanford.edu/~ball"; "hiv-web.lanl.gov"; "ncbi.nlm.nih.gov"; "ebi.ac.uk"; "Pasteur.fr/other/biology"; and "genome.wi.mit.edu".

In particular, the BLAST and BLAST 2.0 algorithms using default parameters are particularly useful for identifying polynucleotide and polypeptides encompassed within the present invention (Altschul et al. (*Nucleic Acids Res.* 25:3389-3402, 1977; *J. Mol. Biol.* 215:403-410, 1990, each of which is incorporated herein by reference). Software for performing BLAST analyses is publicly available through the National Center for Biotechnology Information (http://www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra, 1977, 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4 and a comparison of both strands. For amino acid sequences, the BLASTP program uses as defaults a wordlength of 3, and expectations (E) of 10, and the BLOSUM62 scoring matrix (see Henikoff and Henikoff, *Proc. Natl. Acad. Sci., USA* 89:10915, 1989) alignments (B) of 50, expectation (E) of 10, M=5, N=4, and a comparison of both strands.

The BLAST algorithm also performs a statistical analysis of the similarity between two sequences (see, for example, Karlin and Altschul, *Proc. Natl. Acad. Sci., USA* 90:5873, 1993, which is incorporated herein by reference). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. Significantly, upon identifying polynucleotides that are substantially similar to those of SEQ ID NOS: 1-5379, the identified polynucleotides can be used as query sequences in a BLAST search to identify polynucleotides and polypeptides substantially similar thereto.

It should be noted that the nucleotide sequences set forth as SEQ ID NOS: 1-2703 comprise coding sequences, whereas the nucleotide sequences set forth as SEQ ID NOS:2704-5379 comprise regulatory sequences. In addition, the coding sequences and regulatory sequences are related in that, for example, SEQ ID NO: 1 is the coding sequence of a plant cold regulated gene having a 5' upstream (regulatory) sequence set forth as SEQ ID NO:2704 (see Table 2). Similarly, SEQ ID NO:2705 comprises a regulatory region of SEQ ID NO:2, SEQ ID NO:2706 comprises a regulatory region of SEQ ID NO:3, and so forth as shown in Table 2. As such, reference herein, for example, to a "polynucleotide comprising SEQ ID NO: 1" can, unless indicated otherwise, include at least SEQ ID NO:2704. In some cases, the entire coding region of a plant stress regulated gene or the 5' upstream sequence has not yet been determined (see, for example, SEQ ID NO:43 in Table 3, where "none" indicates that 5' upstream regulatory sequences have not yet been determined). However, the determination of a complete coding sequence where only a portion is known or of regulatory sequences where a portion of the coding sequence is known can be made using methods as disclosed herein or otherwise known in the art.

In one embodiment, protein and nucleic acid sequence homologies are evaluated using the Basic Local Alignment Search Tool ("BLAST"). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., *Science* 256:1443-1445, 1992; Henikoff and Henikoff, *Proteins* 17:49-61, 1993, each of which is incorporated herein by reference). Less preferably, the PAM or PAM250 matrices may also be used (Schwartz and Dayhoff, eds., "Matrices for Detecting Distance Relationships: Atlas of Protein Sequence and Structure" (Washington, National Biomedical Research Foundation 1978)). BLAST programs are accessible through the U.S. National Library of Medicine, for example, on the world wide web at address (url) "ncbi.nlm.nih.gov".

The parameters used with the above algorithms may be adapted depending on the sequence length and degree of homology studied. In some embodiments, the parameters may be the default parameters used by the algorithms in the absence of instructions from the user.

The term "substantially similar" also is used in reference to a comparison of expression profiles of nucleotide sequences, wherein a determination that an expression profile characteristic of a stress response is substantially similar to the profile of nucleic acid molecules expressed in a plant cell being examined ("test plant") is indicative of exposure of the test plant cell to one or a combination of abiotic stress conditions. When used in reference to such a comparison of expression profiles, the term "substantially similar" means that that the individual nucleotide sequences in the test plant cell profile are altered in the same manner as the corresponding nucleotide sequences in the expression profile characteristic of the stress response.

By way of example, where exposure to saline results in an increased expression of nucleotide sequences A, B and C, and a decreased expression of nucleotide sequences D and E, as indicated by the expression profile characteristic of a saline stress response, a determination that corresponding nucleotide sequences A, B and C in the test plant cell are increased and that nucleotides sequences D and E are decreased is indicative of exposure of the test plant cell to a saline stress condition. It should be recognized that, where, for example, only nucleotide sequences A, B, D and E are examined in the test plant cell, an increase in A and B and a decrease in D and E expression of the test plant cells is considered to be substantially similar to the expression profile characteristic of a saline stress condition and, therefore, is indicative of exposure of the plant cell to a saline stress condition. Similarly, where the levels of expression of the nucleotide sequences examined in a test plant are altered in the same manner, i.e., are increased or are decreased, as that observed in an expression profile characteristic of a particular stress response, the absolute levels of expression may vary, for example, two-fold, five-fold, ten-fold, or the like. Nevertheless, the expression profile of the test plant cell is considered to be substantially similar to the expression profile characteristic of the particular stress response and, therefore, indicative of exposure of the plant cell to the stress condition.

As disclosed herein, clusters of stress-regulated genes (and their products), some of which also have been described as having cellular functions such as enzymatic activity or roles as transcription factors, are involved in the response of plant cells to various abiotic stresses (see Tables 29-31; see, also, Tables 1 and 32). As such, the polynucleotide sequences comprising the genes in a cluster likely share common stress-regulated regulatory elements, including, for example, cold-regulated regulatory elements (SEQ ID NOS:2704-3955), salinity-regulated regulatory elements (SEQ ID NOS:4910-5107, and osmotic pressure-regulated regulatory elements (SEQ ID NO:5108-5263), as well as regulatory elements that are responsive to a combination of stress conditions, but not to any of the individual stress conditions, alone (SEQ ID NOS: 3956-4909 and 5263-5379). The identification of such clusters of genes thus provides a means to identify the stress-regulated regulatory elements that control the level of expression of these genes.

As used herein, the term "plant stress-regulated gene" means a polynucleotide sequence of a plant, the transcription of which is altered in response to exposure to a stress condition, and the regulatory elements linked to such a polynucleotide sequence and involved in the stress response, which can be induction or repression. In general, plant stress gene regulatory elements are contained within a sequence including approximately two kilobases upstream (5') of the transcription or translation start site and two kilobases downstream (3') of the transcription or translation termination site. In the absence of an abiotic stress condition, the stress-regulated gene can normally be unexpressed in the cells, can be expressed at a basal level, which is induced to a higher level in response to the stress condition, or can be expressed at a level that is reduced (decreased) in response to the stress condition. The coding region of a plant stress-regulated gene encodes a stress-regulated polypeptide, and also can be the basis for expression of a functional RNA molecule such as an antisense molecule or ribozyme. A stress-regulated polypeptide can have an adaptive effect on a plant, thereby allowing the plant to better tolerate stress conditions; or can have a maladaptive effect, thereby decreasing the ability of the plant to tolerate the stress conditions.

The present invention provides an isolated plant stress-regulated regulatory element, which regulates expression of an operatively linked nucleotide sequence in a plant in response a stress condition. As disclosed herein, a plant stress-regulated regulatory element can be isolated from a polynucleotide sequence of a plant stress-regulated gene comprising a nucleotide sequence as set forth in SEQ ID NOS: 1-2703, for example any of SEQ ID NOS:2704-5379 (see Table 2). It is recognized that certain of the polynucleotides set forth as SEQ ID NOS: 1-5379 previously have been described as being involved in a stress-regulated response in plants, including SEQ ID NOS:156, 229, 233, 558, 573, 606, 625, 635, 787, 813, 1263, 1386, 1391, 1405, 1445, 1484, 1589, 1609, 1634, 1726, 1866, 1918, and 1928 and, therefore, are not encompassed, in whole or in part, within the compositions of the invention, and are encompassed within only certain particular methods of the invention, for example, methods of making a transgenic plant that is resistant to two or more stress conditions, since, even where such a gene was known to be expressed in response to a single stress condition such as cold or saline (e.g., SEQ ID NO:1263), it was not known prior to the present disclosure that any of these genes was responsive to a combination of stress conditions (for example, a combination of cold and osmotic stress for SEQ ID NOS: 1726, 1866, 1918, and 1928; or a combination of cold, osmotic and saline stress for SEQ ID NOS:1263, 1386, 1391, 1405, 1445, 1484, 1589, 1609, and 1634).

Methods for identifying and isolating the stress-regulated regulatory element from the disclosed polynucleotides, or genomic DNA clones corresponding thereto, are well known in the art. For example, methods of making deletion constructs or linker-scanner constructs can be used to identify nucleotide sequences that are responsive to a stress condition. Generally, such constructs include a reporter gene operatively linked to the sequence to be examined for regulatory activity. By performing such assays, a plant stress-regulated regulatory element can be defined within a sequence of about 500 nucleotides or fewer, generally at least about 200 nucleotides or fewer, particularly about 50 to 100 nucleotides, and more particularly at least about 20 nucleotides or fewer. Preferably the minimal (core) sequence required for regulating a stress response of a plant is identified.

The nucleotide sequences of the genes of a cluster also can be examined using a homology search engine such as described herein to identify sequences of conserved identity, particularly in the nucleotide sequence upstream of the transcription start site. Since all of the genes in a cluster as disclosed are induced in response to a particular stress condition or a particular combination of stress conditions, some or all of the nucleotide sequences can share conserved stress-regulated regulatory elements. By performing such a homology search, putative stress-regulated regulatory elements can be identified. The ability of such identified sequences to function as a plant stress-regulated regulatory element can be confirmed, for example, by operatively linking the sequence to a reporter gene and assaying the construct for responsiveness to a stress condition.

As used herein, the term "regulatory element" means a nucleotide sequence that, when operatively linked to a coding region of a gene, effects transcription of the coding region such that a ribonucleic acid (RNA) molecule is transcribed from the coding region. A regulatory element generally can increase or decrease the amount of transcription of a nucleotide sequence, for example, a coding sequence, operatively linked to the element with respect to the level at which the nucleotide sequence would be transcribed absent the regulatory element. Regulatory elements are well known in the art and include promoters, enhancers, silencers, inactivated silencer intron sequences, 3'-untranslated or 5'-untranslated sequences of transcribed sequence, for example, a poly-A signal sequence, or other protein or RNA stabilizing elements, or other gene expression control elements known to regulate gene expression or the amount of expression of a gene product. A regulatory element can be isolated from a naturally occurring genomic DNA sequence or can be synthetic, for example, a synthetic promoter.

Regulatory elements can be constitutively expressed regulatory element, which maintain gene expression at a relative level of activity (basal level), or can be regulated regulatory elements. Constitutively expressed regulatory elements can be expressed in any cell type, or can be tissue specific, which are expressed only in particular cell types, phase specific, which are expressed only during particular developmental or growth stages of a plant cell, or the like. A regulatory element such as a tissue specific or phase specific regulatory element or an inducible regulatory element useful in constructing a recombinant polynucleotide or in a practicing a method of the invention can be a regulatory element that generally, in nature, is found in a plant genome. However, the regulatory element also can be from an organism other than a plant, including, for example, from a plant virus, an animal virus, or a cell from an animal or other multicellular organism.

A regulatory element useful for practicing method of the present is a promoter element. Useful promoters include, but are not limited to, constitutive, inducible, temporally regulated, developmentally regulated, spatially-regulated, chemically regulated, stress-responsive, tissue-specific, viral and synthetic promoters. Promoter sequences are known to be strong or weak. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the Ptac promoter can be induced to varying levels of gene expression depending on the level of isothiopropylgalactoside added to the transformed bacterial cells. An isolated promoter sequence that is a strong promoter for heterologous nucleic acid is advantageous because it provides for a sufficient level of gene expression to allow for easy detection and selection of transformed cells and provides for a high level of gene expression when desired.

Within a plant promoter region there are several domains that are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence that defines the transcription start point for the structural gene.

The presence of the core promoter region defines a sequence as being a promoter: if the region is absent, the promoter is non-functional. The core promoter region, however, is insufficient to provide full promoter activity. A series of regulatory sequences upstream of the core constitute the remainder of the promoter. These regulatory sequences determine expression level, the spatial and temporal pattern of expression and, for an important subset of promoters, expression under inductive conditions (regulation by external factors such as light, temperature, chemicals, hormones).

To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins which are easily measured, including, but not limited to, chloramphenicol acetyl transferase (CAT), beta-glucuronidase (GUS), green fluorescent protein (GFP), β-galactosidase (β-GAL), and luciferase.

The construct containing the reporter gene under the control of the promoter is then introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2-position or 3-position of chloramphenicol. The reaction is monitored by thin layer chromatography, which separates acetylated chloramphenicol from unreacted material. The reaction products are then visualized by autoradiography.

The level of enzyme activity corresponds to the amount of enzyme that was made, which in turn reveals the level of expression from the promoter of interest. This level of expression can be compared to other promoters to determine the relative strength of the promoter under study. In order to be sure that the level of expression is determined by the promoter, rather than by the stability of the mRNA, the level of the reporter mRNA can be measured directly, for example, by northern blot analysis.

Once activity is detected, mutational and/or deletional analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then introduced to cells and their activity determined.

The choice of promoter will vary depending on the temporal and spatial requirements for expression, and also depending on the target species. In some cases, expression in multiple tissues is desirable. While in others, tissue-specific, e.g., leaf-specific, seed-specific, petal-specific, anther-specific, or pith-specific, expression is desirable. Although many promoters from dicotyledons have been shown to be operational in monocotyledons and vice versa, ideally dicotyledonous promoters are selected for expression in dicotyledons, and monocotyledonous promoters for expression in monocotyledons. There is, however, no restriction to the origin or source of a selected promoter. It is sufficient that the promoters are operational in driving the expression of a desired nucleotide sequence in the particular cell.

A range of naturally-occurring promoters are known to be operative in plants and have been used to drive the expression of heterologous (both foreign and endogenous) genes and nucleotide sequences in plants: for example, the constitutive 35S cauliflower mosaic virus (CaMV) promoter, the ripening-enhanced tomato polygalacturonase promoter (Bird et al., 1988), the E8 promoter (Diekman and Fischer, 1988) and the fruit specific 2A1 promoter (Pear et al., 1989). Many other promoters, e.g., U2 and U5 snRNA promoters from maize, the promoter from alcohol dehydrogenase, the Z4 promoter from a gene encoding the Z4 22 kD zein protein, the Z10 promoter from a gene encoding a 10 kD zein protein, a Z27 promoter from a gene encoding a 27 kD zein protein, the A20 promoter from the gene encoding a 19 kD zein protein, inducible promoters, such as the light inducible promoter derived from the pea rbcS gene and the actin promoter from rice, e.g., the actin 2 promoter (WO 00/70067); seed specific promoters, such as the phaseolin promoter from beans, may also be used. The nucleotide sequences of the stress-regulated genes of this invention can also be expressed under the regulation of promoters that are chemically regulated. This enables the nucleic acid sequence or encoded polypeptide to be synthesized only when the crop plants are treated with the inducing chemicals. Chemical induction of gene expression is detailed in EP 0 332 104 and U.S. Pat. No. 5,614,395.

In some instances it may be desirable to link a constitutive promoter to a polynucleotide comprising a stress regulated gene of the invention. Examples of some constitutive promoters include the rice actin 1 (Wang et al., 1992; U.S. Pat. No. 5,641,876), CaMV 35S (Odell et al., 1985), CaMV 19S (Lawton et al., 1987), nos, Adh, sucrose synthase; and the ubiquitin promoters.

In other situations it may be desirable to limit expression of stress-related sequences to specific tissues or stages of development. As used herein, the term "tissue specific or phase specific regulatory element" means a nucleotide sequence that effects transcription in only one or a few cell types, or only during one or a few stages of the life cycle of a plant, for example, only for a period of time during a particular stage of growth, development or differentiation. The terms "tissue specific" and "phase specific" are used together herein in referring to a regulatory element because a single regulatory element can have characteristics of both types of regulatory elements. For example, a regulatory element active only during a particular stage of plant development also can be expressed only in one or a few types of cells in the plant during the particular stage of development. As such, any attempt to classify such regulatory elements as tissue specific or as phase specific can be difficult. Accordingly, unless indicated otherwise, all regulatory elements having the characteristic of a tissue specific regulatory element, or a phase specific regulatory element, or both are considered together for purposes of the present invention.

Examples of tissue specific promoters which have been described include the lectin (Vodkin, 1983; Lindstrom et al., 1990) corn alcohol dehydrogenase 1 (Vogel et al., 1989; Dennis et al., 1984), corn light harvesting complex (Simpson, 1986; Bansal et al., 1992), corn heat shock protein (Odell et al., 1985), pea small subunit RuBP carboxylase (Poulsen et al., 1986), Ti plasmid mannopine synthase and Ti plasmid nopaline synthase (Langridge et al., 1989), petunia chalcone isomerase (vanTunen et al., 1988), bean glycine rich protein 1 (Keller et al., 1989), truncated CaMV 35s (Odell et al., 1985), potato patatin (Wenzler et al., 1989), root cell (Yamamoto et al., 1990), maize zein (Reina et al., 1990; Kriz et al., 1987; Wandelt et al., 1989; Langridge et al., 1983; Reina et al., 1990), globulin-1 (Belanger et al., 1991), α-tubulin, cab (Sullivan et al., 1989), PEPCase (Hudspeth & Grula, 1989), R gene complex-associated promoters (Chandler et al., 1989), histone, and chalcone synthase promoters (Franken et al., 1991). Tissue specific enhancers are described by Fromm et al. (1989).

Several other tissue-specific regulated genes and/or promoters have been reported in plants, including genes encoding seed storage proteins such as napin, cruciferin, beta-conglycinin, and phaseolin, zein or oil body proteins such as oleosin, genes involved in fatty acid biosynthesis, including acyl carrier protein, stearoyl-ACP desaturase, fatty acid desaturases (fad 2-1), and other genes expressed during embryonic development such as Bce4 (see, for example, EP 255378 and Kridl et al., 1991). Particularly useful for seed-specific expression is the pea vicilin promoter (Czako et al., 1992). (See also U.S. Pat. No. 5,625,136, which is incorporated herein by reference.) Other useful promoters for expression in mature leaves are those that are switched on at the onset of senescence, such as the SAG promoter from *Arabidopsis* (Gan et al., 1995).

A class of fruit-specific promoters expressed at or during antithesis through fruit development, at least until the beginning of ripening, is discussed in U.S. Pat. No. 4,943,674. cDNA clones that are preferentially expressed in cotton fiber have been isolated (John et al., 1992). cDNA clones from tomato displaying differential expression during fruit development have been isolated and characterized (Mansson et al., 1985, Slater et al., 1985). The promoter for polygalacturonase gene is active in fruit ripening. The polygalacturonase gene is described in U.S. Pat. Nos. 4,535,060, 4,769,061, 4,801,590, and 5,107,065, each of which is incorporated herein by reference.

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 (John et al., 1992). The E6 gene is most active in fiber, although low levels of transcripts are found in leaf, ovule and flower.

Additional tissue specific or phase specific regulatory elements include, for example, the AGL8/FRUITFULL regulatory element, which is activated upon floral induction (Hempel et al., *Development* 124:3845-3853, 1997, which is incorporated herein by reference); root specific regulatory elements such as the regulatory elements from the RCP1 gene and the LRP1 gene (Tsugeki and Fedoroff, *Proc. Natl. Acad., USA* 96:12941-12946, 1999; Smith and Fedoroff, *Plant Cell* 7:735-745, 1995, each of which is incorporated herein by reference); flower specific regulatory elements such as the regulatory elements from the LEAFY gene and the APETELA1 gene (Blazquez et al., *Development* 124:3835-3844, 1997, which is incorporated herein by reference; Hempel et al., supra, 1997); seed specific regulatory elements such as the regulatory element from the oleosin gene (Plant et al., *Plant Mol. Biol.* 25:193-205, 1994, which is incorporated herein by reference), and dehiscence zone specific regulatory element. Additional tissue specific or phase specific regulatory elements include the Zn13 promoter, which is a pollen specific promoter (Hamilton et al., *Plant Mol. Biol.* 18:211-218, 1992, which is incorporated herein by reference); the UNUSUAL FLORAL ORGANS (UFO) promoter, which is active in apical shoot meristem; the promoter active in shoot meristems (Atanassova et al., *Plant J.* 2:291, 1992, which is incorporated herein by reference), the cdc2a promoter and cyc07 promoter (see, for example, Ito et al., *Plant Mol. Biol.* 24:863, 1994; Martinez et al., *Proc. Natl. Acad. Sci., USA* 89:7360, 1992; Medford et al., *Plant Cell* 3:359, 1991; Terada et al., *Plant J.* 3:241, 1993; Wissenbach et al., *Plant J.* 4:411, 1993, each of which is incorporated herein by reference); the promoter of the APETELA3 gene, which is active in floral meristems (Jack et al., *Cell* 76:703, 1994, which is incorporated herein by reference; Hempel et al., supra, 1997); a promoter of an agamous-like (AGL) family member, for example, AGL8, which is active in shoot meristem upon the transition to flowering (Hempel et al., supra, 1997); floral abscission zone promoters; L1-specific promoters; and the like.

The tissue-specificity of some "tissue-specific" promoters may not be absolute and may be tested by one skilled in the art using the diphtheria toxin sequence. One can also achieve tissue-specific expression with "leaky" expression by a combination of different tissue-specific promoters (Beals et al., 1997). Other tissue-specific promoters can be isolated by one skilled in the art (see U.S. Pat. No. 5,589,379). Several inducible promoters ("gene switches") have been reported, many of which one described in the review by Gatz (1996) and Gatz (1997). These include tetracycline repressor system, Lac repressor system, copper inducible systems, salicylate inducible systems (such as the PR1a system), glucocorticoid (Aoyama et al., 1997) and ecdysone inducible systems. Also included are the benzene sulphonamide (U.S. Pat. No. 5,364,780) and alcohol (WO 97/06269 and WO 97/06268) inducible systems and glutathione S-transferase promoters.

In some instances it might be desirable to inhibit expression of a native DNA sequence within a plant's tissues to achieve a desired phenotype. In this case, such inhibition might be accomplished with transformation of the plant to comprise a constitutive, tissue-independent promoter operably linked to an antisense nucleotide sequence, such that constitutive expression of the antisense sequence produces an RNA transcript that interferes with translation of the mRNA of the native DNA sequence.

Inducible regulatory elements also are useful for purposes of the present invention. As used herein, the term "inducible regulatory element" means a regulatory element that, when exposed to an inducing agent, effects an increased level of transcription of a nucleotide sequence to which it is operatively linked as compared to the level of transcription, if any, in the absence of an inducing agent. Inducible regulatory elements can be those that have no basal or constitutive activity and only effect transcription upon exposure to an inducing agent, or those that effect a basal or constitutive level of transcription, which is increased upon exposure to an inducing agent. Inducible regulatory elements that effect a basal or constitutive level of expression generally are useful in a method or composition of the invention where the induced level of transcription is substantially greater than the basal or constitutive level of expression, for example, at least about two-fold greater, or at least about five-fold greater. Particularly useful inducible regulatory elements do not have a basal or constitutive activity, or increase the level of transcription at least about ten-fold greater than a basal or constitutive level of transcription associated with the regulatory element.

Inducible promoters that have been described include the ABA- and turgor-inducible promoters, the promoter of the auxin-binding protein gene (Schwob et al., 1993), the UDP glucose flavonoid glycosyl-transferase gene promoter (Ralston et al., 1988), the MPI proteinase inhibitor promoter (Cordero et al., 1994), and the glyceraldehyde-3-phosphate dehydrogenase gene promoter (Kohler et al., 1995; Quigley et al., 1989; Martinez et al., 1989).

The term "inducing agent" is used to refer to a chemical, biological or physical agent or environmental condition that effects transcription from an inducible regulatory element. In response to exposure to an inducing agent, transcription from the inducible regulatory element generally is initiated de novo or is increased above a basal or constitutive level of expression. Such induction can be identified using the methods disclosed herein, including detecting an increased level of RNA transcribed from a nucleotide sequence operatively linked to the regulatory element, increased expression of a polypeptide encoded by the nucleotide sequence, or a phenotype conferred by expression of the encoded polypeptide.

An inducing agent useful in a method of the invention is selected based or the particular inducible regulatory element. For example, the inducible regulatory element can be a metallothionein regulatory element, a copper inducible regulatory element or a tetracycline inducible regulatory element, the transcription from which can be effected in response to metal ions, copper or tetracycline, respectively (Furst et al., *Cell* 55:705-717, 1988; Mett et al., *Proc. Natl. Acad. Sci., USA* 90:4567-4571, 1993; Gatz et al., *Plant J.* 2:397-404, 1992; Roder et al., *Mol. Gen. Genet.* 243:32-38, 1994, each of which is incorporated herein by reference). The inducible regulatory element also can be an ecdysone regulatory element or a glucocorticoid regulatory element, the transcription from which can be effected in response to ecdysone or other steroid (Christopherson et al., *Proc. Natl. Acad. Sci., USA* 89:6314-6318, 1992; Schena et al., *Proc. Natl. Acad. Sci., USA* 88:10421-10425, 1991, each of which is incorporated herein by reference). In addition, the regulatory element can be a cold responsive regulatory element or a heat shock regulatory element, the transcription of which can be effected in response to exposure to cold or heat, respectively (Takahashi et al., *Plant Physiol.* 99:383-390, 1992, which is incorporated herein by reference). Additional regulatory elements useful in the methods or compositions of the invention include, for example, the spinach nitrite reductase gene regulatory element (Back et al., *Plant Mol. Biol.* 17:9, 1991, which is incorporated herein by reference); a light inducible regulatory element (Feinbaum et al., *Mol. Gen. Genet.* 226:449, 1991; Lam and Chua, *Science* 248:471, 1990, each of which is incorporated herein by reference), a plant hormone inducible regulatory element (Yamaguchi-Shinozaki et al., *Plant Mol. Biol.* 15:905, 1990; Kares et al., *Plant Mol. Biol.* 15:225, 1990, each of which is incorporated herein by reference), and the like.

An inducible regulatory element also can be a plant stress-regulated regulatory element of the invention. In addition to the known stress conditions that specifically induce or repress expression from such elements, the present invention provides methods of identifying agents that mimic a stress condition. Accordingly, such stress mimics are considered inducing or repressing agents with respect to a plant stress-regulated regulatory element. In addition, a recombinant polypeptide comprising a zinc finger domain, which is specific for the regulatory element, and an effector domain, particularly an activator, can be useful as an inducing agent for a plant stress-regulated regulatory element. Furthermore, such a recombinant polypeptide provides the advantage that the effector domain can be a repressor domain, thereby providing a repressing agent, which decreases expression from the regulatory element. In addition, use of such a method of modulating expression of an endogenous plant stress-regulated gene provides the advantage that the polynucleotide encoding the recombinant polypeptide can be introduced into cells of the plant, thus providing a transgenic plant that can be regulated coordinately with the endogenous plant stress-regulated gene upon exposure to a stress condition. A polynucleotide encoding such a recombinant polypeptide can be operatively linked to and expressed from a constitutively active, inducible or tissue specific or phase specific regulatory element.

In one embodiment, the promoter may be a gamma zein promoter, an oleosin ole16 promoter, a globulin I promoter, an actin I promoter, an actin c1 promoter, a sucrose synthetase promoter, an INOPS promoter, an EXM5 promoter, a globulin2 promoter, a b-32, ADPG-pyrophosphorylase promoter, an LtpI promoter, an Ltp2 promoter, an oleosin ole 17 promoter, an oleosin ole 18 promoter, an actin 2 promoter, a pollen-specific protein promoter, a pollen-specific pectate lyase promoter, an anther-specific protein promoter (Huffman), an anther-specific gene RTS2 promoter, a pollen-specific gene promoter, a tapeturn-specific gene promoter, tapeturn-specific gene RAB24 promoter, an anthranilate synthase alpha subunit promoter, an alpha zein promoter, an anthranilate synthase beta subunit promoter, a dihydrodipicolinate synthase promoter, a Thi 1 promoter, an alcohol dehydrogenase promoter, a cab binding protein promoter, an H3C4 promoter, a RUBISCO SS starch branching enzyme promoter, an ACCase promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphate-1-phosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a metallothionein-like protein promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, an a-tubulin promoter, a cab promoter, a PEPCase promoter, an R gene promoter, a lectin promoter, a light harvesting complex promoter, a heat shock protein promoter, a chalcone synthase promoter, a zein promoter, a globulin-1 promoter, an ABA promoter, an auxin-binding protein promoter, a UDP glucose flavonoid glycosyl-transferase gene promoter, an NTI promoter, an actin promoter, an opaque 2 promoter, a b70 promoter, an oleosin promoter, a CaMV 35S promoter, a CaMV 19S promoter, a histone promoter, a turgor-inducible promoter, a pea small subunit RuBP carboxylase promoter, a Ti plasmid mannopine synthase promoter, Ti plasmid nopaline synthase promoter, a petunia chalcone isomerase promoter, a bean glycine rich protein I promoter, a CaMV 35S transcript promoter, a potato patatin promoter, or a S-E9 small subunit RuBP carboxylase promoter.

In addition to promoters, a variety of 5N and 3N transcriptional regulatory sequences are also available for use in the present invention. Transcriptional terminators are responsible for the termination of transcription and correct mRNA polyadenylation. The 3'-untranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens*, and the 3N end of the protease inhibitor I or II genes from potato or tomato, although other 3N elements known to those of skill in the art can also be employed. Alternatively, one also could use a gamma coixin, oleosin 3 or other terminator from the genus Coix. Preferred 3' elements include those from the nopaline synthase gene of *Agrobacterium tumefaciens* (Bevan et al., 1983), the terminator for the T7 transcript from the octopine synthase gene of *Agrobacterium tumefaciens*, and the 3' end of the protease inhibitor I or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those that include sequences predicted to direct optimum expression of the attached sequence, i.e., to include a preferred consensus leader sequence that may increase or maintain mRNA stability and prevent inappropriate initiation of translation. The choice of such sequences will be known to those of skill in the art in light of the present disclosure. Sequences that are derived from genes that are highly expressed in plants will be most preferred.

Other sequences that have been found to enhance gene expression in transgenic plants include intron sequences (e.g., from Adh1, bronze1, actin1, actin 2 (WO 00/760067), or the sucrose synthase intron) and viral leader sequences (e.g., from TMV, MCMV and AMV). For example, a number of non-translated leader sequences derived from viruses are known to enhance expression. Specifically, leader sequences from tobacco mosaic virus (TMV), maize chlorotic mottle virus (MCMV), and alfalfa mosaic virus (AMV) have been shown to be effective in enhancing expression (e.g., Gallie et al., 1987; Skuzeski et al., 1990). Other leaders known in the art include but are not limited to picornavirus leaders, for example, EMCV leader (encephalomyocarditis virus 5' non-coding region; Elroy-Stein et al., 1989); potyvirus leaders, for example, TEV leader (tobacco etch virus); MDMV leader (maize dwarf mosaic virus); human immunoglobulin heavy chain binding protein (BiP) leader, (Macejak et al., 1991); untranslated leader from the coat protein mRNA of AMV (AMV RNA 4; Jobling et al., 1987), TMV (Gallie et al., 1989), and MCMV (Lommel et al., 1991; see also, della Cioppa et al., 1987).

Regulatory elements such as Adh intron 1 (Callis et al., 1987), sucrose synthase intron (Vasil et al., 1989) or TMV omega element (Gallie, et al., 1989), may further be included where desired. Examples of enhancers include elements from the CaMV 35S promoter, octopine synthase genes (Ellis et al., 1987), the rice actin I gene, the maize alcohol dehydrogenase gene (Callis et al., 1987), the maize shrunken I gene (Vasil et al., 1989), TMV Omega element (Gallie et al., 1989) and promoters from non-plant eukaryotes (e.g. yeast; Ma et al., 1988).

Vectors for use in accordance with the present invention may be constructed to include the ocs enhancer element, which was first identified as a 16 bp palindromic enhancer from the octopine synthase (ocs) gene of ultilane (Ellis et al., 1987), and is present in at least 10 other promoters (Bouchez et al., 1989). The use of an enhancer element, such as the ocs element and particularly multiple copies of the element, will act to increase the level of transcription from adjacent promoters when applied in the context of monocot transformation.

The methods of the invention provide genetically modified plant cells, which can contain, for example, a coding region, or peptide portion thereof, of a plant stress-regulated gene operatively linked to a heterologous inducible regulatory element; or a plant stress-regulated regulatory element operatively linked to a heterologous nucleotide sequence encoding a polypeptide of interest. In such a plant, the expression from the inducible regulatory element can be effected by exposing the plant cells to an inducing agent in any of numerous ways depending, for example, on the inducible regulatory element and the inducing agent. For example, where the inducible regulatory element is a cold responsive regulatory element present in the cells of a transgenic plant, the plant can be exposed to cold conditions, which can be produced artificially, for example, by placing the plant in a thermostatically controlled room, or naturally, for example, by planting the plant in an environment characterized, at least in part, by attaining temperatures sufficient to induce transcription from the promoter but not so cold as to kill the plants. By examining the phenotype of such transgenic plants, those plants that ectopically express a gene product that confers increased resistance of the plant to cold can be identified. Similarly, a transgenic plant containing a metallothionein promoter can be exposed to metal ions such as cadmium or copper by watering the plants with a solution containing the inducing metal ions, or can be planted in soil that is contaminated with a level of such metal ions that is toxic to most plants. The phenotype of surviving plants can be observed, those expressing desirable traits can be selected.

As used herein, the term "phenotype" refers to a physically detectable characteristic. A phenotype can be identified visually by inspecting the physical appearance of a plant following exposure, for example, to increased osmotic conditions; can be identified using an assay to detecting a product produced due to expression of reporter gene, for example, an RNA molecule, a polypeptide such as an enzyme, or other detectable signal such as disclosed herein; or by using any appropriate tool useful for identifying a phenotype of a plant, for example, a microscope, a fluorescence activated cell sorter, or the like.

A transgenic plant containing an inducible regulatory element such as a steroid inducible regulatory element can be exposed to a steroid by watering the plants with a solution containing the steroid. The use of an inducible regulatory element that is induced upon exposure to a chemical or biological inducing agent that can be placed in solution or suspension in an aqueous medium can be particularly useful because the inducing agent can be applied conveniently to a relatively large crop of transgenic plants containing the inducible regulatory element, for example, through a watering system or by spraying the inducing agent over the field. As such, inducible regulatory elements that are responsive to an environmental inducing agent, for example, cold; heat; metal ions or other potentially toxic agents such as a pesticides, which can contaminate a soil; or the like; or inducible regulatory elements that are regulated by inducing agents that conveniently can be applied to plants, can be particularly useful in a method or composition of the invention, and allow the identification and selection of plants that express desirable traits and survive and grow in environments that otherwise would not support growth of the plants.

As disclosed herein, the present invention provides plant stress-regulated regulatory elements, which are identified based on the expression of clusters of plant genes in response to stress. As used herein, the term "stress-regulated regulatory element of a plant" or "plant stress-regulated regulatory element" means a nucleotide sequence of a plant genome that can respond to a stress such that expression of a gene product encoded by a gene comprising the regulatory element (a stress-inducible gene) is increased above or decreased below the level of expression of the gene product in the absence of the stress condition. The regulatory element can be any gene regulatory element, including, for example, a promoter, an enhancer, a silencer, or the like. In one embodiment, the plant stress-regulated regulatory element is a plant stress-regulated promoter.

For purposes of modulating the responsiveness of a plant to a stress condition, it can be useful to introduce a modified plant stress-regulated regulatory element into a plant. Such a modified regulatory element can have any desirable characteristic, for example, it can be inducible to a greater level than the corresponding wild-type promoter, or it can be inactivated such that, upon exposure to a stress, there is little or no induction of expression of a nucleotide sequence operatively linked to the mutant element. A plant stress-regulated regulatory element can be modified by incorporating random mutations using, for example, in vitro recombination or DNA shuffling (Stemmer et al., Nature 370: 389-391, 1994; U.S.

Pat. No. 5,605,793, each of which is incorporated herein by reference). Using such a method, millions of mutant copies of the polynucleotide, for example, stress-regulated regulatory element, can be produced based on the original nucleotide sequence, and variants with improved properties, such as increased inducibility can be recovered.

A mutation method such as DNA shuffling encompasses forming a mutagenized double-stranded polynucleotide from a template double-stranded polynucleotide, wherein the template double-stranded polynucleotide has been cleaved into double stranded random fragments of a desired size, and comprises the steps of adding to the resultant population of double-stranded random fragments one or more single or double stranded oligonucleotides, wherein the oligonucleotides comprise an area of identity and an area of heterology to the double stranded template polynucleotide; denaturing the resultant mixture of double stranded random fragments and oligonucleotides into single stranded fragments; incubating the resultant population of single stranded fragments with a polymerase under conditions that result in the annealing of the single stranded fragments at the areas of identity to form pairs of annealed fragments, the areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. Preferably, the concentration of a single species of double stranded random fragment in the population of double stranded random fragments is less than 1% by weight of the total DNA. In addition, the template double stranded polynucleotide can comprise at least about 100 species of polynucleotides. The size of the double stranded random fragments can be from about 5 base pairs to 5 kilobase pairs. In a further embodiment, the fourth step of the method comprises repeating the second and the third steps for at least 10 cycles.

A plant stress-regulated regulatory element of the invention is useful for expressing a nucleotide sequence operatively linked to the element in a cell, particularly a plant cell. As used herein, the term "expression" refers to the transcription and/or translation of an endogenous gene or a transgene in plants. In the case of an antisense molecule, for example, the term "expression" refers to the transcription of the polynucleotide encoding the antisense molecule.

As used herein, the term "operatively linked," when used in reference to a plant stress-regulated regulatory element, means that the regulatory element is positioned with respect to a second nucleotide sequence such that the regulatory element effects transcription or transcription and translation of the nucleotide sequence in substantially the same manner, but not necessarily to the same extent, as it does when the regulatory element is present in its natural position in a genome. Transcriptional promoters, for example, generally act in a position and orientation dependent manner and usually are positioned at or within about five nucleotides to about fifty nucleotides 5' (upstream) of the start site of transcription of a gene in nature. In comparison, enhancers and silencers can act in a relatively position or orientation independent manner and, therefore, can be positioned several hundred or thousand nucleotides upstream or downstream from a transcription start site, or in an intron within the coding region of a gene, yet still be operatively linked to a coding region so as to effect transcription.

The second nucleotide sequence, i.e., the sequence operatively linked to the plant stress-regulated regulatory element, can be any nucleotide sequence, including, for example, a coding region of a gene or cDNA; a sequence encoding an antisense molecule, an RNAi molecule, ribozyme, triplexing agent (see, for example, Frank-Kamenetskii and Mirkin, *Ann. Rev. Biochem.* 64:65-95, 1995), or the like; or a sequence that, when transcribed, can be detected in the cell using, for example, by hybridization or amplification, or when translated produces a detectable signal. The term "coding region" is used broadly herein to include a nucleotide sequence of a genomic DNA or a cDNA molecule comprising all or part of a coding region of the coding strand. A coding region can be transcribed from an operatively linked regulatory element, and can be translated into a full length polypeptide or a peptide portion of a polypeptide. It should be recognized that, in a nucleotide sequence comprising a coding region, not all of the nucleotides in the sequence need necessarily encode the polypeptide and, particularly, that a gene transcript can contain one or more introns, which do not encode an amino acid sequence of a polypeptide but, nevertheless, are part of the coding region, particularly the coding strand, of the gene.

The present invention also relates to a recombinant polynucleotide, which contains a polynucleotide portion of a plant stress-regulated gene operatively linked to a heterologous nucleotide sequence. As used herein, the term "polynucleotide portion of plant stress-regulated sequence" means a contiguous nucleotide sequence of the plant stress-regulated gene that provides a function. The portion can be any portion of the sequence, particularly a coding sequence, or a sequence encoding a peptide portion of the stress-regulated polypeptide; the stress-regulated regulatory element; a sequence useful as an antisense molecule or triplexing agent; or a sequence useful for disrupting (knocking-out) an endogenous plant stress-regulated gene.

A heterologous nucleotide sequence is a nucleotide sequence that is not normally part of the plant stress-regulated gene from which the polynucleotide portion of the plant stress-regulated gene-component of the recombinant polynucleotide is obtained; or, if it is a part of the plant stress-regulated gene from which the polynucleotide portion is obtained, it is an orientation other than it would normally be in, for example, is an antisense sequence, or comprises at least partially discontinuous as compared to the genomic structure, for example, a single exon operatively linked to the regulatory element. In general, where the polynucleotide portion of the plant stress-regulated gene comprises the coding sequence in a recombinant polynucleotide of the invention, the heterologous nucleotide sequence will function as a regulatory element. The regulatory element can be any heterologous regulatory element, including, for example, a constitutively active regulatory element, an inducible regulatory element, or a tissue specific or phase specific regulatory element, as disclosed above. Conversely, where the polynucleotide portion of the plant stress-regulated polynucleotide comprises the stress-regulated regulatory element of a recombinant polynucleotide of the invention, the heterologous nucleotide sequence generally will be a nucleotide sequence that can be transcribed and, if desired, translated. Where the heterologous nucleotide sequence is expressed from a plant stress-regulated regulatory element, it generally confers a desirable phenotype to a plant cell containing the recombinant polynucleotide, or provides a means to identify a plant cell containing the recombinant polynucleotide. It should be recognized that a "desirable" phenotype can be one that decreases the ability of a plant cell to compete where the plant cell, or a plant containing the cell, is an undesired plant cell. Thus, a heterologous nucleotide sequence can allow a plant to grow, for example, under conditions in which it would not normally be able to grow.

A heterologous nucleotide sequence can be, or encode, a selectable marker. As used herein, the term "selectable marker" is used herein to refer to a molecule that, when present or expressed in a plant cell, provides a means to identify a plant cell containing the marker. As such, a selectable marker can provide a means for screening a population of plants, or plant cells, to identify those having the marker. A selectable marker also can confer a selective advantage to the plant cell, or a plant containing the cell. The selective advantage can be, for example, the ability to grow in the presence of a negative selective agent such as an antibiotic or herbicide, compared to the growth of plant cells that do not contain the selectable marker. The selective advantage also can be due, for example, to an enhanced or novel capacity, to utilize an added compound as a nutrient, growth factor or energy source. A selectable advantage can be conferred, for example, by a single polynucleotide, or its expression product, or to a combination of polynucleotides whose expression in a plant cell gives the cell with a positive selective advantage, a negative selective advantage, or both.

Examples of selectable markers include those that confer antimetabolite resistance, for example, dihydrofolate reductase, which confers resistance to methotrexate (Reiss, *Plant Physiol.* (Life Sci. Adv.) 13:143-149, 1994); neomycin phosphotransferase, which confers resistance to the aminoglycosides neomycin, kanamycin and paromycin (Herrera-Estrella, *EMBO J.* 2:987-995, 1983) and hygro, which confers resistance to hygromycin (Marsh, *Gene* 32:481-485, 1984), trpB, which allows cells to utilize indole in place of tryptophan; hisD, which allows cells to utilize histinol in place of histidine (Hartman, *Proc. Natl. Acad. Sci., USA* 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: Current Communications in Molecular Biology, Cold Spring Harbor Laboratory ed.); and deaminase from *Aspergillus terreus*, which confers resistance to Blasticidin S (Tamura, *Biosci. Biotechnol. Biochem.* 59:2336-2338, 1995). Additional selectable markers include those that confer herbicide resistance, for example, phosphinothricin acetyltransferase gene, which confers resistance to phosphinothricin (White et al., *Nucl. Acids Res.* 18:1062, 1990; Spencer et al., *Theor. Appl. Genet.* 79:625-631, 1990), a mutant EPSPV-synthase, which confers glyphosate resistance (Hinchee et al., *Bio/Technology* 91:915-922, 1998), a mutant acetolactate synthase, which confers imidazolione or sulfonylurea resistance (Lee et al., *EMBO J.* 7:1241-1248, 1988), a mutant psbA, which confers resistance to atrazine (Smeda et al., *Plant Physiol.* 103:911-917, 1993), or a mutant protoporphyrinogen oxidase (see U.S. Pat. No. 5,767,373), or other markers conferring resistance to an herbicide such as glufosinate. In addition, markers that facilitate identification of a plant cell containing the polynucleotide encoding the marker include, for example, luciferase (Giacomin, *Plant Sci.* 116: 59-72, 1996; Scikantha, *J. Bacteriol.* 178:121, 1996), green fluorescent protein (Gerdes, *FEBS Lett.* 389:44-47, 1996) or fl-glucuronidase (Jefferson, *EMBO J.* 6:3901-3907, 1997), and numerous others as disclosed herein or otherwise known in the art. Such markers also can be used as reporter molecules.

A heterologous nucleotide sequence can encode an antisense molecule, particularly an antisense molecule specific for a nucleotide sequence of a plant stress-regulated gene, for example, the gene from which the regulatory component of the recombinant polynucleotide is derived. Such a recombinant polynucleotide can be useful for reducing the expression of a plant stress-regulated polypeptide in response to a stress condition because the antisense molecule, like the polypeptide, only will be induced upon exposure to the stress. A heterologous nucleotide sequence also can be, or can encode, a ribozyme or a triplexing agent. In addition to being useful as heterologous nucleotide sequences, such molecules also can be used directly in a method of the invention, for example, to modulate the responsiveness of a plant cell to a stress condition. Thus, an antisense molecule, ribozyme, or triplexing agent can be contacted directly with a target cell and, upon uptake by the cell, can effect their antisense, ribozyme or triplexing activity; or can be encoded by a heterologous nucleotide sequence that is expressed in a plant cell from a plant stress-regulated regulatory element, whereupon it can effect its activity.

An antisense polynucleotide, ribozyme or triplexing agent is complementary to a target sequence, which can be a DNA or RNA sequence, for example, messenger RNA, and can be a coding sequence, a nucleotide sequence comprising an intron-exon junction, a regulatory sequence such as a Shine-Delgarno-like sequence, or the like. The degree of complementarity is such that the polynucleotide, for example, an antisense polynucleotide, can interact specifically with the target sequence in a cell. Depending on the total length of the antisense or other polynucleotide, one or a few mismatches with respect to the target sequence can be tolerated without losing the specificity of the polynucleotide for its target sequence. Thus, few if any mismatches would be tolerated in an antisense molecule consisting, for example, of twenty nucleotides, whereas several mismatches will not affect the hybridization efficiency of an antisense molecule that is complementary, for example, to the full length of a target mRNA encoding a cellular polypeptide. The number of mismatches that can be tolerated can be estimated, for example, using well known formulas for determining hybridization kinetics (see Sambrook et al., "Molecular Cloning; A Laboratory Manual" 2nd Edition (Cold Spring Harbor Laboratory Press, Cold Spring Harbor, N.Y.; 1989)) or can be determined empirically using methods as disclosed herein or otherwise known in the art, particularly by determining that the presence of the antisense polynucleotide, ribozyme, or triplexing agent in a cell decreases the level of the target sequence or the expression of a polypeptide encoded by the target sequence in the cell.

A nucleotide sequence useful as an antisense molecule, a ribozyme or a triplexing agent can inhibit translation or cleave a polynucleotide encoded by plant stress-regulated gene, thereby modulating the responsiveness of a plant cell to a stress condition. An antisense molecule, for example, can bind to an mRNA to form a double stranded molecule that cannot be translated in a cell. Antisense oligonucleotides of at least about 15 to 25 nucleotides are preferred since they are easily synthesized and can hybridize specifically with a target sequence, although longer antisense molecules can be expressed from a recombinant polynucleotide introduced into the target cell. Specific nucleotide sequences useful as antisense molecules can be identified using well known methods, for example, gene walking methods (see, for example, Seimiya et al., *J. Biol. Chem.* 272:4631-4636 (1997), which is incorporated herein by reference). Where the antisense molecule is contacted directly with a target cell, it can be operatively associated with a chemically reactive group such as iron-linked EDTA, which cleaves a target RNA at the site of hybridization. A triplexing agent, in comparison, can stall transcription (Maher et al., *Antisense Res. Devel.* 1:227 (1991); Helene, *Anticancer Drug Design* 6:569 (1991)).

A plant stress-regulated regulatory element can be included in an expression cassette. As used herein, the term "expression cassette" refers to a nucleotide sequence that can direct expression of an operatively linked polynucleotide. Thus, a plant stress-regulated regulatory element can constitute an expression cassette, or component thereof. An expression cassette is particularly useful for directing expression of a nucleotide sequence, which can be an endogenous nucleotide sequence or a heterologous nucleotide sequence, in a cell, particularly a plant cell. If desired, an expression cassette also can contain additional regulatory elements, for example, nucleotide sequences required for proper translation of a polynucleotide sequence into a polypeptide. In general, an expression cassette can be introduced into a plant cell such that the plant cell, a plant resulting from the plant cell, seeds obtained from such a plant, or plants produced from such seeds are resistant to a stress condition.

Additional regulatory sequences as disclosed above or other desirable sequences such as selectable markers or the like can be incorporated into an expression cassette containing a plant stress-regulated regulatory element (see, for example, WO 99/47552). Examples of suitable markers include dihydrofolate reductase (DHFR) or neomycin resistance for eukaryotic cells and tetracycline or ampicillin resistance for *E. coli*. Selection markers in plants include bleomycin, gentamycin, glyphosate, hygromycin, kanamycin, methotrexate, phleomycin, phosphinotricin, spectinomycin, streptomycin, sulfonamide and sulfonylureas resistance (see, for example, Maliga et al., *Methods in Plant Molecular Biology*, Cold Spring Harbor Laboratory Press, 1995, page 39). The selection marker can have its own promoter or its expression can be driven by the promoter operably linked to the sequence of interest. Additional sequences such as intron sequences (e.g. from Adh1 or bronze1) or viral leader sequences (e.g. from TMV, MCMV and AlVIV), all of which can enhance expression, can be included in the cassette. In addition, where it is desirable to target expression of a nucleotide sequence operatively linked to the stress-regulated regulatory element, a sequence encoding a cellular localization motif can be included in the cassette, for example, such that an encoded transcript or translation product is translocated to and localizes in the cytosol, nucleus, a chloroplast, or another subcellular organelle. Examples of useful transit peptides and transit peptide sequences can be found in Von Heijne et al., *Plant Mol. Biol. Rep.* 9: 104, 1991; Clark et al., *J. Biol. Chem.* 264:17544, 1989; della Cioppa et al., Plant Physiol. 84:965, 1987; Romer et al., *Biochem. Biophys. Res. Comm.* 196:1414, 1993; Shah et al., *Science* 233:478, 1986; Archer et al., *J. Bioenerg Biomemb.* 22:789, 1990; Scandalios, *Prog. Clin. Biol. Res.* 344:515, 1990; Weisbeek et al., *J. Cell Sci. Suppl.* 11:199, 1989; Bruce, *Trends Cell Biol.* 10:440, 2000. The present invention can utilize native or heterologous transit peptides. The encoding sequence for a transit peptide can include all or a portion of the encoding sequence for a particular transit peptide, and may also contain portions of the mature protein encoding sequence associated with a particular transit peptide.

A polynucleotide portion of a plant stress-regulated plant gene, or an expression cassette, can be introduced into a cell as a naked DNA molecule, can be incorporated in a matrix such as a liposome or a particle such as a viral particle, or can be incorporated into a vector. Such vectors can be cloning or expression vectors, but other uses are within the scope of the present invention. A cloning vector is a self-replicating DNA molecule that serves to transfer a DNA segment into a host cell. The three most common types of cloning vectors are bacterial plasmids, phages, and other viruses. An expression vector is a cloning vector designed so that a coding sequence inserted at a particular site will be transcribed and translated into a protein. Incorporation of the polynucleotide into a vector can facilitate manipulation of the polynucleotide, or introduction of the polynucleotide into a plant cell. A vector can be derived from a plasmid or a viral vector such as a T-DNA vector (Horsch et al., *Science* 227:1229-1231, 1985, which is incorporated herein by reference). If desired, the vector can comprise components of a plant transposable element, for example, a Ds transposon (Bancroft and Dean, *Genetics* 134:1221-1229, 1993, which is incorporated herein by reference) or an Spm transposon (Aarts et al., *Mol. Gen. Genet.* 247:555-564, 1995, which is incorporated herein by reference).

In addition to containing the polynucleotide portion of a plant stress-regulated gene, a vector can contain various nucleotide sequences that facilitate, for example, rescue of the vector from a transformed plant cell; passage of the vector in a host cell, which can be a plant, animal, bacterial, or insect host cell; or expression of an encoding nucleotide sequence in the vector, including all or a portion of a rescued coding region. As such, the vector can contain any of a number of additional transcription and translation elements, including constitutive and inducible promoters, enhancers, and the like (see, for example, Bitter et al., *Meth. Enzymol.* 153:516-544, 1987). For example, a vector can contain elements useful for passage, growth or expression in a bacterial system, including a bacterial origin of replication; a promoter, which can be an inducible promoter; and the like. In comparison, a vector that can be passaged in a mammalian host cell system can have a promoter such as a metallothionein promoter, which has characteristics of both a constitutive promoter and an inducible promoter, or a viral promoter such as a retrovirus long terminal repeat, an adenovirus late promoter, or the like. A vector also can contain one or more restriction endonuclease recognition and cleavage sites, including, for example, a polylinker sequence, to facilitate rescue of a nucleotide sequence operably linked to the polynucleotide portion.

The present invention also relates to a method of using a polynucleotide portion of a plant stress-regulated gene to confer a selective advantage on a plant cell. Such a method can be performed by introducing, for example, a plant stress-regulated regulatory element into a plant cell, wherein, upon exposure of the plant cell to a stress condition to which the regulatory element is responsive, a nucleotide sequence operatively linked to the regulatory element is expressed, thereby conferring a selective advantage to plant cell. The operatively linked nucleotide sequence can be a heterologous nucleotide sequence, which can be operatively linked to the regulatory element prior to introduction of the regulatory sequence into the plant cell; or can be an endogenous nucleotide sequence into which the regulatory element was targeted by a method such as homologous recombination. The selective advantage conferred by the operatively linked nucleotide sequence can be such that the plant is better able to tolerate the stress condition; or can be any other selective advantage.

As used herein, the term "selective advantage" refers to the ability of a particular organism to better propagate, develop, grow, survive, or otherwise tolerate a condition as compared to a corresponding reference organism that does not contain a plant-stress regulated polynucleotide portion of the present invention. In one embodiment, a selective advantage is exemplified by the ability of a desired plant, plant cell, or the like, that contains an introduced plant stress-regulated regulatory element, to grow better than an undesired plant, plant cell, or the like, that does not contain the introduced regulatory element. For example, a recombinant polynucleotide comprising a plant stress-regulated regulatory element operatively linked to a heterologous nucleotide sequence encoding an enzyme that inactivates an herbicide can be introduced in a desired plant. Upon exposure of a mixed population of plants comprising the desired plants, which contain the recombinant polynucleotide, and one or more other populations of undesired plants, which lack the recombinant polynucleotide, to a stress condition that induces expression of the regulatory element and to the herbicide, the desired plants will have a greater likelihood of surviving exposure to the toxin and, therefore, a selective advantage over the undesired plants.

In another embodiment, a selective advantage is exemplified by the ability of a desired plant, plant cell, or the like, to better propagate, develop, grow, survive, or otherwise tolerate a condition as compared to an undesired plant, plant cell, or the like, that contains an introduced plant stress-regulated regulatory element. For example, a recombinant polynucleotide comprising a plant stress-regulated regulatory element operatively linked to a plant cell toxin can be introduced into cells of an undesirable plant present in a mixed population of desired and undesired plants, for example, food crops and weeds, respectively, then the plants can be exposed to stress conditions that induce expression from the plant stress-regulated regulatory element, whereby expression of the plant cell toxin results in inhibition of growth or death of the undesired plants, thereby providing a selective advantage to the desired plants, which no longer have to compete with the undesired plants for nutrients, light, or the like. In another example, a plant stress-regulated regulatory element operatively linked to a plant cell toxin can be introduced into cells of plants used as a nurse crop. Nurse crops, also called cover or companion crops, are planted in combination with plants of interest to provide, among other things, shade and soil stability during establishment of the desired plants. Once the desired plants have become established, the presence of the nurse crop may no longer be desirable. Exposure to conditions inducing expression of the gene linked to the plant stress-regulated regulatory element allows elimination of the nurse crop. Alternatively nurse crops can be made less tolerate to abiotic stress by the inhibition of any of the stress-regulated sequences disclosed herein. Inhibition can be accomplished by any of the method described herein. Upon exposure of the nurse crop to the stress, the decreased ability of the nurse crop to respond to the stress will result in elimination of the nurse crop, leaving only the desired plants.

The invention also provides a means of producing a transgenic plant, which comprises plant cells that exhibit altered responsiveness to a stress condition. As such, the present invention further provides a transgenic plant, or plant cells or tissues derived therefrom, which are genetically modified to respond to stress differently than a corresponding wild-type plant or plant not containing constructs of the present invention would respond. As used herein, the term "responsiveness to a stress condition" refers to the ability of a plant to express a plant stress-regulated gene upon exposure to the stress condition. A transgenic plant cell contains a polypeptide portion of a plant stress-regulated gene, or a mutant form thereof, for example, a knock-out mutant. A knock-out mutant form of a plant stress-regulated gene can contain, for example, a mutation such that a STOP codon is introduced into the reading frame of the translated portion of the gene such that expression of a functional stress-regulated polypeptide is prevented; or a mutation in the stress-regulated regulatory element such that inducibility of the element in response to a stress condition is inhibited. Such transgenic plants of the invention can display any of various idiotypic modifications is response to an abiotic stress, including altered tolerance to the stress condition, as well as increased or decreased plant growth, root growth, yield, or the like, as compared to the corresponding wild-type plant.

The term "plant" is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or a cultured cell, or can be part of higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like.

A transgenic plant can be regenerated from a transformed plant cell. As used herein, the term "regenerate" means growing a whole plant from a plant cell; a group of plant cells; a protoplast; a seed; or a piece of a plant such as a callus or tissue. Regeneration from protoplasts varies from species to species of plants. For example, a suspension of protoplasts can be made and, in certain species, embryo formation can be induced from the protoplast suspension, to the stage of ripening and germination. The culture media generally contains various components necessary for growth and regeneration, including, for example, hormones such as auxins and cytokinins; and amino acids such as glutamic acid and proline, depending on the particular plant species. Efficient regeneration will depend, in part, on the medium, the genotype, and the history of the culture. If these variables are controlled, however, regeneration is reproducible.

Regeneration can occur from plant callus, explants, organs or plant parts. Transformation can be performed in the context of organ or plant part regeneration. (see *Meth. Enzymol.* Vol. 118; Klee et al. *Ann. Rev. Plant Physiol.* 38:467, 1987, which is incorporated herein by reference). Utilizing the leaf disk-transformation-regeneration method, for example, disks are cultured on selective media, followed by shoot formation in about two to four weeks (see Horsch et al., supra, 1985). Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated utilizing cuttings or tissue culture techniques to produce multiple identical plants. Selection of desirable transgenotes is made and new varieties are obtained and propagated vegetatively for commercial use. In seed propagated crops, the mature transgenic plants can be self crossed to produce a homozygous inbred plant. The resulting inbred plant produces seeds that contain the introduced plant stress-induced regulatory element, and can be grown to produce plants that express a polynucleotide or polypeptide in response to a stress condition that induces expression from the regulatory element. As such, the invention further provides seeds produced by a transgenic plant obtained by a method of the invention.

In addition, transgenic plants comprising different recombinant sequences can be crossbred, thereby providing a means to obtain transgenic plants containing two or more different transgenes, each of which contributes a desirable characteristic to the plant. Methods for breeding plants and selecting for crossbred plants having desirable characteristics or other characteristics of interest are well known in the art.

A method of the invention can be performed by introducing a polynucleotide portion of a plant stress-regulated gene into the plant. As used herein, the term "introducing" means transferring a polynucleotide into a plant cell. A polynucleotide can be introduced into a cell by a variety of methods well known to those of ordinary skill in the art. For example, the polynucleotide can be introduced into a plant cell using a direct gene transfer method such as electroporation or microprojectile mediated transformation, or using *Agrobacterium* mediated transformation. Non-limiting examples of methods for the introduction of polynucleotides into plants are provided in greater detail herein. As used herein, the term "transformed" refers to a plant cell containing an exogenously introduced polynucleotide portion of a plant stress-regulated gene that is or can be rendered active in a plant cell, or to a plant comprising a plant cell containing such a polynucleotide.

It should be recognized that one or more polynucleotides, which are the same or different can be introduced into a plant, thereby providing a means to obtain a genetically modified plant containing multiple copies of a single transgenic sequence, or containing two or more different transgenic sequences, either or both of which can be present in multiple copies. Such transgenic plants can be produced, for example, by simply selecting plants having multiple copies of a single type of transgenic sequence; by cotransfecting plant cells with two or more populations of different transgenic sequences and identifying those containing the two or more different transgenic sequences; or by crossbreeding transgenic plants, each of which contains one or more desired transgenic sequences, and identifying those progeny having the desired sequences.

Methods for introducing a polynucleotide into a plant cell to obtain a transformed plant also include direct gene transfer (see European Patent A 164 575), injection, electroporation, biolistic methods such as particle bombardment, pollen-mediated transformation, plant RNA virus-mediated transformation, liposome-mediated transformation, transformation using wounded or enzyme-degraded immature embryos, or wounded or enzyme-degraded embryogenic callus, and the like. Transformation methods using *Agrobacterium tumefaciens* tumor inducing (Ti) plasmids or root-inducing (Ri) plasmids, or plant virus vectors are well known in the art (see, for example, WO 99/47552; Weissbach & Weissbach, "Methods for Plant Molecular Biology" (Academic Press, NY 1988), section VIII, pages 421-463; Grierson and Corey, "Plant Molecular Biology" 2d Ed. (Blackie, London 1988), Chapters 7-9, each of which is incorporated herein by reference; Horsch et al., supra, 1985). The wild-type form of *Agrobacterium*, for example, contains a Ti plasmid, which directs production of tumorigenic crown gall growth on host plants. Transfer of the tumor inducing T-DNA region of the Ti plasmid to a plant genome requires the Ti plasmid-encoded virulence genes as well as T-DNA borders, which are a set of direct DNA repeats that delineate the region to be transferred. An *Agrobacterium* based vector is a modified form of a Ti plasmid, in which the tumor inducing functions are replaced by a nucleotide sequence of interest that is to be introduced into the plant host.

Methods of using *Agrobacterium* mediated transformation include cocultivation of *Agrobacterium* with cultured isolated protoplasts; transformation of plant cells or tissues with *Agrobacterium*; and transformation of seeds, apices or meristems with *Agrobacterium*. In addition, in planta transformation by *Agrobacterium* can be performed using vacuum infiltration of a suspension of *Agrobacterium* cells (Bechtold et al., *C. R. Acad. Sci. Paris* 316:1194, 1993, which is incorporated herein by reference).

*Agrobacterium* mediated transformation can employ cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. Binary vectors are well known in the art (see, for example, De Framond, *BioTechnology* 1:262, 1983; Hoekema et al., *Nature* 303:179, 1983, each of which is incorporated herein by reference) and are commercially available (Clontech; Palo Alto Calif.). For transformation, *Agrobacterium* can be cocultured, for example, with plant cells or wounded tissue such as leaf tissue, root explants, hypocotyledons, stem pieces or tubers (see, for example, Glick and Thompson, "Methods in Plant Molecular Biology and Biotechnology" (Boca Raton Fla., CRC Press 1993), which is incorporated herein by reference). Wounded cells within the plant tissue that have been infected by *Agrobacterium* can develop organs de novo when cultured under the appropriate conditions; the resulting transgenic shoots eventually give rise to transgenic plants, which contain an exogenous polynucleotide portion of a plant stress-regulated gene.

*Agrobacterium* mediated transformation has been used to produce a variety of transgenic plants, including, for example, transgenic cruciferous plants such as *Arabidopsis*, mustard, rapeseed and flax; transgenic leguminous plants such as alfalfa, pea, soybean, trefoil and white clover; and transgenic solanaceous plants such as eggplant, petunia, potato, tobacco and tomato (see, for example, Wang et al., "Transformation of Plants and Soil Microorganisms" (Cambridge, University Press 1995), which is incorporated herein by reference). In addition, *Agrobacterium* mediated transformation can be used to introduce an exogeuous polynucleotide sequence, for example, a plant stress-regulated regulatory element into apple, aspen, belladonna, black currant, carrot, celery, cotton, cucumber, grape, horseradish, lettuce, morning glory, muskmelon, neem, poplar, strawberry, sugar beet, sunflower, walnut, asparagus, rice and other plants (see, for example, Glick and Thompson, supra, 1993; Hiei et al., *Plant J.* 6:271-282, 1994; Shimamoto, *Science* 270:1772-1773, 1995).

Suitable strains of *Agrobacterium tumefaciens* and vectors as well as transformation of Agrobacteria and appropriate growth and selection media are well known in the art (GV3101, pMK90RK), Koncz, *Mol. Gen. Genet.* 204:383-396, 1986; (C58C1, pGV3850kan), Deblaere, *Nucl. Acid Res.* 13:4777, 1985; Bevan, *Nucl. Acid Res.* 12:8711, 1984; Koncz, *Proc. Natl. Acad. Sci. USA* 86:8467-8471, 1986; Koncz, *Plant Mol. Biol.* 20:963-976, 1992; Koncz, Specialized vectors for gene tagging and expression studies. In: Plant Molecular Biology Manual Vol. 2, Gelvin and Schilperoort (Eds.), Dordrecht, The Netherlands: Kluwer Academic Publ. (1994), 1-22; European Patent A-1 20 516; Hoekema: The Binary Plant Vector System, Offsetdrukkerij Kanters B. V., Alblasserdam (1985), Chapter V; Fraley, *Crit. Rev. Plant. Sci.*, 4:1-46; An, *EMBO J.* 4:277-287, 1985).

Where a polynucleotide portion of a plant stress-regulated gene is contained in vector, the vector can contain functional elements, for example "left border" and "right border" sequences of the T-DNA of *Agrobacterium*, which allow for stable integration into a plant genome. Furthermore, methods and vectors that permit the generation of marker-free transgenic plants, for example, where a selectable marker gene is lost at a certain stage of plant development or plant breeding, are known, and include, for example, methods of co-transformation (Lyznik, *Plant Mol. Biol.* 13:151-161, 1989; Peng, *Plant Mol. Biol.* 27:91-104, 1995), or methods that utilize enzymes capable of promoting homologous recombination in plants (see, e.g., WO97/08331; Bayley, *Plant Mol. Biol.* 18:353-361, 1992; Lloyd, *Mol. Gen. Genet.* 242:653-657, 1994; Maeser, *Mol. Gen. Genet.* 230:170-176, 1991; Onouchi, *Nucl. Acids Res.* 19:6373-6378, 1991; see, also, Sambrook et al., supra, 1989).

A direct gene transfer method such as electroporation also can be used to introduce a polynucleotide portion of a plant stress-regulated gene into a cell such as a plant cell. For example, plant protoplasts can be electroporated in the presence of the regulatory element, which can be in a vector (Fromm et al., *Proc. Natl. Acad. Sci. USA* 82:5824, 1985, which is incorporated herein by reference). Electrical impulses of high field strength reversibly permeabilize membranes allowing the introduction of the nucleic acid. Electroporated plant protoplasts reform the cell wall, divide and form a plant callus. Microinjection can be performed as described in Potrykus and Spangenberg (eds.), Gene Transfer To Plants (Springer Verlag, Berlin, N.Y. 1995). A transformed plant cell containing the introduced polynucleotide can be identified by detecting a phenotype due to the introduced polynucleotide, for example, increased or decreased tolerance to a stress condition.

Microprojectile mediated transformation also can be used to introduce a polynucleotide into a plant cell (Klein et al., *Nature* 327:70-73, 1987, which is incorporated herein by reference). This method utilizes microprojectiles such as gold or tungsten, which are coated with the desired nucleic acid molecule by precipitation with calcium chloride, spermidine or polyethylene glycol. The microprojectile particles are accelerated at high speed into a plant tissue using a device such as the BIOLISTIC PD-1000 (BioRad; Hercules Calif.).

Microprojectile mediated delivery ("particle bombardment") is especially useful to transform plant cells that are difficult to transform or regenerate using other methods. Methods for the transformation using biolistic methods are well known (Wan, *Plant Physiol.* 104:37-48, 1984; Vasil, *Bio/Technology* 11: 1553-1558, 1993; Christou, *Trends in Plant Science* 1:423-431, 1996). Microprojectile mediated transformation has been used, for example, to generate a variety of transgenic plant species, including cotton, tobacco, corn, hybrid poplar and papaya (see Glick and Thompson, supra, 1993). Important cereal crops such as wheat, oat, barley, sorghum and rice also have been transformed using microprojectile mediated delivery (Duan et al., *Nature Biotech.* 14:494-498, 1996; Shimamoto, *Curr. Opin. Biotech.* 5:158-162, 1994). A rapid transformation regeneration system for the production of transgenic plants such as a system that produces transgenic wheat in two to three months (see European Patent No. EP 0709462A2, which is incorporated herein by reference) also can be useful for producing a transgenic plant using a method of the invention, thus allowing more rapid identification of gene functions. The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, *Agrobacterium* mediated transformation, and the like.

Plastid transformation also can be used to introduce a polynucleotide portion of a plant stress-regulated gene into a plant cell (U.S. Pat. Nos. 5,451,513, 5,545,817, and 5,545,818; WO 95/16783; McBride et al., *Proc. Natl. Acad. Sci., USA* 91:7301-7305, 1994). Chloroplast transformation involves introducing regions of cloned plastid DNA flanking a desired nucleotide sequence, for example, a selectable marker together with polynucleotide of interest into a suitable target tissue, using, for example, a biolistic or protoplast transformation method (e.g., calcium chloride or PEG mediated transformation). One to 1.5 kb flanking regions ("targeting sequences") facilitate homologous recombination with the plastid genome, and allow the replacement or modification of specific regions of the plastome. Using this method, point mutations in the chloroplast 16S rRNA and rps12 genes, which confer resistance to spectinomycin and streptomycin, can be utilized as selectable markers for transformation (Svab et al., *Proc. Natl. Acad. Sci., USA* 87:8526-8530, 1990; Staub and Maliga, *Plant Cell* 4:39-45, 1992), resulted in stable homopiasmic transformants; at a frequency of approximately one per 100 bombardments of target leaves. The presence of cloning sites between these markers allowed creation of a plastid targeting vector for introduction of foreign genes (Staub and Maliga, *EMBO J.* 12:601-606, 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, *Proc. Natl. Acad. Sci., USA* 90:913-917, 1993). Approximately 15 to 20 cell division cycles following transformation are generally required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein.

Plants suitable to treatment according to a method of the invention can be monocots or dicots and include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco) (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea ultilane*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, duckweed (*Lemna*), barley, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*).

Ornamentals such as azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum are also included. Additional ornamentals within the scope of the invention include impatiens, Begonia, Pelargonium, Viola, Cyclamen, Verbena, Vinca, Tagetes, Primula, Saint Paulia, Agertum, Amaranthus, Antihirrhinum, Aquilegia, Cineraria, Clover, Cosmo, Cowpea, Dahlia, Datura, Delphinium, Gerbera, Gladiolus, Gloxinia, Hippeastrum, Mesembryanthemum, Salpiglossos, and Zinnia.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga ultilane*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Leguminous plants which-may be used in the practice of the present invention include beans and peas. Beans include guar, locust bean, fenugreek, soybean, garden beans, cowpea, mungbean, lima bean, fava bean, lentils, chickpea, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, trifolium, *Phaseolus*, e.g., common bean and lima bean, *Pisum*, e.g., field bean, *Melilotus*, e.g., clover, *Medicago*, e.g., alfalfa, Lotus, e.g., trefoil, lens, e.g., lentil, and false indigo. Preferred forage and turf grass for use in the methods of the invention include alfalfa, orchard grass, tall fescue, perennial ryegrass, creeping bent grass, and redtop.

Other plants within the scope of the invention include *Acacia*, aneth, artichoke, arugula, blackberry, canola, cilantro, clementines, escarole, eucalyptus, fennel, grapefruit, honey dew, jicama, kiwifruit, lemon, lime, mushroom, nut, okra, orange, parsley, persimmon, plantain, pomegranate, poplar, radiata pine, radicchio, Southern pine, sweetgum, tangerine, triticale, vine, yams, apple, pear, quince, cherry, apricot, melon, hemp, buckwheat, grape, raspberry, chenopodium, blueberry, nectarine, peach, plum, strawberry, watermelon, eggplant, pepper, cauliflower, *Brassica*, e.g., broccoli, cabbage, ultilan sprouts, onion, carrot, leek, beet, broad bean, celery, radish, pumpkin, endive, gourd, garlic, snapbean, spinach, squash, turnip, ultilane, chicory, groundnut and zucchini.

Angiosperms are divided into two broad classes based on the number of cotyledons, which are seed leaves that generally store or absorb food; a monocotyledonous angiosperm has a single cotyledon, and a dicotyledonous angiosperm has two cotyledons. Angiosperms produce a variety of useful products including materials such as lumber, rubber, and paper; fibers such as cotton and linen; herbs and medicines such as quinine and vinblastine; ornamental flowers such as roses and orchids; and foodstuffs such as grains, oils, fruits and vegetables.

Angiosperms encompass a variety of flowering plants, including, for example, cereal plants, leguminous plants, oilseed plants, hardwood trees, fruit-bearing plants and ornamental flowers, which general classes are not necessarily exclusive. Cereal plants, which produce an edible grain cereal, include, for example, corn, rice, wheat, barley, oat, rye, orchardgrass, guinea grass, sorghum and turfgrass. Leguminous plants include members of the pea family (*Fabaceae*) and produce a characteristic fruit known as a legume. Examples of leguminous plants include, for example, soybean, pea, chickpea, moth bean, broad bean, kidney bean, lima bean, lentil, cowpea, dry bean, and peanut, as well as alfalfa, birdsfoot trefoil, clover and sainfoin. Oilseed plants, which have seeds that are useful as a source of oil, include soybean, sunflower, rapeseed (canola) and cottonseed.

Angiosperms also include hardwood trees, which are perennial woody plants that generally have a single stem (trunk). Examples of such trees include alder, ash, aspen, basswood (linden), beech, birch, cherry, cottonwood, elm, eucalyptus, hickory, locust, maple, oak, persimmon, poplar, sycamore, walnut, sequoia, and willow. Trees are useful, for example, as a source of pulp, paper, structural material and fuel.

Angiosperms are fruit-bearing plants that produce a mature, ripened ovary, which generally contains seeds. A fruit can be suitable for human or animal consumption or for collection of seeds to propagate the species. For example, hops are a member of the mulberry family that are prized for their flavoring in malt liquor. Fruit-bearing angiosperms also include grape, orange, lemon, grapefruit, avocado, date, peach, cherry, olive, plum, coconut, apple and pear trees and blackberry, blueberry, raspberry, strawberry, pineapple, tomato, cucumber and eggplant plants. An ornamental flower is an angiosperm cultivated for its decorative flower. Examples of commercially important ornamental flowers include rose, orchid, lily, tulip and chrysanthemum, snapdragon, camellia, carnation and petunia plants. The skilled artisan will recognize that the methods of the invention can be practiced using these or other angiosperms, as desired, as well as gymnosperms, which do not produce seeds in a fruit.

A method of producing a transgenic plant can be performed by introducing a polynucleotide portion of plant stress-regulated gene into a plant cell genome, whereby the polynucleotide portion of the plant stress-regulated gene modulates a response of the plant cell to a stress condition, thereby producing a transgenic plant, which comprises plant cells that exhibit altered responsiveness to the stress condition. In one embodiment, the polynucleotide portion of the plant stress-regulated gene encodes a stress-regulated polypeptide or functional peptide portion thereof, wherein expression of the stress-regulated polypeptide or functional peptide portion thereof either increases the stress tolerance of the transgenic plant, or decreases the stress tolerance of the transgenic plant. The polynucleotide portion of the plant stress-regulated gene encoding the stress-regulated polypeptide or functional peptide portion thereof can be operatively linked to a heterologous promoter.

In another embodiment, the polynucleotide portion of the plant stress-regulated gene comprises a stress-regulated regulatory element. The stress-regulated regulatory element can integrate into the plant cell genome in a site-specific manner, whereupon it can be operatively linked to an endogenous nucleotide sequence, which can be expressed in response to a stress condition specific for the regulatory element; or can be a mutant regulatory element, which is not responsive to the stress condition, whereby upon integrating into the plant cell genome, the mutant regulatory element disrupts an endogenous stress-regulated regulatory element of a plant stress-regulated gene, thereby altering the responsiveness of the plant stress-regulated gene to the stress condition. Accordingly, the invention also provides genetically modified plants, including transgenic plants, produced by such a method, and a plant cell obtained from such genetically modified plant, wherein said plant cell exhibits altered responsiveness to the stress condition; a seed produced by a transgenic plant; and a cDNA library prepared from a transgenic plant.

Also provided is a method of modulating the responsiveness of a plant cell to a stress condition. Such a method can be performed, for example, by introducing a polynucleotide portion of a plant stress-regulated gene into the plant cell, thereby modulating the responsiveness of the plant cell to a stress condition. As disclosed herein, the responsiveness of the plant cell can be increased or decreased upon exposure to the stress condition, and the altered responsiveness can result in increased or decreased tolerance of the plant cell to a stress condition. The polynucleotide portion of the plant stress-regulated gene can, but need not, be integrated into the genome of the plant cell, thereby modulating the responsiveness of the plant cell to the stress condition. Accordingly, the invention also provide a genetically modified plant, including a transgenic plant, which contains an introduced polynucleotide portion of a plant stress-regulated gene, as well as plant cells, tissues, and the like, which exhibit modulated responsiveness to a stress condition.

The polynucleotide portion of the plant stress-regulated gene can encode a stress-regulated polypeptide or functional peptide portion thereof, which can be operatively linked to a heterologous promoter. As used herein, reference to a "functional peptide portion of a plant stress-regulated polypeptide" means a contiguous amino acid sequence of the polypeptide that has an activity of the full length polypeptide, or that has an antagonist activity with respect to the full length polypeptide, or that presents an epitope unique to the polypeptide. Thus, by expressing a functional peptide portion of a plant stress-regulated polypeptide in a plant cell, the peptide can act as an agonist or an antagonist of the polypeptide, thereby modulating the responsiveness of the plant cell to a stress condition.

A polynucleotide portion of the plant stress-regulated nucleotide sequence also can contain a mutation, whereby upon integrating into the plant cell genome, the polynucleotide disrupts (knocks-out) an endogenous plant stress-regulated nucleotide sequence, thereby modulating the responsiveness of said plant cell to the stress condition. Depending on whether the knocked-out gene encodes an adaptive or a maladaptive stress-regulated polypeptide, the responsiveness of the plant will be modulated accordingly. Thus, a method of the invention provides a means of producing a transgenic plant having a knock-out phenotype of a plant stress-regulated nucleotide sequence.

Alternatively, the responsiveness of a plant or plant cell to a stress condition can be modulated by use of a suppressor construct containing dominant negative mutation for any of the stress-regulated sequences described herein. Expression of a suppressor construct containing a dominant mutant mutation generates a mutant transcript that, when coexpressed with the wild-type transcript inhibits the action of the wild-type transcript. Methods for the design and use of dominant negative constructs are well known (see, for example, in Herskowitz, *Nature* 329:219-222, 1987; Lagna and Hemmati-Brivanlou, *Curr. Topics Devel. Biol.* 36:75-98, 1998).

The polynucleotide portion of the plant stress-regulated gene also can comprise a stress-regulated regulatory element, which can be operatively linked to a heterologous nucleotide sequence, which, upon expression from the regulatory element in response to a stress condition, modulates the responsiveness of the plant cell to the stress condition. Such a heterologous nucleotide sequence can encode, for example, a stress-inducible transcription factor such as DREB1A, which, upon exposure to the stress condition, is expressed such that it can amplify the stress response (see Kasuga et al., supra, 1999). The heterologous nucleotide sequence also can encode a polynucleotide that is specific for a plant stress-regulated gene, for example, an antisense molecule, a ribozyme, and a triplexing agent, either of which, upon expression in the plant cell, reduces or inhibits expression of a stress-regulated polypeptide encoded by the gene, thereby modulating the responsiveness of the plant cell to a stress condition, for example, an abnormal level of cold, osmotic pressure, and salinity. As used herein, the term "abnormal," when used in reference to a condition such as temperature, osmotic pressure, salinity, or any other condition that can be a stress condition, means that the condition varies sufficiently from a range generally considered optimum for growth of a plant that the condition results in an induction of a stress response in a plant. Methods of determining whether a stress response has been induced in a plant are disclosed herein or otherwise known in the art.

A plant stress-regulated regulatory element can be operatively linked to a heterologous polynucleotide sequence, such that the regulatory element can be introduced into a plant genome in a site-specific matter by homologous recombination. For example, a mutant plant stress-regulated regulatory element for a maladaptive stress-induced polypeptide can be transformed into a plant genome in a site specific manner by in vivo mutagenesis, using a hybrid RNA-DNA oligonucleotide ("chimeroplast" (*TIBTECH* 15:441-447, 1997; WO 95/15972; Kren, *Hepatology* 25:1462-1468, 1997; Cole-Strauss, *Science* 273:1386-1389, 1996, each of which is incorporated herein by reference). Part of the DNA component of the RNA-DNA oligonucleotide is homologous to a nucleotide sequence comprising the regulatory element of the maladaptive gene, but includes a mutation or contains a heterologous region which is surrounded by the homologous regions. By means of base pairing of the homologous regions of the RNA-DNA oligonucleotide and of the endogenous nucleic acid molecule, followed by a homologous recombination the mutation contained in the DNA component of the RNA-DNA oligonucleotide or the heterologous region can be transferred to the plant genome, resulting in a "mutant" gene that, for example, is not induced in response to a stress and, therefore, does not confer the maladaptive phenotype. Such a method similarly can be used to knock-out the activity of a stress-regulated gene, for example, in an undesirable plant. Such a method can provide the advantage that a desirable wild-type plant need not compete with the undesirable plant, for example, for light, nutrients, or the like.

A method of modulating the responsiveness of a plant cell to a stress condition also can be performed by introducing a mutation in the chromosomal copy of a plant stress-regulated gene, for example, in the stress-regulated regulatory element, by transforming a cell with a chimeric oligonucleotide composed of a contiguous stretch of RNA and DNA residues in a duplex conformation with double hairpin caps on the ends. An additional feature of the oligonucleotide is the presence of 2'-0-methylation at the RNA residues. The RNA/DNA sequence is designed to align with the sequence of a chromosomal copy of the target regulatory element and to contain the desired nucleotide change (see U.S. Pat. No. 5,501,967, which is incorporated herein by reference).

A plant stress-regulated regulatory element also can be operatively linked to a heterologous polynucleotide such that, upon expression from the regulatory element in the plant cell, confers a desirable phenotype on the plant cell. For example, the heterologous polynucleotide can encode an aptamer, which can bind to a stress-induced polypeptide. Aptamers are nucleic acid molecules that are selected based on their ability to bind to and inhibit the activity of a protein or metabolite. Aptamers can be obtained by the SELEX (Systematic Evolution of Ligands by Exponential Enrichment) method (see U.S. Pat. No. 5,270,163), wherein a candidate mixture of single stranded nucleic acids having regions of randomized sequence is contacted with a target, and those nucleic acids having a specific affinity to the target are partitioned from the remainder of the candidate mixture; and amplified to yield a ligand enriched mixture. After several iterations a nucleic acid molecule (aptamer) having optimal affinity for the target is obtained. For example, such a nucleic acid molecule can be operatively linked to a plant stress-regulated regulatory element and introduced into a plant. Where the aptamer is selected for binding to a polypeptide that normally is expressed from the regulatory element and is involved in an adaptive response of the plant to a stress, the recombinant molecule comprising the aptamer can be useful for inhibiting the activity of the stress-regulated polypeptide, thereby decreasing the tolerance of the plant to the stress condition.

The invention provides a genetically modified plant, which can be a transgenic plant, that is tolerant or resistant to a stress condition. As used herein, the term "tolerant" or "resistant," when used in reference to a stress condition of a plant, means that the particular plant, when exposed to a stress condition, shows less of an effect, or no effect, in response to the condition as compared to a corresponding reference plant (naturally occurring wild-type plant or a plant not containing a construct of the present invention). As a consequence, a plant encompassed within the present invention grows better under more widely varying conditions, has higher yields and/or produces more seeds. Thus, a transgenic plant produced according to a method of the invention can demonstrate protection (as compared to a corresponding reference plant) from a delay to complete inhibition of alteration in cellular metabolism, or reduced cell growth or cell death caused by the stress. Preferably, the transgenic plant is capable of substantially normal growth under environmental conditions where the corresponding reference plant shows reduced growth, metabolism or viability, or increased male or female sterility.

The determination that a plant modified according to a method of the invention has increased resistance to a stress-inducing condition can be made by comparing the treated plant with a control (reference) plant using well known methods. For example, a plant having increased tolerance to saline stress can be identified by growing the plant on a medium such as soil, which contains a higher content of salt in the order of at least about 10% compared to a medium the corresponding reference plant is capable of growing on. Advantageously, a plant treated according to a method of the invention can grow on a medium or soil containing at least about 50%, or more than about 75%, particularly at least about more than 100%, and preferably more than about 200% salt than the medium or soil on which a corresponding reference plant can grow. In particular, such a treated plant can grow on medium or soil containing at least 40 mM, generally at least 100 mM, particularly at least 200 mM, and preferably at least 300 mM salt, including, for example, a water soluble inorganic salt such as sodium sulfate, magnesium sulfate, calcium sulfate, sodium chloride, magnesium chloride, calcium chloride, potassium chloride, or the like; salts of agricultural fertilizers, and salts associated with alkaline or acid soil conditions; particularly NaCl.

In another embodiment, the invention provides a plant that is less tolerant or less resistant to a stress condition as compared to a corresponding reference plant. As used herein, the term "less tolerant" or "less resistant," when used in reference to a stress condition of a plant, means that the particular plant, when exposed to a stress condition, shows an alteration in response to the condition as compared to a corresponding reference plant. As a consequence, such a plant, which generally is an undesirable plant species, is less likely to grow when exposed to a stress condition than an untreated plant.

The present invention also relates to a method of expressing a heterologous nucleotide sequence in a plant cell. Such a method can be performed, for example by introducing into the plant cell a plant stress-regulated regulatory element operatively linked to the heterologous nucleotide sequence, whereby, upon exposure of the plant cell to stress condition, the heterologous nucleotide sequence is expressed in the plant cell. The heterologous nucleotide sequence can encode a selectable marker, or preferably, a polypeptide that confers a desirable trait upon the plant cell, for example, a polypeptide that improves the nutritional value, digestibility or ornamental value of the plant cell, or a plant comprising the plant cell. Accordingly, the invention provides a transgenic plant that, in response to a stress condition, can produce a heterologous polypeptide from a plant stress-regulated regulatory element. Such transgenic plants can provide the advantage that, when grown in a cold environment for example, expression of the heterologous polypeptide from a plant cold-regulated regulatory element can result in increased nutritional value of the plant.

The present invention further relates to a method of modulating the activity of a biological pathway in a plant cell, wherein the pathway involves a stress-regulated polypeptide. As used herein, reference to a pathway that "involves" a stress-regulated polypeptide means that the polypeptide is required for normal function of the pathway. For example, plant stress-regulated polypeptides as disclosed herein include those acting as kinases or as transcription factors, which are well known to be involved in signal transduction pathways. As such, a method of the invention provides a means to modulate biological pathways involving plant stress-regulated polypeptides, for example, by altering the expression of the polypeptides in response to a stress condition. Thus, a method of the invention can be performed, for example, by introducing a polynucleotide portion of a plant stress-regulated gene into the plant cell, thereby modulating the activity of the biological pathway.

A method of the invention can be performed with respect to a pathway involving any of the stress-regulated polypeptides as encoded by a polynucleotide of SEQ ID NOS: 1-2703, including for example, a stress-regulated transcription factor, an enzyme, including a kinase, a channel protein (see, for example, Tables 29-31; see, also, Table 1). Pathways in which the disclosed stress-regulated stress factors are involved can be identified, for example, by searching the Munich Information Center for Protein Sequences (MIPS) *Arabidopsis thaliana* database (MATDB), which is at http://www.mips-.biochem.mpg.de/proj/thal/.

The present invention also relates to a method of identifying a polynucleotide that modulates a stress response in a plant cell. Such a method can be performed, for example, by contacting an array of probes representative of a plant cell genome and nucleic acid molecules expressed in plant cell exposed to the stress; detecting a nucleic acid molecule that is expressed at a level different from a level of expression in the absence of the stress; introducing the nucleic acid molecule that is expressed differently into a plant cell; and detecting a modulated response of the plant cell containing the introduced nucleic acid molecule to a stress, thereby identifying a polynucleotide that modulates a stress response in a plant cell. The contacting is under conditions that allow for selective hybridization of a nucleic acid molecule with probe having sufficient complementarity, for example, under stringent hybridization conditions.

As used herein, the term "array of probes representative of a plant cell genome" means an organized group of oligonucleotide probes that are linked to a solid support, for example, a microchip or a glass slide, wherein the probes can hybridize specifically and selectively to nucleic acid molecules expressed in a plant cell. Such an array is exemplified herein by a GeneChip® *Arabidopsis* Genome Array (Affymetrix; see Example 1). In general, an array of probes that is "representative" of a plant genome will identify at least about 30% or the expressed nucleic acid molecules in a plant cell, generally at least about 50% or 70%, particularly at least about 80% or 90%, and preferably will identify all of the expressed nucleic acid molecules. It should be recognized that the greater the representation, the more likely all nucleotide sequences of cluster of stress-regulated genes will be identified.

A method of the invention is exemplified in Example 1, wherein clusters of *Arabidopsis* genes induced to cold, to increased salinity, to increased osmotic pressure, and to a combination of the above three stress conditions were identified. Based on the present disclosure, the artisan readily can obtain nucleic acid samples for *Arabidopsis* plants exposed to other stress conditions, or combinations of stress conditions, and identify clusters of genes induced in response to the stress conditions. Similarly, the method is readily adaptable to identifying clusters of stress-regulated genes expressed in other plant species, particularly commercially valuable plant species, where a substantial amount of information is known regarding the genome.

The clusters of genes identified herein include those clusters of genes that are induced or repressed in response to a combination of stress conditions, but not to any of the stress conditions alone; and clusters of genes that are induced or repressed in response to a selected stress condition, but not to other stress conditions tested. Furthermore, clusters of genes that respond to a stress condition in a temporally regulated manner are also included, such as gene clusters that are induced early (for example, within about 3 hours), late (for example, after about 8 to 24 hours), or continuously in a stress response. In addition, the genes within a cluster are represented by a variety of cellular proteins, including transcription factors, enzymes such as kinases, channel proteins, and the like (see Tables 1 and 29-31). Thus, the present invention further characterizes nucleotide sequences that previously were known to encode cellular peptides by classifying them within clusters of stress-regulated genes.

The present invention additionally relates to a method of identifying a stress condition to which a plant cell was exposed. Such a method can be performed, for example, by contacting nucleic acid molecules expressed in the plant cell and an array of probes representative of the plant cell genome; and detecting a profile of expressed nucleic acid molecules characteristic of a stress response, thereby identifying the stress condition to which the plant cell was exposed. The contacting generally is under conditions that allow for selective hybridization of a nucleic acid molecule with probe having sufficient complementarity, for example, under stringent hybridization conditions. The profile can be characteristic of exposure to a single stress condition, for example, an abnormal level of cold, osmotic pressure, or salinity (Tables 3-14), or can be characteristic of exposure to more than one stress condition (Tables 15-26, for example, cold, increased osmotic pressure and increased salinity (see Tables 24-26).

The method can be practiced using at least one nucleic acid probe and can identify one or combination of stress conditions by detecting altered expression of one or a plurality of polynucleotides representative of plant stress-regulated genes. As used herein, the term "at least one" includes one, two, three or more, for example, five, ten, twenty, fifty or more polynucleotides, nucleic acid probes, and the like. The term "plurality" is used herein to mean two or more, for example, three, four, five or more, including ten, twenty, fifty or more polynucleotides, nucleic acid probes, and the like.

In a method of the invention, nucleic acid samples from the plant cells to be collected can be contacted with an array, then the profile can be compared with known expression profiles prepared from nucleic acid samples of plants exposed to a known stress condition or combination of stress conditions. By creating a panel of such profiles, representative of various stress conditions, an unknown stress condition to which a plant was exposed can be identified simply by comparing the unknown profile with the known profiles and determining which known profile that matches the unknown profile. Preferably, the comparison is automated. Such a method can be useful, for example, to identify a cause of damage to a crop, where the condition causing the stress is not known or gradually increases over time. For example, accumulation in soils over time of salts from irrigation water can result in gradually decreasing crop yields. Because the accumulation is gradual, the cause of the decreased yield may not be readily apparent. Using the present methods, it is possible to evaluate the stress to which the plants are exposed, thus revealing the cause of the decreased yields.

The present invention, therefore includes a computer readable medium containing executable instructions form receiving expression data for sequences substantially similar to any of those disclosed herein and comparing expression data from a test plant to a reference plant that has been exposed to an abiotic stress. Also provided is a computer-readable medium containing sequence data for sequences substantially similar to any of the sequences described herein, or the complements thereof, and a module for comparing such sequences to other nucleic acid sequences.

Also provided are plants and plant cells comprising plant stress-regulatory elements of the present invention operably linked to a nucleotide sequence encoding a detectable signal. Such plants can be used as diagnostic or "sentinel" plants to provide early warning that nearby plants are being stressed so that appropriate actions can be taken. In one embodiment, the signal is one that alters the appearance of the plant. For example, an osmotic stress regulatory element of the present invention can be operably linked to a nucleotide sequence encoding a fluorescent protein such as green fluorescent protein. When subjected to osmotic stress, the expression of the green fluorescent protein in the sentinel plant provides a visible signal so that appropriate actions can be taken to remove or alleviate the stress. The use of fluorescent proteins in plants is well known (see, for example, in Leffel et al., *BioTechniques* 23:912, 1997).

The invention further relates to a method of identifying an agent that modulates the activity of a stress-regulated regulatory element of a plant. As used herein, the term "modulate the activity," when used in reference to a plant stress-regulated regulatory element, means that expression of a polynucleotide from the regulatory element is increased or decreased. In particular, expression can be increased or decreased with respect to the basal activity of the promoter, i.e., the level of expression, if any, in the absence of a stress condition that normally induces expression from the regulatory element; or can be increased or decreased with respect to the level of expression in the presence of the inducing stress condition. As such, an agent can act as a mimic of a stress condition, or can act to modulate the response to a stress condition.

Such a method can be performed, for example, by contacting the regulatory element with an agent suspected of having the ability to modulate the activity of the regulatory element, and detecting a change in the activity of the regulatory element. In one embodiment, the regulatory element can be operatively linked to a heterologous polynucleotide encoding a reporter molecule, and an agent that modulates the activity of the stress-regulated regulatory element can be identified by detecting a change in expression of the reporter molecule due to contacting the regulatory element with the agent. Such a method can be performed in vitro in a plant cell-free system, or in a plant cell in culture or in a plant in situ.

A method of the invention also can be performed by contacting the agent is contacted with a genetically modified cell or a transgenic plant containing an introduced plant stress-regulated regulatory element, and an agent that modulates the activity of the regulatory element is identified by detecting a phenotypic change in the modified cell or transgenic plant.

A method of the invention can be performed in the presence or absence of the stress condition to which the particularly regulatory element is responsive. As such, the method can identify an agent that modulates the activity of plant stress-regulated promoter in response to the stress, for example, an agent that can enhance the stress response or can reduce the stress response. In particular, a method of the invention can identify an agent that selectively activates the stress-regulated regulatory elements of a cluster of plant stress-regulated genes, but does not affect the activity of other stress-regulated regulatory genes. As such, the method provides a means to identify an agent that acts as a stress mimic. Such agents can be particularly useful to prepare a plant to an expected stress condition. For example, a agent that acts as a cold mimic can be applied to a field of plants prior to the arrival of an expected cold front. Thus, the cold stress response can be induced prior to the actual cold weather, thereby providing the plants with the protection of the stress response, without the plants suffering from any initial damage due to the cold. Similarly, an osmotic pressure mimic can be applied to a crop of plants prior a field being flooded by a rising river.

In one embodiment, the present invention provides a method for marker-assisted selection. Marker-assisted selection involves the selection of plants having desirable phenotypes based on the presence of particular nucleotide sequences ("markers"). The use of markers allows plants to be selected early in development, often before the phenotype would normally be manifest. Because it allows for early selection, marker-assisted selection decreases the amount of time need for selection and thus allows more rapid genetic progress.

Briefly, marker-assisted selection involves obtaining nucleic acid from a plant to be selected. The nucleic acid obtained is then probed with probes that selectively hybridize under stringent, preferably highly stringent, conditions to a nucleotide sequence or sequences associated with the desired phenotype. In one embodiment, the probes hybridize to any of the stress-responsive genes or regulatory regions disclosed herein, for example, any one of SEQ ID NOS:1-2703. The presence of any hybridization products formed is detected and plants are then selected on the presence or absence of the hybridization products.

The following examples are intended to illustrate but not limit the invention.

EXAMPLE 1

Profiling of Plant Stress-Regulated Genes

This example demonstrates that clusters of stress-regulated genes can be identified in plant cells exposed to various stress conditions, either alone or in combination.

A GeneChip® *Arabidopsis* Genome Array (Affymetrix, Santa Clara, Calif.) was used to identify clusters of genes that were coordinately induced in response to various stress conditions. The GeneChip® *Arabidopsis* Genome Array contains probes synthesized in situ and is designed to measure temporal and spatial gene expression of approximately 8700 genes in greater than 100 EST clusters. The sequences used to develop the array were obtained from GenBank (http://www.ncbi.nlm.nih.gov/) in collaboration with Torrey Mesa Research Institute (San Diego, Calif.), formerly known as Novartis Agriculture Discovery Institute. Eighty percent of the nucleotide sequences represented on the array are predicted coding sequences from genomic BAC entries; twenty percent are high quality cDNA sequences. The array also contains over 100 EST clusters that share homology with the predicted coding sequences from BAC clones (see, for example, world wide web at address (url) "affymetrix.com/products/Arabidopsis_content.html".

The Affymetrix GeneChip® array was used to define nucleotide sequences/pathways affected by various abiotic stresses and to define which are uniquely regulated by one stress and those that respond to multiple stress, and to identify candidate nucleotide sequences for screening for insertional mutants. Of the approximately 8,700 nucleotide sequences represented on the Affymetrix GeneChip® array, 2862 nucleotide sequences showed at least a 2-fold change in expression in at least one sample, relative to no-treatment controls. Of those 2,862 nucleotide sequences 1,335 were regulated only by cold stress, 166 were regulated only mannitol stress and 209 were regulated only by saline stress. Furthermore, of the 2,862 nucleotide sequences 123 nucleotide sequences were regulated by salt and mannitol stress, 293 were regulated by mannitol and cold stress, 274 were regulated by cold and saline stress and 462 were regulated by cold, mannitol-and salt. Of the 2,862 nucleotide sequences, 771 passed the higher stringency of showing at least a 2-fold change in expression in at least 2 samples, relative to control. And, 508 of the 771 nucleotide sequences were found in an in-house collection of insertion mutants.

The following describes in more detail how the experiments were done. Transcriptional profiling was performed by hybridizing fluorescence labeled cRNA with the oligonucleotides probes on the chip, washing, and scanning. Each gene is represented on the chip by about sixteen oligonucleotides (25-mers). Expression level is related to fluorescence intensity. Starting material contained 1 to 10 Tg total RNA; detection specificity was about $1:10^6$; approximately a 2-fold change was detectable, with less than 2% false positive; the dynamic range was approximately 500×. Nucleotide sequences having up to 70% to 80% identity could be discriminated using this system.

Seven day old axenic *Arabidopsis* seedlings were transferred to Magenta boxes with rafts floating on MS medium. Three weeks later (28 day old seedlings), stresses were applied as follows: Control—no treatment; Cold—Magenta box placed in ice; Mannitol—medium+200 mM mannitol; Salt—medium+100 mM NaCl. Tissue samples were collected at 3 hours and 27 hours into the stress, roots and aerial portions were harvested, RNA was purified, and the samples were analyzed using the GeneChip® Arabidopsis Genome Array (Affymetrix, Santa Clara, Calif.) following the manufacturer's protocol.

Raw fluorescence values as generated by Affymetrix software were processed as follows: the values were brought into Microsoft Excel and values of 25 or less were set to 25 (an empirically determined baseline, Zhu and Wang, Plant Physiol. 124:1472-1476; 2000). The values from the stressed samples were then converted to fold change relative to control by dividing the values from the stressed samples by the values from the no-treatment control samples. Expression patterns that were altered at least 2-fold with respect to the control were selected. This method gave very robust results and resulted in a larger number of nucleotide sequences called as stress-regulated than previous methods had permitted.

Based on the profiles obtained following hybridization of nucleic acid molecules obtained from plant cells exposed to various stress conditions to the probes in the microarray, clusters of nucleotide sequences that were altered in response to the stress conditions were identified (see Tables 3-6, cold responsive; Tables 7-10, salt (saline) responsive; Tables 11 to 14, mannitol (osmotic) responsive; Tables 15-17, cold and mannitol responsive; Tables 18-20, 6 salt and cold responsive; Tables 21-23, salt and mannitol responsive; Tables 24-26, cold, salt and mannitol responsive. Examples of plant gene sequences that varied in expression at least two-fold in response to a combination of cold, saline and osmotic stress in root cells and leaf cells are shown in Tables 27 and 28, respectively. In addition, examples of plant gene sequences that encode transcription factors (Table 29), phosphatases (Table 30), and kinases (Table 31) and that varied at least two-fold in response to a combination of cold, saline and osmotic stress are provided.

Affymetrix ID numbers and corresponding SEQ ID NOS: for the respective Arabidopsis nucleotide sequences are provided Tables 3-26, and can be used to determine SEQ ID NOS: for the sequences shown by Affymetrix ID number in Tables 27-31. The Affymetrix ID number refers to a particular nucleotide sequence on the GeneChip® Arabidopsis Genome Array. In some cases, a particular plant stress-regulated gene sequence hybridized to more than one nucleotide sequence on the GeneChip® Arabidopsis Genome Array (see, for example, Table 3, where SEQ ID NO:36 is shown to have hybridized to the 12187_AT and 15920_I_AT nucleotide sequences on the GeneChip®). In addition, it should be recognized that the disclosed sequences are not limited to coding sequences but, in some cases, include 5' untranslated sequences (see Table 2) or a longest coding region. As such, while the sequences set forth as SEQ ID NOS:1-2073 generally start with an ATG codon, in most cases each comprises a longer nucleotide sequence, including a regulatory region (see Table 2).

The results disclosed herein demonstrate that several polynucleotides, some of which were known to function as transcription factors, enzymes, and structural proteins, also are involved in the response of a plant cell to stress. The identification of the clusters of stress-regulated genes as disclosed herein provides a means to identify stress-regulated regulatory elements present in Arabidopsis thaliana nucleotide sequences, including consensus regulatory elements. It should be recognized, however that the regulatory elements of the plant genes comprising a sequence as set forth in SEQ ID NOS:156, 229, 233, 558, 573, 606, 625, 635, 787, and 813, which previously have been described as cold regulated genes, are not encompassed within the stress-regulated gene regulatory element of the invention, and the regulatory elements of the plant genes comprising the nucleotide sequences set forth as SEQ ID NOS:1263, 1386, 1391, 1405, 1445, 1484, 1589, 1609, 1634, 1726, 1866, 1918, and 1928, which previously have been identified as genes that are responsive to a single stress condition such as cold or saline stress, are not encompassed within the plant stress-regulated gene regulatory elements of the invention to the extent that they confer stress-regulated expression only with respect to the known single stress. Furthermore, the identification of the Arabidopsis stress-regulated genes provides a means to identify the corresponding homologs and orthologs in other plants, including commercially valuable food crops such as wheat, rice, soy, and barley, and ornamental plants. BLASTN and BLASTP searches to identify such sequences revealed the polynucleotide sequences set forth in Table 32, which is on the CD-R compact disc submitted herewith.

Although the invention has been described with reference to the above example, it will be understood that modifications and variations are encompassed within the spirit and scope of the invention. Accordingly, the invention is limited only by the claims, which follow Tables 1 to 31.

TABLE 1

SEQUENCE DESCRIPTIONS

| Seq ID | Description |
| --- | --- |
| 1 | unknown protein |
| 2 | unknown protein |
| 3 | unknown protein |
| 4 | putative auxin-induced protein |
| 5 | unknown protein |
| 6 | hypothetical protein |
| 7 | putative protein |
| 8 | unknown protein |
| 9 | unknown protein |
| 10 | unknown protein |
| 11 | putative protein |
| 12 | Thioredoxin-like protein |
| 13 | putative RNA helicase |
| 14 | putative protein |
| 15 | putative protein |
| 16 | RING zinc finger protein, putative |
| 17 | putative cyclin |
| 18 | putative protein |
| 19 | putative protein |
| 20 | unknown protein |
| 21 | putative protein |
| 22 | putative protein |
| 23 | hypothetical protein |
| 24 | unknown protein |
| 25 | hypothetical protein |
| 26 | unknown protein |
| 27 | unknown protein |
| 28 | unknown protein |
| 29 | unknown protein |
| 30 | putative protein |
| 31 | putative protein |
| 32 | putative protein |
| 33 | unknown protein |
| 34 | putative ribonuclease III |
| 35 | unknown protein |
| 36 | unknown protein |
| 37 | unknown protein |
| 38 | unknown protein |
| 39 | unknown protein |
| 40 | putative histidine kinase |
| 41 | scarecrow-like 7 (SCL7) |
| 42 | putative protein |
| 43 | No function assigned by TIGR |
| 44 | unknown protein |
| 45 | unknown protein |

TABLE 1-continued

SEQUENCE DESCRIPTIONS

| Seq ID | Description |
|---|---|
| 46 | succinyl-CoA-ligase alpha subunit |
| 47 | putative protein |
| 48 | CLV1 receptor kinase like protein |
| 49 | putative receptor-like protein kinase |
| 50 | putative squalene synthase |
| 51 | putative receptor protein kinase |
| 52 | somatic embryogenesis receptor-like kinase, putative |
| 53 | putative protein |
| 54 | putative beta-glucosidase |
| 55 | multi-drug resistance protein |
| 56 | receptor protein kinase (TMK1), putative |
| 57 | putative receptor-like protein kinase |
| 58 | putative pectate lyase |
| 59 | putative protein kinase |
| 60 | putative peroxidase |
| 61 | cytochrome P450-like protein |
| 62 | putative beta-amylase |
| 63 | monosaccharide transporter STP3 |
| 64 | Lycopersicon esculentum proteinase TMP, Pir2:T07617 |
| 65 | putative receptor-like protein kinase |
| 66 | G-box-binding factor 1 |
| 67 | amino acid carrier, putative |
| 68 | myb-related protein |
| 69 | No function assigned by TIGR |
| 70 | SNF1 like protein kinase |
| 71 | Cu/Zn superoxide dismutase-like protein |
| 72 | putative protein kinase |
| 73 | small nuclear ribonucleoprotein U1A |
| 74 | ras-like GTP-binding protein |
| 75 | oleoyl-[acyl-carrier-protein] hydrolase-like protein |
| 76 | putative heat shock transcription factor |
| 77 | putative protein |
| 78 | membrane-bound small GTP-binding-like protein |
| 79 | putative protein (fragment) |
| 80 | indole-3-acetate beta-glucosyltransferase like protein |
| 81 | HD-zip transcription factor (athb-8) |
| 82 | putative cAMP-dependent protein kinase |
| 83 | glucuronosyl transferase-like protein |
| 84 | putative leucine-rich repeat disease resistance protein |
| 85 | 98b like protein |
| 86 | putative receptor-like protein kinase |
| 87 | IAA-Ala hydrolase (IAR3) |
| 88 | putative AP2 domain transcription factor |
| 89 | putative expansin |
| 90 | putative Ap2 domain protein |
| 91 | expansin (At-EXP1) |
| 92 | cytochrome P450-like protein |
| 93 | putative ATP-dependent RNA helicase A |
| 94 | unknown protein |
| 95 | predicted protein |
| 96 | putative glucosyltransferase |
| 97 | unknown protein |
| 98 | putative xyloglucan-specific glucanase |
| 99 | cysteine synthase |
| 100 | clathrin assembly protein AP19 homolog |
| 101 | dynein light chain like protein |
| 102 | chaperonin CPN10 |
| 103 | putative bHLH transcription factor |
| 104 | putative glyoxysomal malate dehydrogenase precursor |
| 105 | ATP-dependent RNA helicase, putative |
| 106 | chlorophyll synthetase |
| 107 | similar to epoxide hydrolases |
| 108 | putative protein |
| 109 | unknown protein |
| 110 | hypothetical protein |
| 111 | putative membrane transporter |
| 112 | putative tyrosyl-tRNA synthetase |
| 113 | ARGININE/SERINE-RICH SPLICING FACTOR RSP31 |
| 114 | putative oxidoreductase |
| 115 | unknown protein |
| 116 | linker histone protein, putative |
| 117 | hypothetical protein |
| 118 | putative protein |
| 119 | putative mitochondrial carrier protein |
| 120 | putative transcription factor |
| 121 | MYB-related protein |
| 122 | myb-related transcription factor, putative |
| 123 | unknown protein |
| 124 | unknown protein |
| 125 | putative glycine-rich protein |
| 126 | No function assigned by TIGR |
| 127 | unknown protein |
| 128 | unknown protein |
| 129 | unknown protein |
| 130 | unknown protein |
| 131 | putative membrane channel protein |
| 132 | putative protein |
| 133 | unknown protein |
| 134 | gamma glutamyl hydrolase, putative |
| 135 | 40S ribosomal protein S5 |
| 136 | DnaJ-like protein |
| 137 | 40S ribosomal protein S26 |
| 138 | putative WRKY-type DNA binding protein |
| 139 | putative protein |
| 140 | hypothetical protein |
| 141 | putative ubiquitin-conjugating enzyme |
| 142 | peptidylprolyl isomerase ROC1 |
| 143 | glyceraldehyde-3-phosphate dehydrogenase C subunit (GapC) |
| 144 | No function assigned by TIGR |
| 145 | putative protein |
| 146 | putative thioredoxin |
| 147 | thioredoxin h, putative |
| 148 | thioredoxin-like |
| 149 | allene oxide synthase (emb|CAA73184.1) |
| 150 | anthranilate synthase component I-1 precursor (sp|P32068) |
| 151 | CELL DIVISION CONTROL PROTEIN 2 HOMOLOG A |
| 152 | protein kinase cdc2 homolog B |

TABLE 1-continued

SEQUENCE DESCRIPTIONS

| Seq ID | Description |
|---|---|
| 153 | ethylene responsive element binding factor 1 (frameshift !) |
| 154 | ethylene responsive element binding factor 2 (ATERF2) (sp|O80338) |
| 155 | ethylene responsive element binding factor 5 (ATERF5) (sp|O80341) |
| 156 | glucose-6-phosphate dehydrogenase |
| 157 | photomorphogenesis repressor (COP1) |
| 158 | unknown protein |
| 159 | DNA (cytosine-5)-methyltransferase (DNA methyltransferase) (DNA metase) (sp|P34881) |
| 160 | PROLIFERA |
| 161 | putative photomorphogenesis repressor protein |
| 162 | SNF1-like protein kinase(Akin11) |
| 163 | thioredoxin h |
| 164 | thioredoxin |
| 165 | Ca2+-dependent lipid-binding protein, putative |
| 166 | putative auxin-induced protein |
| 167 | putative bZIP transcription factor |
| 168 | hypothetical protein |
| 169 | putative AVR9 elicitor response protein |
| 170 | putative serine/threonine protein kinase |
| 171 | bZIP transcription factor ATB2 |
| 172 | putative spliceosome associated protein |
| 173 | 3-hydroxyisobutyryl-coenzyme A hydrolase-like protein |
| 174 | putative protein |
| 175 | putative Mutator-like transposase |
| 176 | putative protein |
| 177 | unknown protein |
| 178 | putative protein |
| 179 | putative protein |
| 180 | putative galactinol synthase |
| 181 | putative transcriptional regulator |
| 182 | nuclear matrix constituent protein 1 (NMCP1)-like |
| 183 | putative DNA-binding protein RAV2 |
| 184 | No function assigned by TIGR |
| 185 | basic blue protein, 5' partial |
| 186 | unknown protein |
| 187 | putative calcium-binding protein, calreticulin |
| 188 | putative pyrophosphate-fructose-6-phosphate 1-phosphotransferase |
| 189 | ribosomal protein L11, cytosolic |
| 190 | putative dTDP-glucose 4-6-dehydratase |
| 191 | 40S ribosomal protein S20-like protein |
| 192 | 60S ribosomal protein L24 |
| 193 | coatomer-like protein, epsilon subunit |
| 194 | glycoprotein(EP1), putative |
| 195 | putative SPLI-related protein |
| 196 | unknown protein |
| 197 | putative transport protein SEC61 beta-subunit |
| 198 | unknown protein |
| 199 | putative cytochrome P450 |
| 200 | UTP-glucose glucosyltransferase-like protein |
| 201 | 60S ribosomal protein L23 |
| 202 | 40S ribosomal protein S17 |
| 203 | 40S ribosomal protein S26 |
| 204 | protein translation factor Sui1 homolog, putative |
| 205 | unknown protein |
| 206 | gamma glutamyl hydrolase, putative |
| 207 | dTDP-glucose 4,6-dehydratase, putative |
| 208 | extensin-like protein |
| 209 | unknown protein |
| 210 | protein phosphatase 2C-like protein |
| 211 | ubiquitin-like protein |
| 212 | protein phosphatase 2C-like protein |
| 213 | unknown protein |
| 214 | putative RING zinc finger ankyrin protein |
| 215 | unknown protein |
| 216 | putative rubisco subunit binding-protein alpha subunit |
| 217 | putative acetone-cyanohydrin lyase |
| 218 | putative isoamylase |
| 219 | putative protein |
| 220 | HSP associated protein like |
| 221 | 60S ribosomal protein L39 |
| 222 | unknown protein |
| 223 | putative SF16 protein {Helianthus annuus} |
| 224 | unknown protein |
| 225 | thioredoxin |
| 226 | trehalose-6-phosphate phosphatase (AtTPPB) |
| 227 | chlorophyll a/b-binding protein |
| 228 | class IV chitinase (CHIV) |
| 229 | chalcone synthase (naringenin-chalcone synthase) (testa 4 protein) (sp|P13114) |
| 230 | unknown protein |
| 231 | cinnamyl-alcohol dehydrogenase ELI3-2 |
| 232 | farnesyl-pyrophosphate synthetase FPS2 |
| 233 | phospholipid hydroperoxide glutathione peroxidase |
| 234 | heat shock transcription factor HSF4 |
| 235 | heat shock protein 101 |
| 236 | 17.6 kDa heat shock protein (AA 1-156) |
| 237 | heat shock protein 17.6A |
| 238 | heat-shock protein |
| 239 | HY5 |
| 240 | putative auxin-induced protein, IAA12 |
| 241 | early auxin-induced protein, IAA19 |
| 242 | auxin-inducible gene (IAA2) |
| 243 | putative protein |
| 244 | putative choline kinase |
| 245 | thymidylate kinase-like protein |
| 246 | CTP synthase like protein |
| 247 | putative protein |
| 248 | putative amidase |
| 249 | 4-alpha-glucanotransferase |
| 250 | hypothetical protein |
| 251 | similar to auxin-induced protein |
| 252 | putative protein |

TABLE 1-continued

SEQUENCE DESCRIPTIONS

| Seq ID | Description |
|---|---|
| 253 | putative protein |
| 254 | putative protein |
| 255 | hyuC-like protein |
| 256 | putative tetracycline transporter protein |
| 257 | similar to early nodulins |
| 258 | putative protein |
| 259 | putative peptidyl-prolyl cis-trans isomerase |
| 260 | unknown protein |
| 261 | unknown protein |
| 262 | putative endochitinase |
| 263 | putative ABC transporter |
| 264 | No function assigned by TIGR |
| 265 | CONSTANS-like B-box zinc finger protein |
| 266 | unknown protein |
| 267 | unknown protein |
| 268 | putative mitochondrial processing peptidase alpha subunit |
| 269 | putative pre-mRNA splicing factor |
| 270 | putative phosphatidylserine decarboxylase |
| 271 | unknown protein |
| 272 | unknown protein |
| 273 | unknown protein |
| 274 | putative casein kinase I |
| 275 | unknown protein |
| 276 | 60S ribosomal protein L23A |
| 277 | putative mitochondrial dicarboxylate carrier protein |
| 278 | enoyl-ACP reductase (enr-A) |
| 279 | putative isoamylase |
| 280 | formamidase-like protein |
| 281 | reticuline oxidase-like protein |
| 282 | unknown protein |
| 283 | putative transketolase precursor |
| 284 | putative protein |
| 285 | unknown protein |
| 286 | unknown protein |
| 287 | unknown protein |
| 288 | putative esterase D |
| 289 | predicted protein of unknown function |
| 290 | unknown protein |
| 291 | putative indole-3-glycerol phosphate synthase |
| 292 | isopentenyl pyrophosphate:dimethyllallyl pyrophosphate isomerase |
| 293 | kinase associated protein phosphatase |
| 294 | putative K+ channel, beta subunit |
| 295 | KNAT1 homeobox-like protein |
| 296 | PSI type II chlorophyll a/b-binding protein, putative |
| 297 | transcription factor |
| 298 | putative WD-40 repeat protein, MSI2 |
| 299 | WD-40 repeat protein (MSI3) |
| 300 | putative WD-40 repeat protein, MSI4 |
| 301 | unknown protein |
| 302 | hypothetical protein |
| 303 | putative protein |
| 304 | No function assigned by TIGR |
| 305 | polyphosphoinositide binding protein, putative |
| 306 | hypothetical protein |
| 307 | unknown protein |
| 308 | chloroplast ribosomal L1-like protein |
| 309 | cold-regulated protein cor15b precursor |
| 310 | cyanohydrin lyase like protein |
| 311 | putative replication protein Al |
| 312 | putative protein |
| 313 | possible apospory-associated like protein |
| 314 | DNA binding protein GT-1, putative |
| 315 | AT-hook DNA-binding protein (AHP1) |
| 316 | putative phospholipase |
| 317 | chloroplast FtsH protease, putative |
| 318 | enoyl-CoA hydratase like protein |
| 319 | berberine bridge enzyme-like protein |
| 320 | putative sugar transporter |
| 321 | unknown protein |
| 322 | No function assigned by TIGR |
| 323 | hypothetical protein |
| 324 | putative acidic ribosomal protein |
| 325 | putative protein |
| 326 | unknown protein |
| 327 | hypothetical protein |
| 328 | putative protein |
| 329 | dihydroxypolyprenylbenzoate methyltransferase |
| 330 | unknown protein |
| 331 | myb-related protein |
| 332 | No function assigned by TIGR |
| 333 | putative protein |
| 334 | putative disease resistance response protein |
| 335 | hypothetical protein |
| 336 | No function assigned by TIGR |
| 337 | starch branching enzyme II |
| 338 | No function assigned by TIGR |
| 339 | putative enolase (2-phospho-D-glycerate hydroylase) |
| 340 | putative protein kinase |
| 341 | HD-Zip protein, putative |
| 342 | putative protein kinase |
| 343 | phenylalanyl-trna synthetase-like protein |
| 344 | putative aconitase |
| 345 | NAM(no apical meristem) protein, putative |
| 346 | unknown protein |
| 347 | putative phosphomannomutase |
| 348 | putative farnesylated protein |
| 349 | unknown protein |
| 350 | water stress-induced protein, putative |
| 351 | unknown protein |
| 352 | unknown protein |
| 353 | PEROXISOMAL MEMBRANE PROTEIN PMP22 |
| 354 | putative peroxisomal membrane carrier protein |
| 355 | putative protein |
| 356 | unknown protein |
| 357 | putative protein |
| 358 | putative protein |

TABLE 1-continued

SEQUENCE DESCRIPTIONS

| Seq ID | Description |
|---|---|
| 359 | argininosuccinate synthase-like protein |
| 360 | 1-phosphatidylinositol-4,5-bisphosphate phosphodiesterase |
| 361 | putative JUN kinase activator protein |
| 362 | putative 60S ribosomal protein L35 |
| 363 | nucleoid DNA-binding protein cnd41-like protein |
| 364 | SigA binding protein |
| 365 | hypothetical protein |
| 366 | putative protein kinase |
| 367 | unknown protein |
| 368 | regulatory protein NPR1-like; transcription factor inhibitor I kappa B-like |
| 369 | putative protein |
| 370 | hypothetical protein |
| 371 | phosphoribosylanthranilate isomerase |
| 372 | phosphoribosylanthranilate isomerase |
| 373 | sterol glucosyltransferase, putative |
| 374 | putative gigantea protein |
| 375 | putative MYB family transcription factor |
| 376 | hypothetical protein |
| 377 | hypothetical protein |
| 378 | predicted protein |
| 379 | cytochrome P450, putative |
| 380 | putative Na+ dependent ileal bile acid transporter |
| 381 | unknown protein |
| 382 | RING-H2 finger protein RHF1a |
| 383 | putative protein |
| 384 | unknown protein |
| 385 | putative protein |
| 386 | putative auxin-regulated protein |
| 387 | hypothetical protein |
| 388 | unknown protein |
| 389 | unknown protein |
| 390 | putative protein |
| 391 | putative protein |
| 392 | unknown protein |
| 393 | histone H1 |
| 394 | Argonaute (AGO 1)-like protein |
| 395 | unknown protein |
| 396 | putative protein with C-terminal RING finger |
| 397 | unknown protein |
| 398 | unknown protein |
| 399 | unknown protein |
| 400 | unknown protein |
| 401 | unknown protein |
| 402 | putative copper amine oxidase |
| 403 | unknown protein |
| 404 | unknown protein |
| 405 | unknown protein |
| 406 | putative protein |
| 407 | putative protein |
| 408 | unknown protein |
| 409 | unknown protein |
| 410 | putative protein |
| 411 | putative protein |
| 412 | unknown protein |
| 413 | serine/threonine kinase-like protein |
| 414 | alcohol dehydrogenase, putative |
| 415 | anthranilate phosphoribosyltransferase, chloroplast precursor (sp|Q02166) |
| 416 | phytochrome C (sp|P14714) |
| 417 | putative phytochrome-associated protein 3 |
| 418 | receptor serine/threonine kinase PR5K |
| 419 | Ran-binding protein (atranbp1a) |
| 420 | small Ras-like GTP-binding protein (gb|AAB58478.1) |
| 421 | sterol-C5-desaturase |
| 422 | tryptophan synthase beta chain 1 precursor (sp|P14671) |
| 423 | thioredoxin f2 (gb|AAD35004.1) |
| 424 | No function assigned by TIGR |
| 425 | putative WRKY DNA-binding protein |
| 426 | putative protein |
| 427 | unknown protein |
| 428 | unknown protein |
| 429 | 14-3-3 protein homolog RCI1 (pir||S47969) |
| 430 | unknown protein |
| 431 | putative CCCH-type zinc finger protein |
| 432 | PINHEAD (gb|AAD40098.1); translation initiation factor |
| 433 | plasma membrane proton ATPase (PMA) |
| 434 | CHLOROPHYLL A-B BINDING PROTEIN 4 PRECURSOR homolog |
| 435 | membrane related protein CP5, putative |
| 436 | ABC transporter (AtMRP2) |
| 437 | putative embryo-abundant protein |
| 438 | putative anthocyanidin-3-glucoside rhamnosyltransferase |
| 439 | putative lipid transfer protein |
| 440 | unknown protein |
| 441 | unknown protein |
| 442 | galactinol synthase, putative |
| 443 | putative protein |
| 444 | putative protein |
| 445 | SCARECROW-like protein |
| 446 | unknown protein |
| 447 | unknown protein |
| 448 | unknown protein |
| 449 | unknown protein |
| 450 | asparagine- tRNA ligase |
| 451 | putative protein |
| 452 | glutamate-1-semialdehyde 2,1-aminomutase 1 precursor (GSA 1) (glutamate-1-semialdehyde aminotransferase 1) (GSA-AT 1) (sp|P42799) |
| 453 | hypothetical protein |
| 454 | putative serine protease-like protein |
| 455 | No function assigned by TIGR |
| 456 | unknown protein |
| 457 | unknown protein |
| 458 | gamma-adaptin, putative |
| 459 | UDP rhamnose-anthocyanidin-3-glucoside rhamnosyltransferase-like protein |
| 460 | carbonate dehydratase-like protein |
| 461 | putative microtubule-associated protein |
| 462 | putative ribophorin I |

TABLE 1-continued

SEQUENCE DESCRIPTIONS

| Seq ID | Description |
| --- | --- |
| 463 | putative zinc finger protein |
| 464 | chloroplast FtsH protease, putative |
| 465 | putative protein |
| 466 | unknown protein |
| 467 | putative LEA protein |
| 468 | putative protein |
| 469 | putative protein |
| 470 | unknown protein |
| 471 | putative purple acid phosphatase |
| 472 | unknown protein |
| 473 | putative protein |
| 474 | unknown protein |
| 475 | chlorophyll binding protein, putative |
| 476 | phosphoenolpyruvate carboxylase (PPC) |
| 477 | chlorophyll a/b-binding protein-like |
| 478 | AtAGP4 |
| 479 | putative cryptochrome 2 apoprotein |
| 480 | type 2 peroxiredoxin, putative |
| 481 | Atpm24.1 glutathione S transferase |
| 482 | delta tonoplast integral protein (delta-TIP) |
| 483 | 20S proteasome subunit (PAA2) |
| 484 | dormancy-associated protein, putative |
| 485 | putative cytidine deaminase |
| 486 | No function assigned by TIGR |
| 487 | putative phospholipase D-gamma |
| 488 | cell elongation protein, Dwarf1 |
| 489 | germin-like protein |
| 490 | hevein-like protein precursor (PR-4) |
| 491 | rac-like GTP binding protein (ARAC5) |
| 492 | phosphoprotein phosphatase, type 1 catalytic subunit |
| 493 | ubiquitin-protein ligase UBC9 |
| 494 | xyloglucan endotransglycosylase-related protein XTR-7 |
| 495 | cysteine synthase |
| 496 | putative villin 2 |
| 497 | glutathione S-transferase |
| 498 | 5-adenylylsulfate reductase |
| 499 | arginine decarboxylase |
| 500 | ATHP2, putative |
| 501 | ornithine carbamoyltransferase precursor |
| 502 | puative protein |
| 503 | putative protein |
| 504 | unknown protein |
| 505 | putative protein |
| 506 | putative protein |
| 507 | unknown protein |
| 508 | unknown protein |
| 509 | unknown protein |
| 510 | unknown protein |
| 511 | hypothetical protein |
| 512 | putative protein |
| 513 | putative DnaJ protein |
| 514 | plastocyanin |
| 515 | unknown protein |
| 516 | unknown protein |
| 517 | unknown protein |
| 518 | unknown protein |
| 519 | unknown protein |
| 520 | unknown protein |
| 521 | putative ATP-dependent RNA helicase |
| 522 | non-race specific disease resistance protein (NDR1) |
| 523 | hypothetical protein |
| 524 | putative protein |
| 525 | putative protein |
| 526 | putative protein |
| 527 | copper transport protein |
| 528 | putative protein |
| 529 | unknown protein |
| 530 | unknown protein |
| 531 | unknown protein |
| 532 | putative protein kinase |
| 533 | unknown protein |
| 534 | putative protein |
| 535 | putative protein |
| 536 | hypothetical protein |
| 537 | putative protein |
| 538 | putative AP2 domain transcription factor |
| 539 | putative nitrilase |
| 540 | putative protein |
| 541 | putative tetrahydrofolate synthase |
| 542 | heat-shock protein |
| 543 | unkown protein |
| 544 | unknown protein |
| 545 | histone H4 |
| 546 | hypothetical protein |
| 547 | unknown protein |
| 548 | putative protein |
| 549 | predicted protein |
| 550 | putative dihydrolipoamide succinyltransferase |
| 551 | actin3 |
| 552 | putative CCCH-type zinc finger protein |
| 553 | MAP kinase kinase 2 |
| 554 | ethylene-insensitive3-like 1 (EIL1) |
| 555 | histidine transport protein (PTR2-B) |
| 556 | putative auxin-induced protein AUX2-11 |
| 557 | hydroxyacylglutathione hydrolase cytoplasmic (glyoxalase II) (GLX II) |
| 558 | delta-8 sphingolipid desaturase |
| 559 | cellulose synthase catalytic subunit (Ath-A) |
| 560 | nitrate transporter (NTL1) |
| 561 | DNA-binding homeotic protein Athb-2 |
| 562 | hypothetical protein |
| 563 | aspartate aminotransferase |
| 564 | 4-coumarate:CoA ligase 1 |
| 565 | pyruvate dehydrogenase E1 beta subunit, putative |
| 566 | nucleotide diphosphate kinase Ia (emb|CAB58230.1) |
| 567 | chloroplast Cpn21 protein |
| 568 | ATP dependent copper transporter |
| 569 | very-long-chain fatty acid condensing enzyme (CUT1) |
| 570 | putative purine-rich single-stranded DNA-binding protein |
| 571 | serine/threonine protein phosphatase (type 2A) |
| 572 | isopentenyl diphosphate:dimethylallyl diphosphate isomerase (IPP2) |
| 573 | putative c2h2 zinc finger transcription factor |
| 574 | putative 20S proteasome beta subunit PBC2 |
| 575 | nucleoside diphosphate kinase 3 (ndpk3) |
| 576 | ras-related small GTP-binding protein |
| 577 | putative 4-coumarate:CoA ligase 2 |

TABLE 1-continued

SEQUENCE DESCRIPTIONS

| Seq ID | Description |
|---|---|
| 578 | transcription factor HBP-1b homolog (sp\|P43273) |
| 579 | biotin synthase (Bio B) |
| 580 | homeobox protein HAT22 |
| 581 | putative preprotein translocase SECY protein |
| 582 | carbamoylphosphate synthetase, putative |
| 583 | putative protein kinase, ADK 1 |
| 584 | putative nuclear DNA-binding protein G2p |
| 585 | hypothetical protein |
| 586 | hypothetical protein |
| 587 | unknown protein |
| 588 | unknown protein |
| 589 | molybdopterin synthase (CNX2) |
| 590 | putative ribosomal protein L6 |
| 591 | unknown protein |
| 592 | En/Spm-like transposon protein |
| 593 | putative protein |
| 594 | putative protein |
| 595 | unknown protein |
| 596 | hypothetical protein |
| 597 | unknown protein |
| 598 | unknown protein |
| 599 | putative lysosomal acid lipase |
| 600 | unknown protein |
| 601 | unknown protein |
| 602 | NifS-like aminotranfserase |
| 603 | actin 8 |
| 604 | hypothetical protein |
| 605 | putative protein |
| 606 | heat-shock protein (At-hsc70-3) |
| 607 | putative protein disulfide isomerase precursor |
| 608 | adenosine nucleotide translocator |
| 609 | photosystem II oxygen-evolving complex protein 3-like |
| 610 | sedoheptulose-bisphosphatase precursor |
| 611 | glutathione S-transferase (GST6) |
| 612 | geranylgeranyl reductase |
| 613 | hypothetical protein |
| 614 | hypothetical protein |
| 615 | phosphoribulokinase precursor |
| 616 | high mobility group protein (HMG1), putative |
| 617 | protease inhibitor II |
| 618 | protease inhibitor II |
| 619 | cytochrome P450 90A1 (sp\|Q42569) |
| 620 | unknown protein |
| 621 | heat shock protein 90 |
| 622 | tubulin beta-9 chain |
| 623 | putative ubiquitin carboxyl terminal hydrolase |
| 624 | protein kinase |
| 625 | DRE/CRT-binding protein DREB1C |
| 626 | histidyl-tRNA synthetase |
| 627 | splicing factor, putative |
| 628 | glutamyl-tRNA synthetase |
| 629 | putative RING zinc finger protein |
| 630 | phytochelatin synthase (gb\|AAD41794.1) |
| 631 | putative C2H2-type zinc finger protein |
| 632 | putative ligand-gated ion channel protein |
| 633 | putative ribosomal-protein S6 kinase (ATPK6) |
| 634 | MOLYBDOPTERIN BIOSYNTHESIS CNX1 PROTEIN |
| 635 | temperature-sensitive omega-3 fatty acid desaturase, chloroplast precursor (sp\|P48622) |
| 636 | adenylosuccinate synthetase |
| 637 | putative 14-3-3 protein |
| 638 | putative cytochrome P450 |
| 639 | putative two-component response regulator 3 protein |
| 640 | putative RING-H2 zinc finger protein ATL6 |
| 641 | No function assigned by TIGR |
| 642 | small zinc finger-like protein |
| 643 | hypothetical protein |
| 644 | MAP kinase (ATMPK6) |
| 645 | vacuolar ATP synthase, putative |
| 646 | kinesin-like protein |
| 647 | serine/threonine-specific protein kinase NAK |
| 648 | No function assigned by TIGR |
| 649 | ACTIN 2/7 (sp\|P53492) |
| 650 | phosphoglycerate kinase, putative |
| 651 | homeotic protein BEL1 homolog |
| 652 | proline iminopeptidase |
| 653 | pasticcino 1 |
| 654 | serine/threonine protein kinase |
| 655 | cytochrome P450 monooxygenase (CYP71B4) |
| 656 | No function assigned by TIGR |
| 657 | putative GDSL-motif lipase/hydrolase |
| 658 | putative protein |
| 659 | unknown protein |
| 660 | hypothetical protein |
| 661 | putative glycosylation enzyme |
| 662 | No function assigned by TIGR |
| 663 | No function assigned by TIGR |
| 664 | unknown protein |
| 665 | putative ABC transporter |
| 666 | nifU-like protein |
| 667 | putative receptor-like protein kinase |
| 668 | putative disease resistance protein |
| 669 | receptor-like protein kinase-like |
| 670 | ubiquitin activating enzyme 2 (gb\|AAB37569.1) |
| 671 | No function assigned by TIGR |
| 672 | putative receptor-like protein kinase |
| 673 | K+ transporter, AKT1 |
| 674 | shaggy-like kinase beta |
| 675 | heat shock protein 70 |
| 676 | plasma membrane intrinsic protein 1a |
| 677 | HSP90-like protein |
| 678 | histone H1, putative |
| 679 | unknown protein |

TABLE 1-continued
SEQUENCE DESCRIPTIONS

| Seq ID | Description |
|---|---|
| 680 | dnaK-type molecular chaperone hsc70.1-like |
| 681 | gamma-glutamylcysteine synthetase |
| 682 | peroxidase (ATP22a) |
| 683 | putative serine carboxypeptidase precursor |
| 684 | putative dioxygenase |
| 685 | glucose transporter |
| 686 | NOI protein, nitrate-induced |
| 687 | putative protein |
| 688 | putative protein |
| 689 | unknown protein |
| 690 | putative photosystem I reaction center subunit II precursor |
| 691 | putative protein |
| 692 | unknown protein |
| 693 | cobalamin biosynthesis protein |
| 694 | adenine nucleotide translocase |
| 695 | glutathione transferase, putative |
| 696 | putative 60S ribosomal protein L21 |
| 697 | cytochrome P450 like protein |
| 698 | cytochrome b245 beta chain homlog RbohApl08, putative |
| 699 | RNA helicase, DRH1 |
| 700 | putative aldolase |
| 701 | farnesyltransferase subunit A (FTA) |
| 702 | No function assigned by TIGR |
| 703 | putative putative sister-chromatide cohesion protein |
| 704 | calcium-dependent protein kinase |
| 705 | serine/threonine protein phosphatase type 2A, putative |
| 706 | 40S ribosomal protein S28 (sp|P34789) |
| 707 | RNA polymerase subunit |
| 708 | DNA-damage-repair/toleration protein DRT102 |
| 709 | putative C2H2-type zinc finger protein |
| 710 | putative adenosine phosphosulfate kinase |
| 711 | lipase |
| 712 | putative violaxanthin de-epoxidase precursor (U44133) |
| 713 | aromatic rich glycoprotein, putative |
| 714 | putative fumarase |
| 715 | flavonol synthase (FLS) (sp|Q96330) |
| 716 | response regulator 5, putative |
| 717 | sulfate transporter |
| 718 | putative floral homeotic protein, AGL9 |
| 719 | putative ethylene-inducible protein |
| 720 | C-8,7 sterol isomerase |
| 721 | TCH4 protein (gb|AAA92363.1) |
| 722 | hypothetical protein |
| 723 | putative urease accessory protein |
| 724 | molybdopterin synthase sulphurylase (gb|AAD18050.1) |
| 725 | putative protein |
| 726 | NBD-like protein (gb|AAD20643.1) |
| 727 | AtHVA22c |
| 728 | unknown protein |
| 729 | phytoene synthase (gb|AAB65697.1) |
| 730 | protein kinase (AME2/AFC1) |
| 731 | hypothetical protein |
| 732 | cyclin-dependent protein kinase-like protein |
| 733 | photosystem II stability/assembly factor HCF136 (sp|O82660) |
| 734 | hypothetical protein |
| 735 | DNA binding-like protein |
| 736 | putative protein |
| 737 | chorismate mutase |
| 738 | putative LRR receptor protein kinase |
| 739 | putative chalcone synthase |
| 740 | putative protein kinase |
| 741 | replicase, putative |
| 742 | putative cysteine proteinase |
| 743 | 60S ribosomal protein L36 |
| 744 | unknown protein |
| 745 | CLC-b chloride channel protein |
| 746 | putative ribosomal protein S14 |
| 747 | histone H2B like protein (emb|CAA69025.1) |
| 748 | 60S ribosomal protein L2 |
| 749 | 60S ribosomal protein L15 homolog |
| 750 | ribosomal protein S27 |
| 751 | ribosomal protein |
| 752 | 60S ribosomal protein L12 |
| 753 | 60s ribosomal protein L34 |
| 754 | putative ribosomal protein S10 |
| 755 | drought-induced protein like |
| 756 | blue copper-binding protein, 15K (lamin) |
| 757 | calmodulin-like protein |
| 758 | putative protein |
| 759 | No function assigned by TIGR |
| 760 | alpha-mannosidase, putative |
| 761 | uncoupling protein (ucp/PUMP) |
| 762 | homeodomain-like protein |
| 763 | ribosomal protein S18, putative |
| 764 | similar to SOR1 from the fungus Cercospora nicotianae |
| 765 | 60S ribosomal protein L13, BBC1 protein |
| 766 | 50S ribosomal protein L24, chloroplast precursor |
| 767 | putative ribosomal protein |
| 768 | unknown protein |
| 769 | aspartate aminotransferase (AAT1) |
| 770 | potassium channel protein AtKC |
| 771 | unknown protein |
| 772 | peroxisomal targeting signal type 2 receptor |
| 773 | putative protein |
| 774 | Ras-related GTP-binding protein (ARA-4) |
| 775 | S-receptor kinase homolog 2 precursor |
| 776 | pathogenesis-related group 5 protein, putative |
| 777 | Nitrilase 4 (sp|P46011) |
| 778 | biotin carboxyl carrier protein of acetyl-CoA carboxylase precursor (BCCP) (sp|Q42533) |

TABLE 1-continued

SEQUENCE DESCRIPTIONS

| Seq ID | Description |
|---|---|
| 779 | photosystem I reaction centre subunit psaN precursor (PSI-N) (sp|P49107) |
| 780 | 3(2),5-bisphosphate nucleotidase |
| 781 | high affinity Ca2+ antiporter |
| 782 | putative cytoskeletal protein |
| 783 | putative peroxidase |
| 784 | respiratory burst oxidase protein |
| 785 | beta-glucosidase |
| 786 | calcium-dependent protein kinase (pir||S71196) |
| 787 | phosphoinositide specific phospholipase C |
| 788 | similarity to S-domain receptor-like protein kinase, Zea mays |
| 789 | mitosis-specific cyclin 1b |
| 790 | 4-coumarate: CoA ligase 3 |
| 791 | transcription factor IIB (TFIIB) |
| 792 | unknown protein |
| 793 | hypothetical protein |
| 794 | hypothetical protein |
| 795 | sugar transporter like protein |
| 796 | putative trypsin inhibitor |
| 797 | unknown protein |
| 798 | putative multispanning membrane protein |
| 799 | receptor-like kinase, putative |
| 800 | putative inosine-5-monophosphate dehydrogenase |
| 801 | inosine-5'-monophosphate dehydrogenase, putative |
| 802 | amino acid permease 6 (emb|CAA65051.1) |
| 803 | NADPH-ferrihemoprotein reductase (ATR2) |
| 804 | putative WRKY-type DNA binding protein |
| 805 | putative ankyrin |
| 806 | putative hexose transporter |
| 807 | aquaporin/MIP-like protein |
| 808 | Ser/Thr protein kinase isolog |
| 809 | pectate lyase like protein |
| 810 | putative 60S ribosomal protein L17 |
| 811 | putative protein |
| 812 | unknown protein |
| 813 | phenylalanine ammonia-lyase |
| 814 | putative cytochrome P450 monooxygenase |
| 815 | ARR1 protein; putative |
| 816 | putative bHLH transcription factor |
| 817 | aminomethyltransferase-like precursor protein |
| 818 | purple acid phosphatase precursor |
| 819 | AP2 domain containing protein, putative |
| 820 | ubiquitin-conjugating enzyme E2-21 kD 1 (ubiquitin-protein ligase 4) (ubiquitin carrier protein 4) (sp|P42748) |
| 821 | translation initiation factor |
| 822 | putative VAMP-associated protein |
| 823 | spermidine synthase, putative |
| 824 | putative protein |
| 825 | unknown protein |
| 826 | AtKAP alpha |
| 827 | glyceraldehyde-3-phosphate dehydrogenase, putative |
| 828 | putative poly(A) binding protein |
| 829 | alpha-tubulin, putative |
| 830 | serine/threonine-specific protein kinase ATPK64 (pir||S20918) |
| 831 | putative aspartate-tRNA ligase |
| 832 | ras-related small GTP-binding protein RAB1c |
| 833 | cycloartenol synthase |
| 834 | No function assigned by TIGR |
| 835 | cytochrome P450 |
| 836 | GTPase AtRAB8 |
| 837 | 3-phosphoserine phosphatase |
| 838 | transcription factor CRC |
| 839 | nuclear cap-binding protein; CBP20 (gb|AAD29697.1) |
| 840 | chloroplast membrane protein (ALBINO3) |
| 841 | biotin holocarboxylase synthetase |
| 842 | expansin AtEx6 |
| 843 | unknown protein |
| 844 | mercaptopyruvate sulfurtransferase, putative |
| 845 | putative thiosulfate sulfurtransferase |
| 846 | dihydrolipoamide S-acetyltransferase |
| 847 | auxin transport protein REH1, putative |
| 848 | putative auxin transport protein |
| 849 | apyrase (Atapy1) |
| 850 | root cap 1 (RCP1) |
| 851 | hypothetical protein |
| 852 | putative protein |
| 853 | predicted protein of unknown function |
| 854 | hypothetical protein |
| 855 | hypothetical protein |
| 856 | hypothetical protein |
| 857 | putative aldehyde dehydrogenase |
| 858 | putative peroxidase |
| 859 | UDP-glucose 4-epimerase-like protein |
| 860 | indole-3-acetate beta glucosyltransferase like protein |
| 861 | putative beta-1,3-glucanase |
| 862 | disease resistance protein-like |
| 863 | putative respiratory burst oxidase protein B |
| 864 | ubiquitin-conjugating enzyme UBC3 |
| 865 | cytoplasmic aconitate hydratase |
| 866 | NADPH oxidoreductase, putative |
| 867 | PROTEIN TRANSPORT PROTEIN SEC61 GAMMA SUBUNIT-like |
| 868 | putative protein |
| 869 | unknown protein |
| 870 | 60S acidic ribosomal protein P2 |
| 871 | No function assigned by TIGR |
| 872 | 1,4-alpha-glucan branching enzyme protein soform SBE2.2 precursor |
| 873 | calcium binding protein (CaBP-22) |
| 874 | putative phosphoglucomutase |

TABLE 1-continued

SEQUENCE DESCRIPTIONS

| Seq ID | Description |
|---|---|
| 875 | shaggy-like protein kinase etha (EC 2.7.1.—) |
| 876 | pyruvate decarboxylase (gb|AAB16855.1) |
| 877 | hypothetical protein |
| 878 | putative protein kinase |
| 879 | putative protein kinase |
| 880 | putative leucine aminopeptidase |
| 881 | probable cytochrome P450 |
| 882 | protein kinase 6-like protein |
| 883 | arginine methyltransferase (pam1) |
| 884 | MYB96 transcription factor-like protein |
| 885 | putative protein |
| 886 | metal ion transporter |
| 887 | No function assigned by TIGR |
| 888 | flax rust resistance protein, putative |
| 889 | fructose-2,6 bisphosphatase, putative |
| 890 | exonuclease RRP41 |
| 891 | squamosa promoter binding protein-like 2 (emb|CAB56576.1) |
| 892 | putative squamosa promoter binding protein |
| 893 | O-acetylserine(thiol) lyase, putative |
| 894 | snoRNA |
| 895 | snoRNA |
| 896 | ferredoxin-NADP+ reductase |
| 897 | H+-transporting ATP synthase chain 9-like protein |
| 898 | photosystem I subunit III precursor, putative |
| 899 | photosystem I subunit VI precursor |
| 900 | auxin-binding protein 1 precursor |
| 901 | putative RAS superfamily GTP-binding protein |
| 902 | disease resistance protein-like |
| 903 | protein kinase like protein |
| 904 | glucuronosyl transferase-like protein |
| 905 | putative homeodomain transcription factor |
| 906 | putative flavonol reductase |
| 907 | putative protein |
| 908 | salt-tolerance protein |
| 909 | 40S ribosomal protein S30 |
| 910 | putative bZIP transcription factor |
| 911 | putative protein |
| 912 | putative cinnamoyl CoA reductase |
| 913 | unknown protein |
| 914 | putative RNA-binding protein |
| 915 | phosphatidylinositol synthase (PIS1) |
| 916 | unknown protein |
| 917 | hydroxyproline-rich glycoprotein homolog |
| 918 | 50S ribosomal protein L15, chloroplast precursor |
| 919 | unknown protein |
| 920 | putative YME1 ATP-dependant protease |
| 921 | unknown protein |
| 922 | putative ribosomal protein L28 |
| 923 | unknown protein |
| 924 | putative protein |
| 925 | protein ch-42 precursor, chloroplast |
| 926 | protein serine/threonine kinase, putative |
| 927 | beta-VPE |
| 928 | putative vacuolar sorting receptor |
| 929 | putative translation initiation factor IF-2 |
| 930 | predicted protein of unknown function |
| 931 | putative protein |
| 932 | hypothetical protein |
| 933 | hypothetical protein |
| 934 | phosphate transporter, putative |
| 935 | No function assigned by TIGR |
| 936 | beta subunit of protein farnesyl transferase ERA1 |
| 937 | putative glutamate decarboxylase |
| 938 | putative indole-3-acetate beta-glucosyltransferase |
| 939 | putative receptor-like protein kinase |
| 940 | UDP-galactose 4-epimerase-like protein |
| 941 | putative proliferating cell nuclear antigen, PCNA |
| 942 | ubiquitin conjugating enzyme E2 (UBC13) |
| 943 | cyclophilin (CYP2) |
| 944 | cystatin (emb|CAA03929.1) |
| 945 | putative alcohol dehydrogenase |
| 946 | acidic ribosomal protein p1 |
| 947 | glutathione transferase AtGST 10 (emb|CAA10457.1) |
| 948 | putative tropinone reductase |
| 949 | ZIP4, a putative zinc transporter |
| 950 | unknown protein |
| 951 | putative protein |
| 952 | putative protein |
| 953 | putative C2H2-type zinc finger protein |
| 954 | putative RING zinc finger protein |
| 955 | putative microtubule-associated protein |
| 956 | unknown protein |
| 957 | putative protein |
| 958 | putative protein phosphatase-2c |
| 959 | V-ATPase subunit G (vag2 gene) |
| 960 | hypothetical protein |
| 961 | unknown protein |
| 962 | unknown protein |
| 963 | unknown protein |
| 964 | myrosinase-associated protein, putative |
| 965 | hypothetical protein |
| 966 | hypothetical protein |
| 967 | No function assigned by TIGR |
| 968 | unknown protein |
| 969 | hypothetical protein |
| 970 | LAX1/AUX1-like permease |
| 971 | putative UDP-N-acetylglucosamine-dolichyl-phosphate N-acetylglucosaminephosphotransferase |
| 972 | chorismate mutase CM2 |

TABLE 1-continued

SEQUENCE DESCRIPTIONS

| Seq ID | Description |
|---|---|
| 973 | inner mitochondrial membrane protein |
| 974 | DEF (CLA1) protein |
| 975 | decoy |
| 976 | citrate synthase |
| 977 | myosin |
| 978 | 40S ribosomal protein S19 |
| 979 | ripening-related protein-like |
| 980 | putative signal peptidase I |
| 981 | methionyl-tRNA synthetase (AtcpMetRS) |
| 982 | ribosomal protein precursor-like |
| 983 | 50S ribosomal protein L21 chloroplast precursor (CL21) |
| 984 | putative MYB family transcription factor |
| 985 | cyclophilin-like protein |
| 986 | hypothetical protein |
| 987 | naringenin 3-dioxygenase like protein |
| 988 | WD-repeat protein-like protein |
| 989 | putative serine carboxypeptidase II |
| 990 | prenyltransferase, putative |
| 991 | putative ligand-gated ion channel protein |
| 992 | clathrin adaptor medium chain protein MU1B, putative |
| 993 | No function assigned by TIGR |
| 994 | putative Tall-like non-LTR retroelement protein |
| 995 | putative 3-isopropylmalate dehydrogenase |
| 996 | 3-isopropylmalate dehydratase, small subunit |
| 997 | unknown protein |
| 998 | unknown protein |
| 999 | unknown protein |
| 1000 | hypothetical protein |
| 1001 | putative protein |
| 1002 | No function assigned by TIGR |
| 1003 | putative beta-glucosidase |
| 1004 | putative pectate lyase A11 |
| 1005 | putative beta-glucosidase |
| 1006 | HD-Zip protein |
| 1007 | putative ubiquitin conjugating enzyme |
| 1008 | homeobox-leucine zipper protein-like |
| 1009 | cytochrome P450 like protein |
| 1010 | putative cysteine proteinase inhibitor B (cystatin B) |
| 1011 | ethylene response sensor (ERS) |
| 1012 | putative SWH1 protein |
| 1013 | putative glutathione S-transferase |
| 1014 | putative protein |
| 1015 | unknown protein |
| 1016 | putative protein phosphatase 2C |
| 1017 | dnaJ protein homolog atj3 |
| 1018 | ferredoxin |
| 1019 | hypothetical protein |
| 1020 | putative sugar transport protein, ERD6 |
| 1021 | putative DnaJ protein |
| 1022 | putative AP2 domain transcription factor |
| 1023 | putative protein |
| 1024 | putative cyclin-dependent kinase regulatory subunit |
| 1025 | putative tropinone reductase |
| 1026 | signal response protein (GAI) |
| 1027 | putative steroid sulfotransferase |
| 1028 | hypothetical protein |
| 1029 | nucleic acid binding protein-like |
| 1030 | putative protein |
| 1031 | blue copper binding protein |
| 1032 | farnesylated protein (ATFP6) |
| 1033 | unknown protein |
| 1034 | putative PCF2-like DNA binding protein |
| 1035 | teosinte branched1-like protein |
| 1036 | putative protein |
| 1037 | unknown protein |
| 1038 | unknown protein |
| 1039 | 2-oxoglutarate dehydrogenase, E1 component |
| 1040 | unknown protein |
| 1041 | unknown protein |
| 1042 | CCAAT-binding transcription factor subunit A(CBF-A) |
| 1043 | hypothetical protein |
| 1044 | putative growth regulator protein |
| 1045 | putative presenilin |
| 1046 | putative expansin |
| 1047 | ribosomal-like protein |
| 1048 | unknown protein |
| 1049 | unknown protein |
| 1050 | putative protein |
| 1051 | putative protein |
| 1052 | unknown protein |
| 1053 | unknown protein |
| 1054 | unknown protein |
| 1055 | unknown protein |
| 1056 | unknown protein |
| 1057 | putative protein |
| 1058 | putative protein |
| 1059 | argininosuccinate lyase (AtArgH) |
| 1060 | disease resistance protein homolog |
| 1061 | aldehyde dehydrogenase like protein |
| 1062 | GBF2, G-box binding factor |
| 1063 | CDPK-related kinase |
| 1064 | endo-1,4-beta-glucanase |
| 1065 | putative serine protease |
| 1066 | serine/threonine-specific kinase lecRK1 precursor, lectin receptor-like |
| 1067 | putative MAP kinase |
| 1068 | RNase L inhibitor-like protein |
| 1069 | No function assigned by TIGR |
| 1070 | AP2 domain transcription factor |
| 1071 | polygalacturonase isoenzyme 1 beta subunit, putative |
| 1072 | putative lipid transfer protein |
| 1073 | putative protein kinase |
| 1074 | putative protein |
| 1075 | ATP-dependent RNA helicase like protein |
| 1076 | putative cyclic nucleotide-regulated ion channel protein |
| 1077 | COP1 like protein |
| 1078 | putative peroxidase |
| 1079 | putative NAK-like ser/thr protein kinase |
| 1080 | putative cytochrome C |
| 1081 | cytochrome c |
| 1082 | putative serine carboxypeptidase II |
| 1083 | acyl-(acyl carrier protein) thioesterase |

TABLE 1-continued

SEQUENCE DESCRIPTIONS

| Seq ID | Description |
|---|---|
| 1084 | DNA-binding factor, putative |
| 1085 | MAP3K delta-1 protein kinase |
| 1086 | AtMlo-hl-like protein |
| 1087 | No function assigned by TIGR |
| 1088 | putative expansin |
| 1089 | defender against cell death protein, putative |
| 1090 | glycolate oxidase-like protein |
| 1091 | putative ATP-dependent RNA helicase |
| 1092 | putative protein |
| 1093 | putative HMG protein |
| 1094 | squalene monooxygenase 2 (squalene epoxidase 2) (SE 2) (sp|O65403) |
| 1095 | eukaryotic peptide chain release factor subunit 1, putative |
| 1096 | auxin-induced protein-like |
| 1097 | putative lipoamide dehydrogenase |
| 1098 | putative protein |
| 1099 | unknown protein |
| 1100 | putative oligopeptide transporter |
| 1101 | putative translation elongation factor ts |
| 1102 | putative CCAAT-binding transcription factor subunit |
| 1103 | putative ABC transporter |
| 1104 | putative superoxide-generating NADPH oxidase flavocytochrome |
| 1105 | aspartate kinase-homoserine dehydrogenase-like protein |
| 1106 | putative bHLH transcription factor |
| 1107 | putative geranylgeranyl transferase type I beta subunit |
| 1108 | putative ARP2/3 protein complex subunit p41 |
| 1109 | sulphite reductase |
| 1110 | putative auxin-regulated protein |
| 1111 | transcription factor scarecrow-like 14, putative |
| 1112 | unknown protein |
| 1113 | monooxygenase 2 (MO2) |
| 1114 | putative amine oxidase |
| 1115 | zinc finger protein, putative |
| 1116 | DNA-binding protein, putative |
| 1117 | putative protein |
| 1118 | putative protein |
| 1119 | Avr9 elicitor response like protein |
| 1120 | putative protein |
| 1121 | hypothetical protein |
| 1122 | putative nucleotide-sugar dehydratase |
| 1123 | UFD1 like protein |
| 1124 | putative transprenyltransferase |
| 1125 | outward rectifying potassium channel KCO |
| 1126 | unknown protein |
| 1127 | putative pectinacetylesterase |
| 1128 | putative protein |
| 1129 | No function assigned by TIGR |
| 1130 | unknown protein |
| 1131 | unknown protein |
| 1132 | unknown protein |
| 1133 | protein phosphatase homolog (PPH1) |
| 1134 | unknown protein |
| 1135 | No function assigned by TIGR |
| 1136 | unknown protein |
| 1137 | unknown protein |
| 1138 | unknown protein |
| 1139 | putative protein |
| 1140 | unknown protein |
| 1141 | putative ubiquinol-cytochrome-c reductase |
| 1142 | unknown protein |
| 1143 | contains similarity to high-glucose-regulated protein 8 GB: AAF08813 GI: 6449083 from [*Homo sapiens*] |
| 1144 | unknown protein |
| 1145 | putative cis-Golgi SNARE protein |
| 1146 | unknown protein |
| 1147 | glutamate-1-semialdehyde aminotransferase |
| 1148 | No function assigned by TIGR |
| 1149 | hypothetical protein |
| 1150 | unknown protein |
| 1151 | unknown protein |
| 1152 | unknown protein |
| 1153 | scarecrow-like 3 |
| 1154 | putative proline-rich protein |
| 1155 | cytocrome c oxidoreductase like protein |
| 1156 | putative carboxymethylenebutenolidase |
| 1157 | unknown protein |
| 1158 | unknown protein |
| 1159 | unknown protein |
| 1160 | unknown protein |
| 1161 | unknown protein |
| 1162 | unknown protein |
| 1163 | auxin-induced protein (IAA20) |
| 1164 | 50S ribosomal protein L4 |
| 1165 | putative DNA topoisomerase III beta |
| 1166 | No function assigned by TIGR |
| 1167 | isp4 like protein |
| 1168 | putative protein kinase |
| 1169 | hypothetical protein |
| 1170 | putative pyrophosphate-fructose-6-phosphate 1-phosphotransferase |
| 1171 | putative protein |
| 1172 | putative protein |
| 1173 | putative protein |
| 1174 | unknown protein |
| 1175 | unknown protein |
| 1176 | putative protein |
| 1177 | putative protein |
| 1178 | unknown protein |
| 1179 | unknown protein |
| 1180 | putative protein |
| 1181 | brassinosteroid insensitive 1 gene (BRI1) |
| 1182 | putative receptor protein kinase |
| 1183 | vacuolar-type H+-translocating inorganic pyrophosphatase |
| 1184 | protein kinase-like protein |
| 1185 | glycyl tRNA synthetase, putative |
| 1186 | subtilisin proteinase-like |
| 1187 | hypothetical protein |
| 1188 | cytochrome P450-like protein |
| 1189 | cytochrome p450 like protein |
| 1190 | putative protein kinase |
| 1191 | pectinesterase-like protein |
| 1192 | putative receptor-like protein kinase |
| 1193 | peroxidase ATP17a-like protein |
| 1194 | No function assigned by TIGR |

TABLE 1-continued

SEQUENCE DESCRIPTIONS

| Seq ID | Description |
|---|---|
| 1195 | cellulose synthase catalytic subunit-like protein |
| 1196 | RAS-related protein, RAB7 |
| 1197 | putative aspartate aminotransferase |
| 1198 | cyclophilin |
| 1199 | putative SF2/ASF splicing modulator, Srp30 |
| 1200 | putative cytochrome b5 |
| 1201 | glutamyl-tRNA reductase, putative |
| 1202 | putative MADS-box protein |
| 1203 | ammonium transport protein (AMT1) |
| 1204 | No function assigned by TIGR |
| 1205 | putative beta-ketoacyl-CoA synthase |
| 1206 | thaumatin-like protein |
| 1207 | putative methionine aminopeptidase |
| 1208 | putative protein phosphatase 2C |
| 1209 | kinase-like protein |
| 1210 | receptor-associated kinase isolog |
| 1211 | mitochondrial ribosomal protein S14 |
| 1212 | oleosin, 18.5K |
| 1213 | chalcone isomerase |
| 1214 | putative cyclin-dependent kinase regulatory subunit |
| 1215 | putative thaumatin-like protein |
| 1216 | putative two-component response regulator protein |
| 1217 | TATA binding protein associated factor, putative |
| 1218 | predicted protein of unknown function |
| 1219 | putative AP2 domain transcription factor |
| 1220 | brassinosteroid receptor kinase, putative |
| 1221 | TINY-like protein |
| 1222 | glucose-6-phosphate isomerase |
| 1223 | putative protein |
| 1224 | putative NAM (no apical meristem)-like protein |
| 1225 | unknown protein |
| 1226 | putative nucleotide-binding protein |
| 1227 | bZIP transcription factor (POSF21) |
| 1228 | ubiquitin activating enzyme-like protein |
| 1229 | telomere repeat-binding protein |
| 1230 | unknown protein |
| 1231 | mevalonate kinase |
| 1232 | putative protein |
| 1233 | hypothetical protein |
| 1234 | disease resistance RPP5 like protein |
| 1235 | putative protein |
| 1236 | putative pectinesterase |
| 1237 | Ttg1 protein (emb|CAB45372.1) |
| 1238 | FUSCA PROTEIN FUS6 |
| 1239 | NHE1 Na+/H+ exchanger |
| 1240 | No function assigned by TIGR |
| 1241 | Phospholipase like protein |
| 1242 | unknown protein |
| 1243 | unknown protein |
| 1244 | unknown protein |
| 1245 | AUX1-like amino acid permease |
| 1246 | unknown protein |
| 1247 | putative C2H2-type zinc finger protein |
| 1248 | putative protein |
| 1249 | putative protein |
| 1250 | putative glucosyltransferase |
| 1251 | putative lipase |
| 1252 | putative protein |
| 1253 | putative thioredoxin |
| 1254 | AIG2-like protein |
| 1255 | short-chain alcohol dehydrogenase like protein |
| 1256 | hypothetical protein |
| 1257 | putative protein |
| 1258 | putative protein |
| 1259 | glutathione peroxidase-like protein |
| 1260 | putative protein |
| 1261 | putative disease resistance response protein |
| 1262 | putative protein |
| 1263 | senescence-associated protein (SAG29) |
| 1264 | glycolate oxidase, putative |
| 1265 | extensin-like protein |
| 1266 | putative protein |
| 1267 | unknown protein |
| 1268 | putative disease resistance protein |
| 1269 | putative receptor-like protein kinase |
| 1270 | putative receptor-like protein kinase |
| 1271 | basic chitinase |
| 1272 | putative pectin methylesterase |
| 1273 | peroxidase ATP N |
| 1274 | class 2 non-symbiotic hemoglobin |
| 1275 | nitrate transporter |
| 1276 | Ca2+/H+-exchanging protein-like |
| 1277 | putative protein |
| 1278 | hydroxynitrile lyase like protein |
| 1279 | putative AP2 domain transcription factor |
| 1280 | pectin methylesterase, putative |
| 1281 | putative protein |
| 1282 | beta-glucosidase-like protein |
| 1283 | CCAAT box binding factor/transcription factor Hap2a |
| 1284 | putative fibrillin |
| 1285 | xyloglucan endo transglycosylase |
| 1286 | putative 10 kd chaperonin |
| 1287 | No function assigned by TIGR |
| 1288 | serine/threonine protein kinase ATPK10 |
| 1289 | putative lipase |
| 1290 | choline kinase GmCK2p-like protein |
| 1291 | putative sugar transport protein, ERD6 |
| 1292 | MYB27 protein-like |
| 1293 | DNA-binding protein, putative |
| 1294 | similar to cold acclimation protein WCOR413 [*Triticum aestivum*] |
| 1295 | unknown protein |
| 1296 | aquaporin (plasma membrane intrinsic protein 2B) |
| 1297 | No function assigned by TIGR |
| 1298 | P-Protein-like protein |
| 1299 | No function assigned by TIGR |
| 1300 | putative cytochrome P450 monooxygenase |

TABLE 1-continued

SEQUENCE DESCRIPTIONS

| Seq ID | Description |
|---|---|
| 1301 | putative cytochrome P450 monooxygenase |
| 1302 | putative thioredoxin |
| 1303 | stromal ascorbate peroxidase |
| 1304 | ethylene responsive element binding factor-like protein (AtERF6) |
| 1305 | auxin transport protein EIR1 (gb|AAC39513.1) |
| 1306 | putative CONSTANS-like B-box zinc finger protein |
| 1307 | putative protein kinase |
| 1308 | mitochondrial Lon protease homolog 1 precursor (sp|O64948) |
| 1309 | putative protein |
| 1310 | heme activated protein, putative |
| 1311 | putative cytochrome P450 |
| 1312 | No function assigned by TIGR |
| 1313 | putative lipase |
| 1314 | putative protein |
| 1315 | putative sugar transporter protein |
| 1316 | putative sucrose transport protein, SUC2 |
| 1317 | putative protein |
| 1318 | putative protein |
| 1319 | putative endochitinase |
| 1320 | putative acetone-cyanohydrin lyase |
| 1321 | putative protein |
| 1322 | calmodulin-like protein |
| 1323 | hypothetical protein |
| 1324 | cysteine proteinase like protein |
| 1325 | heat shock protein 17.6-II |
| 1326 | heat shock protein 18 |
| 1327 | Arabidopsis mitochondrion-localized small heat shock protein (AtHSP23.6-mito) |
| 1328 | unknown protein |
| 1329 | putative WRKY-type DNA binding protein |
| 1330 | No function assigned by TIGR |
| 1331 | hypothetical protein |
| 1332 | putative integral membrane protein nodulin |
| 1333 | putative protein |
| 1334 | unknown protein |
| 1335 | 3-isopropylmalate dehydratase, small subunit |
| 1336 | unknown protein |
| 1337 | putative homeodomain transcription factor |
| 1338 | unknown protein |
| 1339 | putative protein |
| 1340 | peroxidase ATP19a |
| 1341 | putative Na+/H+ exchanging protein |
| 1342 | putative auxin-regulated protein |
| 1343 | unknown protein |
| 1344 | unknown protein |
| 1345 | putative trehalose-6-phosphate synthase |
| 1346 | putative lectin |
| 1347 | Mlo protein-like |
| 1348 | unknown protein |
| 1349 | ethylene response factor, putative |
| 1350 | unknown protein |
| 1351 | unknown protein |
| 1352 | bZIP transcription factor-like protein |
| 1353 | Medicago nodulin N21-like protein |
| 1354 | putative endo-1,4-beta glucanase |
| 1355 | 1-aminocyclopropane-1-carboxylate oxidase |
| 1356 | putative anion exchange protein |
| 1357 | SRG1-like protein |
| 1358 | putative protein |
| 1359 | putative phi-1-like phosphate induced protein |
| 1360 | putative protein |
| 1361 | putative embryo-abundant protein |
| 1362 | putative hydrolase |
| 1363 | unknown protein |
| 1364 | unknown protein |
| 1365 | hexose transporter-like protein |
| 1366 | unknown protein |
| 1367 | unknown protein |
| 1368 | peptide transport-like protein |
| 1369 | unknown protein |
| 1370 | putative peptide transporter |
| 1371 | disease resistance protein, putative |
| 1372 | cysteine protease component of protease-inhibitor complex |
| 1373 | putative cytochrome P450 |
| 1374 | putative protein |
| 1375 | hypothetical protein |
| 1376 | unknown protein |
| 1377 | putative phosphoribosylaminoimidazolecarboxamide formyltransferase |
| 1378 | putative protein |
| 1379 | HSP like protein |
| 1380 | unknown protein |
| 1381 | unknown protein |
| 1382 | putative cytochrome P450 |
| 1383 | similar to pectinesterase |
| 1384 | putative glucosyltransferase |
| 1385 | thaumatin-like protein |
| 1386 | drought-inducible cysteine proteinase RD19A precursor |
| 1387 | vegetative storage protein Vsp2 |
| 1388 | unknown protein |
| 1389 | unknown protein |
| 1390 | anthranilate N-benzoyltransferase-like protein |
| 1391 | delta-1-pyrroline 5-carboxylase synthetase (P5C1) |
| 1392 | glutathione S-conjugate transporting ATPase (AtMRP1) |
| 1393 | hypothetical protein |
| 1394 | hypothetical protein |
| 1395 | unknown protein |
| 1396 | putative protein |
| 1397 | putative protein |
| 1398 | No function assigned by TIGR |
| 1399 | unknown protein |
| 1400 | putative protein kinase |
| 1401 | unknown protein |
| 1402 | hypothetical protein |
| 1403 | unknown protein |
| 1404 | putative calcium-binding EF-hand protein |
| 1405 | cinnamyl-alcohol dehydrogenase ELI3-1 |
| 1406 | putative protein |
| 1407 | unknown protein |
| 1408 | senescence-associated protein sen1 |
| 1409 | hypothetical protein |
| 1410 | putative cytochrome P450 |

TABLE 1-continued

SEQUENCE DESCRIPTIONS

| Seq ID | Description |
|---|---|
| 1411 | proline oxidase, mitochondrial precursor (osmotic stress-induced proline dehydrogenase) |
| 1412 | putative response regulator 3 |
| 1413 | hypothetical protein |
| 1414 | glutamine-dependent asparagine synthetase |
| 1415 | lysine-ketoglutarate reductase/saccharopine |
| 1416 | En/Spm-like transposon protein |
| 1417 | G-box binding bZIP transcription factor |
| 1418 | putative protein |
| 1419 | putative protein |
| 1420 | putative protein |
| 1421 | ATFP4-like |
| 1422 | unknown protein |
| 1423 | unknown protein |
| 1424 | putative protein |
| 1425 | invertase inhibitor homolog (emb|CAA73335.1) |
| 1426 | unknown protein |
| 1427 | unknown protein |
| 1428 | putative cytochrome b5 |
| 1429 | putative protein |
| 1430 | putative protein |
| 1431 | putative protein |
| 1432 | No function assigned by TIGR |
| 1433 | putative copper/zinc superoxide dismutase |
| 1434 | protein phosphatase ABI1 |
| 1435 | glutamate dehydrogenase 2 |
| 1436 | No function assigned by TIGR |
| 1437 | low-temperature-induced protein 78 (sp|Q06738) |
| 1438 | putative myo-inositol 1-phosphate synthase |
| 1439 | phosphate transporter (gb|AAB17265.1) |
| 1440 | 4-hydroxyphenylpyruvate dioxygenase (HPD) |
| 1441 | histone HI |
| 1442 | hypothetical protein |
| 1443 | No function assigned by TIGR |
| 1444 | neoxanthin cleavage enzyme-like protein |
| 1445 | dehydration-induced protein RD22 |
| 1446 | zinc finger protein ZAT7 |
| 1447 | unknown protein |
| 1448 | unknown protein |
| 1449 | unknown protein |
| 1450 | unknown protein |
| 1451 | putative protein |
| 1452 | putative protein |
| 1453 | RNA helicase, putative |
| 1454 | putative glycine-rich protein |
| 1455 | hypothetical protein |
| 1456 | putative protein |
| 1457 | peroxidase |
| 1458 | peroxidase ATP3a (emb|CAA67340.1) |
| 1459 | metallothionein-like protein |
| 1460 | endomembrane-associated Protein |
| 1461 | ferritin 1 precursor |
| 1462 | dehydrin RAB18-like protein (sp|P30185) |
| 1463 | HSR201 like protein |
| 1464 | light regulated protein, putative |
| 1465 | Dr4(protease inhibitor) |
| 1466 | mitogen activated protein kinase kinase (nMAPKK) |
| 1467 | glutathione S-transferase |
| 1468 | transcriptional activator CBF1/CRT/CRE binding factor 1 |
| 1469 | homeobox-leucine zipper protein ATHB-12 |
| 1470 | amino acid permease I |
| 1471 | MAP kinase (ATMPK7) |
| 1472 | potassium channel protein AKT3 |
| 1473 | cytochrome P450 monooxygenase (CYP91A2) |
| 1474 | putative transport protein |
| 1475 | putative protein |
| 1476 | hypothetical protein |
| 1477 | putative protein |
| 1478 | hypothetical protein |
| 1479 | receptor protein kinase-like protein |
| 1480 | serine/threonine protein kinase-like protein |
| 1481 | putative auxin-regulated protein |
| 1482 | amino acid transport protein AAP2 |
| 1483 | unknown protein |
| 1484 | cold and ABA inducible protein kin1 |
| 1485 | gamma-VPE (vacuolar processing enzyme) |
| 1486 | putative protein 1 photosystem II oxygen-evolving complex |
| 1487 | myrosinase-associated protein, putative |
| 1488 | transcription factor ATMYB4 |
| 1489 | H-protein promoter binding factor-2a |
| 1490 | ammonium transporter, putative |
| 1491 | putative zeta-carotene desaturase precursor |
| 1492 | high-affinity nitrate transporter NRT2 |
| 1493 | light induced protein like |
| 1494 | putative AT-hook DNA-binding protein |
| 1495 | putative glycogenin |
| 1496 | putative light repressible receptor protein kinase |
| 1497 | serine/threonine kinase-like protein |
| 1498 | putative peroxidase |
| 1499 | cytochrome P450 monooxygenase (CYP83A1) |
| 1500 | MYB-related transcription factor (CCA1) |
| 1501 | Terminal flower1 (TFL1) |
| 1502 | sulfate transporter ATST1 |
| 1503 | RING-H2 finger protein RHA3b |
| 1504 | lipoxygenase, putative |
| 1505 | seine 0-acetyltransferase (EC 2.3.1.30) Sat-52 (pir||S71207) |
| 1506 | ferulate-5-hydroxylase (FAH1) |
| 1507 | En/Spm-like transposon protein, putative |
| 1508 | calmodulin-binding-like protein |
| 1509 | hypothetical protein |
| 1510 | somatic embryogenesis receptor-like kinase-like protein |
| 1511 | putative giberellin beta-hydroxylase |
| 1512 | putative pectinesterase |
| 1513 | putative protein |

TABLE 1-continued

SEQUENCE DESCRIPTIONS

| Seq ID | Description |
|---|---|
| 1514 | unknown protein |
| 1515 | ribosomal protein |
| 1516 | low-temperature-induced 65 kD protein (sp|Q04980) |
| 1517 | putative glucosyltransferase |
| 1518 | peroxidase (emb|CAA67551.1) |
| 1519 | ankyrin-like protein |
| 1520 | ribosomal protein S11-like |
| 1521 | hypothetical protein |
| 1522 | glycoprotein(EP1), putative |
| 1523 | calnexin-like protein |
| 1524 | SRG1-like protein |
| 1525 | ethylene response factor 1 (ERF1) |
| 1526 | transcriptional activator CBF1-like protein |
| 1527 | xyloglucan endo-1,4-beta D-glucanase (XTR-6) |
| 1528 | putative cinnamyl alcohol dehydrogenase |
| 1529 | gibberellin 3 beta-hydroxylase, putative |
| 1530 | auxin response transcription factor 3 (ETTIN/ARF3) |
| 1531 | No function assigned by TIGR |
| 1532 | putative protein |
| 1533 | similar to avrRpt2-induced protein 1 |
| 1534 | unknown protein |
| 1535 | hypothetical protein |
| 1536 | putative protein kinase |
| 1537 | respiratory burst oxidase-like protein |
| 1538 | glucose-6-phosphate/phosphate-translocator precursor, putative |
| 1539 | class 1 non-symbiotic hemoglobin (AHB1) |
| 1540 | endochitinase isolog |
| 1541 | putative cytochrome P450 |
| 1542 | 60S acidic ribosomal protein P0 |
| 1543 | putative protein |
| 1544 | auxin-induced protein, putative |
| 1545 | unknown protein |
| 1546 | hypothetical protein |
| 1547 | protein phosphatase 2C ABI2 (PP2C) (sp|O04719) |
| 1548 | peroxidase, prxr2 |
| 1549 | putative peroxidase ATP12a |
| 1550 | putative beta-amylase |
| 1551 | putative acetone-cyanohydrin lyase |
| 1552 | fatty acid elongase 3-ketoacyl-CoA synthase 1 |
| 1553 | putative citrate synthase |
| 1554 | pEARLI 1-like protein |
| 1555 | putative MYB family transcription factor |
| 1556 | putative transcription factor MYB28 |
| 1557 | RNA helicase-like protein |
| 1558 | snoRNA |
| 1559 | putative protein kinase |
| 1560 | growth regulator like protein |
| 1561 | putative potassium transporter |
| 1562 | putative protein |
| 1563 | 60S ribosomal protein L14 |
| 1564 | unknown protein |
| 1565 | putative RING-H2 zinc finger protein |
| 1566 | putative pollen surface protein |
| 1567 | unknown protein |
| 1568 | unknown protein |
| 1569 | unknown protein |
| 1570 | putative Ca2+-ATPase |
| 1571 | 1-aminocyclopropane-1-carboxylate synthase-like protein |
| 1572 | putative beta-glucosidase |
| 1573 | transcription factor ZAP1 |
| 1574 | oligopeptide transporter, putative |
| 1575 | putative protein |
| 1576 | putative glucosyltransferase |
| 1577 | putative serine/threonine kinase |
| 1578 | squalene epoxidase-like protein |
| 1579 | similar to 14 KD proline-rich protein DC2.15 precursor (sp|P14009); similar to ESTs emb|Z17709 and emb|Z47685 |
| 1580 | unknown protein |
| 1581 | unknown protein |
| 1582 | hypothetical protein |
| 1583 | 60S ribosomal protein L38 |
| 1584 | flavin-containing monooxygenase, putative |
| 1585 | remorin |
| 1586 | unknown protein |
| 1587 | putative protein |
| 1588 | lipoxygenase |
| 1589 | cold-regulated protein COR6.6 (KIN2) |
| 1590 | Myb transcription factor homolog (ATR1) |
| 1591 | putative protein |
| 1592 | unknown protein |
| 1593 | unknown protein |
| 1594 | Ca2+-transporting ATPase-like protein |
| 1595 | protein phosphatase 2C (AtP2C-HA) |
| 1596 | peroxidase ATP24a |
| 1597 | branched-chain alpha keto-acid dehydrogenase, putative |
| 1598 | putative beta-ketoacyl-CoA synthase |
| 1599 | putative protein |
| 1600 | putative beta-galactosidase |
| 1601 | putative protein |
| 1602 | 60S ribosomal protein L27 |
| 1603 | putative annexin |
| 1604 | NAC domain protein, putative |
| 1605 | unknown protein |
| 1606 | late embryogenesis abundant protein LEA like |
| 1607 | unknown protein |
| 1608 | putative protein |
| 1609 | dehydrin Xero2 |
| 1610 | putative zinc finger protein |
| 1611 | unknown protein |
| 1612 | DnaJ-like protein |
| 1613 | putative inositol polyphosphate-5-phosphatase- |
| 1614 | putative cytochrome P450 |
| 1615 | putative protein |
| 1616 | unknown protein |
| 1617 | putative protein |
| 1618 | hypothetical protein |
| 1619 | putative protein |
| 1620 | sucrose-UDP glucosyltransferase |
| 1621 | glucose-6-phosphate 1-dehydrogenase |
| 1622 | unknown protein |
| 1623 | mitochondria chaperonin (HSP60) |
| 1624 | sucrose transport protein SUC1 |
| 1625 | putative protein disulfide isomerase |
| 1626 | putative pollen-specific protein |

TABLE 1-continued

SEQUENCE DESCRIPTIONS

| Seq ID | Description |
|---|---|
| 1627 | integral membrane protein, putative |
| 1628 | rubredoxin, putative |
| 1629 | putative protein |
| 1630 | disease resistance protein RPS4, putative |
| 1631 | putative peptide/amino acid Transporter |
| 1632 | peroxidase, putative |
| 1633 | ethylene receptor, putative (ETR2) |
| 1634 | protein phosphatase 2C (PP2C) |
| 1635 | putative glutathione S-transferase |
| 1636 | homeodomain transcription factor (ATHB-7) |
| 1637 | putative nitrate transporter |
| 1638 | putative ribosomal protein L9, cytosolic |
| 1639 | putative DNA-binding protein |
| 1640 | beta-1,3-glucanase-like protein |
| 1641 | putative zinc transporter |
| 1642 | transcription factor TINY |
| 1643 | putative aspartate kinase-homoserine dehydrogenase |
| 1644 | ethylene reponse factor-like AP2 domain transcription factor |
| 1645 | peptide transporter-like protein |
| 1646 | trehalose-6-phosphate synthase like protein |
| 1647 | putative ribonuclease |
| 1648 | hypothetical protein |
| 1649 | putative DNA-binding protein |
| 1650 | nodulin-like protein |
| 1651 | trehalose-6-phosphate phosphatase-like protein |
| 1652 | succinate dehydrogenase flavoprotein alpha subunit (emb|CAA05025.1) |
| 1653 | unknown protein |
| 1654 | stress related protein, putative |
| 1655 | putative chloroplast initiation factor 3 |
| 1656 | putative protein |
| 1657 | hypothetical protein |
| 1658 | putative CCCH-type zinc finger protein |
| 1659 | similar to harpin-induced protein hin 1 from tobacco |
| 1660 | unknown protein |
| 1661 | unknown protein |
| 1662 | hypothetical protein |
| 1663 | No function assigned by TIGR |
| 1664 | putative protein |
| 1665 | putative glutathione S transferase TSI-1 |
| 1666 | putative protein |
| 1667 | putative PTR2 family peptide transporter |
| 1668 | receptor kinase-like protein |
| 1669 | putative sugar transport protein, ERD6 |
| 1670 | putative protein |
| 1671 | nodulin-like protein |
| 1672 | unknown protein |
| 1673 | putative receptor-like protein kinase |
| 1674 | glutathione-conjugate transporter AtMRP4 |
| 1675 | ascorbate oxidase-like protein |
| 1676 | pathogenesis-related protein 1 precursor, 19.3K |
| 1677 | R2R3-MYB transcription factor |
| 1678 | hypothetical protein |
| 1679 | putative chitinase |
| 1680 | Mlo protein, putative |
| 1681 | putative WRKY-type DNA binding protein |
| 1682 | putative acyl-CoA synthetase |
| 1683 | putative pathogenesis-related protein |
| 1684 | putative chitinase |
| 1685 | germin precursor oxalate oxidase |
| 1686 | endoxyloglucan transferase, putative |
| 1687 | putative protein |
| 1688 | putative cytochrome P450 |
| 1689 | similar to Mlo proteins from *H. vulgare* |
| 1690 | putative tropinone reductase |
| 1691 | extensin-like protein |
| 1692 | putative sarcosine oxidase |
| 1693 | putative protein |
| 1694 | hypothetical protein |
| 1695 | late embryogenesis-abundant protein, putative |
| 1696 | beta-carotene hydroxylase |
| 1697 | putative calcium binding protein |
| 1698 | unknown protein |
| 1699 | unknown protein |
| 1700 | predicted glycosyl transferase |
| 1701 | hypothetical protein |
| 1702 | hypothetical protein |
| 1703 | hypothetical protein |
| 1704 | putative protein |
| 1705 | unknown protein |
| 1706 | putative protein |
| 1707 | putative protein |
| 1708 | serine/threonine kinase-like protein |
| 1709 | No function assigned by TIGR |
| 1710 | putative pectinesterase |
| 1711 | peroxidase like protein |
| 1712 | No function assigned by TIGR |
| 1713 | phenylalanine ammonia lyase (PAL1) |
| 1714 | peroxidase (emb|CAA68212.1) |
| 1715 | putative AMP deaminase |
| 1716 | putative MYB family transcription factor |
| 1717 | DNA-directed RNA polymerase II, third largest subunit |
| 1718 | nucleotide pyrophosphatase-like protein |
| 1719 | putative peroxidase |
| 1720 | calcium sensor homolog (gb|AAC26110.1) |
| 1721 | putative GDSL-motif lipase/hydrolase |
| 1722 | putative nonspecific lipid-transfer protein |
| 1723 | acyl-carrier protein (ACP), putative |
| 1724 | putative glycine dehydrogenase |
| 1725 | AIG1 |
| 1726 | ACC synthase (AtACS-6) |
| 1727 | cyclin delta-3 |
| 1728 | putative RING zinc finger protein |
| 1729 | aldose 1-epimerase-like protein |
| 1730 | putative phospholipase |
| 1731 | phosphoenolpyruvate carboxylase |
| 1732 | putative galactinol synthase |
| 1733 | unknown protein |
| 1734 | putative protein |

TABLE 1-continued

SEQUENCE DESCRIPTIONS

| Seq ID | Description |
|---|---|
| 1735 | 1-aminocyclopropane-1-carboxylate oxidase |
| 1736 | thioredoxin (clone GIF1) (pir||S58118) |
| 1737 | trehalose-6-phosphate phosphatase |
| 1738 | beta-1,3-glucanase 2 (BG2) (PR-2) |
| 1739 | putative S-adenosyl-L-methionine:trans-caffeoyl-Coenzyme A 3-O-methyltransferase |
| 1740 | disease resistance protein EDS1 |
| 1741 | putative protein kinase |
| 1742 | Gluthatione reductase, chloroplast precursor |
| 1743 | putative heat shock protein |
| 1744 | aspartate kinase |
| 1745 | putative major intrinsic (channel) protein |
| 1746 | matrix metalloproteinase, putative |
| 1747 | putative GDSL-motif lipase/hydrolase |
| 1748 | putative protein |
| 1749 | DAG-like protein |
| 1750 | serine/threonine kinase-like protein |
| 1751 | formamidase-like protein |
| 1752 | CER2 |
| 1753 | 26S proteasome subunit 4 |
| 1754 | pectinesterase like protein |
| 1755 | putative disease resistance protein |
| 1756 | putative RNA methyltransferase |
| 1757 | unknown protein |
| 1758 | HOMEOBOX PROTEIN KNOTTED-1 LIKE 4 (KNAT4) |
| 1759 | glycine-rich RNA-binding protein AtGRP2-like |
| 1760 | putative acetylornithine transaminase |
| 1761 | putative Sec24-like COPII protein |
| 1762 | putative berberine bridge enzyme |
| 1763 | putative GH3-like protein |
| 1764 | putative ABC transporter |
| 1765 | putative reticuline oxidase-like protein |
| 1766 | pectate lyase-like protein |
| 1767 | protein disulfide-isomerase-like protein |
| 1768 | putative protein |
| 1769 | putative membrane transporter |
| 1770 | unknown protein |
| 1771 | unknown protein |
| 1772 | putative RING-H2 zinc finger protein |
| 1773 | unknown protein |
| 1774 | unknown protein |
| 1775 | unknown protein |
| 1776 | MADS-box protein (AGL20) |
| 1777 | amidophosphoribosyltransferase 2 precursor |
| 1778 | putative dihydrodipicolinate synthase |
| 1779 | hypothetical protein |
| 1780 | ABA-responsive protein-like |
| 1781 | putative protein |
| 1782 | hypothetical protein |
| 1783 | DNA-binding protein-like |
| 1784 | No function assigned by TIGR |
| 1785 | transcription factor, putative |
| 1786 | nitrate reductase, putative |
| 1787 | putative protein |
| 1788 | putative protein |
| 1789 | putative protein |
| 1790 | putative protein |
| 1791 | unknown protein |
| 1792 | unknown protein |
| 1793 | tryptophan synthase beta-subunit (TSB2) |
| 1794 | hypothetical protein |
| 1795 | putative protein |
| 1796 | putative DNA-binding protein |
| 1797 | putative 40S ribosomal protein S10 |
| 1798 | putative protein |
| 1799 | putative cytochrome P450 |
| 1800 | putative protein |
| 1801 | putative protein |
| 1802 | putative glucosyltransferase |
| 1803 | No function assigned by TIGR |
| 1804 | putative protein |
| 1805 | putative protein |
| 1806 | unknown protein |
| 1807 | glycine-rich RNA binding protein 7 |
| 1808 | dehydrin, putative |
| 1809 | putative endoxyloglucan glycosyltransferase |
| 1810 | glutamate decarboxylase 1 (GAD 1) (sp|Q42521) |
| 1811 | delta 9 desaturase |
| 1812 | UDP-glucose glucosyltransferase |
| 1813 | CARBONIC ANHYDRASE 2 |
| 1814 | response reactor 2 (ATRR2) |
| 1815 | S-adenosyl-methionine-sterol-C-methyltransferase, putative |
| 1816 | putative DNA-binding protein (RAV2-like) |
| 1817 | gamma glutamyl hydrolase, putative |
| 1818 | protein phosphatase-like |
| 1819 | unknown protein |
| 1820 | unknown protein |
| 1821 | unknown protein |
| 1822 | copper transport protein-like protein |
| 1823 | hypothetical protein |
| 1824 | unknown protein |
| 1825 | putative peptide methionine sulfoxide reductase |
| 1826 | putative obtusifoliol 14-alpha demethylase |
| 1827 | glutamate dehydrogenase (EC 1.4.1.—) 1 (pir||S71217) |
| 1828 | unknown protein |
| 1829 | xyloglucan endo-1,4-beta-D-glucanase precursor |
| 1830 | unknown protein |
| 1831 | SNF1 related protein kinase (ATSRPK1) |
| 1832 | putative protein |
| 1833 | putative chloroplast nucleoid DNA binding protein |
| 1834 | hypothetical protein |
| 1835 | putative protein |
| 1836 | putative thiamin biosynthesis protein |
| 1837 | unknown protein |
| 1838 | unknown protein |
| 1839 | putative RNA helicase |
| 1840 | putative SF21 protein {Helianthus annuus} |
| 1841 | unknown protein |
| 1842 | NBS/LRR disease resistance protein, putative |

TABLE 1-continued

SEQUENCE DESCRIPTIONS

| Seq ID | Description |
|---|---|
| 1843 | hypothetical protein |
| 1844 | unknown protein |
| 1845 | No function assigned by TIGR |
| 1846 | glycine-rich protein (AtGRP2) |
| 1847 | No function assigned by TIGR |
| 1848 | putative protein |
| 1849 | putative glucosyltransferase |
| 1850 | hypothetical protein |
| 1851 | hypothetical protein |
| 1852 | putative protein |
| 1853 | putative disease resistance protein |
| 1854 | thaumatin, putative |
| 1855 | putative proline-rich protein |
| 1856 | sterol-C-methyltransferase |
| 1857 | superoxidase dismutase |
| 1858 | TINY-like protein |
| 1859 | calcium-dependent protein kinase, putative |
| 1860 | hypothetical protein |
| 1861 | putative protein kinase |
| 1862 | DNA-directed RNA polymerase (mitochondrial) |
| 1863 | putaive DNA-binding protein |
| 1864 | late embryogenesis abundant M17 protein |
| 1865 | putative protein |
| 1866 | delta-1-pyrroline-5-carboxylate synthetase |
| 1867 | putative 60s ribosomal protein L10 |
| 1868 | cytochrome P450 CYP86A1 |
| 1869 | putative tyrosine aminotransferase |
| 1870 | thionin |
| 1871 | No function assigned by TIGR |
| 1872 | APETALA2 protein |
| 1873 | MADS-box protein (AGL3) |
| 1874 | putative monooxygenase |
| 1875 | ZFP3 zinc finger protein |
| 1876 | cell division protein FtsZ chloroplast homolog precursor (sp|Q42545) |
| 1877 | calreticulin, putative |
| 1878 | phosphoserine aminotransferase |
| 1879 | 12-oxophytodienoate-10,11-reductase |
| 1880 | putative bHLH transcription factor |
| 1881 | pectin methylesterase (PMEU1), putative |
| 1882 | DNA-binding protein |
| 1883 | carnitine racemase like protein |
| 1884 | putative protein |
| 1885 | endoxyloglucan transferase (dbj|BAA81669.1) |
| 1886 | RMA1 RING zinc finger protein |
| 1887 | ammonium transporter |
| 1888 | apyrase (gb|AAF00612.1) |
| 1889 | potassium uptake transporter-like protein |
| 1890 | putative ABC transporter |
| 1891 | potassium transporter-like protein |
| 1892 | integral membrane protein, putative |
| 1893 | putative protein |
| 1894 | pyruvate decarboxylase-1 (Pdc 1) |
| 1895 | putative malate oxidoreductase |
| 1896 | putative histone H2B |
| 1897 | snoRNA |
| 1898 | symbiosis-related like protein |
| 1899 | unknown protein |
| 1900 | unknown protein |
| 1901 | hypothetical protein |
| 1902 | putative protein |
| 1903 | copper-binding protein-like |
| 1904 | putative protein |
| 1905 | unknown protein |
| 1906 | putative glyoxalase II |
| 1907 | No function assigned by TIGR |
| 1908 | hypothetical protein |
| 1909 | flavanone 3-hydroxylase (FH3) |
| 1910 | putative laccase |
| 1911 | putative protein kinase |
| 1912 | myb-related protein, 33.3K (pir||S71284) |
| 1913 | unknown protein |
| 1914 | endo-xyloglucan transferase-like protein |
| 1915 | TMV resistance protein N-like |
| 1916 | putative xyloglucan endotransglycosylase |
| 1917 | unknown protein |
| 1918 | proline transporter 2 |
| 1919 | resistance protein, putative |
| 1920 | actin, putative |
| 1921 | putative related to microbial divalent cation tolerance proteins |
| 1922 | unknown protein |
| 1923 | putative glycosyl transferase |
| 1924 | unknown protein |
| 1925 | putative protein phosphatase 2C |
| 1926 | unknown protein |
| 1927 | serpin, putative |
| 1928 | cinnamyl-alcohol dehydrogenase CAD1 |
| 1929 | putative protein import receptor |
| 1930 | unknown protein |
| 1931 | unknown protein |
| 1932 | putative protein |
| 1933 | putative CDP-diacylglycerol-glycerol-3-phosphate 3-phosphatidyltransferase |
| 1934 | unknown protein |
| 1935 | putative LRR receptor-like protein kinase |
| 1936 | serine/threonine protein kinase, putative |
| 1937 | potassium transporter-like protein |
| 1938 | lactate dehydrogenase (LDH1) |
| 1939 | hypothetical protein |
| 1940 | unknown protein |
| 1941 | putative thaumatin |
| 1942 | putative reticuline oxidase-like protein |
| 1943 | uracil phosphoribosyltransferase, putative |
| 1944 | transcription factor, putative |
| 1945 | unknown protein |
| 1946 | unknown protein |
| 1947 | GATA transcription factor 4 |
| 1948 | unknown protein |
| 1949 | unknown protein |
| 1950 | senescence-associated protein-like |
| 1951 | putative pollen allergen |
| 1952 | unknown protein |
| 1953 | putative protein |
| 1954 | glycine-rich protein |
| 1955 | putative protein |

TABLE 1-continued

SEQUENCE DESCRIPTIONS

| Seq ID | Description |
|---|---|
| 1956 | 3-methyladenine DNA glycosylase, putative |
| 1957 | endoplasmic reticulum-type calcium-transporting ATPase 4 |
| 1958 | putative pectinesterase |
| 1959 | cytochrome P450-like protein |
| 1960 | RNA-binding protein (cp33) |
| 1961 | CONSTANS-like 1 |
| 1962 | putative small heat shock protein |
| 1963 | hypothetical protein |
| 1964 | unknown protein |
| 1965 | cytochrome P450-like protein |
| 1966 | cysteine proteinase inhibitor like protein |
| 1967 | nicotianamine synthase (dbj|BAA74589.1) |
| 1968 | copper amine oxidase like protein (fragment2) |
| 1969 | putative SCARECROW gene regulator |
| 1970 | unknown protein |
| 1971 | unknown protein |
| 1972 | putative alanine acetyl transferase |
| 1973 | unknown protein |
| 1974 | unknown protein |
| 1975 | unknown protein |
| 1976 | putative extensin |
| 1977 | putative protein kinase |
| 1978 | putative protein kinase |
| 1979 | NADPH-dependent codeinone reductase, putative |
| 1980 | peroxidase |
| 1981 | putative cytochrome P450 |
| 1982 | No function assigned by TIGR |
| 1983 | putative zinc-finger protein (B-box zinc finger domain) |
| 1984 | putative tyrosine aminotransferase |
| 1985 | hypothetical protein |
| 1986 | DNA binding protein |
| 1987 | putative fatty acid elongase |
| 1988 | bZIP transcription factor-like protein |
| 1989 | xyloglucan fucosyltransferase, putative |
| 1990 | unknown protein |
| 1991 | unknown protein |
| 1992 | putative protein |
| 1993 | myb factor, putative |
| 1994 | Myb-family transcription factor, putative |
| 1995 | putative fructose bisphosphate aldolase |
| 1996 | myrosinase-associated protein, putative |
| 1997 | cytochrome P450 like protein |
| 1998 | similar to SOR1 from the fungus Cercospora nicotianae |
| 1999 | similar to embryo-abundant protein GB: L47672 GI: 1350530 from [*Picea glauca*] |
| 2000 | alcohol dehydrogenase |
| 2001 | auxin response factor 1 |
| 2002 | pathogenesis-related protein 1 precursor, 18.9K |
| 2003 | hypothetical protein. |
| 2004 | unknown protein |
| 2005 | zinc finger protein Zat12 |
| 2006 | unknown protein |
| 2007 | unknown protein |
| 2008 | cyclin, putative |
| 2009 | 2-dehydro-3-deoxyphosphoheptonate aldolase |
| 2010 | glutathione synthetase gsh2 |
| 2011 | heat shock protein 17 |
| 2012 | putative Na+-dependent inorganic phosphate cotransporter |
| 2013 | No function assigned by TIGR |
| 2014 | unknown protein |
| 2015 | putative protein |
| 2016 | similar to RING-H2 finger protein RHC1a GB: AAC69854 GI: 3790583 from [*Arabidopsis thaliana*] |
| 2017 | calcium-binding protein-like |
| 2018 | putative protein |
| 2019 | putative aldehyde dehydrogenase |
| 2020 | auxin-responsive GH3-like protein |
| 2021 | putative protein |
| 2022 | Phosphoglycerate dehydrogenase-like protein |
| 2023 | unknown protein |
| 2024 | unknown protein |
| 2025 | PSI type III chlorophyll a/b-binding protein, putative |
| 2026 | putative protein |
| 2027 | putative protein |
| 2028 | glutaredoxin, putative |
| 2029 | hypothetical protein |
| 2030 | No function assigned by TIGR |
| 2031 | putative protein |
| 2032 | jasmonate inducible protein, putative |
| 2033 | putative polygalacuronase isoenzyme 1 beta subunit |
| 2034 | putative small heat shock protein |
| 2035 | unknown protein |
| 2036 | putative disease resistance protein |
| 2037 | putative protein |
| 2038 | ethylene-responsive element binding factor, putative |
| 2039 | putative protein |
| 2040 | Pollen-specific protein precursor like |
| 2041 | putative protein |
| 2042 | unknown protein |
| 2043 | EF-Hand containing protein-like |
| 2044 | unknown protein |
| 2045 | puative calcium transporting ATPase |
| 2046 | antifungal protein-like (PDF1.2) |
| 2047 | pathogenesis-related PR-1-like protein |
| 2048 | similar to Mlo proteins from H. vulgare |
| 2049 | putative steroid sulfotransferase |
| 2050 | trehalase-like protein |
| 2051 | thioredoxin f1 |
| 2052 | unknown protein |
| 2053 | alanine-glyoxylate aminotransferase |
| 2054 | integral membrane protein, putative |
| 2055 | hypothetical protein |
| 2056 | unknown protein |
| 2057 | hypothetical protein |
| 2058 | unknown protein |
| 2059 | unknown protein |
| 2060 | unknown protein |

TABLE 1-continued

SEQUENCE DESCRIPTIONS

| Seq ID | Description |
|---|---|
| 2061 | drought-induced-19-like 1 |
| 2062 | unknown protein |
| 2063 | putative protein |
| 2064 | putative protein |
| 2065 | AIG2-like protein |
| 2066 | Lhca2 protein |
| 2067 | phytocyanin |
| 2068 | putative chlorophyll A-B binding protein |
| 2069 | Lhcb3 chlorophyll a/b binding protein (gb|AAD28773.1) |
| 2070 | luminal binding protein (dbj|BAA13948.1) |
| 2071 | hydroxypyruvate reductase (HPR) |
| 2072 | epoxide hydrolase (ATsEH) |
| 2073 | putative protein (fragment) |
| 2074 | unknown protein |
| 2075 | hypothetical protein |
| 2076 | putative glucosyl transferase |
| 2077 | putative glucosyl transferase |
| 2078 | putative 3-methylcrotonyl-CoA carboxylase |
| 2079 | putative peroxidase |
| 2080 | acyl-CoA oxidase (gb|AAC13497.1) |
| 2081 | alternative oxidase 1a precursor |
| 2082 | putative transcription factor (MYB4) |
| 2083 | serine acetyltransferase |
| 2084 | ATP-sulfurylase |
| 2085 | calreticulin (crtl) |
| 2086 | putative prohibitin 2 |
| 2087 | putative monodehydroascorbate reductase |
| 2088 | branched-chain alpha-keto acid decarboxylase E1 beta subunit |
| 2089 | cytokinin oxidase-like protein |
| 2090 | putative receptor-like protein kinase |
| 2091 | unknown protein |
| 2092 | hypothetical protein |
| 2093 | No function assigned by TIGR |
| 2094 | putative APG protein |
| 2095 | glutathione S-transferase, putative |
| 2096 | phytochrome-associated protein 1 (PAP1) |
| 2097 | amidophosphoribosyltransferase |
| 2098 | nonphototropic hypocotyl 1 |
| 2099 | 3-keto-acyl-CoA thiolase 2 (gb|AAC17877.1) |
| 2100 | pEARLI 1 |
| 2101 | glutathione reductase, cytosolic |
| 2102 | putative protein |
| 2103 | putative protein |
| 2104 | putative aldehyde oxidase |
| 2105 | probable photosystem I chain XI precursor |
| 2106 | photosystem II polypeptide, putative |
| 2107 | photosystem II reaction center 6.1 KD protein |
| 2108 | 33 kDa polypeptide of oxygen-evolving complex (OEC) in photosystem II (emb|CAA75629.1) |
| 2109 | 60S ribosomal protein L11B |
| 2110 | extA (emb|CAA47807.1) |
| 2111 | zinc finger protein OBP4-like |
| 2112 | sterol delta7 reductase |
| 2113 | putative RAS-related protein, RAB11C |
| 2114 | glucosyltransferase like protein |
| 2115 | zinc finger protein (PMZ), putative |
| 2116 | 6,7-dimethyl-8-ribityllumazine synthase precursor |
| 2117 | putative protein |
| 2118 | osmotin precursor |
| 2119 | No function assigned by TIGR |
| 2120 | ferredoxin precursor isolog |
| 2121 | GH3 like protein |
| 2122 | non-specific lipid transfer protein |
| 2123 | homeodomain transcription factor (HAT9) |
| 2124 | putative cytochrome P450 monooxygenase |
| 2125 | putative protein kinase |
| 2126 | putative protein |
| 2127 | glyceraldehyde-3-phosphate dehydrogenase |
| 2128 | putative protein disulfide-isomerase |
| 2129 | unknown protein |
| 2130 | beta-1,3-glucanase class I precursor |
| 2131 | homeobox-leucine zipper protein HAT5 (HD-ZIP protein 5) (HD-ZIP protein ATHB-1) |
| 2132 | putative cyclic nucleotide-regulated ion channel protein |
| 2133 | P II nitrogen sensing protein GLBI |
| 2134 | H-protein promoter binding factor 1 (gb|AAC24592.1) |
| 2135 | GAST1-like protein |
| 2136 | cytochrome P450 GA3 |
| 2137 | putative protein |
| 2138 | Myb-related transcription factor-like protein |
| 2139 | putative phloem-specific lectin |
| 2140 | protein kinase-like protein |
| 2141 | unknown protein |
| 2142 | SCARECROW transcriptional regulator-like |
| 2143 | unknown protein |
| 2144 | unknown protein |
| 2145 | putative protein |
| 2146 | calnexin homolog |
| 2147 | PP1/PP2A phosphatases pleiotropic regulator PRL2 |
| 2148 | xyloglucan endotransglycosylase, putative |
| 2149 | putative calmodulin |
| 2150 | spermine synthase (ACL5) |
| 2151 | snoRNA |
| 2152 | photosystem I subunit V precursor, putative |
| 2153 | putative potassium transporter |
| 2154 | Homeodomain-like protein |
| 2155 | putative protein |
| 2156 | unknown protein |
| 2157 | CALMODULIN-RELATED PROTEIN 2, TOUCH-INDUCED (TCH2) |
| 2158 | putative protein phosphatase 2C |
| 2159 | monosaccharide transport protein, STP4 |
| 2160 | hypothetical protein |
| 2161 | unknown protein |
| 2162 | hypothetical protein |
| 2163 | putative protein kinase |
| 2164 | putative serine/threonine protein kinase |
| 2165 | jasmonate inducible protein, putative |

TABLE 1-continued

SEQUENCE DESCRIPTIONS

| Seq ID | Description |
|---|---|
| 2166 | similar to several small proteins (~100aa) that are induced by heat, auxin, ethylene and wounding such as Phaseolus aureus indole-3-acetic acid induced protein ARG (SW: 32292) |
| 2167 | unknown protein |
| 2168 | MYB-like protein |
| 2169 | putative protein kinase |
| 2170 | unknown protein |
| 2171 | CLC-d chloride channel protein |
| 2172 | cytochrome P450-like protein |
| 2173 | putative glutathione S-transferase |
| 2174 | putative mandelonitrile lyase |
| 2175 | hypothetical protein |
| 2176 | putative trypsin inhibitor |
| 2177 | male sterility 2-like protein (emb|CAA68191.1) |
| 2178 | unknown protein |
| 2179 | unknown protein |
| 2180 | putative protein |
| 2181 | putative peroxidase |
| 2182 | putative thromboxane-A synthase |
| 2183 | putative cytochrome P450 |
| 2184 | peroxidase ATP21a |
| 2185 | unknown protein |
| 2186 | putative glutathione S-transferase |
| 2187 | defender against cell death protein |
| 2188 | AP2 domain containing protein, putative |
| 2189 | actin depolymerizing factor-like protein |
| 2190 | putative calcium-dependent protein kinase (U90439) |
| 2191 | phosphoribosylanthranilate transferase, putative |
| 2192 | oligopeptide transporter, putative |
| 2193 | calmodulin-like protein |
| 2194 | putative protease inhibitor |
| 2195 | MAP kinase |
| 2196 | DNA binding protein MybSt1, putative |
| 2197 | putative protein |
| 2198 | putative protein |
| 2199 | unknown protein |
| 2200 | unknown protein |
| 2201 | unknown protein |
| 2202 | putative protein |
| 2203 | unknown protein |
| 2204 | unknown protein |
| 2205 | hypothetical protein |
| 2206 | uncharacterized protein |
| 2207 | putative protein |
| 2208 | hypothetical protein |
| 2209 | peroxidase (emb|CAA66967.1) |
| 2210 | putative flavonol 3-O-glucosyltransferase |
| 2211 | putative flavonol 3-O-glucosyltransferase |
| 2212 | putative protein |
| 2213 | glycerol-3-phosphate acyltransferase |
| 2214 | putative beta-1,3-glucanase |
| 2215 | putative ethylene response element binding protein (EREBP) |
| 2216 | putative CONSTANS-like B-box zinc finger protein |
| 2217 | putative protein |
| 2218 | unknown protein |
| 2219 | putative trehalose-6-phosphate phosphatase (AtTPPA) |
| 2220 | putative protein |
| 2221 | putative protein |
| 2222 | unknown protein |
| 2223 | unknown protein |
| 2224 | unknown protein |
| 2225 | hypothetical protein |
| 2226 | putative metal-binding protein |
| 2227 | putative phosphoribosylglycinamide synthetase |
| 2228 | unknown protein |
| 2229 | putative protein |
| 2230 | unknown protein |
| 2231 | unknown protein |
| 2232 | putative beta-galactosidase |
| 2233 | putative protein kinase |
| 2234 | putative protein |
| 2235 | putative protein phosphatase 2C |
| 2236 | putative growth regulator protein |
| 2237 | putative ABC transporter |
| 2238 | chloride channel (emb|CAA70310.1) |
| 2239 | adrenodoxin-like protein |
| 2240 | NAM (no apical meristem)-like protein |
| 2241 | putative transcription factor MYB41 |
| 2242 | Myb DNA binding protein-like |
| 2243 | AtMYB84 |
| 2244 | photosystem II type I chlorophyll a/b binding protein |
| 2245 | putative aspartic proteinase |
| 2246 | jasmonate inducible protein, putative |
| 2247 | putative protein |
| 2248 | No function assigned by TIGR |
| 2249 | putative phosphatidylserine synthase |
| 2250 | putative nicotianamine synthase |
| 2251 | lysine and histidine specific transporter, putative |
| 2252 | putative protein |
| 2253 | putative protein |
| 2254 | putative sugar transporter protein |
| 2255 | 12S cruciferin seed storage protein |
| 2256 | putative auxin-induced protein, IAA17/AXR3-1 |
| 2257 | putative cyclin D |
| 2258 | farnesyl diphosphate synthase precursor (gb|AAB49290.1) |
| 2259 | putative potassium transport protein (TRH1) |
| 2260 | putative NPK1-related MAP kinase |
| 2261 | putative protein |
| 2262 | putative ABC transporter |
| 2263 | putative DNA-directed RNA polymerase subunit |
| 2264 | putative small nuclear ribonucleoprotein E |
| 2265 | unknown protein |
| 2266 | reticuline oxidase-like protein |
| 2267 | putative 1-aminocyclopropane-1-carboxylate oxidase |
| 2268 | similar to Mlo proteins from H. vulgare |

TABLE 1-continued

SEQUENCE DESCRIPTIONS

| Seq ID | Description |
|---|---|
| 2269 | long-chain-fatty-acid-CoA ligase-like protein |
| 2270 | putative protein |
| 2271 | chromatin remodelling complex ATPase chain ISWI-like protein |
| 2272 | hypothetical protein |
| 2273 | latex-abundant protein, putative |
| 2274 | N-acetylornithine deacetylase-like protein, fragment |
| 2275 | putative DNA-binding protein |
| 2276 | putative anthranilate N-hydroxycinnamoyl/lbenzoyltransferase |
| 2277 | putative DNA binding protein |
| 2278 | cytochrome P450-like protein |
| 2279 | putative DNA-binding protein |
| 2280 | putative peptide transporter |
| 2281 | putative reticuline oxidase-like protein |
| 2282 | thioredoxin, putative |
| 2283 | nodulin-like protein |
| 2284 | UDP-galactose transporter-like protein |
| 2285 | putative fibrillin |
| 2286 | unknown protein |
| 2287 | unknown protein |
| 2288 | unknown protein |
| 2289 | hypothetical protein |
| 2290 | glyceraldehyde 3-phosphate dehydrogenase A subunit (GapA) |
| 2291 | predicted protein of unknown function |
| 2292 | putative protein |
| 2293 | putative protein |
| 2294 | myb-like protein |
| 2295 | hypothetical protein |
| 2296 | putative U5 small nuclear ribonucleoprotein, an RNA helicase |
| 2297 | unknown protein |
| 2298 | cinnamyl alcohol dehydrogenase-like protein |
| 2299 | hypothetical protein similar to extensin-like protein |
| 2300 | unknown protein |
| 2301 | putative chlorophyll a/b binding protein |
| 2302 | probable plasma membrane intrinsic protein 1c |
| 2303 | hexokinase (ATHXK2) |
| 2304 | calcium-dependent protein kinase |
| 2305 | 5'-adenylylphosphosulfate reductase, putative |
| 2306 | Erd1 protein precursor (sp|P42762) |
| 2307 | putative protein |
| 2308 | putative protein |
| 2309 | unknown protein |
| 2310 | BCS1 protein-like protein |
| 2311 | putative protein |
| 2312 | putative protein |
| 2313 | putative protein kinase |
| 2314 | indoleacetic acid (IAA)-inducible gene (IAA7) |
| 2315 | ATP-dependent Clp protease regulatory subunit CLPX |
| 2316 | DNA-binding protein RAV1 |
| 2317 | putative protein |
| 2318 | hypothetical protein |
| 2319 | unknown protein |
| 2320 | unknown protein |
| 2321 | putative protein |
| 2322 | putative thioredoxin reductase |
| 2323 | unknown protein |
| 2324 | putative lectin |
| 2325 | No function assigned by TIGR |
| 2326 | beta-fructosidase |
| 2327 | chlorophyll a/b-binding protein CP29 |
| 2328 | photosystem I subunit PSI-E-like protein |
| 2329 | peroxidase ATP8a |
| 2330 | putative fructose bisphosphate aldolase |
| 2331 | zinc finger protein ATZF1, putative |
| 2332 | DegP protease precursor |
| 2333 | transcription factor-like protein |
| 2334 | calcium-dependent protein kinase |
| 2335 | hypothetical protein |
| 2336 | putative protein |
| 2337 | glucose-1-phosphate adenylyltransferase (APL3) |
| 2338 | No function assigned by TIGR |
| 2339 | putative Eukaryotic initiation factor 4A |
| 2340 | No function assigned by TIGR |
| 2341 | unknown protein |
| 2342 | beta tubulin 1, putative |
| 2343 | one helix protein (OHP) |
| 2344 | No function assigned by TIGR |
| 2345 | zinc finger protein 5, ZFP5 |
| 2346 | putative MYB family transcription factor |
| 2347 | putative amino acid transporter protein |
| 2348 | putative potassium transporter |
| 2349 | protein kinase (AFC2) |
| 2350 | putative protein |
| 2351 | No function assigned by TIGR |
| 2352 | putative ubiquitin-conjugating enzyme E2 |
| 2353 | unknown protein |
| 2354 | cytochrome P450 monooxygenase (CYP7IB3) |
| 2355 | putative myrosinase binding protein |
| 2356 | putative vacuolar sorting receptor |
| 2357 | uridine diphosphate glucose epimerase |
| 2358 | shaggy related protein kinase, ASK-GAMMA |
| 2359 | ankyrin repeat protein EMB506 |
| 2360 | putative beta-alanine pyruvate aminotransferase |
| 2361 | putative alcohol dehydrogenase |
| 2362 | putative receptor-like protein kinase |
| 2363 | unknown protein |
| 2364 | putative methylmalonate semi-aldehyde dehydrogenase |
| 2365 | hypothetical protein |
| 2366 | unknown protein |
| 2367 | peroxidase ATP13a |
| 2368 | putative glutathione peroxidase |
| 2369 | squamosa promoter binding protein-like 7 |
| 2370 | photosystem II core complex protein, putative |
| 2371 | snoRNA |

TABLE 1-continued

SEQUENCE DESCRIPTIONS

| Seq ID | Description |
|---|---|
| 2372 | photosystem I subunit X precursor |
| 2373 | MYB transcription factor (Atmyb2) |
| 2374 | putative PHD-type zinc finger protein |
| 2375 | nuclear RNA binding protein A-like protein |
| 2376 | unknown protein |
| 2377 | unknown protein |
| 2378 | unknown protein |
| 2379 | putative amino-cyclopropane-carboxylic acid oxidase (ACC oxidase) |
| 2380 | hypothetical protein |
| 2381 | indole-3-acetate beta glucosyltransferase like protein |
| 2382 | predicted protein |
| 2383 | unknown protein |
| 2384 | No function assigned by TIGR |
| 2385 | putative photosystem I reaction center subunit IV |
| 2386 | putative homeodomain transcription factor |
| 2387 | putative purple acid phosphatase precursor |
| 2388 | No function assigned by TIGR |
| 2389 | nitrate reductase 1(NR1) |
| 2390 | putative casein kinase II beta subunit |
| 2391 | pEARLI 1-like protein |
| 2392 | putative protein |
| 2393 | No function assigned by TIGR |
| 2394 | unknown protein |
| 2395 | putative cell wall-plasma membrane disconnecting CLCT protein (AIR1A) |
| 2396 | unknown protein |
| 2397 | scarecrow-like 11-like |
| 2398 | putative anthocyanidin synthase |
| 2399 | putative AP2 domain transcription factor |
| 2400 | caffeoyl-CoA O-methyltransferase-like protein |
| 2401 | unknown protein |
| 2402 | putative protein kinase |
| 2403 | cytochrome P450-like protein |
| 2404 | putative MADS-box protein ANR1 |
| 2405 | putative glutathione S-transferase |
| 2406 | hypothetical protein |
| 2407 | similar to gibberellin-regulated proteins |
| 2408 | unknown protein |
| 2409 | putative sensory transduction histidine Kinase |
| 2410 | similar to late embryogenesis abundant proteins |
| 2411 | unknown protein |
| 2412 | putative protein |
| 2413 | putative ATP-dependent RNA helicase |
| 2414 | putative protein |
| 2415 | putative sucrose synthetase |
| 2416 | beta-fructofuranosidase 1 |
| 2417 | putative indole-3-acetate beta-glucosyltransferase |
| 2418 | hypothetical protein |
| 2419 | DNA-directed RNA polymerase II, third largest subunit |
| 2420 | putative transcription factor |
| 2421 | homeobox-leucine zipper protein ATHB-5 (HD-zip protein ATHB-5) (sp|P46667) |
| 2422 | putative ftsH chloroplast protease |
| 2423 | replication protein A1-like |
| 2424 | hypothetical protein |
| 2425 | unknown protein |
| 2426 | unknown protein |
| 2427 | putative methionine aminopeptidase |
| 2428 | unknown protein |
| 2429 | fatty acid elongase-like protein (cer2-like) |
| 2430 | unknown protein |
| 2431 | putative disease resistance response protein |
| 2432 | putative protein |
| 2433 | unknown protein |
| 2434 | putative protein |
| 2435 | putative protein |
| 2436 | unknown protein |
| 2437 | putative protein |
| 2438 | unknown protein |
| 2439 | unknown protein |
| 2440 | putative protein |
| 2441 | No function assigned by TIGR |
| 2442 | MADS-box protein AGL14 |
| 2443 | No function assigned by TIGR |
| 2444 | peptidylprolyl isomerase |
| 2445 | putative s-adenosylmethionine synthetase |
| 2446 | peroxidase |
| 2447 | ferrochelatase-I |
| 2448 | putative eukaryotic initiation factor 4, eIF4 |
| 2449 | drought-inducible cysteine proteinase RD21A precursor-like protein |
| 2450 | unknown protein |
| 2451 | unknown protein |
| 2452 | No function assigned by TIGR |
| 2453 | No function assigned by TIGR |
| 2454 | salt-inducible like protein |
| 2455 | glucose-6-phosphate 1-Dehydrogenase |
| 2456 | 3-hydroxy-3-methylglutaryl CoA reductase (AA 1-592) |
| 2457 | hypothetical protein |
| 2458 | putative protein |
| 2459 | putative putative 60S ribosomal protein L17 |
| 2460 | putative inorganic pyrophosphatase |
| 2461 | putative gamma-glutamyltransferase |
| 2462 | heat shock transcription factor-like protein |
| 2463 | mitochondrial chaperonin hsp60 |
| 2464 | unknown protein |
| 2465 | putative zinc finger protein identical to T10M13.22 |
| 2466 | putative uridylyl transferase |
| 2467 | nodulin-like protein |
| 2468 | putative B-box zinc finger protein |
| 2469 | No function assigned by TIGR |
| 2470 | putative metalloproteinase |
| 2471 | putative cellular apoptosis susceptibility protein |
| 2472 | hypothetical protein |
| 2473 | hypothetical protein |
| 2474 | scarecrow-like 13 (SCL13) |
| 2475 | putative nucleoside triphosphatase |
| 2476 | unknown protein |
| 2477 | No function assigned by TIGR |
| 2478 | hypothetical protein |
| 2479 | putative phospholipase |

TABLE 1-continued

SEQUENCE DESCRIPTIONS

| Seq ID | Description |
|---|---|
| 2480 | putative snRNP protein |
| 2481 | putative protein |
| 2482 | putative lipase |
| 2483 | putative nonsense-mediated mRNA decay protein |
| 2484 | No function assigned by TIGR |
| 2485 | protochlorophyllide reductase precursor |
| 2486 | No function assigned by TIGR |
| 2487 | trehalose-6-phosphate synthase, putative |
| 2488 | unknown protein |
| 2489 | germin-like protein |
| 2490 | plastid protein |
| 2491 | putative protein |
| 2492 | hypothetical protein |
| 2493 | unknown protein |
| 2494 | unknown protein |
| 2495 | histone deacetylase-like protein |
| 2496 | unknown protein |
| 2497 | unknown protein |
| 2498 | putative protein |
| 2499 | putative protein |
| 2500 | No function assigned by TIGR |
| 2501 | putative zinc transporter ZIP2-like |
| 2502 | unknown protein |
| 2503 | putative ribosomal-protein S6 kinase (ATPK19) |
| 2504 | unknown protein |
| 2505 | unknown protein |
| 2506 | 60S ribosomal protein L10A |
| 2507 | putative protein |
| 2508 | receptor protein kinase (IRK1), putative |
| 2509 | putative nematode-resistance protein |
| 2510 | tubulin alpha-5 chain-like protein |
| 2511 | putative DNA-binding protein |
| 2512 | unknown protein |
| 2513 | putative RGA1, giberellin repsonse modulation protein |
| 2514 | non phototropic hypocotyl 1-like |
| 2515 | RING-H2 finger protein RHA1b |
| 2516 | putative myb-protein |
| 2517 | hydroperoxide lyase (HPOL) like protein |
| 2518 | serine/threonine-protein kinase, PK7 |
| 2519 | putative vacuolar proton-ATPase subunit |
| 2520 | putative polygalacturonase |
| 2521 | putative ribosomal protein L8 |
| 2522 | putative adenylate kinase |
| 2523 | germin-like protein (GLP10) |
| 2524 | putative chlorophyll a/b binding protein |
| 2525 | chloroplast single subunit DNA-dependent RNA polymerase |
| 2526 | putative protein |
| 2527 | hypothetical protein |
| 2528 | hypothetical protein |
| 2529 | b-keto acyl reductase, putative |
| 2530 | cellulose synthase catalytic subunit |
| 2531 | putative 1-aminocyclopropane-1-carboxylate oxidase |
| 2532 | S-linalool synthase, putative |
| 2533 | phosphoribosyl-ATP pyrophosphohydrolase (At-IE) |
| 2534 | disease resistance RPP5 like protein (fragment) |
| 2535 | putative protein |
| 2536 | beta-galactosidase like protein |
| 2537 | putative translation initiation factor eIF-2, gamma subunit |
| 2538 | ankyrin like protein |
| 2539 | histone H2A-like protein |
| 2540 | putative protein |
| 2541 | salt-tolerance zinc finger protein |
| 2542 | unknown protein |
| 2543 | putative protein |
| 2544 | fructose-bisphosphate aldolase |
| 2545 | peroxidase (emb|CAA66964.1) |
| 2546 | patatin-like protein |
| 2547 | salt-inducible protein homolog |
| 2548 | hypothetical protein |
| 2549 | xyloglucan endo-transglycosylase-like protein |
| 2550 | trihelix DNA-binding protein (GT2) |
| 2551 | ubiquitin-conjugating enzyme 16, putative |
| 2552 | homeobox protein |
| 2553 | envelope Ca2+-ATPase |
| 2554 | snap25a |
| 2555 | putative annexin |
| 2556 | putative protein |
| 2557 | homeodomain transcription factor (ATHB-14) |
| 2558 | heat shock protein, putative |
| 2559 | peroxidase ATP23a |
| 2560 | p68 RNA helicase, putative |
| 2561 | potassium transporter, putative |
| 2562 | putative eukaryotic translation initiation factor 2 alpha subunit, eIF2 |
| 2563 | hypothetical protein |
| 2564 | carnitine racemase like protein |
| 2565 | No function assigned by TIGR |
| 2566 | unknown protein |
| 2567 | unknown protein |
| 2568 | unknown protein |
| 2569 | serine/threonine kinase-like protein |
| 2570 | peroxidase (emb|CAA66960.1) |
| 2571 | putative protein |
| 2572 | hypothetical protein |
| 2573 | glycine-rich protein 2 (GRP2) |
| 2574 | unknown protein |
| 2575 | berberine bridge enzyme-like protein |
| 2576 | unknown protein |
| 2577 | putative WD-repeat protein |
| 2578 | serine/threonine kinase-like protein |
| 2579 | serine/threonine kinase-like protein |
| 2580 | Cu2+-transporting ATPase-like protein |
| 2581 | translation initiation factor eIF4E |
| 2582 | O-methyltransferase-like protein |
| 2583 | translation initiation factor eIF3-like protein |
| 2584 | No function assigned by TIGR |
| 2585 | unknown protein |
| 2586 | hypothetical protein |
| 2587 | unknown protein |
| 2588 | unknown protein |
| 2589 | glycine-rich protein like |
| 2590 | putative disease resistance protein |
| 2591 | putative Na+/Ca2+ antiporter |
| 2592 | putative hydroxymethylglutaryl-CoA lyase |

TABLE 1-continued

SEQUENCE DESCRIPTIONS

| Seq ID | Description |
|---|---|
| 2593 | putative phosphoribosylaminoimidazole carboxylase |
| 2594 | SAR DNA-binding protein-like |
| 2595 | response regulator, putative |
| 2596 | fibrillin precursor-like protein |
| 2597 | beta-ketoacyl-CoA synthase (FIDDLEHEAD) |
| 2598 | lectin like protein |
| 2599 | No function assigned by TIGR |
| 2600 | acidic endochitinase (dbj|BAA21861.1) |
| 2601 | unknown protein |
| 2602 | hypothetical protein |
| 2603 | predicted OR23 protein of unknown function |
| 2604 | putative protein |
| 2605 | hypothetical protein |
| 2606 | glycerol-3-phosphate dehydrogenase |
| 2607 | hypothetical protein |
| 2608 | tat-binding protein, putative |
| 2609 | putative protein |
| 2610 | putative trehalose-6-phosphate phosphatase |
| 2611 | hypothetical protein |
| 2612 | putative flavonol 3-O-glucosyltransferase |
| 2613 | 60S ribosomal protein L30 |
| 2614 | putative auxin-induced protein |
| 2615 | putative nonspecific lipid-transfer protein precursor |
| 2616 | AtRerlA |
| 2617 | putative aquaporin (tonoplast intrinsic protein gamma) |
| 2618 | hypothetical protein |
| 2619 | putative alanine acetyl transferase |
| 2620 | putative NADP-dependent glyceraldehyde-3-phosphate dehydrogenase |
| 2621 | putative DNA binding protein |
| 2622 | putative cystathionine gamma-synthase |
| 2623 | unknown protein |
| 2624 | malate oxidoreductase (malic enzyme) |
| 2625 | unknown protein |
| 2626 | cyclic nucleotide-gated cation channel |
| 2627 | glyoxalase II, putative |
| 2628 | putative trypsin inhibitor |
| 2629 | unknown protein |
| 2630 | unknown protein |
| 2631 | unknown protein |
| 2632 | nucleosome assembly protein I-like protein |
| 2633 | membrane channel like protein |
| 2634 | anthocyanin2, putative |
| 2635 | TWIN SISTER OF FT (TSF) |
| 2636 | putative myb-related transcription factor |
| 2637 | hypothetical protein |
| 2638 | putative RING zinc finger protein |
| 2639 | amino acid transport protein AAT1 |
| 2640 | putative protein |
| 2641 | putative protein |
| 2642 | xanthine dehydrogenase |
| 2643 | xanthine dehydrogenase-like protein |
| 2644 | receptor protein kinase (IRK1), putative |
| 2645 | dehydrin-like protein |
| 2646 | unknown protein |
| 2647 | aldehyde dehydrogenase homolog, putative |
| 2648 | Ran binding protein (AtRanBPlb) |
| 2649 | putative squamosa-promoter binding protein |
| 2650 | putative protein |
| 2651 | kinesin like protein |
| 2652 | putative cellulose synthase |
| 2653 | calmodulin (cam2) |
| 2654 | fibrillarin-like protein |
| 2655 | putative transmembrane protein G5p |
| 2656 | putative peroxidase |
| 2657 | putative SNF1-related protein kinase |
| 2658 | glutathione S-transferase, putative |
| 2659 | unknown protein |
| 2660 | hypothetical protein |
| 2661 | putative protein |
| 2662 | phosphatidylinositol-4-phosphate 5-kinase isolog |
| 2663 | putative tyrosine decarboxylase |
| 2664 | unknown protein |
| 2665 | SGP1 monomeric G-protein (emb|CAB54517.1) |
| 2666 | putative serine carboxypeptidase II |
| 2667 | putative L5 ribosomal protein |
| 2668 | putative glucosyltransferase |
| 2669 | flavonoid 3,5-hydroxylase like protein |
| 2670 | putative protein |
| 2671 | putative protein |
| 2672 | putative Fe(II)/ascorbate oxidase |
| 2673 | putative anthocyanin 5-aromatic acyltransferase |
| 2674 | casein kinase I |
| 2675 | putative 2,3-bisphosphoglycerate-independent phosphoglycerate mutase |
| 2676 | putative glutathione S-transferase TSI-1 |
| 2677 | ATP-dependent RNA helicase |
| 2678 | putative cytochrome P450 |
| 2679 | putative WD-40 repeat protein |
| 2680 | No function assigned by TIGR |
| 2681 | No function assigned by TIGR |
| 2682 | putative protein |
| 2683 | putative extension |
| 2684 | nodulin-26-like protein |
| 2685 | RINA helicase (emb/CAA09212.1) |
| 2686 | predicted protein of unknown function |
| 2687 | putative berberine bridge enzyme |
| 2688 | thioredoxin, putative |
| 2689 | putative serine carboxypeptidase I |
| 2690 | cytochrome P450-like protein |
| 2691 | putative pyrophosphate-dependent phosphofructokinase alpha subunit |
| 2692 | putative flavonol glucosyltransferase |
| 2693 | peroxidase ATP20a (emb|CAA67338.1) |

TABLE 1-continued

SEQUENCE DESCRIPTIONS

| Seq ID | Description |
| --- | --- |
| 2694 | TOPP8 serine/threonine protein phosphatase type one |
| 2695 | auxin regulated protein IAA18, putative |
| 2696 | putative WRKY-type DNA binding protein |
| 2697 | putative glucan synthase |
| 2698 | squalene monooxygenase |
| 2699 | putative proline-rich protein |
| 2700 | G2484-1 protein |
| 2701 | heat shock protein 70 like protein |
| 2702 | unknown protein |
| 2703 | unknown protein |

TABLE 2

ABIOTIC STRESS RESPONSIVE GENE REGULATORY SEQUENCES

| SEQ ID NO: | REGULATORY REGION |
| --- | --- |
| 1 | 2704 |
| 2 | 2705 |
| 3 | 2706 |
| 4 | 2707 |
| 5 | 2708 |
| 6 | 2709 |
| 7 | 2710 |
| 8 | 2711 |
| 9 | 2712 |
| 10 | 2713 |
| 11 | 2714 |
| 12 | 2715 |
| 13 | 2716 |
| 14 | 2717 |
| 15 | 2718 |
| 16 | 2719 |
| 17 | 2720 |
| 18 | 2721 |
| 19 | 2722 |
| 20 | 2723 |
| 21 | 2724 |
| 22 | 2725 |
| 23 | 2726 |
| 24 | 2727 |
| 25 | 2728 |
| 26 | 2729 |
| 27 | 2730 |
| 28 | 2731 |
| 29 | 2732 |
| 30 | 2733 |
| 31 | 2734 |
| 32 | 2735 |
| 33 | 2736 |
| 34 | 2737 |
| 35 | 2738 |
| 36 | 2739 |
| 37 | 2740 |
| 38 | 2741 |
| 39 | 2742 |
| 40 | 2743 |
| 41 | 2744 |
| 42 | 2745 |
| 43 | NONE |
| 44 | 2746 |
| 45 | 2747 |
| 46 | 2748 |
| 47 | 2749 |
| 48 | 2750 |
| 49 | 2751 |
| 50 | 2752 |

TABLE 2-continued

ABIOTIC STRESS RESPONSIVE GENE REGULATORY SEQUENCES

| SEQ ID NO: | REGULATORY REGION |
| --- | --- |
| 51 | 2753 |
| 52 | 2754 |
| 53 | 2755 |
| 54 | 2756 |
| 55 | 2757 |
| 56 | 2758 |
| 57 | 2759 |
| 58 | 2760 |
| 59 | 2761 |
| 60 | 2762 |
| 61 | 2763 |
| 62 | 2764 |
| 63 | 2765 |
| 64 | 2766 |
| 65 | 2767 |
| 66 | 2768 |
| 67 | 2769 |
| 68 | 2770 |
| 69 | NONE |
| 70 | 2771 |
| 71 | 2772 |
| 72 | 2773 |
| 73 | 2774 |
| 74 | 2775 |
| 75 | 2776 |
| 76 | 2777 |
| 77 | 2778 |
| 78 | 2779 |
| 79 | 2780 |
| 80 | 2781 |
| 81 | 2782 |
| 82 | 2783 |
| 83 | 2784 |
| 84 | 2785 |
| 85 | 2786 |
| 86 | 2787 |
| 87 | 2788 |
| 88 | 2789 |
| 89 | 2790 |
| 90 | 2791 |
| 91 | 2792 |
| 92 | 2793 |
| 93 | 2794 |
| 94 | 2795 |
| 95 | 2796 |
| 96 | 2797 |
| 97 | 2798 |
| 98 | 2799 |
| 99 | 2800 |
| 100 | 2801 |
| 101 | 2802 |
| 102 | 2803 |
| 103 | 2804 |
| 104 | 2805 |
| 105 | 2806 |
| 106 | 2807 |
| 107 | 2808 |
| 108 | 2809 |
| 109 | 2810 |
| 110 | 2811 |
| 111 | 2812 |
| 112 | 2813 |
| 113 | 2814 |
| 114 | 2815 |
| 115 | 2816 |
| 116 | 2817 |
| 117 | 2818 |
| 118 | 2819 |
| 119 | 2820 |
| 120 | 2821 |
| 121 | 2822 |
| 122 | 2823 |
| 123 | 2824 |
| 124 | 2825 |

TABLE 2-continued

ABIOTIC STRESS RESPONSIVE GENE REGULATORY SEQUENCES

| SEQ ID NO: | REGULATORY REGION |
|---|---|
| 125 | 2826 |
| 126 | 2827 |
| 127 | 2828 |
| 128 | 2829 |
| 129 | 2830 |
| 130 | 2831 |
| 131 | 2832 |
| 132 | 2833 |
| 133 | 2834 |
| 134 | 2835 |
| 135 | 2836 |
| 136 | 2837 |
| 137 | 2838 |
| 138 | 2839 |
| 139 | 2840 |
| 140 | 2841 |
| 141 | 2842 |
| 142 | 2843 |
| 143 | 2844 |
| 144 | NONE |
| 145 | 2845 |
| 146 | 2846 |
| 147 | 2847 |
| 148 | 2848 |
| 149 | 2849 |
| 150 | 2850 |
| 151 | 2851 |
| 152 | 2852 |
| 153 | 2853 |
| 154 | 2854 |
| 155 | 2855 |
| 156 | 2856 |
| 157 | 2857 |
| 158 | 2858 |
| 159 | 2859 |
| 160 | 2860 |
| 161 | 2861 |
| 162 | 2862 |
| 163 | 2863 |
| 164 | 2864 |
| 165 | 2865 |
| 166 | 2866 |
| 167 | 2867 |
| 168 | 2868 |
| 169 | 2869 |
| 170 | 2870 |
| 171 | 2871 |
| 172 | 2872 |
| 173 | 2873 |
| 174 | 2874 |
| 175 | 2875 |
| 176 | 2876 |
| 177 | 2877 |
| 178 | 2878 |
| 179 | 2879 |
| 180 | 2880 |
| 181 | 2881 |
| 182 | 2882 |
| 183 | 2883 |
| 184 | 2884 |
| 185 | 2885 |
| 186 | 2886 |
| 187 | 2887 |
| 188 | 2888 |
| 189 | 2889 |
| 190 | 2890 |
| 191 | 2891 |
| 192 | 2892 |
| 193 | 2893 |
| 194 | 2894 |
| 195 | 2895 |
| 196 | 2896 |
| 197 | 2897 |
| 198 | 2898 |
| 199 | 2899 |
| 200 | 2900 |
| 201 | 2901 |
| 202 | 2902 |
| 203 | 2903 |
| 204 | 2904 |
| 205 | 2905 |
| 206 | 2906 |
| 207 | 2907 |
| 208 | 2908 |
| 209 | 2909 |
| 210 | 2910 |
| 211 | 2911 |
| 212 | 2912 |
| 213 | 2913 |
| 214 | 2914 |
| 215 | 2915 |
| 216 | 2916 |
| 217 | 2917 |
| 218 | 2918 |
| 219 | 2919 |
| 220 | 2920 |
| 221 | 2921 |
| 222 | 2922 |
| 223 | 2923 |
| 224 | 2924 |
| 225 | 2925 |
| 226 | 2926 |
| 227 | 2927 |
| 228 | 2928 |
| 229 | 2929 |
| 230 | 2930 |
| 231 | 2931 |
| 232 | 2932 |
| 233 | 2933 |
| 234 | 2934 |
| 235 | 2935 |
| 236 | 2936 |
| 237 | 2937 |
| 238 | 2938 |
| 239 | 2939 |
| 240 | 2940 |
| 241 | 2941 |
| 242 | 2942 |
| 243 | 2943 |
| 244 | 2944 |
| 245 | 2945 |
| 246 | 2946 |
| 247 | 2947 |
| 248 | 2948 |
| 249 | 2949 |
| 250 | 2950 |
| 251 | 2951 |
| 252 | 2952 |
| 253 | 2953 |
| 254 | 2954 |
| 255 | 2955 |
| 256 | 2956 |
| 257 | 2957 |
| 258 | 2958 |
| 259 | 2959 |
| 260 | 2960 |
| 261 | 2961 |
| 262 | 2962 |
| 263 | 2963 |
| 264 | 2964 |
| 265 | 2965 |
| 266 | 2966 |
| 267 | 2967 |
| 268 | 2968 |
| 269 | 2969 |
| 270 | 2970 |
| 271 | 2971 |
| 272 | 2972 |

TABLE 2-continued

ABIOTIC STRESS RESPONSIVE GENE REGULATORY SEQUENCES

| SEQ ID NO: | REGULATORY REGION |
|---|---|
| 273 | 2973 |
| 274 | 2974 |
| 275 | 2975 |
| 276 | 2976 |
| 277 | 2977 |
| 278 | 2978 |
| 279 | 2979 |
| 280 | 2980 |
| 281 | 2981 |
| 282 | 2982 |
| 283 | 2983 |
| 284 | 2984 |
| 285 | 2985 |
| 286 | 2986 |
| 287 | 2987 |
| 288 | 2988 |
| 289 | 2989 |
| 290 | 2990 |
| 291 | 2991 |
| 292 | 2992 |
| 293 | 2993 |
| 295 | 2995 |
| 296 | 2996 |
| 297 | 2997 |
| 298 | 2998 |
| 299 | 2999 |
| 300 | 3000 |
| 301 | 3001 |
| 302 | 3002 |
| 303 | 3003 |
| 304 | NONE |
| 305 | 3004 |
| 306 | 3005 |
| 307 | 3006 |
| 308 | 3007 |
| 309 | 3008 |
| 310 | 3009 |
| 311 | 3010 |
| 312 | 3011 |
| 313 | 3012 |
| 314 | 3013 |
| 315 | 3014 |
| 316 | 3015 |
| 317 | 3016 |
| 318 | 3017 |
| 319 | 3018 |
| 320 | 3019 |
| 321 | 3020 |
| 322 | 3021 |
| 323 | 3022 |
| 324 | 3023 |
| 325 | 3024 |
| 326 | 3025 |
| 327 | 3026 |
| 328 | 3027 |
| 329 | 3028 |
| 330 | 3029 |
| 331 | 3030 |
| 332 | 3031 |
| 333 | 3032 |
| 334 | 3033 |
| 335 | 3034 |
| 336 | 3035 |
| 337 | 3036 |
| 338 | 3037 |
| 339 | 3038 |
| 340 | 3039 |
| 341 | 3040 |
| 342 | 3041 |
| 343 | 3042 |
| 344 | 3043 |
| 345 | 3044 |
| 346 | 3045 |
| 347 | 3046 |
| 348 | 3047 |
| 349 | 3048 |
| 350 | 3049 |
| 351 | 3050 |
| 352 | 3051 |
| 353 | 3052 |
| 354 | 3053 |
| 355 | 3054 |
| 356 | 3055 |
| 357 | 3056 |
| 358 | 3057 |
| 359 | 3058 |
| 360 | 3059 |
| 361 | 3060 |
| 362 | 3061 |
| 363 | 3062 |
| 364 | 3063 |
| 365 | 3064 |
| 366 | 3065 |
| 367 | 3066 |
| 368 | 3067 |
| 369 | 3068 |
| 370 | 3069 |
| 371 | 3070 |
| 372 | 3071 |
| 373 | 3072 |
| 374 | 3073 |
| 375 | 3074 |
| 376 | 3075 |
| 377 | 3076 |
| 378 | 3077 |
| 379 | 3078 |
| 380 | 3079 |
| 381 | 3080 |
| 382 | 3081 |
| 383 | 3082 |
| 384 | 3083 |
| 385 | 3084 |
| 386 | 3085 |
| 387 | 3086 |
| 388 | 3087 |
| 389 | 3088 |
| 390 | 3089 |
| 391 | 3090 |
| 392 | 3091 |
| 393 | 3092 |
| 394 | 3093 |
| 395 | 3094 |
| 396 | 3095 |
| 397 | 3096 |
| 398 | 3097 |
| 399 | 3098 |
| 400 | 3099 |
| 401 | 3100 |
| 402 | 3101 |
| 403 | 3102 |
| 404 | 3103 |
| 405 | 3104 |
| 406 | 3105 |
| 407 | 3106 |
| 408 | 3107 |
| 409 | 3108 |
| 410 | 3109 |
| 411 | 3110 |
| 412 | 3111 |
| 413 | 3112 |
| 414 | 3113 |
| 415 | 3114 |
| 416 | 3115 |
| 417 | 3116 |
| 418 | 3117 |
| 419 | 3118 |
| 420 | 3119 |
| 421 | 3120 |

TABLE 2-continued

ABIOTIC STRESS RESPONSIVE GENE REGULATORY SEQUENCES

| SEQ ID NO: | REGULATORY REGION |
|---|---|
| 422 | 3121 |
| 423 | 3122 |
| 424 | 3123 |
| 425 | 3124 |
| 426 | 3125 |
| 427 | 3126 |
| 428 | 3127 |
| 429 | 3128 |
| 430 | 3129 |
| 431 | 3130 |
| 432 | 3131 |
| 433 | 3132 |
| 434 | 3133 |
| 435 | 3134 |
| 436 | 3135 |
| 437 | 3136 |
| 438 | 3137 |
| 439 | 3138 |
| 440 | 3139 |
| 441 | 3140 |
| 442 | 3141 |
| 443 | 3142 |
| 444 | 3143 |
| 445 | 3144 |
| 446 | 3145 |
| 447 | 3146 |
| 448 | 3147 |
| 449 | 3148 |
| 450 | 3149 |
| 451 | 3150 |
| 452 | 3151 |
| 453 | 3152 |
| 454 | 3153 |
| 455 | 3154 |
| 456 | 3155 |
| 457 | 3156 |
| 458 | 3157 |
| 459 | 3158 |
| 460 | 3159 |
| 461 | 3160 |
| 462 | 3161 |
| 463 | 3162 |
| 464 | 3163 |
| 465 | 3164 |
| 466 | 3165 |
| 467 | 3166 |
| 468 | 3167 |
| 469 | 3168 |
| 470 | 3169 |
| 471 | 3170 |
| 472 | 3171 |
| 473 | 3172 |
| 474 | 3173 |
| 475 | 3174 |
| 476 | 3175 |
| 477 | 3176 |
| 478 | 3177 |
| 479 | 3178 |
| 480 | 3179 |
| 481 | 3180 |
| 482 | 3181 |
| 483 | 3182 |
| 484 | 3183 |
| 485 | 3184 |
| 486 | 3185 |
| 487 | 3186 |
| 488 | 3187 |
| 489 | 3188 |
| 490 | 3189 |
| 491 | 3190 |
| 492 | 3191 |
| 493 | 3192 |
| 494 | 3193 |
| 495 | 3194 |
| 496 | 3195 |
| 497 | 3196 |
| 498 | 3197 |
| 499 | 3198 |
| 500 | 3199 |
| 501 | 3200 |
| 502 | 3201 |
| 503 | 3202 |
| 504 | 3203 |
| 505 | 3204 |
| 506 | 3205 |
| 507 | 3206 |
| 508 | 3207 |
| 509 | 3208 |
| 510 | 3209 |
| 511 | 3210 |
| 512 | 3211 |
| 513 | 3212 |
| 514 | 3213 |
| 515 | 3214 |
| 516 | 3215 |
| 517 | 3216 |
| 518 | 3217 |
| 519 | 3218 |
| 520 | 3219 |
| 521 | 3220 |
| 522 | 3221 |
| 523 | 3222 |
| 524 | 3223 |
| 525 | 3224 |
| 526 | 3225 |
| 527 | 3226 |
| 528 | 3227 |
| 529 | 3228 |
| 530 | 3229 |
| 531 | 3230 |
| 532 | 3231 |
| 533 | 3232 |
| 534 | 3233 |
| 535 | 3234 |
| 536 | 3235 |
| 537 | 3236 |
| 538 | 3237 |
| 539 | 3238 |
| 540 | 3239 |
| 541 | 3240 |
| 542 | 3241 |
| 543 | 3242 |
| 544 | 3243 |
| 545 | 3244 |
| 546 | 3245 |
| 547 | 3246 |
| 548 | 3247 |
| 549 | 3248 |
| 550 | 3249 |
| 551 | 3250 |
| 552 | 3251 |
| 553 | 3252 |
| 554 | 3253 |
| 555 | 3254 |
| 556 | 3255 |
| 557 | 3256 |
| 558 | 3257 |
| 559 | 3258 |
| 560 | 3259 |
| 561 | 3260 |
| 562 | 3261 |
| 563 | 3262 |
| 564 | 3263 |
| 565 | 3264 |
| 566 | 3265 |
| 567 | 3266 |
| 568 | 3267 |
| 569 | 3268 |

TABLE 2-continued

ABIOTIC STRESS RESPONSIVE GENE REGULATORY SEQUENCES

| SEQ ID NO: | REGULATORY REGION |
|---|---|
| 570 | 3269 |
| 571 | 3270 |
| 572 | 3271 |
| 573 | 3272 |
| 574 | 3273 |
| 575 | 3274 |
| 576 | 3275 |
| 577 | 3276 |
| 578 | 3277 |
| 579 | 3278 |
| 580 | 3279 |
| 581 | 3280 |
| 582 | 3281 |
| 583 | 3282 |
| 584 | 3283 |
| 585 | 3284 |
| 586 | 3285 |
| 587 | 3286 |
| 588 | 3287 |
| 589 | 3288 |
| 590 | 3289 |
| 591 | 3290 |
| 592 | 3291 |
| 593 | 3292 |
| 594 | 3293 |
| 595 | 3294 |
| 596 | 3295 |
| 597 | 3296 |
| 598 | 3297 |
| 599 | 3298 |
| 600 | 3299 |
| 601 | 3300 |
| 602 | 3301 |
| 603 | 3302 |
| 604 | 3303 |
| 605 | 3304 |
| 606 | 3305 |
| 607 | 3306 |
| 608 | 3307 |
| 609 | 3308 |
| 610 | 3309 |
| 611 | 3310 |
| 612 | 3311 |
| 613 | 3312 |
| 614 | 3313 |
| 615 | 3314 |
| 616 | 3315 |
| 617 | 3316 |
| 618 | 3317 |
| 619 | 3318 |
| 620 | 3319 |
| 621 | 3320 |
| 622 | 3321 |
| 623 | 3322 |
| 624 | 3323 |
| 625 | 3324 |
| 626 | 3325 |
| 627 | 3326 |
| 628 | 3327 |
| 629 | 3328 |
| 630 | 3329 |
| 631 | 3330 |
| 632 | 3331 |
| 633 | 3332 |
| 634 | 3333 |
| 635 | 3334 |
| 636 | 3335 |
| 637 | 3336 |
| 638 | 3337 |
| 639 | 3338 |
| 640 | 3339 |
| 641 | 3340 |
| 642 | 3341 |
| 643 | 3342 |
| 644 | 3343 |
| 645 | 3344 |
| 646 | 3345 |
| 647 | 3346 |
| 648 | 3347 |
| 649 | 3348 |
| 650 | 3349 |
| 651 | 3350 |
| 652 | 3351 |
| 653 | 3352 |
| 654 | 3353 |
| 655 | 3354 |
| 656 | 3355 |
| 657 | 3356 |
| 658 | 3357 |
| 659 | 3358 |
| 660 | 3359 |
| 661 | 3360 |
| 662 | 3361 |
| 663 | 3362 |
| 664 | 3363 |
| 665 | 3364 |
| 666 | 3365 |
| 667 | 3366 |
| 668 | 3367 |
| 669 | 3368 |
| 670 | 3369 |
| 671 | 3370 |
| 672 | 3371 |
| 673 | 3372 |
| 674 | 3373 |
| 675 | 3374 |
| 676 | 3375 |
| 677 | 3376 |
| 678 | 3377 |
| 679 | 3378 |
| 680 | 3379 |
| 681 | 3380 |
| 682 | 3381 |
| 683 | 3382 |
| 684 | 3383 |
| 685 | 3384 |
| 686 | 3385 |
| 687 | 3386 |
| 688 | 3387 |
| 689 | 3388 |
| 690 | 3389 |
| 691 | 3390 |
| 692 | 3391 |
| 693 | 3392 |
| 694 | 3393 |
| 695 | 3394 |
| 696 | 3395 |
| 697 | 3396 |
| 698 | 3397 |
| 699 | 3398 |
| 700 | 3399 |
| 701 | 3400 |
| 702 | 3401 |
| 703 | 3402 |
| 704 | 3403 |
| 705 | 3404 |
| 706 | 3405 |
| 707 | 3406 |
| 708 | 3407 |
| 709 | 3408 |
| 710 | 3409 |
| 711 | 3410 |
| 712 | 3411 |
| 713 | 3412 |
| 714 | 3413 |
| 715 | 3414 |
| 716 | 3415 |
| 717 | 3416 |

TABLE 2-continued

ABIOTIC STRESS RESPONSIVE GENE REGULATORY SEQUENCES

| SEQ ID NO: | REGULATORY REGION |
|---|---|
| 718 | 3417 |
| 719 | 3418 |
| 720 | 3419 |
| 721 | 3420 |
| 722 | 3421 |
| 723 | 3422 |
| 724 | 3423 |
| 725 | 3424 |
| 726 | 3425 |
| 727 | 3426 |
| 728 | 3427 |
| 729 | 3428 |
| 730 | 3429 |
| 731 | 3430 |
| 732 | 3431 |
| 733 | 3432 |
| 734 | 3433 |
| 735 | 3434 |
| 736 | 3435 |
| 737 | 3436 |
| 738 | 3437 |
| 739 | 3438 |
| 740 | 3439 |
| 741 | 3440 |
| 742 | 3441 |
| 743 | 3442 |
| 744 | 3443 |
| 745 | 3444 |
| 746 | 3445 |
| 747 | 3446 |
| 748 | 3447 |
| 749 | 3448 |
| 750 | 3449 |
| 751 | 3450 |
| 752 | 3451 |
| 753 | 3452 |
| 754 | 3453 |
| 755 | 3454 |
| 756 | 3455 |
| 757 | 3456 |
| 758 | 3457 |
| 759 | 3458 |
| 760 | 3459 |
| 761 | 3460 |
| 762 | 3461 |
| 763 | 3462 |
| 764 | 3463 |
| 765 | 3464 |
| 766 | 3465 |
| 767 | 3466 |
| 768 | 3467 |
| 769 | 3468 |
| 770 | 3469 |
| 771 | 3470 |
| 772 | 3471 |
| 773 | 3472 |
| 774 | 3473 |
| 775 | 3474 |
| 776 | 3475 |
| 777 | 3476 |
| 778 | 3477 |
| 779 | 3478 |
| 780 | 3479 |
| 781 | 3480 |
| 782 | 3481 |
| 783 | 3482 |
| 784 | 3483 |
| 785 | 3484 |
| 786 | 3485 |
| 787 | 3486 |
| 788 | 3487 |
| 789 | 3488 |
| 790 | 3489 |
| 791 | 3490 |
| 792 | 3491 |
| 793 | 3492 |
| 794 | 3493 |
| 795 | 3494 |
| 796 | 3495 |
| 797 | 3496 |
| 798 | 3497 |
| 799 | 3498 |
| 800 | 3499 |
| 801 | 3500 |
| 802 | 3501 |
| 803 | 3502 |
| 804 | 3503 |
| 805 | 3504 |
| 806 | 3505 |
| 807 | 3506 |
| 808 | 3507 |
| 809 | 3508 |
| 810 | 3509 |
| 811 | 3510 |
| 812 | 3511 |
| 813 | 3512 |
| 814 | 3513 |
| 815 | 3514 |
| 816 | 3515 |
| 817 | 3516 |
| 818 | 3517 |
| 819 | 3518 |
| 820 | 3519 |
| 821 | 3520 |
| 822 | 3521 |
| 823 | 3522 |
| 824 | 3523 |
| 825 | 3524 |
| 826 | 3525 |
| 827 | 3526 |
| 828 | 3527 |
| 829 | 3528 |
| 830 | 3529 |
| 831 | 3530 |
| 832 | 3531 |
| 833 | 3532 |
| 834 | 3533 |
| 835 | 3534 |
| 836 | 3535 |
| 837 | 3536 |
| 838 | 3537 |
| 839 | 3538 |
| 840 | 3539 |
| 841 | 3540 |
| 842 | 3541 |
| 843 | 3542 |
| 844 | 3543 |
| 845 | 3544 |
| 846 | 3545 |
| 847 | 3546 |
| 848 | 3547 |
| 849 | 3548 |
| 850 | 3549 |
| 851 | 3550 |
| 852 | 3551 |
| 853 | 3552 |
| 854 | 3553 |
| 855 | 3554 |
| 856 | 3555 |
| 857 | 3556 |
| 858 | 3557 |
| 859 | 3558 |
| 860 | 3559 |
| 861 | 3560 |
| 862 | 3561 |
| 863 | 3562 |
| 864 | 3563 |
| 865 | 3564 |

TABLE 2-continued

ABIOTIC STRESS RESPONSIVE GENE REGULATORY SEQUENCES

| SEQ ID NO: | REGULATORY REGION |
|---|---|
| 866 | 3565 |
| 867 | 3566 |
| 868 | 3567 |
| 869 | 3568 |
| 870 | 3569 |
| 871 | 3570 |
| 872 | 3571 |
| 873 | 3572 |
| 874 | 3573 |
| 875 | 3574 |
| 876 | 3575 |
| 877 | 3576 |
| 878 | 3577 |
| 879 | 3578 |
| 880 | 3579 |
| 881 | 3580 |
| 882 | 3581 |
| 883 | 3582 |
| 884 | 3583 |
| 885 | 3584 |
| 886 | 3585 |
| 887 | NONE |
| 888 | 3586 |
| 889 | 3587 |
| 890 | 3588 |
| 891 | 3589 |
| 892 | 3590 |
| 893 | 3591 |
| 894 | NONE |
| 895 | NONE |
| 896 | 3592 |
| 897 | 3593 |
| 898 | 3594 |
| 899 | 3595 |
| 900 | 3596 |
| 901 | 3597 |
| 902 | 3598 |
| 903 | 3599 |
| 904 | 3600 |
| 905 | 3601 |
| 906 | 3602 |
| 907 | 3603 |
| 908 | 3604 |
| 909 | 3605 |
| 910 | 3606 |
| 911 | 3607 |
| 912 | 3608 |
| 913 | 3609 |
| 914 | 3610 |
| 915 | 3611 |
| 916 | 3612 |
| 917 | 3613 |
| 918 | 3614 |
| 919 | 3615 |
| 920 | 3616 |
| 921 | 3617 |
| 922 | 3618 |
| 923 | 3619 |
| 924 | 3620 |
| 925 | 3621 |
| 926 | 3622 |
| 927 | 3623 |
| 928 | 3624 |
| 929 | 3625 |
| 930 | 3626 |
| 931 | 3627 |
| 932 | 3628 |
| 933 | 3629 |
| 934 | 3630 |
| 935 | NONE |
| 936 | 3631 |
| 937 | 3632 |
| 938 | 3633 |
| 939 | 3634 |
| 940 | 3635 |
| 941 | 3636 |
| 942 | 3637 |
| 943 | 3638 |
| 944 | 3639 |
| 945 | 3640 |
| 946 | 3641 |
| 947 | 3642 |
| 948 | 3643 |
| 949 | 3644 |
| 950 | 3645 |
| 951 | 3646 |
| 952 | 3647 |
| 953 | 3648 |
| 954 | 3649 |
| 955 | 3650 |
| 956 | 3651 |
| 957 | 3652 |
| 958 | 3653 |
| 959 | 3654 |
| 960 | 3655 |
| 961 | 3656 |
| 962 | 3657 |
| 963 | 3658 |
| 964 | 3659 |
| 965 | 3660 |
| 966 | 3661 |
| 967 | 3662 |
| 968 | 3663 |
| 969 | 3664 |
| 970 | 3665 |
| 971 | 3666 |
| 972 | 3667 |
| 973 | 3668 |
| 974 | 3669 |
| 975 | 3670 |
| 976 | 3671 |
| 977 | 3672 |
| 978 | 3673 |
| 979 | 3674 |
| 980 | 3675 |
| 981 | 3676 |
| 982 | 3677 |
| 983 | 3678 |
| 984 | 3679 |
| 985 | 3680 |
| 986 | 3681 |
| 987 | 3682 |
| 988 | 3683 |
| 989 | 3684 |
| 990 | 3685 |
| 991 | 3686 |
| 992 | 3687 |
| 993 | 3688 |
| 994 | 3689 |
| 995 | 3690 |
| 996 | 3691 |
| 997 | 3692 |
| 998 | 3693 |
| 999 | 3694 |
| 1000 | 3695 |
| 1001 | 3696 |
| 1002 | 3697 |
| 1003 | 3698 |
| 1004 | 3699 |
| 1005 | 3700 |
| 1006 | 3701 |
| 1007 | 3702 |
| 1008 | 3703 |
| 1009 | 3704 |
| 1010 | 3705 |
| 1011 | 3706 |
| 1012 | 3707 |
| 1013 | 3708 |

TABLE 2-continued

ABIOTIC STRESS RESPONSIVE GENE REGULATORY SEQUENCES

| SEQ ID NO: | REGULATORY REGION |
|---|---|
| 1014 | 3709 |
| 1015 | 3710 |
| 1016 | 3711 |
| 1017 | 3712 |
| 1018 | 3713 |
| 1019 | 3714 |
| 1020 | 3715 |
| 1021 | 3716 |
| 1022 | 3717 |
| 1023 | 3718 |
| 1024 | 3719 |
| 1025 | 3720 |
| 1026 | 3721 |
| 1027 | 3722 |
| 1028 | 3723 |
| 1029 | 3724 |
| 1030 | 3725 |
| 1031 | 3726 |
| 1032 | 3727 |
| 1033 | 3728 |
| 1034 | 3729 |
| 1035 | 3730 |
| 1036 | 3731 |
| 1037 | 3732 |
| 1038 | 3733 |
| 1039 | 3734 |
| 1040 | 3735 |
| 1041 | 3736 |
| 1042 | 3737 |
| 1043 | 3738 |
| 1044 | 3739 |
| 1045 | 3740 |
| 1046 | 3741 |
| 1047 | 3742 |
| 1048 | 3743 |
| 1049 | 3744 |
| 1050 | 3745 |
| 1051 | 3746 |
| 1052 | 3747 |
| 1053 | 3748 |
| 1054 | 3749 |
| 1055 | 3750 |
| 1056 | 3751 |
| 1057 | 3752 |
| 1058 | 3753 |
| 1059 | 3754 |
| 1060 | 3755 |
| 1061 | 3756 |
| 1062 | 3757 |
| 1063 | 3758 |
| 1064 | 3759 |
| 1065 | 3760 |
| 1066 | 3761 |
| 1067 | 3762 |
| 1068 | 3763 |
| 1069 | 3764 |
| 1070 | 3765 |
| 1071 | 3766 |
| 1072 | 3767 |
| 1073 | 3768 |
| 1074 | 3769 |
| 1075 | 3770 |
| 1076 | 3771 |
| 1077 | 3772 |
| 1078 | 3773 |
| 1079 | 3774 |
| 1080 | 3775 |
| 1081 | 3776 |
| 1082 | 3777 |
| 1083 | 3778 |
| 1084 | 3779 |
| 1085 | 3780 |
| 1086 | 3781 |
| 1087 | NONE |
| 1088 | 3782 |
| 1089 | 3783 |
| 1090 | 3784 |
| 1091 | 3785 |
| 1092 | 3786 |
| 1093 | 3787 |
| 1094 | 3788 |
| 1095 | 3789 |
| 1096 | 3790 |
| 1097 | 3791 |
| 1098 | 3792 |
| 1099 | 3793 |
| 1100 | 3794 |
| 1101 | 3795 |
| 1102 | 3796 |
| 1103 | 3797 |
| 1104 | 3798 |
| 1105 | 3799 |
| 1106 | 3800 |
| 1107 | 3801 |
| 1108 | 3802 |
| 1109 | 3803 |
| 1110 | 3804 |
| 1111 | 3805 |
| 1112 | 3806 |
| 1113 | 3807 |
| 1114 | 3808 |
| 1115 | 3809 |
| 1116 | 3810 |
| 1117 | 3811 |
| 1118 | 3812 |
| 1119 | 3813 |
| 1120 | 3814 |
| 1121 | 3815 |
| 1122 | 3816 |
| 1123 | 3817 |
| 1124 | 3818 |
| 1125 | 3819 |
| 1126 | 3820 |
| 1127 | 3821 |
| 1128 | 3822 |
| 1129 | 3823 |
| 1130 | 3824 |
| 1131 | 3825 |
| 1132 | 3826 |
| 1133 | 3827 |
| 1134 | 3828 |
| 1135 | 3829 |
| 1136 | 3830 |
| 1137 | 3831 |
| 1138 | 3832 |
| 1139 | 3833 |
| 1140 | 3834 |
| 1141 | 3835 |
| 1142 | 3836 |
| 1143 | 3837 |
| 1144 | 3838 |
| 1145 | 3839 |
| 1146 | 3840 |
| 1147 | 3841 |
| 1148 | 3842 |
| 1149 | 3843 |
| 1150 | 3844 |
| 1151 | 3845 |
| 1152 | 3846 |
| 1153 | 3847 |
| 1154 | 3848 |
| 1155 | 3849 |
| 1156 | 3850 |
| 1157 | 3851 |
| 1158 | 3852 |
| 1159 | 3853 |
| 1160 | 3854 |
| 1161 | 3855 |

TABLE 2-continued

ABIOTIC STRESS RESPONSIVE GENE REGULATORY SEQUENCES

| SEQ ID NO: | REGULATORY REGION |
|---|---|
| 1162 | 3856 |
| 1163 | 3857 |
| 1164 | 3858 |
| 1165 | 3859 |
| 1166 | 3860 |
| 1167 | 3861 |
| 1168 | 3862 |
| 1169 | 3863 |
| 1170 | 3864 |
| 1171 | 3865 |
| 1172 | 3866 |
| 1173 | 3867 |
| 1174 | 3868 |
| 1175 | 3869 |
| 1176 | 3870 |
| 1177 | 3871 |
| 1178 | 3872 |
| 1179 | 3873 |
| 1180 | 3874 |
| 1181 | 3875 |
| 1182 | 3876 |
| 1183 | 3877 |
| 1184 | 3878 |
| 1185 | 3879 |
| 1186 | 3880 |
| 1187 | 3881 |
| 1188 | 3882 |
| 1189 | 3883 |
| 1190 | 3884 |
| 1191 | 3885 |
| 1192 | 3886 |
| 1193 | 3887 |
| 1194 | 3888 |
| 1195 | 3889 |
| 1196 | 3890 |
| 1197 | 3891 |
| 1198 | 3892 |
| 1199 | 3893 |
| 1200 | 3894 |
| 1201 | 3895 |
| 1202 | 3896 |
| 1203 | 3897 |
| 1204 | 3898 |
| 1205 | 3899 |
| 1206 | 3900 |
| 1207 | 3901 |
| 1208 | 3902 |
| 1209 | 3903 |
| 1210 | 3904 |
| 1211 | 3905 |
| 1212 | 3906 |
| 1213 | 3907 |
| 1214 | 3908 |
| 1215 | 3909 |
| 1216 | 3910 |
| 1217 | 3911 |
| 1218 | 3912 |
| 1219 | 3913 |
| 1220 | 3914 |
| 1221 | 3915 |
| 1222 | 3916 |
| 1223 | 3917 |
| 1224 | 3918 |
| 1225 | 3919 |
| 1226 | 3920 |
| 1227 | 3921 |
| 1228 | 3922 |
| 1229 | 3923 |
| 1230 | 3924 |
| 1231 | 3925 |
| 1232 | 3926 |
| 1233 | 3927 |
| 1234 | 3928 |
| 1235 | 3929 |
| 1236 | 3930 |
| 1237 | 3931 |
| 1238 | 3932 |
| 1239 | 3933 |
| 1240 | 3934 |
| 1241 | 3935 |
| 1242 | 3936 |
| 1243 | 3937 |
| 1244 | 3938 |
| 1245 | 3939 |
| 1246 | 3940 |
| 1247 | 3941 |
| 1248 | 3942 |
| 1249 | 3943 |
| 1250 | 3944 |
| 1251 | 3945 |
| 1252 | 3946 |
| 1253 | 3947 |
| 1254 | 3948 |
| 1255 | 3949 |
| 1256 | 3950 |
| 1257 | 3951 |
| 1258 | 3952 |
| 1259 | 3953 |
| 1260 | 3954 |
| 1261 | 3955 |
| 1262 | 3956 |
| 1263 | 3957 |
| 1264 | 3958 |
| 1265 | 3959 |
| 1266 | 3960 |
| 1267 | 3961 |
| 1268 | 3962 |
| 1269 | 3963 |
| 1270 | 3964 |
| 1271 | 3965 |
| 1272 | 3966 |
| 1273 | 3967 |
| 1274 | 3968 |
| 1275 | 3969 |
| 1276 | 3970 |
| 1277 | 3971 |
| 1278 | 3972 |
| 1279 | 3973 |
| 1280 | 3974 |
| 1281 | 3975 |
| 1282 | 3976 |
| 1283 | 3977 |
| 1284 | 3978 |
| 1285 | 3979 |
| 1286 | 3980 |
| 1287 | 3981 |
| 1288 | 3982 |
| 1289 | 3983 |
| 1290 | 3984 |
| 1291 | 3985 |
| 1292 | 3986 |
| 1293 | 3987 |
| 1294 | 3988 |
| 1295 | 3989 |
| 1296 | 3990 |
| 1297 | 3991 |
| 1298 | 3992 |
| 1299 | 3993 |
| 1300 | 3994 |
| 1301 | 3995 |
| 1302 | 3996 |
| 1303 | 3997 |
| 1304 | 3998 |
| 1305 | 3999 |
| 1306 | 4000 |
| 1307 | 4001 |
| 1308 | 4002 |
| 1309 | 4003 |

TABLE 2-continued

ABIOTIC STRESS RESPONSIVE GENE REGULATORY SEQUENCES

| SEQ ID NO: | REGULATORY REGION |
|---|---|
| 1310 | 4004 |
| 1311 | 4005 |
| 1312 | 4006 |
| 1313 | 4007 |
| 1314 | 4008 |
| 1315 | 4009 |
| 1316 | 4010 |
| 1317 | 4011 |
| 1318 | 4012 |
| 1319 | 4013 |
| 1320 | 4014 |
| 1321 | 4015 |
| 1322 | 4016 |
| 1323 | 4017 |
| 1324 | 4018 |
| 1325 | 4019 |
| 1326 | 4020 |
| 1327 | 4021 |
| 1328 | 4022 |
| 1329 | 4023 |
| 1330 | NONE |
| 1331 | 4024 |
| 1332 | 4025 |
| 1333 | 4026 |
| 1334 | 4027 |
| 1335 | 4028 |
| 1336 | 4029 |
| 1337 | 4030 |
| 1338 | 4031 |
| 1339 | 4032 |
| 1340 | 4033 |
| 1341 | 4034 |
| 1342 | 4035 |
| 1343 | 4036 |
| 1344 | 4037 |
| 1345 | 4038 |
| 1346 | 4039 |
| 1347 | 4040 |
| 1348 | 4041 |
| 1349 | 4042 |
| 1350 | 4043 |
| 1351 | 4044 |
| 1352 | 4045 |
| 1353 | 4046 |
| 1354 | 4047 |
| 1355 | 4048 |
| 1356 | 4049 |
| 1357 | 4050 |
| 1358 | 4051 |
| 1359 | 4052 |
| 1360 | 4053 |
| 1361 | 4054 |
| 1362 | 4055 |
| 1363 | 4056 |
| 1364 | 4057 |
| 1365 | 4058 |
| 1366 | 4059 |
| 1367 | 4060 |
| 1368 | 4061 |
| 1369 | 4062 |
| 1370 | 4063 |
| 1371 | 4064 |
| 1372 | 4065 |
| 1373 | 4066 |
| 1374 | 4067 |
| 1375 | 4068 |
| 1376 | 4069 |
| 1377 | 4070 |
| 1378 | 4071 |
| 1379 | 4072 |
| 1380 | 4073 |
| 1381 | 4074 |
| 1382 | 4075 |
| 1383 | 4076 |
| 1384 | 4077 |
| 1385 | 4078 |
| 1386 | 4079 |
| 1387 | 4080 |
| 1388 | 4081 |
| 1389 | 4082 |
| 1390 | 4083 |
| 1391 | 4084 |
| 1392 | 4085 |
| 1393 | 4086 |
| 1394 | 4087 |
| 1395 | 4088 |
| 1396 | 4089 |
| 1397 | 4090 |
| 1398 | 4091 |
| 1399 | 4092 |
| 1400 | 4093 |
| 1401 | 4094 |
| 1402 | 4095 |
| 1403 | 4096 |
| 1404 | 4097 |
| 1405 | 4098 |
| 1406 | 4099 |
| 1407 | 4100 |
| 1408 | 4101 |
| 1409 | 4102 |
| 1410 | 4103 |
| 1411 | 4104 |
| 1412 | 4105 |
| 1413 | 4106 |
| 1414 | 4107 |
| 1415 | 4108 |
| 1416 | 4109 |
| 1417 | 4110 |
| 1418 | 4111 |
| 1419 | 4112 |
| 1420 | 4113 |
| 1421 | 4114 |
| 1422 | 4115 |
| 1423 | 4116 |
| 1424 | 4117 |
| 1425 | 4118 |
| 1426 | 4119 |
| 1427 | 4120 |
| 1428 | 4121 |
| 1429 | 4122 |
| 1430 | 4123 |
| 1431 | 4124 |
| 1432 | NONE |
| 1433 | 4125 |
| 1434 | 4126 |
| 1435 | 4127 |
| 1436 | 4128 |
| 1437 | 4129 |
| 1438 | 4130 |
| 1439 | 4131 |
| 1440 | 4132 |
| 1441 | 4133 |
| 1442 | 4134 |
| 1443 | 4135 |
| 1444 | 4136 |
| 1445 | 4137 |
| 1446 | 4138 |
| 1447 | 4139 |
| 1448 | 4140 |
| 1449 | 4141 |
| 1450 | 4142 |
| 1451 | 4143 |
| 1452 | 4144 |
| 1453 | 4145 |
| 1454 | 4146 |
| 1455 | 4147 |
| 1456 | 4148 |
| 1457 | 4149 |

TABLE 2-continued

ABIOTIC STRESS RESPONSIVE GENE REGULATORY SEQUENCES

| SEQ ID NO: | REGULATORY REGION |
|---|---|
| 1458 | 4150 |
| 1459 | 4151 |
| 1460 | 4152 |
| 1461 | 4153 |
| 1462 | 4154 |
| 1463 | 4155 |
| 1464 | 4156 |
| 1465 | 4157 |
| 1466 | 4158 |
| 1467 | 4159 |
| 1468 | 4160 |
| 1469 | 4161 |
| 1470 | 4162 |
| 1471 | 4163 |
| 1472 | 4164 |
| 1473 | 4165 |
| 1474 | 4166 |
| 1475 | 4167 |
| 1476 | 4168 |
| 1477 | 4169 |
| 1478 | 4170 |
| 1479 | 4171 |
| 1480 | 4172 |
| 1481 | 4173 |
| 1482 | 4174 |
| 1483 | 4175 |
| 1484 | 4176 |
| 1485 | 4177 |
| 1486 | 4178 |
| 1487 | 4179 |
| 1488 | 4180 |
| 1489 | 4181 |
| 1490 | 4182 |
| 1491 | 4183 |
| 1492 | 4184 |
| 1493 | 4185 |
| 1494 | 4186 |
| 1495 | 4187 |
| 1496 | 4188 |
| 1497 | 4189 |
| 1498 | 4190 |
| 1499 | 4191 |
| 1500 | 4192 |
| 1501 | 4193 |
| 1502 | 4194 |
| 1503 | 4195 |
| 1504 | 4196 |
| 1505 | 4197 |
| 1506 | 4198 |
| 1507 | 4199 |
| 1508 | 4200 |
| 1509 | 4201 |
| 1510 | 4202 |
| 1511 | 4203 |
| 1512 | 4204 |
| 1513 | 4205 |
| 1514 | 4206 |
| 1515 | 4207 |
| 1516 | 4208 |
| 1517 | 4209 |
| 1518 | 4210 |
| 1519 | 4211 |
| 1520 | 4212 |
| 1521 | 4213 |
| 1522 | 4214 |
| 1523 | 4215 |
| 1524 | 4216 |
| 1525 | 4217 |
| 1526 | 4218 |
| 1527 | 4219 |
| 1528 | 4220 |
| 1529 | 4221 |
| 1530 | 4222 |
| 1531 | 4223 |
| 1532 | 4224 |
| 1533 | 4225 |
| 1534 | 4226 |
| 1535 | 4227 |
| 1536 | 4228 |
| 1537 | 4229 |
| 1538 | 4230 |
| 1539 | 4231 |
| 1540 | 4232 |
| 1541 | 4233 |
| 1542 | 4234 |
| 1543 | 4235 |
| 1544 | 4236 |
| 1545 | 4237 |
| 1546 | 4238 |
| 1547 | 4239 |
| 1548 | 4240 |
| 1549 | 4241 |
| 1550 | 4242 |
| 1551 | 4243 |
| 1552 | 4244 |
| 1553 | 4245 |
| 1554 | 4246 |
| 1555 | 4247 |
| 1556 | 4248 |
| 1557 | 4249 |
| 1558 | NONE |
| 1559 | 4250 |
| 1560 | 4251 |
| 1561 | 4252 |
| 1562 | 4253 |
| 1563 | 4254 |
| 1564 | 4255 |
| 1565 | 4256 |
| 1566 | 4257 |
| 1567 | 4258 |
| 1568 | 4259 |
| 1569 | 4260 |
| 1570 | 4261 |
| 1571 | 4262 |
| 1572 | 4263 |
| 1573 | 4264 |
| 1574 | 4265 |
| 1575 | 4266 |
| 1576 | 4267 |
| 1577 | 4268 |
| 1578 | 4269 |
| 1579 | 4270 |
| 1580 | 4271 |
| 1581 | 4272 |
| 1582 | 4273 |
| 1583 | 4274 |
| 1584 | 4275 |
| 1585 | 4276 |
| 1586 | 4277 |
| 1587 | 4278 |
| 1588 | 4279 |
| 1589 | 4280 |
| 1590 | 4281 |
| 1591 | 4282 |
| 1592 | 4283 |
| 1593 | 4284 |
| 1594 | 4285 |
| 1595 | 4286 |
| 1596 | 4287 |
| 1597 | 4288 |
| 1598 | 4289 |
| 1599 | 4290 |
| 1600 | 4291 |
| 1601 | 4292 |
| 1602 | 4293 |
| 1603 | 4294 |
| 1604 | 4295 |
| 1605 | 4296 |

TABLE 2-continued

ABIOTIC STRESS RESPONSIVE GENE REGULATORY SEQUENCES

| SEQ ID NO: | REGULATORY REGION |
|---|---|
| 1606 | 4297 |
| 1607 | 4298 |
| 1608 | 4299 |
| 1609 | 4300 |
| 1610 | 4301 |
| 1611 | 4302 |
| 1612 | 4303 |
| 1613 | 4304 |
| 1614 | 4305 |
| 1615 | 4306 |
| 1616 | 4307 |
| 1617 | 4308 |
| 1618 | 4309 |
| 1619 | 4310 |
| 1620 | 4311 |
| 1621 | 4312 |
| 1622 | 4313 |
| 1623 | 4314 |
| 1624 | 4315 |
| 1625 | 4316 |
| 1626 | 4317 |
| 1627 | 4318 |
| 1628 | 4319 |
| 1629 | 4320 |
| 1630 | 4321 |
| 1631 | 4322 |
| 1632 | 4323 |
| 1633 | 4324 |
| 1634 | 4325 |
| 1635 | 4326 |
| 1636 | 4327 |
| 1637 | 4328 |
| 1638 | 4329 |
| 1639 | 4330 |
| 1640 | 4331 |
| 1641 | 4332 |
| 1642 | 4333 |
| 1643 | 4334 |
| 1644 | 4335 |
| 1645 | 4336 |
| 1646 | 4337 |
| 1647 | 4338 |
| 1648 | 4339 |
| 1649 | 4340 |
| 1650 | 4341 |
| 1651 | 4342 |
| 1652 | 4343 |
| 1653 | 4344 |
| 1654 | 4345 |
| 1655 | 4346 |
| 1656 | 4347 |
| 1657 | 4348 |
| 1658 | 4349 |
| 1659 | 4350 |
| 1660 | 4351 |
| 1661 | 4352 |
| 1662 | 4353 |
| 1663 | NONE |
| 1664 | 4354 |
| 1665 | 4355 |
| 1666 | 4356 |
| 1667 | 4357 |
| 1668 | 4358 |
| 1669 | 4359 |
| 1670 | 4360 |
| 1671 | 4361 |
| 1672 | 4362 |
| 1673 | 4363 |
| 1674 | 4364 |
| 1675 | 4365 |
| 1676 | 4366 |
| 1677 | 4367 |
| 1678 | 4368 |
| 1679 | 4369 |
| 1680 | 4370 |
| 1681 | 4371 |
| 1682 | 4372 |
| 1683 | 4373 |
| 1684 | 4374 |
| 1685 | 4375 |
| 1686 | 4376 |
| 1687 | 4377 |
| 1688 | 4378 |
| 1689 | 4379 |
| 1690 | 4380 |
| 1691 | 4381 |
| 1692 | 4382 |
| 1693 | 4383 |
| 1694 | 4384 |
| 1695 | 4385 |
| 1696 | 4386 |
| 1697 | 4387 |
| 1698 | 4388 |
| 1699 | 4389 |
| 1700 | 4390 |
| 1701 | 4391 |
| 1702 | 4392 |
| 1703 | 4393 |
| 1704 | 4394 |
| 1705 | 4395 |
| 1706 | 4396 |
| 1707 | 4397 |
| 1708 | 4398 |
| 1709 | 4399 |
| 1710 | 4400 |
| 1711 | 4401 |
| 1712 | NONE |
| 1713 | 4402 |
| 1714 | 4403 |
| 1715 | 4404 |
| 1716 | 4405 |
| 1717 | 4406 |
| 1718 | 4407 |
| 1719 | 4408 |
| 1720 | 4409 |
| 1721 | 4410 |
| 1722 | 4411 |
| 1723 | 4412 |
| 1724 | 4413 |
| 1725 | 4414 |
| 1726 | 4415 |
| 1727 | 4416 |
| 1728 | 4417 |
| 1729 | 4418 |
| 1730 | 4419 |
| 1731 | 4420 |
| 1732 | 4421 |
| 1733 | 4422 |
| 1734 | 4423 |
| 1735 | 4424 |
| 1736 | 4425 |
| 1737 | 4426 |
| 1738 | 4427 |
| 1739 | 4428 |
| 1740 | 4429 |
| 1741 | 4430 |
| 1742 | 4431 |
| 1743 | 4432 |
| 1744 | 4433 |
| 1745 | 4434 |
| 1746 | 4435 |
| 1747 | 4436 |
| 1748 | 4437 |
| 1749 | 4438 |
| 1750 | 4439 |
| 1751 | 4440 |
| 1752 | 4441 |
| 1753 | 4442 |

TABLE 2-continued

ABIOTIC STRESS RESPONSIVE GENE REGULATORY SEQUENCES

| SEQ ID NO: | REGULATORY REGION |
|---|---|
| 1754 | 4443 |
| 1755 | 4444 |
| 1756 | 4445 |
| 1757 | 4446 |
| 1758 | 4447 |
| 1759 | 4448 |
| 1760 | 4449 |
| 1761 | 4450 |
| 1762 | 4451 |
| 1763 | 4452 |
| 1764 | 4453 |
| 1765 | 4454 |
| 1766 | 4455 |
| 1767 | 4456 |
| 1768 | 4457 |
| 1769 | 4458 |
| 1770 | 4459 |
| 1771 | 4460 |
| 1772 | 4461 |
| 1773 | 4462 |
| 1774 | 4463 |
| 1775 | 4464 |
| 1776 | 4465 |
| 1777 | 4466 |
| 1778 | 4467 |
| 1779 | 4468 |
| 1780 | 4469 |
| 1781 | 4470 |
| 1782 | 4471 |
| 1783 | 4472 |
| 1784 | NONE |
| 1785 | 4473 |
| 1786 | 4474 |
| 1787 | 4475 |
| 1788 | 4476 |
| 1789 | 4477 |
| 1790 | 4478 |
| 1791 | 4479 |
| 1792 | 4480 |
| 1793 | 4481 |
| 1794 | 4482 |
| 1795 | 4483 |
| 1796 | 4484 |
| 1797 | 4485 |
| 1798 | 4486 |
| 1799 | 4487 |
| 1800 | 4488 |
| 1801 | 4489 |
| 1802 | 4490 |
| 1803 | NONE |
| 1804 | 4491 |
| 1805 | 4492 |
| 1806 | 4493 |
| 1807 | 4494 |
| 1808 | 4495 |
| 1809 | 4496 |
| 1810 | 4497 |
| 1811 | 4498 |
| 1812 | 4499 |
| 1813 | 4500 |
| 1814 | 4501 |
| 1815 | 4502 |
| 1816 | 4503 |
| 1817 | 4504 |
| 1818 | 4505 |
| 1819 | 4506 |
| 1820 | 4507 |
| 1821 | 4508 |
| 1822 | 4509 |
| 1823 | 4510 |
| 1824 | 4511 |
| 1825 | 4512 |
| 1826 | 4513 |
| 1827 | 4514 |
| 1828 | 4515 |
| 1829 | 4516 |
| 1830 | 4517 |
| 1831 | 4518 |
| 1832 | 4519 |
| 1833 | 4520 |
| 1834 | 4521 |
| 1835 | 4522 |
| 1836 | 4523 |
| 1837 | 4524 |
| 1838 | 4525 |
| 1839 | 4526 |
| 1840 | 4527 |
| 1841 | 4528 |
| 1842 | 4529 |
| 1843 | 4530 |
| 1844 | 4531 |
| 1845 | 4532 |
| 1846 | 4533 |
| 1847 | 4534 |
| 1848 | 4535 |
| 1849 | 4536 |
| 1850 | 4537 |
| 1851 | 4538 |
| 1852 | 4539 |
| 1853 | 4540 |
| 1854 | 4541 |
| 1855 | 4542 |
| 1856 | 4543 |
| 1857 | 4544 |
| 1858 | 4545 |
| 1859 | 4546 |
| 1860 | 4547 |
| 1861 | 4548 |
| 1862 | 4549 |
| 1863 | 4550 |
| 1864 | 4551 |
| 1865 | 4552 |
| 1866 | 4553 |
| 1867 | 4554 |
| 1868 | 4555 |
| 1869 | 4556 |
| 1870 | 4557 |
| 1871 | 4558 |
| 1872 | 4559 |
| 1873 | 4560 |
| 1874 | 4561 |
| 1875 | 4562 |
| 1876 | 4563 |
| 1877 | 4564 |
| 1878 | 4565 |
| 1879 | 4566 |
| 1880 | 4567 |
| 1881 | 4568 |
| 1882 | 4569 |
| 1883 | 4570 |
| 1884 | 4571 |
| 1885 | 4572 |
| 1886 | 4573 |
| 1887 | 4574 |
| 1888 | 4575 |
| 1889 | 4576 |
| 1890 | 4577 |
| 1891 | 4578 |
| 1892 | 4579 |
| 1893 | 4580 |
| 1894 | 4581 |
| 1895 | 4582 |
| 1896 | 4583 |
| 1897 | NONE |
| 1898 | 4584 |
| 1899 | 4585 |
| 1900 | 4586 |
| 1901 | 4587 |

TABLE 2-continued

ABIOTIC STRESS RESPONSIVE GENE REGULATORY SEQUENCES

| SEQ ID NO: | REGULATORY REGION |
|---|---|
| 1902 | 4588 |
| 1903 | 4589 |
| 1904 | 4590 |
| 1905 | 4591 |
| 1906 | 4592 |
| 1907 | NONE |
| 1908 | 4593 |
| 1909 | 4594 |
| 1910 | 4595 |
| 1911 | 4596 |
| 1912 | 4597 |
| 1913 | 4598 |
| 1914 | 4599 |
| 1915 | 4600 |
| 1916 | 4601 |
| 1917 | 4602 |
| 1918 | 4603 |
| 1919 | 4604 |
| 1920 | 4605 |
| 1921 | 4606 |
| 1922 | 4607 |
| 1923 | 4608 |
| 1924 | 4609 |
| 1925 | 4610 |
| 1926 | 4611 |
| 1927 | 4612 |
| 1928 | 4613 |
| 1929 | 4614 |
| 1930 | 4615 |
| 1931 | 4616 |
| 1932 | 4617 |
| 1933 | 4618 |
| 1934 | 4619 |
| 1935 | 4620 |
| 1936 | 4621 |
| 1937 | 4622 |
| 1938 | 4623 |
| 1939 | 4624 |
| 1940 | 4625 |
| 1941 | 4626 |
| 1942 | 4627 |
| 1943 | 4628 |
| 1944 | 4629 |
| 1945 | 4630 |
| 1946 | 4631 |
| 1947 | 4632 |
| 1948 | 4633 |
| 1949 | 4634 |
| 1950 | 4635 |
| 1951 | 4636 |
| 1952 | 4637 |
| 1953 | 4638 |
| 1954 | 4639 |
| 1955 | 4640 |
| 1956 | 4641 |
| 1957 | 4642 |
| 1958 | 4643 |
| 1959 | 4644 |
| 1960 | 4645 |
| 1961 | 4646 |
| 1962 | 4647 |
| 1963 | 4648 |
| 1964 | 4649 |
| 1965 | 4650 |
| 1966 | 4651 |
| 1967 | 4652 |
| 1968 | 4653 |
| 1969 | 4654 |
| 1970 | 4655 |
| 1971 | 4656 |
| 1972 | 4657 |
| 1973 | 4658 |
| 1974 | 4659 |
| 1975 | 4660 |
| 1976 | 4661 |
| 1977 | 4662 |
| 1978 | 4663 |
| 1979 | 4664 |
| 1980 | 4665 |
| 1981 | 4666 |
| 1982 | 4667 |
| 1983 | 4668 |
| 1984 | 4669 |
| 1985 | 4670 |
| 1986 | 4671 |
| 1987 | 4672 |
| 1988 | 4673 |
| 1989 | 4674 |
| 1990 | 4675 |
| 1991 | 4676 |
| 1992 | 4677 |
| 1993 | 4678 |
| 1994 | 4679 |
| 1995 | 4680 |
| 1996 | 4681 |
| 1997 | 4682 |
| 1998 | 4683 |
| 1999 | 4684 |
| 2000 | 4685 |
| 2001 | 4686 |
| 2002 | 4687 |
| 2003 | 4688 |
| 2004 | 4689 |
| 2005 | 4690 |
| 2006 | 4691 |
| 2007 | 4692 |
| 2008 | 4693 |
| 2009 | 4694 |
| 2010 | 4695 |
| 2011 | 4696 |
| 2012 | 4697 |
| 2013 | 4698 |
| 2014 | 4699 |
| 2015 | 4700 |
| 2016 | 4701 |
| 2017 | 4702 |
| 2018 | 4703 |
| 2019 | 4704 |
| 2020 | 4705 |
| 2021 | 4706 |
| 2022 | 4707 |
| 2023 | 4708 |
| 2024 | 4709 |
| 2025 | 4710 |
| 2026 | 4711 |
| 2027 | 4712 |
| 2028 | 4713 |
| 2029 | 4714 |
| 2030 | NONE |
| 2031 | 4715 |
| 2032 | 4716 |
| 2033 | 4717 |
| 2034 | 4718 |
| 2035 | 4719 |
| 2036 | 4720 |
| 2037 | 4721 |
| 2038 | 4722 |
| 2039 | 4723 |
| 2040 | 4724 |
| 2041 | 4725 |
| 2042 | 4726 |
| 2043 | 4727 |
| 2044 | 4728 |
| 2045 | 4729 |
| 2046 | 4730 |
| 2047 | 4731 |
| 2048 | 4732 |
| 2049 | 4733 |

TABLE 2-continued

ABIOTIC STRESS RESPONSIVE GENE REGULATORY SEQUENCES

| SEQ ID NO: | REGULATORY REGION |
|---|---|
| 2050 | 4734 |
| 2051 | 4735 |
| 2052 | 4736 |
| 2053 | 4737 |
| 2054 | 4738 |
| 2055 | 4739 |
| 2056 | 4740 |
| 2057 | 4741 |
| 2058 | 4742 |
| 2059 | 4743 |
| 2060 | 4744 |
| 2061 | 4745 |
| 2062 | 4746 |
| 2063 | 4747 |
| 2064 | 4748 |
| 2065 | 4749 |
| 2066 | 4750 |
| 2067 | 4751 |
| 2068 | 4752 |
| 2069 | 4753 |
| 2070 | 4754 |
| 2071 | 4755 |
| 2072 | 4756 |
| 2073 | 4757 |
| 2074 | 4758 |
| 2075 | 4759 |
| 2076 | 4760 |
| 2077 | 4761 |
| 2078 | 4762 |
| 2079 | 4763 |
| 2080 | 4764 |
| 2081 | 4765 |
| 2082 | 4766 |
| 2083 | 4767 |
| 2084 | 4768 |
| 2085 | 4769 |
| 2086 | 4770 |
| 2087 | 4771 |
| 2088 | 4772 |
| 2089 | 4773 |
| 2090 | 4774 |
| 2091 | 4775 |
| 2092 | 4776 |
| 2093 | 4777 |
| 2094 | 4778 |
| 2095 | 4779 |
| 2096 | 4780 |
| 2097 | 4781 |
| 2098 | 4782 |
| 2099 | 4783 |
| 2100 | 4784 |
| 2101 | 4785 |
| 2102 | 4786 |
| 2103 | 4787 |
| 2104 | 4788 |
| 2105 | 4789 |
| 2106 | 4790 |
| 2107 | 4791 |
| 2108 | 4792 |
| 2109 | 4793 |
| 2110 | 4794 |
| 2111 | 4795 |
| 2112 | 4796 |
| 2113 | 4797 |
| 2114 | 4798 |
| 2115 | 4799 |
| 2116 | 4800 |
| 2117 | 4801 |
| 2118 | 4802 |
| 2119 | 4803 |
| 2120 | 4804 |
| 2121 | 4805 |
| 2122 | 4806 |
| 2123 | 4807 |
| 2124 | 4808 |
| 2125 | 4809 |
| 2126 | 4810 |
| 2127 | 4811 |
| 2128 | 4812 |
| 2129 | 4813 |
| 2130 | 4814 |
| 2131 | 4815 |
| 2132 | 4816 |
| 2133 | 4817 |
| 2134 | 4818 |
| 2135 | 4819 |
| 2136 | 4820 |
| 2137 | 4821 |
| 2138 | 4822 |
| 2139 | 4823 |
| 2140 | 4824 |
| 2141 | 4825 |
| 2142 | 4826 |
| 2143 | 4827 |
| 2144 | 4828 |
| 2145 | 4829 |
| 2146 | 4830 |
| 2147 | 4831 |
| 2148 | 4832 |
| 2149 | 4833 |
| 2150 | 4834 |
| 2151 | NONE |
| 2152 | 4835 |
| 2153 | 4836 |
| 2154 | 4837 |
| 2155 | 4838 |
| 2156 | 4839 |
| 2157 | 4840 |
| 2158 | 4841 |
| 2159 | 4842 |
| 2160 | 4843 |
| 2161 | 4844 |
| 2162 | 4845 |
| 2163 | 4846 |
| 2164 | 4847 |
| 2165 | 4848 |
| 2166 | 4849 |
| 2167 | 4850 |
| 2168 | 4851 |
| 2169 | 4852 |
| 2170 | 4853 |
| 2171 | 4854 |
| 2172 | 4855 |
| 2173 | 4856 |
| 2174 | 4857 |
| 2175 | 4858 |
| 2176 | 4859 |
| 2177 | 4860 |
| 2178 | 4861 |
| 2179 | 4862 |
| 2180 | 4863 |
| 2181 | 4864 |
| 2182 | 4865 |
| 2183 | 4866 |
| 2184 | 4867 |
| 2185 | 4868 |
| 2186 | 4869 |
| 2187 | 4870 |
| 2188 | 4871 |
| 2189 | 4872 |
| 2190 | 4873 |
| 2191 | 4874 |
| 2192 | 4875 |
| 2193 | 4876 |
| 2194 | 4877 |
| 2195 | 4878 |
| 2196 | 4879 |
| 2197 | 4880 |

TABLE 2-continued

ABIOTIC STRESS RESPONSIVE GENE REGULATORY SEQUENCES

| SEQ ID NO: | REGULATORY REGION |
|---|---|
| 2198 | 4881 |
| 2199 | 4882 |
| 2200 | 4883 |
| 2201 | 4884 |
| 2202 | 4885 |
| 2203 | 4886 |
| 2204 | 4887 |
| 2205 | 4888 |
| 2206 | 4889 |
| 2207 | 4890 |
| 2208 | 4891 |
| 2209 | 4892 |
| 2210 | 4893 |
| 2211 | 4894 |
| 2212 | 4895 |
| 2213 | 4896 |
| 2214 | 4897 |
| 2215 | 4898 |
| 2216 | 4899 |
| 2217 | 4900 |
| 2218 | 4901 |
| 2219 | 4902 |
| 2220 | 4903 |
| 2221 | 4904 |
| 2222 | 4905 |
| 2223 | 4906 |
| 2224 | 4907 |
| 2225 | 4908 |
| 2226 | 4909 |
| 2227 | 4910 |
| 2228 | 4911 |
| 2229 | 4912 |
| 2230 | 4913 |
| 2231 | 4914 |
| 2232 | 4915 |
| 2233 | 4916 |
| 2234 | 4917 |
| 2235 | 4918 |
| 2236 | 4919 |
| 2237 | 4920 |
| 2238 | 4921 |
| 2239 | 4922 |
| 2240 | 4923 |
| 2241 | 4924 |
| 2242 | 4925 |
| 2243 | 4926 |
| 2244 | 4927 |
| 2245 | 4928 |
| 2246 | 4929 |
| 2247 | 4930 |
| 2248 | NONE |
| 2249 | 4931 |
| 2250 | 4932 |
| 2251 | 4933 |
| 2252 | 4934 |
| 2253 | 4935 |
| 2254 | 4936 |
| 2255 | 4937 |
| 2256 | 4938 |
| 2257 | 4939 |
| 2258 | 4940 |
| 2259 | 4941 |
| 2260 | 4942 |
| 2261 | 4943 |
| 2262 | 4944 |
| 2263 | 4945 |
| 2264 | 4946 |
| 2265 | 4947 |
| 2266 | 4948 |
| 2267 | 4949 |
| 2268 | 4950 |
| 2269 | 4951 |
| 2270 | 4952 |
| 2271 | 4953 |
| 2272 | 4954 |
| 2273 | 4955 |
| 2274 | 4956 |
| 2275 | 4957 |
| 2276 | 4958 |
| 2277 | 4959 |
| 2278 | 4960 |
| 2279 | 4961 |
| 2280 | 4962 |
| 2281 | 4963 |
| 2282 | 4964 |
| 2283 | 4965 |
| 2284 | 4966 |
| 2285 | 4967 |
| 2286 | 4968 |
| 2287 | 4969 |
| 2288 | 4970 |
| 2289 | 4971 |
| 2290 | 4972 |
| 2291 | 4973 |
| 2292 | 4974 |
| 2293 | 4975 |
| 2294 | 4976 |
| 2295 | 4977 |
| 2296 | 4978 |
| 2297 | 4979 |
| 2298 | 4980 |
| 2299 | 4981 |
| 2300 | 4982 |
| 2301 | 4983 |
| 2302 | 4984 |
| 2303 | 4985 |
| 2304 | 4986 |
| 2305 | 4987 |
| 2306 | 4988 |
| 2307 | 4989 |
| 2308 | 4990 |
| 2309 | 4991 |
| 2310 | 4992 |
| 2311 | 4993 |
| 2312 | 4994 |
| 2313 | 4995 |
| 2314 | 4996 |
| 2315 | 4997 |
| 2316 | 4998 |
| 2317 | 4999 |
| 2318 | 5000 |
| 2319 | 5001 |
| 2320 | 5002 |
| 2321 | 5003 |
| 2322 | 5004 |
| 2323 | 5005 |
| 2324 | 5006 |
| 2325 | 5007 |
| 2326 | 5008 |
| 2327 | 5009 |
| 2328 | 5010 |
| 2329 | 5011 |
| 2330 | 5012 |
| 2331 | 5013 |
| 2332 | 5014 |
| 2333 | 5015 |
| 2334 | 5016 |
| 2335 | 5017 |
| 2336 | 5018 |
| 2337 | 5019 |
| 2338 | 5020 |
| 2339 | 5021 |
| 2340 | NONE |
| 2341 | 5022 |
| 2342 | 5023 |
| 2343 | 5024 |
| 2344 | 5025 |
| 2345 | 5026 |

TABLE 2-continued

ABIOTIC STRESS RESPONSIVE GENE REGULATORY SEQUENCES

| SEQ ID NO: | REGULATORY REGION |
|---|---|
| 2346 | 5027 |
| 2347 | 5028 |
| 2348 | 5029 |
| 2349 | 5030 |
| 2350 | 5031 |
| 2351 | 5032 |
| 2352 | 5033 |
| 2353 | 5034 |
| 2354 | 5035 |
| 2355 | 5036 |
| 2356 | 5037 |
| 2357 | 5038 |
| 2358 | 5039 |
| 2359 | 5040 |
| 2360 | 5041 |
| 2361 | 5042 |
| 2362 | 5043 |
| 2363 | 5044 |
| 2364 | 5045 |
| 2365 | 5046 |
| 2366 | 5047 |
| 2367 | 5048 |
| 2368 | 5049 |
| 2369 | 5050 |
| 2370 | 5051 |
| 2371 | NONE |
| 2372 | 5052 |
| 2373 | 5053 |
| 2374 | 5054 |
| 2375 | 5055 |
| 2376 | 5056 |
| 2377 | 5057 |
| 2378 | 5058 |
| 2379 | 5059 |
| 2380 | 5060 |
| 2381 | 5061 |
| 2382 | 5062 |
| 2383 | 5063 |
| 2384 | 5064 |
| 2385 | 5065 |
| 2386 | 5066 |
| 2387 | 5067 |
| 2388 | 5068 |
| 2389 | 5069 |
| 2390 | 5070 |
| 2391 | 5071 |
| 2392 | 5072 |
| 2393 | 5073 |
| 2394 | 5074 |
| 2395 | 5075 |
| 2396 | 5076 |
| 2397 | 5077 |
| 2398 | 5078 |
| 2399 | 5079 |
| 2400 | 5080 |
| 2401 | 5081 |
| 2402 | 5082 |
| 2403 | 5083 |
| 2404 | 5084 |
| 2405 | 5085 |
| 2406 | 5086 |
| 2407 | 5087 |
| 2408 | 5088 |
| 2409 | 5089 |
| 2410 | 5090 |
| 2411 | 5091 |
| 2412 | 5092 |
| 2413 | 5093 |
| 2414 | 5094 |
| 2415 | 5095 |
| 2416 | 5096 |
| 2417 | 5097 |
| 2418 | 5098 |
| 2419 | 5099 |
| 2420 | 5100 |
| 2421 | 5101 |
| 2422 | 5102 |
| 2423 | 5103 |
| 2424 | 5104 |
| 2425 | 5105 |
| 2426 | 5106 |
| 2427 | 5107 |
| 2428 | 5108 |
| 2429 | 5109 |
| 2430 | 5110 |
| 2431 | 5111 |
| 2432 | 5112 |
| 2433 | 5113 |
| 2434 | 5114 |
| 2435 | 5115 |
| 2436 | 5116 |
| 2437 | 5117 |
| 2438 | 5118 |
| 2439 | 5119 |
| 2440 | 5120 |
| 2441 | 5121 |
| 2442 | 5122 |
| 2443 | NONE |
| 2444 | 5123 |
| 2445 | 5124 |
| 2446 | 5125 |
| 2447 | 5126 |
| 2448 | 5127 |
| 2449 | 5128 |
| 2450 | 5129 |
| 2451 | 5130 |
| 2452 | 5131 |
| 2453 | 5132 |
| 2454 | 5133 |
| 2455 | 5134 |
| 2456 | 5135 |
| 2457 | 5136 |
| 2458 | 5137 |
| 2459 | 5138 |
| 2460 | 5139 |
| 2461 | 5140 |
| 2462 | 5141 |
| 2463 | 5142 |
| 2464 | 5143 |
| 2465 | 5144 |
| 2466 | 5145 |
| 2467 | 5146 |
| 2468 | 5147 |
| 2469 | NONE |
| 2470 | 5148 |
| 2471 | 5149 |
| 2472 | 5150 |
| 2473 | 5151 |
| 2474 | 5152 |
| 2475 | 5153 |
| 2476 | 5154 |
| 2477 | 5155 |
| 2478 | 5156 |
| 2479 | 5157 |
| 2480 | 5158 |
| 2481 | 5159 |
| 2482 | 5160 |
| 2483 | 5161 |
| 2484 | 5162 |
| 2485 | 5163 |
| 2486 | 5164 |
| 2487 | 5165 |
| 2488 | 5166 |
| 2489 | 5167 |
| 2490 | 5168 |
| 2491 | 5169 |
| 2492 | 5170 |
| 2493 | 5171 |

TABLE 2-continued

ABIOTIC STRESS RESPONSIVE GENE REGULATORY SEQUENCES

| SEQ ID NO: | REGULATORY REGION |
|---|---|
| 2494 | 5172 |
| 2495 | 5173 |
| 2496 | 5174 |
| 2497 | 5175 |
| 2498 | 5176 |
| 2499 | 5177 |
| 2500 | 5178 |
| 2501 | 5179 |
| 2502 | 5180 |
| 2503 | 5181 |
| 2504 | 5182 |
| 2505 | 5183 |
| 2506 | 5184 |
| 2507 | 5185 |
| 2508 | 5186 |
| 2509 | 5187 |
| 2510 | 5188 |
| 2511 | 5189 |
| 2512 | 5190 |
| 2513 | 5191 |
| 2514 | 5192 |
| 2515 | 5193 |
| 2516 | 5194 |
| 2517 | 5195 |
| 2518 | 5196 |
| 2519 | 5197 |
| 2520 | 5198 |
| 2521 | 5199 |
| 2522 | 5200 |
| 2523 | 5201 |
| 2524 | 5202 |
| 2525 | 5203 |
| 2526 | 5204 |
| 2527 | 5205 |
| 2528 | 5206 |
| 2529 | 5207 |
| 2530 | 5208 |
| 2531 | 5209 |
| 2532 | 5210 |
| 2533 | 5211 |
| 2534 | 5212 |
| 2535 | 5213 |
| 2536 | 5214 |
| 2537 | 5215 |
| 2538 | 5216 |
| 2539 | 5217 |
| 2540 | 5218 |
| 2541 | 5219 |
| 2542 | 5220 |
| 2543 | 5221 |
| 2544 | 5222 |
| 2545 | 5223 |
| 2546 | 5224 |
| 2547 | 5225 |
| 2548 | 5226 |
| 2549 | 5227 |
| 2550 | 5228 |
| 2551 | 5229 |
| 2552 | 5230 |
| 2553 | 5231 |
| 2554 | 5232 |
| 2555 | 5233 |
| 2556 | 5234 |
| 2557 | 5235 |
| 2558 | 5236 |
| 2559 | 5237 |
| 2560 | 5238 |
| 2561 | 5239 |
| 2562 | 5240 |
| 2563 | 5241 |
| 2564 | 5242 |
| 2565 | 5243 |
| 2566 | 5244 |
| 2567 | 5245 |
| 2568 | 5246 |
| 2569 | 5247 |
| 2570 | 5248 |
| 2571 | 5249 |
| 2572 | 5250 |
| 2573 | 5251 |
| 2574 | 5252 |
| 2575 | 5253 |
| 2576 | 5254 |
| 2577 | 5255 |
| 2578 | 5256 |
| 2579 | 5257 |
| 2580 | 5258 |
| 2581 | 5259 |
| 2582 | 5260 |
| 2583 | 5261 |
| 2584 | 5262 |
| 2585 | 5263 |
| 2586 | 5264 |
| 2587 | 5265 |
| 2588 | 5266 |
| 2589 | 5267 |
| 2590 | 5268 |
| 2591 | 5269 |
| 2592 | 5270 |
| 2593 | 5271 |
| 2594 | 5272 |
| 2595 | 5273 |
| 2596 | 5274 |
| 2597 | 5275 |
| 2598 | 5276 |
| 2599 | NONE |
| 2600 | 5277 |
| 2601 | 5278 |
| 2602 | 5279 |
| 2603 | 5280 |
| 2604 | 5281 |
| 2605 | 5282 |
| 2606 | 5283 |
| 2607 | 5284 |
| 2608 | 5285 |
| 2609 | 5286 |
| 2610 | 5287 |
| 2611 | 5288 |
| 2612 | 5289 |
| 2613 | 5290 |
| 2614 | 5291 |
| 2615 | 5292 |
| 2616 | 5293 |
| 2617 | 5294 |
| 2618 | 5295 |
| 2619 | 5296 |
| 2620 | 5297 |
| 2621 | 5298 |
| 2622 | 5299 |
| 2623 | 5300 |
| 2624 | 5301 |
| 2625 | 5302 |
| 2626 | 5303 |
| 2627 | 5304 |
| 2628 | 5305 |
| 2629 | 5306 |
| 2630 | 5307 |
| 2631 | 5308 |
| 2632 | 5309 |
| 2633 | 5310 |
| 2634 | 5311 |
| 2635 | 5312 |
| 2636 | 5313 |
| 2637 | 5314 |
| 2638 | 5315 |
| 2639 | 5316 |
| 2640 | 5317 |
| 2641 | 5318 |

TABLE 2-continued

ABIOTIC STRESS RESPONSIVE GENE REGULATORY SEQUENCES

| SEQ ID NO: | REGULATORY REGION |
|---|---|
| 2642 | 5319 |
| 2643 | 5320 |
| 2644 | 5321 |
| 2645 | 5322 |
| 2646 | 5323 |
| 2647 | 5324 |
| 2648 | 5325 |
| 2649 | 5326 |
| 2650 | 5327 |
| 2651 | 5328 |
| 2652 | 5329 |
| 2653 | 5330 |
| 2654 | 5331 |
| 2655 | 5332 |
| 2656 | 5333 |
| 2657 | 5334 |
| 2658 | 5335 |
| 2659 | 5336 |
| 2660 | 5337 |
| 2661 | 5338 |
| 2662 | 5339 |
| 2663 | 5340 |
| 2664 | 5341 |
| 2665 | 5342 |
| 2666 | 5343 |
| 2667 | 5344 |
| 2668 | 5345 |
| 2669 | 5346 |
| 2670 | 5347 |
| 2671 | 5348 |
| 2672 | 5349 |
| 2673 | 5350 |
| 2674 | 5351 |
| 2675 | 5352 |
| 2676 | 5353 |
| 2677 | 5354 |
| 2678 | 5355 |
| 2679 | 5356 |
| 2680 | 5357 |
| 2681 | NONE |
| 2682 | 5358 |
| 2683 | 5359 |
| 2684 | 5360 |
| 2685 | 5361 |
| 2686 | 5362 |
| 2687 | 5363 |
| 2688 | 5364 |
| 2689 | 5365 |
| 2690 | 5366 |
| 2691 | 5367 |
| 2692 | 5368 |
| 2693 | 5369 |
| 2694 | 5370 |
| 2695 | 5371 |
| 2696 | 5372 |
| 2697 | 5373 |
| 2698 | 5374 |
| 2699 | 5375 |
| 2700 | 5376 |
| 2701 | 5377 |
| 2702 | 5378 |
| 2703 | 5379 |

TABLE 3

COLD RESPONSIVE SEQUENCES

| SEQ ID NO: | AFFYMETRIX ID NO: |
|---|---|
| 1 | 11991_G_AT |
| 2 | 11992_AT |
| 3 | 11997_AT |

TABLE 3-continued

COLD RESPONSIVE SEQUENCES

| SEQ ID NO: | AFFYMETRIX ID NO: |
|---|---|
| 4 | 11998_AT |
| 5 | 12001_AT |
| 6 | 12006_S_AT |
| 7 | 12007_AT |
| 8 | 12009_AT |
| 9 | 12018_AT |
| 10 | 12022_AT |
| 11 | 12026_AT |
| 12 | 12031_AT |
| 13 | 12047_AT |
| 14 | 12051_AT |
| 15 | 12052_AT |
| 16 | 12053_AT |
| 17 | 12060_AT |
| 18 | 12072_AT |
| 19 | 12074_AT |
| 20 | 12102_AT |
| 21 | 12112_AT |
| 22 | 12117_AT |
| 23 | 12125_AT |
| 24 | 12130_AT |
| 25 | 12143_AT |
| 26 | 12145_S_AT |
| 27 | 12149_AT |
| 28 | 12156_AT |
| 29 | 12163_AT |
| 30 | 12166_I_AT |
| 31 | 12167_AT |
| 32 | 12169_I_AT |
| 33 | 12175_AT |
| 34 | 12176_AT |
| 35 | 12179_AT |
| 36 | 12187_AT 15920_I_AT |
| 37 | 12195_AT |
| 38 | 12196_AT |
| 39 | 12198_AT |
| 40 | 12200_AT |
| 41 | 12202_AT |
| 42 | 12214_G_AT |
| 43 | 12219_AT |
| 44 | 12224_AT |
| 45 | 12226_AT |
| 46 | 12233_AT |
| 47 | 12240_AT |
| 48 | 12253_G_AT |
| 49 | 12256_AT |
| 50 | 12269_S_AT |
| 51 | 12270_AT |
| 52 | 12284_AT |
| 53 | 12287_S_AT 17570_G_AT |
| 54 | 12293_AT |
| 55 | 12294_S_AT |
| 56 | 12300_AT |
| 57 | 12307_AT |
| 58 | 12312_AT |
| 59 | 12315_AT |
| 60 | 12324_I_AT |
| 61 | 12331_S_AT |
| 62 | 12336_AT |
| 63 | 12344_AT |
| 64 | 12348_AT |
| 65 | 12353_AT |
| 66 | 12359_S_AT |
| 67 | 12372_AT |
| 68 | 12374_I_AT 12726_F_AT |
| 69 | 12390_AT |
| 70 | 12395_S_AT |
| 71 | 12405_AT |
| 72 | 12408_AT |

TABLE 3-continued

COLD RESPONSIVE SEQUENCES

| SEQ ID NO: | AFFYMETRIX ID NO: |
|---|---|
| 73 | 12410_G_AT |
| 74 | 12419_AT |
| 75 | 12427_AT |
| 76 | 12431_AT |
| 77 | 12436_AT |
| 78 | 12438_AT |
| 79 | 12443_S_AT |
| 80 | 12447_AT |
| 81 | 12450_S_AT |
| 82 | 12452_AT |
| 83 | 12474_AT |
| 84 | 12477_AT |
| 85 | 12491_AT |
| 86 | 12497_AT |
| 87 | 12500_S_AT |
| 88 | 12503_AT |
| 89 | 12515_AT |
| 90 | 12516_S_AT |
| 91 | 12523_AT |
| 92 | 12526_AT |
| 93 | 12527_AT |
| 94 | 12532_AT |
| 95 | 12534_G_AT |
| 96 | 12544_AT |
| 97 | 12549_S_AT |
| 98 | 12550_S_AT |
|  | 17103_S_AT |
| 99 | 12552_AT |
| 100 | 12555_S_AT |
| 101 | 12576_S_AT |
| 102 | 12581_S_AT |
|  | 16645_S_AT |
| 103 | 12587_AT |
| 104 | 12597_AT |
| 105 | 12602_AT |
| 106 | 12610_AT |
| 107 | 12631_AT |
| 108 | 12646_AT |
| 109 | 12649_AT |
| 110 | 12650_AT |
| 111 | 12653_AT |
| 112 | 12661_AT |
| 113 | 12666_AT |
| 114 | 12674_AT |
| 115 | 12675_S_AT |
| 116 | 12678_I_AT |
| 117 | 12681_S_AT |
| 118 | 12688_AT |
| 119 | 12702_AT |
| 120 | 12705_F_AT |
| 121 | 12736_F_AT |
| 122 | 12737_F_AT |
| 123 | 12758_AT |
| 124 | 12760_G_AT |
| 125 | 12762_R_AT |
| 126 | 12764_F_AT |
| 127 | 12766_AT |
|  | 15115_F_AT |
| 128 | 12767_AT |
| 129 | 12768_AT |
| 130 | 12772_AT |
| 131 | 12773_AT |
| 132 | 12776_AT |
| 133 | 12788_AT |
| 134 | 12793_AT |
| 135 | 12794_AT |
| 136 | 12802_AT |
| 137 | 12809_G_AT |
| 138 | 12812_AT |
| 139 | 12815_AT |
| 140 | 12816_AT |
| 141 | 12818_AT |
| 142 | 12824_S_AT |

TABLE 3-continued

COLD RESPONSIVE SEQUENCES

| SEQ ID NO: | AFFYMETRIX ID NO: |
|---|---|
| 143 | 12828_S_AT |
| 144 | 12842_S_AT |

TABLE 6

(cont): 2X DOWN COLD, ONLY

| SEQ ID NO: | AFFYMETRIX ID NO: |
|---|---|
| 145 | 12846_S_AT |
| 146 | 12858_AT |
| 147 | 12860_S_AT |
| 148 | 12861_S_AT |
| 149 | 12881_S_AT |
|  | 17600_S_AT |
| 150 | 12889_S_AT |
| 151 | 12901_S_AT |
| 152 | 12902_AT |
| 153 | 12904_S_AT |
| 154 | 12905_S_AT |
| 155 | 12908_S_AT |
| 156 | 12910_S_AT |
|  | 16385_S_AT |
| 157 | 12914_S_AT |
|  | 15783_S_AT |
|  | 17645_S_AT |
| 158 | 12916_S_AT |
| 159 | 12923_S_AT |
| 160 | 12926_S_AT |
| 161 | 12927_S_AT |
| 162 | 12931_S_AT |
| 163 | 12937_R_AT |
| 164 | 12941_G_AT |
| 165 | 12942_AT |
| 166 | 12947_AT |
| 167 | 12949_AT |
| 168 | 12953_AT |
| 169 | 12956_I_AT |
| 170 | 12959_AT |
| 171 | 12966_S_AT |
| 172 | 12975_AT |
| 173 | 12983_AT |
| 174 | 12984_AT |
| 175 | 12987_S_AT |
| 176 | 12994_S_AT |
| 177 | 13002_AT |
| 178 | 13009_I_AT |
| 179 | 13011_AT |
| 180 | 13018_AT |
| 181 | 13023_AT |
| 182 | 13024_AT |
| 183 | 13034_S_AT |
| 184 | 13046_G_AT |
| 185 | 13048_S_AT |
|  | 13495_S_AT |
| 186 | 13054_AT |
| 187 | 13067_S_AT |
| 188 | 13068_AT |
| 189 | 13073_S_AT |
| 190 | 13078_S_AT |
| 191 | 13079_AT |
| 192 | 13081_S_AT |
| 193 | 13083_AT |
| 194 | 13086_R_AT |
| 195 | 13087_AT |
| 196 | 13090_AT |
| 197 | 13092_S_AT |
|  | 16950_S_AT |
| 198 | 13098_AT |
| 199 | 13100_AT |
| 200 | 13103_AT |
| 201 | 13105_AT |
| 202 | 13107_S_AT |
| 203 | 13108_AT |

TABLE 6-continued (cont): 2X DOWN COLD, ONLY

| | |
|---|---|
| 204 | 13109_AT |
| 205 | 13114_AT |
| 206 | 13118_F_AT |
| 207 | 13119_AT |
| 208 | 13120_AT |
| 209 | 13123_AT |
| 210 | 13128_AT |
| 211 | 13133_S_AT |
| | 17430_S_AT |
| 212 | 13135_S_AT |
| 213 | 13139_AT |
| 214 | 13140_AT |
| 215 | 13143_AT |
| 216 | 13151_G_AT |
| 217 | 13160_AT |
| 218 | 13161_AT |
| 219 | 13162_AT |
| 220 | 13165_AT |
| 221 | 13166_AT |
| 222 | 13167_AT |
| 223 | 13179_AT |
| 224 | 13181_AT |
| 225 | 13185_AT |
| 226 | 13193_S_AT |
| 227 | 13213_S_AT |
| | 16004_S_AT |
| 228 | 13219_S_AT |
| | 20288_G_AT |
| 229 | 13220_S_AT |
| | 13221_AT |
| | 18929_S_AT |
| 230 | 13233_AT |
| | 14301_S_AT |
| 231 | 13243_R_AT |
| 232 | 13254_S_AT |
| 233 | 13260_S_AT |
| | 15660_S_AT |
| 234 | 13273_S_AT |
| | 16105_S_AT |
| 235 | 13274_S_AT |
| | 17077_S_AT |
| 236 | 13276_S_AT |
| 237 | 13278_F_AT |
| 238 | 13285_S_AT |
| 239 | 13288_S_AT |
| | 17043_S_AT |
| 240 | 13292_S_AT |
| 241 | 13296_S_AT |
| 242 | 13297_S_AT |
| 243 | 13299_S_AT |
| | 15166_S_AT |
| 244 | 13332_AT |
| 245 | 13347_AT |
| 246 | 13351_AT |
| 247 | 13352_AT |
| 248 | 13355_AT |
| 249 | 13404_AT |
| 250 | 13422_AT |
| 251 | 13459_AT |
| 252 | 13460_AT |
| 253 | 13461_S_AT |
| 254 | 13467_AT |
| 255 | 13488_AT |
| 256 | 13523_S_AT |
| 257 | 13529_AT |
| 258 | 13539_I_AT |
| | 14631_S_AT |
| 259 | 13541_AT |
| 260 | 13542_AT |
| 261 | 13545_S_AT |
| 262 | 13552_AT |
| 263 | 13556_I_AT |
| 264 | 13561_AT |
| 265 | 13563_S_AT |
| 266 | 13567_AT |
| 267 | 13568_AT |
| 268 | 13571_AT |

TABLE 6-continued (cont): 2X DOWN COLD, ONLY

| | |
|---|---|
| 269 | 13575_AT |
| 270 | 13576_AT |
| 271 | 13583_AT |
| 272 | 13598_AT |
| 273 | 13601_AT |
| 274 | 13604_AT |
| 275 | 13613_AT |
| 276 | 13616_S_AT |
| | 16544_S_AT |
| 277 | 13617_AT |
| 278 | 13618_S_AT |
| 279 | 13619_AT |
| 280 | 13621_G_AT |
| 281 | 13623_R_AT |
| 282 | 13629_S_AT |
| 283 | 13631_AT |
| 284 | 13635_AT |
| 285 | 13646_AT |
| 286 | 13650_AT |
| 287 | 13653_AT |
| 288 | 13655_AT |
| 289 | 13656_AT |
| 290 | 13657_AT |
| 291 | 13666_S_AT |
| | 17083_S_AT |
| 292 | 13667_S_AT |
| 293 | 13669_SAT |
| | 17074_S_AT |
| 294 | 13670_S_AT |
| | 15206_S_AT |
| 295 | 13671_S_AT |
| | 16805_S_AT |
| 296 | 13678_S_AT |
| 297 | 13688_S_AT |
| 298 | 13690_S_AT |
| | 16065_S_AT |
| 299 | 13691_S_AT |
| | 16117_S_AT |
| 300 | 13692_S_AT |
| | 16118_S_AT |
| 301 | 13700_AT |
| 302 | 13704_S_AT |
| 303 | 13714_AT |
| 304 | 13715_AT |
| 305 | 13724_AT |
| 306 | 13748_AT |
| 307 | 13759_AT |
| 308 | 13767_AT |
| 309 | 13785_AT |
| 310 | 13803_AT |
| 311 | 13850_I_AT |
| 312 | 13876_AT |
| 313 | 13880_S_AT |
| 314 | 13883_AT |
| 315 | 13887_S_AT |
| 316 | 13895_AT |
| 317 | 13904_S_AT |
| | 18722_S_AT |
| 318 | 13906_S_AT |
| 319 | 13908_S_AT |
| | 18597_AT |
| 320 | 13923_AT |
| 321 | 13927_AT |
| 322 | 13932_AT |
| 323 | 13935_AT |
| 324 | 13940_AT |
| 325 | 13949_S_AT |
| 326 | 13954_G_AT |
| 327 | 13971_S_AT |
| 328 | 13973_AT |
| 329 | 13983_AT |
| 330 | 13985_S_AT |
| 331 | 13987_S_AT |
| | 18738_F_AT |
| 332 | 13989_AT |
| | 20674_S_AT |
| 333 | 14010_AT |

TABLE 6-continued (cont): 2X DOWN COLD, ONLY

| | |
|---|---|
| 334 | 14013_AT |
| 335 | 14014_AT |
| 336 | 14019_AT |
| 337 | 14021_R_AT |
| 338 | 14025_S_AT |
| | 18909_S_AT |
| 339 | 14027_AT |
| 340 | 14030_AT |
| 341 | 14044_AT |
| 342 | 14048_AT |
| 343 | 14056_AT |
| 344 | 14057_AT |
| 345 | 14058_AT |
| 346 | 14059_AT |
| 347 | 14061_AT |
| 348 | 14068_S_AT |
| 349 | 14072_AT |
| 350 | 14073_AT |
| 351 | 14074_AT |
| 352 | 14084_AT |
| 353 | 14095_S_AT |
| 354 | 14100_AT |
| 355 | 14101_AT |
| 356 | 14103_AT |
| 357 | 14105_AT |
| 358 | 14106_AT |
| 359 | 14121_AT |
| 360 | 14129_S_AT |
| 361 | 14133_S_AT |
| 362 | 14143_AT |
| 363 | 14145_AT |
| 364 | 14148_AT |
| 365 | 14186_AT |
| 366 | 14194_AT |
| 367 | 14196_AT |
| 368 | 14223_AT |
| 369 | 14234_AT |
| 370 | 14236_AT |
| 371 | 14251_F_AT |
| 372 | 14252_F_AT |
| 373 | 14270_AT |
| 374 | 14298_G_AT |
| | 17581_G_AT |
| 375 | 14303_S_AT |
| 376 | 14312_AT |
| 377 | 14316_AT |
| 378 | 14339_AT |
| 379 | 14366_AT |
| 380 | 14369_AT |
| 381 | 14388_AT |
| 382 | 14392_G_AT |
| 383 | 14393_AT |
| 384 | 14421_AT |
| 385 | 14436_AT |
| 386 | 14448_AT |
| 387 | 14450_AT |
| 388 | 14454_AT |
| 389 | 14459_AT |
| 390 | 14478_AT |
| 391 | 14482_AT |
| 392 | 14485_AT |
| 393 | 14492_S_AT |
| 394 | 14505_AT |
| 395 | 14510_AT |
| 396 | 14511_AT |
| 397 | 14517_AT |
| 398 | 14519_AT |
| 399 | 14525_S_AT |
| 400 | 14527_AT |
| 401 | 14534_S_AT |
| 402 | 14538_R_AT |
| 403 | 14554_AT |
| 404 | 14558_AT |
| 405 | 14559_S_AT |
| 406 | 14566_AT |
| 407 | 14572_AT |
| 408 | 14579_AT |
| 409 | 14587_AT |
| 410 | 14591_AT |
| 411 | 14595_AT |
| 412 | 14602_AT |
| 413 | 14603_AT |
| 414 | 14605_AT |
| 415 | 14620_S_AT |
| 416 | 14626_S_AT |
| 417 | 14630_S_AT |
| | 16559_S_AT |
| 418 | 14637_S_AT |
| | 17122_S_AT |
| 419 | 14642_F_AT |
| 420 | 14650_S_AT |
| | 15150_S_AT |
| 421 | 14654_S_AT |
| 422 | 14667_S_AT |
| | 18299_S_AT |
| 423 | 14669_S_AT |
| | 16136_S_AT |
| 424 | 14672_S_AT |
| 425 | 14679_S_AT |
| 426 | 14682_I_AT |
| 427 | 14689_AT |
| 428 | 14697_G_AT |
| | 16902_AT |
| 429 | 14701_S_AT |
| | 14734_S_AT |
| 430 | 14703_AT |
| 431 | 14711_S_AT |
| 432 | 14712_S_AT |
| | 20530_S_AT |
| 433 | 14713_S_AT |
| 434 | 14715_S_AT |
| 435 | 14728_S_AT |
| 436 | 14731_S_AT |
| 437 | 14781_AT |
| 438 | 14797_S_AT |
| 439 | 14800_AT |
| 440 | 14809_AT |
| 441 | 14843_AT |
| 442 | 14847_AT |
| 443 | 14872_AT |
| 444 | 14886_AT |
| 445 | 14896_AT |
| 446 | 14900_AT |
| 447 | 14908_AT |
| 448 | 14912_AT |
| 449 | 14914_AT |
| 450 | 14942_AT |
| 451 | 14945_AT |
| 452 | 14955_AT |
| 453 | 14957_S_AT |
| 454 | 14958_AT |
| 455 | 14965_AT |
| 456 | 14974_AT |
| 457 | 14980_AT |
| 458 | 14981_AT |
| 459 | 14984_S_AT |
| 460 | 14995_AT |
| 461 | 15004_AT |
| 462 | 15009_AT |
| 463 | 15010_AT |
| 464 | 15024_AT |
| 465 | 15026_AT |
| 466 | 15036_R_AT |
| 467 | 15054_AT |
| 468 | 15056_AT |
| 469 | 15057_AT |
| 470 | 15066_AT |
| 471 | 15073_AT |
| 472 | 15081_AT |
| 473 | 15083_AT |
| 474 | 15091_AT |
| 475 | 15097_S_AT |
| 476 | 15101_S_AT |
| 477 | 15102_S_AT |

TABLE 6-continued (cont): 2X DOWN COLD, ONLY

| | |
|---|---|
| 478 | 15107_S_AT |
| 479 | 15112_S_AT |
| 480 | 15116_F_AT |
| 481 | 15118_S_AT |
| 482 | 15122_S_AT |
| 483 | 15130_S_AT |
| 484 | 15131_S_AT |
| 485 | 15132_S_AT |
| | 17585_S_AT |
| 486 | 15139_S_AT |
| 487 | 15143_S_AT |
| 488 | 15146_S_AT |
| 489 | 15159_S_AT |
| | 15160_S_AT |
| 490 | 15162_S_AT |
| 491 | 15167_S_AT |
| 492 | 15171_S_AT |
| 493 | 15174_F_AT |
| 494 | 15178_S_AT |
| 495 | 15185_S_AT |
| | 18023_S_AT |
| 496 | 15188_S_AT |
| 497 | 15193_S_AT |
| 498 | 15196_S_AT |
| 499 | 15197_S_AT |
| 500 | 15201_F_AT |
| 501 | 15213_S_AT |
| 502 | 15243_AT |
| 503 | 15256_AT |
| 504 | 15270_AT |
| 505 | 15319_AT |
| 506 | 15325_AT |
| 507 | 15337_AT |
| 508 | 15341_AT |
| 509 | 15343_AT |
| 510 | 15348_AT |
| 511 | 15350_AT |
| 512 | 15355_S_AT |
| 513 | 15367_AT |
| 514 | 15372_AT |
| 515 | 15379_AT |
| 516 | 15381_AT |
| 517 | 15383_AT |
| 518 | 15384_AT |
| 519 | 15385_AT |
| 520 | 15387_AT |
| 521 | 15410_AT |
| 522 | 15417_S_AT |
| 523 | 15422_AT |
| 524 | 15423_AT |
| 525 | 15431_AT |
| 526 | 15433_AT |
| 527 | 15452_AT |
| 528 | 15464_AT |
| 529 | 15468_AT |
| 530 | 15471_AT |
| 531 | 15472_AT |
| 532 | 15475_S_AT |
| 533 | 15485_AT |
| 534 | 15489_AT |
| 535 | 15490_AT |
| 536 | 15503_AT |
| 537 | 15505_AT |
| 538 | 15510_R_AT |
| 539 | 15512_AT |
| 540 | 15514_AT |
| 541 | 15515_R_AT |
| 542 | 15517_S_AT |
| 543 | 15518_AT |
| 544 | 15529_AT |
| 545 | 15534_F_AT |
| 546 | 15538_AT |
| 547 | 15541_AT |
| 548 | 15543_AT |
| 549 | 15544_AT |
| 550 | 15551_AT |
| 551 | 15574_AT |

TABLE 6-continued (cont): 2X DOWN COLD, ONLY

| | |
|---|---|
| 552 | 15576_S_AT |
| 553 | 15577_S_AT |
| 554 | 15578_S_AT |
| 555 | 15583_S_AT |
| 556 | 15588_S_AT |
| 557 | 15595_S_AT |
| 558 | 15600_S_AT |
| 559 | 15602_F_AT |
| 560 | 15608_S_AT |
| 561 | 15613_S_AT |
| 562 | 15616_S_AT |
| 563 | 15618_S_AT |
| 564 | 15620_S_AT |
| 565 | 15627_S_AT |
| 566 | 15634_S_AT |
| | 16125_S_AT |
| | 18046_S_AT |
| 567 | 15637_S_AT |
| 568 | 15639_S_AT |
| 569 | 15642_S_AT |
| 570 | 15643_S_AT |
| 571 | 15651_F_AT |
| 572 | 15652_S_AT |
| 573 | 15665_S_AT |
| 574 | 15667_S_AT |
| | 18610_S_AT |
| 575 | 15668_S_AT |
| 576 | 15671_S_AT |
| 577 | 15675_S_AT |
| 578 | 15679_S_AT |
| 579 | 15685_S_AT |
| 580 | 15687_F_AT |
| 581 | 15688_S_AT |
| 582 | 15689_S_AT |
| 583 | 15692_S_AT |
| 584 | 15694_S_AT |
| 585 | 15712_S_AT |
| 586 | 15808_AT |
| 587 | 15845_AT |
| 588 | 15848_AT |
| 589 | 15850_AT |
| | 20406_G_AT |
| 590 | 15858_AT |
| 591 | 15862_AT |
| 592 | 15868_AT |
| 593 | 15878_AT |
| 594 | 15894_AT |
| 595 | 15900_AT |
| 596 | 15901_AT |
| 597 | 15902_AT |
| 598 | 15912_AT |
| 599 | 15913_AT |
| 600 | 15928_AT |
| 601 | 15940_AT |
| 602 | 15941_AT |
| 603 | 15945_AT |
| 604 | 15948_S_AT |
| 605 | 15956_AT |
| 606 | 15960_AT |
| | 16466_S_AT |
| 607 | 15976_AT |
| 608 | 15978_AT |
| 609 | 15986_S_AT |
| 610 | 15990_AT |
| 611 | 16009_S_AT |
| 612 | 16015_AT |
| 613 | 16019_AT |
| 614 | 16024_AT |
| 615 | 16034_AT |
| 616 | 16036_I_AT |
| | 18729_AT |
| 617 | 16039_S_AT |
| 618 | 16040_AT |
| 619 | 16042_S_AT |
| 620 | 16047_AT |
| 621 | 16049_S_AT |
| 622 | 16051_S_AT |

TABLE 6-continued

(cont): 2X DOWN COLD, ONLY

| | |
|---|---|
| 623 | 16055_S_AT |
| 624 | 16059_S_AT |
| 625 | 16062_S_AT |
| 626 | 16066_S_AT |
| 627 | 16069_S_AT |
| 628 | 16074_S_AT |
| 629 | 16076_S_AT |
| 630 | 16077_S_AT |
| | 17579_S_AT |
| 631 | 16079_S_AT |
| 632 | 16084_S_AT |
| | 17998_S_AT |
| 633 | 16087_S_AT |
| 634 | 16089_S_AT |
| 635 | 16090_S_AT |
| 636 | 16102_S_AT |
| 637 | 16103_S_AT |
| 638 | 16108_S_AT |
| 639 | 16112_S_AT |
| 640 | 16134_S_AT |
| 641 | 16137_S_AT |
| 642 | 16138_S_AT |
| 643 | 16140_S_AT |
| 644 | 16143_S_AT |
| 645 | 16145_S_AT |
| 646 | 16148_S_AT |
| 647 | 16151_S_AT |
| 648 | 16155_S_AT |
| 649 | 16158_F_AT |
| 650 | 16160_F_AT |
| 651 | 16162_S_AT |
| 652 | 16168_S_AT |
| 653 | 16169_S_AT |
| 654 | 16171_S_AT |
| 655 | 16172_S_AT |
| 656 | 16184_AT |
| 657 | 16192_AT |
| 658 | 16222_AT |
| 659 | 16242_AT |
| 660 | 16244_AT |
| 661 | 16250_AT |
| 662 | 16286_AT |
| 663 | 16288_AT |
| 664 | 16294_S_AT |
| 665 | 16296_AT |
| 666 | 16297_AT |
| 667 | 16325_AT |
| 668 | 16346_S_AT |
| 669 | 16357_AT |
| 670 | 16380_AT |
| 671 | 16382_AT |
| 672 | 16393_S_AT |
| 673 | 16402_S_AT |
| 674 | 16411_S_AT |
| 675 | 16442_S_AT |
| 676 | 16446_AT |
| 677 | 16448_G_AT |
| 678 | 16453_S_AT |
| 679 | 16457_S_AT |
| 680 | 16465_AT |
| | 16916_S_AT |
| 681 | 16470_S_AT |
| | 18735_S_AT |
| 682 | 16481_S_AT |
| 683 | 16486_AT |
| 684 | 16487_AT |
| 685 | 16488_AT |
| 686 | 16496_S_AT |
| 687 | 16499_AT |
| 688 | 16510_AT |
| 689 | 16511_AT |
| 690 | 16512_S_AT |
| | 18085_R_AT |
| 691 | 16514_AT |
| 692 | 16516_AT |
| 693 | 16517_AT |
| 694 | 16526_AT |
| 695 | 16528_AT |
| 696 | 16531_S_AT |
| 697 | 16535_S_AT |
| 698 | 16537_S_AT |
| 699 | 16538_S_AT |
| 700 | 16543_S_AT |
| 701 | 16550_S_AT |
| 702 | 16554_S_AT |
| 703 | 16567_S_AT |
| 704 | 16571_S_AT |
| 705 | 16576_F_AT |
| 706 | 16577_S_AT |
| 707 | 16579_S_AT |
| 708 | 16580_S_AT |
| 709 | 16583_S_AT |
| 710 | 16584_S_AT |
| | 18706_S_AT |
| 711 | 16593_S_AT |
| 712 | 16595_S_AT |
| 713 | 16598_S_AT |
| 714 | 16604_S_AT |
| 715 | 16605_S_AT |
| 716 | 16610_S_AT |
| 717 | 16611_S_AT |
| 718 | 16614_S_AT |
| 719 | 16617_S_AT |
| 720 | 16618_S_AT |
| 721 | 16620_S_AT |
| 722 | 16621_S_AT |
| 723 | 16631_S_AT |
| 724 | 16634_S_AT |
| 725 | 16635_S_AT |
| 726 | 16636_S_AT |
| 727 | 16639_S_AT |
| 728 | 16640_S_AT |
| 729 | 16650_S_AT |
| 730 | 16652_S_AT |
| 731 | 16654_AT |
| 732 | 16672_AT |
| 733 | 16673_AT |
| 734 | 16687_S_AT |
| 735 | 16747_AT |
| 736 | 16753_AT |
| 737 | 16768_AT |
| 738 | 16777_AT |
| 739 | 16784_AT |
| 740 | 16807_AT |
| 741 | 16811_AT |
| 742 | 16845_AT |
| 743 | 16894_AT |
| 744 | 16899_AT |
| 745 | 16911_AT |
| 746 | 16920_AT |
| 747 | 16921_AT |
| 748 | 16924_S_AT |
| 749 | 16926_S_AT |
| 750 | 16931_S_AT |
| 751 | 16934_S_AT |
| 752 | 16937_AT |
| 753 | 16938_AT |
| 754 | 16942_AT |
| 755 | 16943_S_AT |
| | 18231_AT |
| 756 | 16949_S_AT |
| 757 | 16952_S_AT |
| 758 | 16956_AT |
| 759 | 16962_S_AT |
| 760 | 16965_S_AT |
| 761 | 16970_S_AT |
| | 18010_S_AT |
| 762 | 16977_AT |
| 763 | 16984_AT |
| 764 | 16996_S_AT |
| 765 | 16997_AT |
| 766 | 17000_AT |
| 767 | 17005_AT |
| 768 | 17010_S_AT |

TABLE 6-continued (cont): 2X DOWN COLD, ONLY

| | |
|---|---|
| 769 | 17017_S_AT |
| 770 | 17031_S_AT |
| 771 | 17033_S_AT |
| 772 | 17053_S_AT |
| 773 | 17055_S_AT |
| 774 | 17063_S_AT |
| 775 | 17068_S_AT |
| 776 | 17070_S_AT |
| 777 | 17075_S_AT |
| 778 | 17084_S_AT |
| 779 | 17087_S_AT |
| 780 | 17092_S_AT |
| 781 | 17095_S_AT |
| 782 | 17096_S_AT |
| 783 | 17102_S_AT |
| 784 | 17105_S_AT |
| 785 | 17109_S_AT |
| 786 | 17110_S_AT |
| 787 | 17113_S_AT |
| 788 | 17115_S_AT |
| 789 | 17116_S_AT |
| 790 | 17123_S_AT |
| 791 | 17129_S_AT |
| 792 | 17132_AT |
| 793 | 17166_AT |
| 794 | 17206_AT |
| 795 | 17207_AT |
| 796 | 17215_AT |
| 797 | 17237_AT |
| 798 | 17247_AT |
| 799 | 17254_AT |
| 800 | 17286_AT |
| 801 | 17288_S_AT |
| 802 | 17292_AT |
| 803 | 17300_AT |
| 804 | 17303_S_AT |
| 805 | 17318_AT |
| 806 | 17319_AT |
| 807 | 17322_AT |
| 808 | 17323_AT |
| 809 | 17332_S_AT |
| 810 | 17374_AT |
| 811 | 17381_AT |
| 812 | 17388_AT |
| 813 | 17392_S_AT |
| 814 | 17405_AT |
| 815 | 17415_AT |
| 816 | 17418_S_AT |
| 817 | 17420_AT |
| 818 | 17423_S_AT |
| 819 | 17426_AT |
| 820 | 17427_AT |
| 821 | 17429_S_AT |
| 822 | 17431_AT |
| 823 | 17439_G_AT |
| 824 | 17457_AT |
| 825 | 17458_AT |
| 826 | 17462_S_AT |
| 827 | 17463_AT |
| 828 | 17465_AT |
| 829 | 17466_S_AT |
| 830 | 17475_AT |
| 831 | 17479_AT |
| 832 | 17482_S_AT |
| 833 | 17495_S_AT |
| 834 | 17508_S_AT |
| 835 | 17522_S_AT |
| 836 | 17523_S_AT |
| 837 | 17537_S_AT |
| 838 | 17538_S_AT |
| 839 | 17539_S_AT |
| 840 | 17546_S_AT |
| | 18694_S_AT |
| 841 | 17557_S_AT |
| 842 | 17560_S_AT |
| 843 | 17562_AT |

TABLE 6-continued (cont): 2X DOWN COLD, ONLY

| | |
|---|---|
| 844 | 17564_S_AT |
| | 19361_S_AT |
| 845 | 17565_S_AT |
| 846 | 17568_AT |
| 847 | 17573_AT |
| 848 | 17577_G_AT |
| 849 | 17578_AT |
| 850 | 17596_AT |
| 851 | 17627_AT |
| 852 | 17631_AT |
| 853 | 17632_AT |
| 854 | 17672_AT |
| 855 | 17675_AT |
| 856 | 17677_AT |
| 857 | 17732_AT |
| 858 | 17743_AT |
| 859 | 17748_AT |
| 860 | 17782_AT |
| 861 | 17823_S_AT |
| 862 | 17841_AT |
| 863 | 17849_S_AT |
| 864 | 17852_G_AT |
| 865 | 17857_AT |
| 866 | 17865_AT |
| 867 | 17882_AT |
| 868 | 17885_AT |
| 869 | 17900_S_AT |
| 870 | 17910_AT |
| 871 | 17911_AT |
| 872 | 17916_AT |
| 873 | 17917_S_AT |
| 874 | 17918_AT |
| 875 | 17921_S_AT |
| 876 | 17922_AT |
| 877 | 17926_S_AT |
| 878 | 17933_AT |
| 879 | 17935_AT |
| 880 | 17956_I_AT |
| 881 | 17966_AT |
| 882 | 17967_AT |
| 883 | 17970_I_AT |
| 884 | 17978_S_AT |
| | 20635_S_AT |
| 885 | 17986_S_AT |
| 886 | 17993_AT |
| 887 | 18001_AT |
| 888 | 18003_AT |
| 889 | 18004_AT |
| 890 | 18005_AT |
| 891 | 18029_G_AT |
| | 18030_I_AT |
| 892 | 18040_S_AT |
| 893 | 18045_AT |
| 894 | 18064_R_AT |
| 895 | 18065_R_AT |
| 896 | 18074_AT |
| 897 | 18076_S_AT |
| 898 | 18077_AT |
| 899 | 18081_AT |
| 900 | 18154_S_AT |
| | 18365_S_AT |
| 901 | 18165_AT |
| 902 | 18174_AT |
| 903 | 18176_AT |
| 904 | 18194_I_AT |
| 905 | 18197_AT |
| 906 | 18198_AT |
| 907 | 18213_AT |
| 908 | 18219_AT |
| 909 | 18221_AT |
| 910 | 18222_AT |
| 911 | 18226_S_AT |
| 912 | 18232_AT |
| 913 | 18237_AT |
| 914 | 18241_AT |
| 915 | 18257_AT |
| 916 | 18258_S_AT |

TABLE 6-continued (cont): 2X DOWN COLD, ONLY

| | |
|---|---|
| 917 | 18269_S_AT |
| 918 | 18274_S_AT |
| 919 | 18275_AT |
| 920 | 18278_AT |
| 921 | 18282_AT |
| 922 | 18283_AT |
| 923 | 18290_AT |
| 924 | 18291_AT |
| 925 | 18306_AT |
| 926 | 18316_AT |
| 927 | 18317_AT |
| 928 | 18327_S_AT |
| 929 | 18337_S_AT |
| 930 | 18339_AT |
| 931 | 18347_S_AT |
| 932 | 18383_AT |
| 933 | 18390_AT |
| 934 | 18439_S_AT |
| 935 | 18465_S_AT |
| 936 | 18487_AT |
| 937 | 18508_S_AT |
| 938 | 18512_AT |
| 939 | 18543_AT |
| 940 | 18544_AT |
| 941 | 18552_AT |
| 942 | 18555_AT |
| 943 | 18556_AT |
| 944 | 18561_AT |
| 945 | 18567_AT |
| 946 | 18573_AT |
| 947 | 18580_AT |
| 948 | 18581_AT |
| 949 | 18584_AT |
| 950 | 18587_S_AT |
| 951 | 18588_AT |
| 952 | 18591_AT |
| 953 | 18592_S_AT |
| 954 | 18600_AT |
| 955 | 18601_S_AT |
| 956 | 18607_S_AT |
| 957 | 18611_AT |
| 958 | 18616_AT |
| 959 | 18622_G_AT |
| 960 | 18623_AT |
| 961 | 18628_AT |
| 962 | 18631_AT |
| 963 | 18635_AT |
| 964 | 18636_AT |
| 965 | 18638_AT |
| 966 | 18652_AT |
| 967 | 18657_AT |
| 968 | 18659_AT |
| 969 | 18660_S_AT |
| 970 | 18667_AT |
| 971 | 18675_AT |
| 972 | 18684_AT |
| 973 | 18686_S_AT |
| 974 | 18688_S_AT |
| 975 | 18693_S_AT |
| 976 | 18698_S_AT |
| 977 | 18705_AT |
| 978 | 18707_AT |
| 979 | 18708_AT |
| 980 | 18726_S_AT |
| 981 | 18727_AT |
| 982 | 18732_I_AT |
| 983 | 18736_AT |
| 984 | 18750_F_AT |
| 985 | 18754_AT |
| 986 | 18778_AT |
| 987 | 18806_S_AT |
| 988 | 18823_S_AT |
| 989 | 18829_AT |
| 990 | 18835_AT |
| 991 | 18844_AT |
| 992 | 18859_AT |
| 993 | 18864_AT |
| 994 | 18866_AT |
| 995 | 18880_AT |
| 996 | 18883_G_AT |
| 997 | 18885_AT |
| 998 | 18886_AT |
| 999 | 18887_AT |
| 1000 | 18888_AT |
| 1001 | 18889_AT |
| 1002 | 18892_S_AT |
| 1003 | 18901_AT |
| 1004 | 18911_AT |
| 1005 | 18917_I_AT |
| 1006 | 18939_AT |
| 1007 | 18947_I_AT |
| 1008 | 18950_AT |
| 1009 | 18951_S_AT |
| 1010 | 18954_AT |
| 1011 | 18956_AT |
| 1012 | 18959_AT |
| 1013 | 18966_AT |
| 1014 | 18974_AT |
| 1015 | 18976_AT |
| 1016 | 18980_AT |
| 1017 | 18989_S_AT |
| 1018 | 18994_AT |
| 1019 | 19030_AT |
| 1020 | 19039_AT |
| 1021 | 19049_AT |
| 1022 | 19083_AT |
| 1023 | 19115_AT |
| 1024 | 19117_S_AT |
| 1025 | 19122_AT |
| 1026 | 19125_S_AT |
| 1027 | 19127_AT |
| 1028 | 19130_AT |
| 1029 | 19144_AT |
| 1030 | 19157_S_AT |
| 1031 | 19178_AT |
| 1032 | 19190_G_AT |
| 1033 | 19198_AT |
| 1034 | 19202_AT |
| 1035 | 19209_S_AT |
| 1036 | 19211_AT |
| 1037 | 19218_AT |
| 1038 | 19222_AT |
| 1039 | 19226_G_AT |
| 1040 | 19229_AT |
| 1041 | 19230_AT |
| 1042 | 19232_S_AT |
| 1043 | 19285_AT |
| 1044 | 19326_AT |
| 1045 | 19332_AT |
| 1046 | 19346_AT |
| 1047 | 19347_AT |
| 1048 | 19362_AT |
| 1049 | 19363_AT |
| 1050 | 19364_AT |
| 1051 | 19367_AT |
| 1052 | 19373_AT |
| 1053 | 19381_AT |
| 1054 | 19382_AT |
| 1055 | 19384_AT |
| 1056 | 19401_AT |
| 1057 | 19406_AT |
| 1058 | 19413_AT |
| 1059 | 19416_AT |
| 1060 | 19426_S_AT |
| 1061 | 19439_AT |
| 1062 | 19441_S_AT |
| 1063 | 19442_AT |
| 1064 | 19448_S_AT |
| 1065 | 19454_AT |
| 1066 | 19462_S_AT |
| 1067 | 19464_AT |
| 1068 | 19470_AT |
| 1069 | 19483_AT |
| 1070 | 19489_S_AT |

TABLE 6-continued (cont): 2X DOWN COLD, ONLY

| | |
|---|---|
| 1071 | 19513_AT |
| 1072 | 19548_AT |
| 1073 | 19562_AT |
| 1074 | 19563_S_AT |
| 1075 | 19567_AT |
| 1076 | 19581_AT |
| 1077 | 19589_S_AT |
| 1078 | 19595_S_AT |
| 1079 | 19606_AT |
| 1080 | 19623_AT |
| 1081 | 19624_AT |
| 1082 | 19627_S_AT |
| 1083 | 19636_AT |
| 1084 | 19652_AT |
| 1085 | 19655_AT |
| 1086 | 19657_S_AT |
| 1087 | 19658_AT |
| 1088 | 19660_AT |
| 1089 | 19665_S_AT |
| 1090 | 19667_AT |
| 1091 | 19671_AT |
| 1092 | 19677_AT |
| 1093 | 19686_AT |
| 1094 | 19689_AT |
| 1095 | 19690_S_AT |
| 1096 | 19695_AT |
| 1097 | 19698_AT |
| 1098 | 19700_S_AT |
| 1099 | 19708_AT |
| 1100 | 19717_AT |
| 1101 | 19726_S_AT |
| 1102 | 19744_AT |
| 1103 | 19752_S_AT |
| 1104 | 19759_AT |
| 1105 | 19782_AT |
| 1106 | 19803_S_AT |
| 1107 | 19828_AT |
| 1108 | 19831_I_AT |
| 1109 | 19833_S_AT |
| 1110 | 19834_AT |
| 1111 | 19836_AT |
| 1112 | 19841_AT |
| 1113 | 19845_G_AT |
| 1114 | 19854_AT |
| 1115 | 19855_AT |
| 1116 | 19866_AT |
| 1117 | 19867_AT |
| 1118 | 19870_S_AT |
| 1119 | 19871_AT |
| 1120 | 19872_AT |
| 1121 | 19875_S_AT |
| 1122 | 19876_AT |
| 1123 | 19879_S_AT |
| 1124 | 19881_AT |
| 1125 | 19897_S_AT |
| 1126 | 19903_AT |
| 1127 | 19905_AT |
| 1128 | 19906_AT |
| 1129 | 19907_AT |
| 1130 | 19910_AT |
| 1131 | 19913_AT |
| 1132 | 19920_S_AT |
| 1133 | 19932_AT |
| 1134 | 19939_AT |
| 1135 | 19945_AT |
| 1136 | 19947_AT |
| 1137 | 19951_AT |
| 1138 | 19956_AT |
| 1139 | 19962_AT |
| 1140 | 19963_AT |
| 1141 | 19969_AT |
| 1142 | 19970_S_AT |
| 1143 | 19971_AT |
| 1144 | 19972_AT |
| 1145 | 19981_AT |
| 1146 | 19990_AT |
| 1147 | 19996_AT |
| 1148 | 20003_S_AT |
| 1149 | 20009_S_AT |
| 1150 | 20013_AT |
| 1151 | 20018_AT |
| 1152 | 20024_S_AT |
| 1153 | 20027_AT |
| 1154 | 20045_AT |
| 1155 | 20047_AT |
| 1156 | 20048_AT |
| 1157 | 20050_AT |
| 1158 | 20051_AT |
| 1159 | 20058_AT |
| 1160 | 20067_AT |
| 1161 | 20068_AT |
| 1162 | 20069_AT |
| 1163 | 20093_I_AT |
| 1164 | 20099_AT |
| 1165 | 20100_AT |
| 1166 | 20113_S_AT |
| 1167 | 20117_AT |
| 1168 | 20123_AT |
| 1169 | 20127_S_AT |
| 1170 | 20129_AT |
| 1171 | 20150_AT |
| 1172 | 20154_AT |
| 1173 | 20156_AT |
| 1174 | 20165_AT |
| 1175 | 20173_AT |
| 1176 | 20178_S_AT |
| 1177 | 20183_AT |
| 1178 | 20188_AT |
| 1179 | 20189_AT |
| 1180 | 20197_AT |
| 1181 | 20210_G_AT |
| 1182 | 20213_AT |
| 1183 | 20229_AT |
| 1184 | 20232_S_AT |
| 1185 | 20255_AT |
| 1186 | 20257_AT |
| 1187 | 20262_AT |
| 1188 | 20275_AT |
| 1189 | 20278_S_AT |
| 1190 | 20282_S_AT |
| 1191 | 20284_AT |
| 1192 | 20293_AT |
| 1193 | 20294_AT |
| 1194 | 20312_S_AT |
| 1195 | 20315_I_AT |
| 1196 | 20330_S_AT |
| 1197 | 20331_AT |
| 1198 | 20350_S_AT |
| 1199 | 20354_S_AT |
| 1200 | 20355_AT |
| 1201 | 20360_AT |
| 1202 | 20363_AT |
| 1203 | 20369_S_AT |
| 1204 | 20378_G_AT |
| 1205 | 20383_AT |
| 1206 | 20384_AT |
| 1207 | 20387_AT |
| 1208 | 20393_AT |
| 1209 | 20396_AT |
| 1210 | 20399_AT |
| 1211 | 20409_G_AT |
| 1212 | 20412_S_AT |
| 1213 | 20413_AT |
| 1214 | 20439_AT |
| 1215 | 20440_AT |
| 1216 | 20444_AT |
| 1217 | 20445_AT |
| 1218 | 20449_AT |
| 1219 | 20456_AT |
| 1220 | 20462_AT |
| 1221 | 20471_AT |
| 1222 | 20474_AT |
| 1223 | 20495_S_AT |
| 1224 | 20499_AT |

TABLE 6-continued

(cont): 2X DOWN COLD, ONLY

| | |
|---|---|
| 1225 | 20501_AT |
| 1226 | 20511_AT |
| 1227 | 20515_S_AT |
| 1228 | 20516_AT |
| 1229 | 20517_AT |
| 1230 | 20518_AT |
| 1231 | 20520_S_AT |
| 1232 | 20536_S_AT |
| 1233 | 20538_S_AT |
| 1234 | 20539_S_AT |
| 1235 | 20558_AT |
| 1236 | 20561_AT |
| 1237 | 20567_AT |
| 1238 | 20571_AT |
| 1239 | 20582_S_AT |
| 1240 | 20586_I_AT |
| 1241 | 20590_AT |
| 1242 | 20592_AT |
| 1243 | 20594_AT |
| 1244 | 20608_S_AT |
| 1245 | 20612_S_AT |
| 1246 | 20616_AT |
| 1247 | 20620_G_AT |
| 1248 | 20637_AT |
| 1249 | 20643_AT |
| 1250 | 20649_AT |
| 1251 | 20651_AT |
| 1252 | 20654_S_AT |
| 1253 | 20670_AT |
| 1254 | 20684_AT |
| 1255 | 20685_AT |
| 1256 | 20693_AT |
| 1257 | 20701_S_AT |
| 1258 | 20704_AT |
| 1259 | 20705_AT |
| 1260 | 20715_AT |
| 1261 | 20719_AT |

TABLE 4

2X UP IN COLD, ONLY

11997_at
11998_at
12018_at
12031_at
12047_at
12051_at
12053_at
12060_at
12072_at
12074_at
12102_at
12112_at
12117_at
12130_at
12145_s_at
12151_at
12163_at
12175_at
12187_at
12195_at
12219_at
12256_at
12269_s_at
12307_at
12315_at
12336_at
12349_s_at
12353_at
12359_s_at
12390_at
12395_s_at
12431_at

TABLE 4-continued

2X UP IN COLD, ONLY

12436_at
12443_s_at
12447_at
12452_at
12477_at
12503_at
12516_s_at
12532_at
12544_at
12561_at
12602_at
12610_at
12631_at
12647_s_at
12650_at
12656_at
12674_at
12675_s_at
12676_s_at
12681_s_at
12686_s_at
12688_at
12701_i_at
12702_at
12719_f_at
12726_f_at
12736_f_at
12754_g_at
12762_r_at
12766_at
12767_at
12768_at
12773_at
12788_at
12802_at
12860_s_at
12861_s_at
12879_s_at
12891_at
12914_s_at
12927_s_at
12947_at
12956_i_at
12966_s_at
12974_at
12987_s_at
12994_s_at
12998_at
13002_at
13018_at
13023_at
13046_g_at
13054_at
13086_r_at
13087_at
13100_at
13109_at
13119_at
13120_at
13128_at
13134_s_at
13140_at
13143_at
13167_at
13172_s_at
13178_at
13179_at
13181_at
13187_i_at
13209_s_at
13219_s_at
13221_at
13243_r_at
13260_s_at
13274_s_at
13278_f_at
13279_s_at

TABLE 4-continued

2X UP IN COLD, ONLY

| |
|---|
| 13285_s_at |
| 13288_s_at |
| 13292_s_at |
| 13297_s_at |
| 13299_s_at |
| 13332_at |
| 13351_at |
| 13352_at |
| 13422_at |
| 13435_at |
| 13461_s_at |
| 13467_at |
| 13488_at |
| 13495_s_at |
| 13539_i_at |
| 13542_at |
| 13575_at |
| 13577_s_at |
| 13617_at |
| 13634_s_at |
| 13656_at |
| 13671_s_at |
| 13691_s_at |
| 13700_at |
| 13704_s_at |
| 13709_s_at |
| 13715_at |
| 13785_at |
| 13803_at |
| 13812_s_at |
| 13825_s_at |
| 13850_i_at |
| 13904_s_at |
| 13908_s_at |
| 13927_at |
| 13971_s_at |
| 13985_s_at |
| 14013_at |
| 14019_at |
| 14021_r_at |
| 14028_at |
| 14048_at |
| 14058_at |
| 14059_at |
| 14064_at |
| 14073_at |
| 14105_at |
| 14106_at |
| 14126_s_at |
| 14140_at |
| 14145_at |
| 14170_at |
| 14186_at |
| 14196_at |
| 14227_at |
| 14234_at |
| 14250_r_at |
| 14270_at |
| 14298_g_at |
| 14303_s_at |
| 14312_at |
| 14339_at |
| 14388_at |
| 14393_at |
| 14511_at |
| 14525_s_at |
| 14527_at |
| 14534_s_at |
| 14554_at |
| 14566_at |
| 14579_at |
| 14591_at |
| 14595_at |
| 14600_at |
| 14631_s_at |
| 14635_s_at |
| 14679_s_at |

TABLE 4-continued

2X UP IN COLD, ONLY

| |
|---|
| 14691_at |
| 14697_g_at |
| 14709_at |
| 14711_s_at |
| 14728_s_at |
| 14731_s_at |
| 14797_s_at |
| 14809_at |
| 14843_at |
| 14847_at |
| 14872_at |
| 14886_at |
| 14896_at |
| 14897_at |
| 14900_at |
| 14956_s_at |
| 14958_at |
| 14965_at |
| 14984_s_at |
| 15004_at |
| 15010_at |
| 15036_r_at |
| 15040_g_at |
| 15046_s_at |
| 15057_at |
| 15073_at |
| 15083_at |
| 15084_at |
| 15096_at |
| 15101_s_at |
| 15105_s_at |
| 15112_s_at |
| 15115_f_at |
| 15116_f_at |
| 15122_s_at |
| 15126_s_at |
| 15131_s_at |
| 15132_s_at |
| 15137_s_at |
| 15144_s_at |
| 15148_s_at |
| 15153_s_at |
| 15159_s_at |
| 15160_s_at |
| 15166_s_at |
| 15174_f_at |
| 15197_s_at |
| 15270_at |
| 15319_at |
| 15325_at |
| 15337_at |
| 15341_at |
| 15343_at |
| 15355_s_at |
| 15367_at |
| 15379_at |
| 15381_at |
| 15410_at |
| 15417_s_at |
| 15422_at |
| 15433_at |
| 15451_at |
| 15452_at |
| 15453_s_at |
| 15472_at |
| 15489_at |
| 15490_at |
| 15503_at |
| 15510_r_at |
| 15517_s_at |
| 15518_at |
| 15544_at |
| 15588_s_at |
| 15600_s_at |
| 15605_s_at |
| 15613_s_at |
| 15614_s_at |

TABLE 4-continued

2X UP IN COLD, ONLY

| |
|---|
| 15616_s_at |
| 15633_s_at |
| 15639_s_at |
| 15641_s_at |
| 15660_s_at |
| 15665_s_at |
| 15687_f_at |
| 15694_s_at |
| 15712_s_at |
| 15783_s_at |
| 15808_at |
| 15837_at |
| 15850_at |
| 15862_at |
| 15868_at |
| 15878_at |
| 15901_at |
| 15912_at |
| 15920_i_at |
| 15941_at |
| 15945_at |
| 15960_at |
| 15990_at |
| 16001_at |
| 16009_s_at |
| 16010_s_at |
| 16034_at |
| 16036_i_at |
| 16039_s_at |
| 16040_at |
| 16042_s_at |
| 16047_at |
| 16049_s_at |
| 16051_s_at |
| 16062_s_at |
| 16079_s_at |
| 16087_s_at |
| 16090_s_at |
| 16117_s_at |
| 16118_s_at |
| 16137_s_at |
| 16155_s_at |
| 16162_s_at |
| 16184_at |
| 16192_at |
| 16222_at |
| 16244_at |
| 16250_at |
| 16260_at |
| 16286_at |
| 16296_at |
| 16297_at |
| 16342_at |
| 16367_i_at |
| 16411_s_at |
| 16442_s_at |
| 16465_at |
| 16466_s_at |
| 16468_at |
| 16486_at |
| 16487_at |
| 16488_at |
| 16489_at |
| 16496_s_at |
| 16499_at |
| 16511_at |
| 16517_at |
| 16538_s_at |
| 16554_s_at |
| 16571_s_at |
| 16576_f_at |
| 16595_s_at |
| 16605_s_at |
| 16610_s_at |
| 16620_s_at |
| 16621_s_at |
| 16635_s_at |

TABLE 4-continued

2X UP IN COLD, ONLY

| |
|---|
| 16636_s_at |
| 16638_s_at |
| 16650_s_at |
| 16672_at |
| 16673_at |
| 16687_s_at |
| 16747_at |
| 16753_at |
| 16768_s_at |
| 16805_s_at |
| 16807_at |
| 16845_at |
| 16847_at |
| 16896_s_at |
| 16899_at |
| 16902_at |
| 16911_at |
| 16914_s_at |
| 16943_s_at |
| 16956_at |
| 16996_s_at |
| 17010_s_at |
| 17016_s_at |
| 17032_s_at |
| 17033_s_at |
| 17043_s_at |
| 17050_s_at |
| 17055_at |
| 17068_at |
| 17071_s_at |
| 17075_s_at |
| 17077_s_at |
| 17102_s_at |
| 17109_s_at |
| 17113_s_at |
| 17123_s_at |
| 17128_s_at |
| 17129_s_at |
| 17132_at |
| 17166_at |
| 17206_at |
| 17237_at |
| 17300_at |
| 17319_at |
| 17322_at |
| 17332_s_at |
| 17381_at |
| 17388_at |
| 17392_s_at |
| 17408_at |
| 17424_at |
| 17429_s_at |
| 17457_at |
| 17458_at |
| 17466_s_at |
| 17477_s_at |
| 17482_s_at |
| 17538_s_at |
| 17546_s_at |
| 17562_at |
| 17581_g_at |
| 17627_at |
| 17631_at |
| 17632_at |
| 17645_s_at |
| 17672_at |
| 17675_at |
| 17677_at |
| 17693_at |
| 17732_at |
| 17743_at |
| 17748_at |
| 17775_at |
| 17782_at |
| 17841_at |
| 17852_g_at |
| 17900_s_at |

TABLE 4-continued

2X UP IN COLD, ONLY

17901_at
17911_at
17921_s_at
17922_at
17933_at
17967_at
17970_i_at
17978_s_at
17999_at
18001_at
18004_at
18012_s_at
18040_s_at
18176_at
18194_i_at
18197_at
18198_at
18213_at
18219_at
18222_at
18231_at
18232_at
18241_at
18269_s_at
18272_at
18282_at
18298_at
18316_at
18317_at
18331_s_at
18347_s_at
18383_at
18390_at
18455_at
18465_s_at
18544_at
18555_at
18556_at
18560_at
18561_at
18571_at
18588_at
18597_at
18601_s_at
18611_at
18623_at
18635_at
18659_at
18660_s_at
18673_at
18694_s_at
18705_at
18708_at
18738_f_at
18750_f_at
18778_at
18829_at
18835_at
18866_at
18875_s_at
18885_at
18887_at
18888_at
18889_at
18901_at
18907_s_at
18917_i_at
18939_at
18947_i_at
18949_at
18954_at
18959_at
18974_at
18976_at
18980_at
18989_s_at
19019_i_at

TABLE 4-continued

2X UP IN COLD, ONLY

19049_at
19083_at
19130_at
19156_s_at
19178_at
19190_g_at
19199_at
19202_at
19209_s_at
19211_at
19218_at
19229_at
19322_at
19326_at
19359_s_at
19367_at
19384_at
19389_at
19397_at
19406_at
19426_s_at
19441_s_at
19442_at
19470_at
19489_s_at
19562_at
19577_at
19589_s_at
19597_s_at
19611_s_at
19624_at
19657_s_at
19667_at
19671_at
19677_at
19686_at
19689_at
19698_at
19700_s_at
19707_s_at
19708_at
19713_at
19718_at
19744_at
19836_at
19839_at
19840_s_at
19845_g_at
19854_at
19855_at
19860_at
19866_at
19871_at
19875_s_at
19879_s_at
19881_at
19913_at
19939_at
19945_at
19947_at
19951_at
19956_at
19971_at
19976_at
19998_at
20003_s_at
20015_at
20027_at
20051_at
20068_at
20093_i_at
20117_at
20150_at
20156_at
20165_at
20257_at
20262_at

TABLE 4-continued

2X UP IN COLD, ONLY

20275_at
20282_s_at
20288_g_at
20293_at
20315_i_at
20330_s_at
20360_at
20363_at
20369_s_at
20384_at
20393_at
20396_at
20412_s_at
20413_at
20432_at
20433_at
20456_at
20462_at
20471_at
20511_at
20515_s_at
20517_at
20518_at
20529_at
20536_s_at
20538_s_at
20539_s_at
20576_at
20582_s_at
20586_i_at
20608_s_at
20649_at
20651_at
20684_at
20685_at
20699_at
20705_at
20715_at

TABLE 5

2X UP COLD 3 HR, ONLY

12117_at
12145_s_at
12151_at
12163_at
12187_at
12256_at
12315_at
12349_s_at
12353_at
12359_s_at
12544_at
12602_at
12610_at
12676_s_at
12686_s_at
12701_i_at
12702_at
12719_f_at
12736_f_at
12754_g_at
12766_at
12767_at
12768_at
12773_at
12788_at
12879_s_at
12891_at
12947_at
12966_s_at
12974_at
12994_s_at

TABLE 5-continued

2X UP COLD 3 HR, ONLY

13002_at
13100_at
13140_at
13167_at
13172_s_at
13179_at
13187_i_at
13219_s_at
13260_s_at
13278_f_at
13279_s_at
13285_s_at
13288_s_at
13292_s_at
13297_s_at
13351_at
13352_at
13435_at
13467_at
13488_at
13495_s_at
13656_at
13671_s_at
13691_s_at
13785_at
13803_at
13825_s_at
13904_s_at
14013_at
14021_r_at
14028_at
14064_at
14126_s_at
14145_at
14170_at
14196_at
14250_r_at
14298_g_at
14303_s_at
14339_at
14527_at
14534_s_at
14554_at
14595_at
14635_s_at
14679_s_at
14691_at
14697_g_at
14709_at
14728_s_at
14809_at
14896_at
14965_at
14984_s_at
15046_s_at
15083_at
15096_at
15105_s_at
15115_f_at
15116_f_at
15122_s_at
15126_s_at
15131_s_at
15132_s_at
15137_s_at
15153_s_at
15159_s_at
15160_s_at
15197_s_at
15355_s_at
15379_at
15417_s_at
15422_at
15451_at
15452_at
15453_s_at
15489_at

TABLE 5-continued

2X UP COLD 3 HR, ONLY

15518_at
15588_s_at
15613_s_at
15614_s_at
15616_s_at
15639_s_at
15641_s_at
15660_s_at
15687_f_at
15694_s_at
15862_at
15868_at
15878_at
15901_at
16034_at
16039_s_at
16040_at
16042_s_at
16047_at
16062_s_at
16087_s_at
16117_s_at
16118_at
16162_s_at
16184_at
16222_at
16250_at
16411_s_at
16442_s_at
16465_at
16486_at
16488_at
16489_at
16517_at
16571_s_at
16605_s_at
16610_s_at
16620_s_at
16636_s_at
16650_s_at
16805_s_at
16845_at
16899_at
16914_s_at
16943_s_at
16996_s_at
17010_s_at
17043_s_at
17068_s_at
17109_s_at
17128_s_at
17237_at
17319_at
17392_s_at
17429_s_at
17477_s_at
17538_s_at
17581_g_at
17627_at
17672_at
17693_at
17782_at
17841_at
17900_s_at
17933_at
17978_s_at
18001_at
18012_s_at
18198_at
18219_at
18241_at
18269_s_at
18272_at
18282_at
18298_at
18383_at
18556_at

TABLE 5-continued

2X UP COLD 3 HR, ONLY

18588_at
18601_s_at
18611_at
18694_s_at
18708_at
18738_f_at
18778_at
18829_at
18835_at
18866_at
18875_s_at
18888_at
18907_s_at
18917_i_at
18939_at
18974_at
19190_g_at
19199_at
19202_at
19211_at
19384_at
19406_at
19426_s_at
19442_at
19470_at
19577_at
19597_s_at
19624_at
19657_s_at
19667_at
19845_g_at
19855_at
19866_at
19945_at
19951_at
19998_at
20003_s_at
20015_at
20051_at
20093_i_at
20117_at
20288_g_at
20360_at
20369_s_at
20384_at
20462_at
20471_at
20515_s_at
20538_s_at
20576_at
20608_s_at
20651_at
20685_at
20705_at

TABLE 6

2X DOWN COLD, ONLY

11991_g_at
11992_at
12001_at
12006_s_at
12007_at
12009_at
12022_at
12023_s_at
12026_at
12037_at
12052_at
12125_at
12143_at
12149_at
12156_at

TABLE 6-continued

2X DOWN COLD, ONLY

| |
|---|
| 12166_i_at |
| 12167_at |
| 12169_i_at |
| 12176_at |
| 12179_at |
| 12196_at |
| 12198_at |
| 12200_at |
| 12202_at |
| 12212_at |
| 12214_g_at |
| 12224_at |
| 12226_at |
| 12233_at |
| 12240_at |
| 12253_g_at |
| 12270_at |
| 12278_at |
| 12284_at |
| 12287_s_at |
| 12293_at |
| 12294_s_at |
| 12300_at |
| 12312_at |
| 12315_at |
| 12324_i_at |
| 12331_s_at |
| 12344_at |
| 12348_at |
| 12353_at |
| 12372_at |
| 12374_i_at |
| 12405_at |
| 12408_at |
| 12410_g_at |
| 12419_at |
| 12427_at |
| 12438_at |
| 12450_s_at |
| 12474_at |
| 12491_at |
| 12497_at |
| 12500_s_at |
| 12515_at |
| 12521_at |
| 12523_at |
| 12526_at |
| 12527_at |
| 12534_g_at |
| 12549_s_at |
| 12550_s_at |
| 12552_at |
| 12555_s_at |
| 12556_at |
| 12575_s_at |
| 12576_s_at |
| 12581_s_at |
| 12587_at |
| 12597_at |
| 12606_at |
| 12609_at |
| 12646_at |
| 12649_at |
| 12653_at |
| 12661_at |
| 12666_at |
| 12678_i_at |
| 12705_f_at |
| 12736_f_at |
| 12737_f_at |
| 12758_at |
| 12760_g_at |
| 12764_f_at |
| 12765_at |
| 12772_at |
| 12776_at |
| 12784_at |
| 12793_at |
| 12794_at |
| 12795_at |
| 12809_g_at |
| 12812_at |
| 12815_at |
| 12816_at |
| 12818_at |
| 12824_s_at |
| 12828_s_at |
| 12842_s_at |
| 12846_s_at |
| 12858_at |
| 12869_s_at |
| 12881_s_at |
| 12889_s_at |
| 12901_s_at |
| 12902_at |
| 12904_s_at |
| 12905_s_at |
| 12908_s_at |
| 12910_s_at |
| 12916_at |
| 12923_s_at |
| 12926_s_at |
| 12931_s_at |
| 12937_r_at |
| 12941_g_at |
| 12942_at |
| 12949_at |
| 12953_at |
| 12958_at |
| 12959_at |
| 12966_s_at |
| 12975_at |
| 12983_at |
| 12984_at |
| 13002_at |
| 13009_i_at |
| 13011_at |
| 13014_at |
| 13024_at |
| 13034_s_at |
| 13041_s_at |
| 13048_s_at |
| 13067_s_at |
| 13068_at |
| 13073_s_at |
| 13078_s_at |
| 13079_at |
| 13081_s_at |
| 13083_at |
| 13090_at |
| 13092_s_at |
| 13098_at |
| 13103_at |
| 13105_at |
| 13107_s_at |
| 13108_at |
| 13114_at |
| 13118_f_at |
| 13123_at |
| 13124_at |
| 13133_s_at |
| 13135_s_at |
| 13139_at |
| 13146_s_at |
| 13151_g_at |
| 13160_at |
| 13161_at |
| 13162_at |
| 13165_at |
| 13166_at |
| 13185_at |
| 13193_s_at |
| 13211_s_at |
| 13213_s_at |

TABLE 6-continued

2X DOWN COLD, ONLY

| |
|---|
| 13219_s_at |
| 13233_at |
| 13236_s_at |
| 13239_s_at |
| 13241_s_at |
| 13254_s_at |
| 13266_s_at |
| 13273_s_at |
| 13275_f_at |
| 13276_s_at |
| 13278_f_at |
| 13280_s_at |
| 13285_s_at |
| 13296_s_at |
| 13347_at |
| 13355_at |
| 13361_at |
| 13404_at |
| 13406_at |
| 13459_at |
| 13460_at |
| 13464_at |
| 13523_s_at |
| 13529_at |
| 13541_at |
| 13545_s_at |
| 13550_at |
| 13552_at |
| 13556_i_at |
| 13561_at |
| 13563_s_at |
| 13567_at |
| 13568_at |
| 13571_at |
| 13576_at |
| 13583_at |
| 13598_at |
| 13601_at |
| 13604_at |
| 13613_at |
| 13616_s_at |
| 13618_s_at |
| 13619_at |
| 13621_g_at |
| 13623_r_at |
| 13629_s_at |
| 13631_at |
| 13635_at |
| 13646_at |
| 13650_at |
| 13652_at |
| 13653_at |
| 13655_at |
| 13657_at |
| 13666_s_at |
| 13667_s_at |
| 13669_s_at |
| 13670_s_at |
| 13672_s_at |
| 13678_s_at |
| 13679_s_at |
| 13688_s_at |
| 13690_s_at |
| 13691_s_at |
| 13692_s_at |
| 13714_at |
| 13724_at |
| 13748_at |
| 13751_at |
| 13759_at |
| 13767_at |
| 13789_at |
| 13876_at |
| 13880_s_at |
| 13883_at |
| 13887_s_at |
| 13895_at |

TABLE 6-continued

2X DOWN COLD, ONLY

| |
|---|
| 13906_s_at |
| 13919_at |
| 13923_at |
| 13932_at |
| 13935_at |
| 13940_at |
| 13949_s_at |
| 13954_g_at |
| 13973_at |
| 13983_at |
| 13989_at |
| 14010_at |
| 14014_at |
| 14015_s_at |
| 14016_s_at |
| 14025_s_at |
| 14027_at |
| 14030_at |
| 14044_at |
| 14056_at |
| 14057_at |
| 14061_at |
| 14067_at |
| 14068_s_at |
| 14072_at |
| 14074_at |
| 14075_at |
| 14083_at |
| 14084_at |
| 14089_at |
| 14095_s_at |
| 14096_at |
| 14100_at |
| 14101_at |
| 14103_at |
| 14121_at |
| 14129_s_at |
| 14133_s_at |
| 14143_at |
| 14148_at |
| 14162_at |
| 14194_at |
| 14208_at |
| 14217_at |
| 14223_at |
| 14235_at |
| 14236_at |
| 14251_f_at |
| 14252_f_at |
| 14285_at |
| 14301_s_at |
| 14316_at |
| 14366_at |
| 14369_at |
| 14392_g_at |
| 14421_at |
| 14431_at |
| 14436_at |
| 14448_at |
| 14450_at |
| 14454_at |
| 14459_at |
| 14478_at |
| 14482_at |
| 14485_at |
| 14492_s_at |
| 14505_at |
| 14510_at |
| 14517_at |
| 14519_at |
| 14534_s_at |
| 14538_r_at |
| 14558_at |
| 14559_s_at |
| 14572_at |
| 14584_at |
| 14587_at |

TABLE 6-continued

2X DOWN COLD, ONLY

14595_at
14602_at
14603_at
14605_at
14620_s_at
14626_s_at
14630_s_at
14637_s_at
14640_s_at
14642_f_at
14650_s_at
14654_s_at
14667_s_at
14668_s_at
14669_s_at
14672_s_at
14673_s_at
14675_s_at
14679_s_at
14681_g_at
14682_i_at
14689_at
14701_s_at
14703_at
14712_s_at
14713_s_at
14715_s_at
14734_s_at
14781_at
14800_at
14856_s_at
14882_at
14908_at
14912_at
14914_at
14924_at
14942_at
14945_at
14955_at
14957_s_at
14974_at
14980_at
14981_at
14995_at
15009_at
15018_at
15024_at
15026_at
15047_at
15054_at
15056_at
15058_s_at
15063_at
15066_at
15081_at
15091_at
15097_s_at
15102_s_at
15107_s_at
15118_s_at
15127_s_at
15130_s_at
15132_s_at
15133_s_at
15139_s_at
15143_s_at
15146_s_at
15150_s_at
15161_s_at
15162_s_at
15167_s_at
15170_s_at
15171_s_at
15178_s_at
15182_s_at
15185_s_at
15188_s_at

TABLE 6-continued

2X DOWN COLD, ONLY

15193_s_at
15196_s_at
15201_f_at
15206_s_at
15207_s_at
15213_s_at
15243_at
15256_at
15348_at
15350_at
15372_at
15383_at
15384_at
15385_at
15387_at
15406_at
15423_at
15431_at
15464_at
15468_at
15471_at
15475_s_at
15485_at
15505_at
15512_at
15514_at
15515_r_at
15529_at
15534_f_at
15538_at
15541_at
15543_at
15551_at
15574_s_at
15576_s_at
15577_s_at
15578_s_at
15581_s_at
15583_s_at
15591_s_at
15595_s_at
15602_f_at
15606_s_at
15608_s_at
15616_s_at
15618_s_at
15620_s_at
15627_s_at
15634_s_at
15637_s_at
15642_s_at
15643_s_at
15646_s_at
15651_f_at
15652_s_at
15667_s_at
15668_s_at
15670_s_at
15671_s_at
15675_s_at
15679_s_at
15685_s_at
15688_s_at
15689_s_at
15692_s_at
15775_at
15776_at
15845_at
15848_at
15858_at
15866_s_at
15894_at
15900_at
15901_at
15902_at
15913_at
15928_at

TABLE 6-continued

2X DOWN COLD, ONLY

| |
|---|
| 15940_at |
| 15948_s_at |
| 15956_at |
| 15976_at |
| 15978_at |
| 15986_s_at |
| 16004_s_at |
| 16015_at |
| 16017_at |
| 16019_at |
| 16024_at |
| 16031_at |
| 16055_s_at |
| 16059_s_at |
| 16065_s_at |
| 16066_s_at |
| 16069_s_at |
| 16074_s_at |
| 16076_s_at |
| 16077_s_at |
| 16084_s_at |
| 16089_s_at |
| 16102_s_at |
| 16103_s_at |
| 16105_s_at |
| 16108_s_at |
| 16112_s_at |
| 16117_s_at |
| 16118_s_at |
| 16125_s_at |
| 16127_s_at |
| 16134_s_at |
| 16136_s_at |
| 16138_s_at |
| 16140_s_at |
| 16143_s_at |
| 16144_s_at |
| 16145_s_at |
| 16148_s_at |
| 16151_s_at |
| 16158_f_at |
| 16160_f_at |
| 16168_s_at |
| 16169_s_at |
| 16171_s_at |
| 16172_s_at |
| 16222_at |
| 16232_s_at |
| 16242_at |
| 16288_at |
| 16294_s_at |
| 16325_at |
| 16346_s_at |
| 16357_at |
| 16380_at |
| 16382_at |
| 16385_s_at |
| 16393_s_at |
| 16402_s_at |
| 16417_s_at |
| 16442_s_at |
| 16446_at |
| 16448_g_at |
| 16453_at |
| 16457_s_at |
| 16470_s_at |
| 16481_s_at |
| 16510_at |
| 16512_s_at |
| 16514_at |
| 16516_at |
| 16523_s_at |
| 16526_at |
| 16528_at |
| 16531_s_at |
| 16535_s_at |
| 16537_s_at |

TABLE 6-continued

2X DOWN COLD, ONLY

| |
|---|
| 16543_s_at |
| 16544_s_at |
| 16550_s_at |
| 16559_s_at |
| 16567_s_at |
| 16577_s_at |
| 16579_s_at |
| 16580_s_at |
| 16583_s_at |
| 16584_s_at |
| 16593_s_at |
| 16598_s_at |
| 16603_s_at |
| 16604_s_at |
| 16611_s_at |
| 16614_s_at |
| 16617_s_at |
| 16618_s_at |
| 16620_s_at |
| 16631_s_at |
| 16634_s_at |
| 16639_s_at |
| 16640_s_at |
| 16652_s_at |
| 16654_at |
| 16777_at |
| 16784_at |
| 16811_at |
| 16893_at |
| 16894_at |
| 16899_at |
| 16920_at |
| 16921_at |
| 16924_s_at |
| 16926_s_at |
| 16931_s_at |
| 16934_s_at |
| 16937_at |
| 16938_at |
| 16942_at |
| 16949_s_at |
| 16950_s_at |
| 16952_s_at |
| 16962_s_at |
| 16965_s_at |
| 16970_s_at |
| 16977_at |
| 16984_at |
| 16989_at |
| 16993_s_at |
| 16997_s_at |
| 17000_at |
| 17005_at |
| 17010_s_at |
| 17017_s_at |
| 17031_s_at |
| 17040_s_at |
| 17053_s_at |
| 17056_s_at |
| 17063_s_at |
| 17070_s_at |
| 17074_s_at |
| 17084_s_at |
| 17085_s_at |
| 17087_s_at |
| 17092_s_at |
| 17095_s_at |
| 17096_s_at |
| 17097_s_at |
| 17103_s_at |
| 17105_s_at |
| 17110_s_at |
| 17115_s_at |
| 17116_s_at |
| 17119_s_at |
| 17122_s_at |
| 17207_at |

TABLE 6-continued

2X DOWN COLD, ONLY

| |
|---|
| 17215_at |
| 17247_at |
| 17254_at |
| 17286_at |
| 17288_s_at |
| 17292_at |
| 17303_s_at |
| 17305_at |
| 17318_at |
| 17323_at |
| 17374_at |
| 17405_at |
| 17415_at |
| 17418_s_at |
| 17420_at |
| 17423_s_at |
| 17426_at |
| 17427_at |
| 17430_s_at |
| 17431_at |
| 17439_g_at |
| 17442_i_at |
| 17449_s_at |
| 17462_s_at |
| 17463_at |
| 17465_at |
| 17475_at |
| 17479_at |
| 17495_s_at |
| 17508_s_at |
| 17522_s_at |
| 17523_s_at |
| 17529_s_at |
| 17537_s_at |
| 17539_s_at |
| 17543_s_at |
| 17555_s_at |
| 17557_s_at |
| 17560_s_at |
| 17564_s_at |
| 17565_s_at |
| 17568_at |
| 17570_g_at |
| 17573_at |
| 17577_g_at |
| 17578_at |
| 17579_s_at |
| 17585_s_at |
| 17596_at |
| 17600_s_at |
| 17823_s_at |
| 17840_s_at |
| 17849_s_at |
| 17857_at |
| 17865_at |
| 17882_at |
| 17885_at |
| 17902_s_at |
| 17910_at |
| 17916_at |
| 17917_s_at |
| 17918_at |
| 17926_s_at |
| 17935_at |
| 17956_i_at |
| 17961_at |
| 17966_at |
| 17978_s_at |
| 17986_s_at |
| 17993_at |
| 17998_s_at |
| 18003_at |
| 18005_at |
| 18010_s_at |
| 18013_r_at |
| 18023_s_at |
| 18029_g_at |

TABLE 6-continued

2X DOWN COLD, ONLY

| |
|---|
| 18030_i_at |
| 18045_at |
| 18046_s_at |
| 18059_i_at |
| 18064_r_at |
| 18065_r_at |
| 18074_at |
| 18076_s_at |
| 18077_at |
| 18078_at |
| 18081_at |
| 18083_r_at |
| 18085_r_at |
| 18091_at |
| 18154_s_at |
| 18165_at |
| 18174_at |
| 18221_at |
| 18226_s_at |
| 18230_at |
| 18237_at |
| 18255_at |
| 18257_at |
| 18258_s_at |
| 18274_s_at |
| 18275_at |
| 18278_at |
| 18283_at |
| 18290_at |
| 18291_at |
| 18299_s_at |
| 18300_at |
| 18306_at |
| 18327_s_at |
| 18337_s_at |
| 18339_at |
| 18365_s_at |
| 18402_at |
| 18439_s_at |
| 18487_at |
| 18508_s_at |
| 18512_at |
| 18543_at |
| 18552_at |
| 18567_at |
| 18573_at |
| 18580_at |
| 18581_at |
| 18584_at |
| 18587_s_at |
| 18590_at |
| 18591_at |
| 18592_s_at |
| 18600_at |
| 18601_s_at |
| 18607_s_at |
| 18610_s_at |
| 18611_at |
| 18616_at |
| 18622_g_at |
| 18628_at |
| 18631_at |
| 18636_at |
| 18638_at |
| 18652_at |
| 18657_at |
| 18667_at |
| 18675_at |
| 18684_at |
| 18686_s_at |
| 18688_s_at |
| 18693_s_at |
| 18698_s_at |
| 18706_s_at |
| 18707_at |
| 18726_s_at |
| 18727_at |

TABLE 6-continued

2X DOWN COLD, ONLY

| |
|---|
| 18732_i_at |
| 18735_s_at |
| 18736_at |
| 18738_f_at |
| 18747_f_at |
| 18754_at |
| 18782_at |
| 18789_at |
| 18806_s_at |
| 18814_at |
| 18823_s_at |
| 18844_at |
| 18859_at |
| 18864_at |
| 18880_at |
| 18883_g_at |
| 18886_at |
| 18892_s_at |
| 18909_s_at |
| 18911_at |
| 18913_s_at |
| 18916_s_at |
| 18921_g_at |
| 18950_at |
| 18951_s_at |
| 18956_at |
| 18966_at |
| 18972_at |
| 18994_at |
| 19030_at |
| 19039_at |
| 19068_i_at |
| 19108_at |
| 19115_at |
| 19117_s_at |
| 19122_at |
| 19125_s_at |
| 19127_at |
| 19135_at |
| 19144_at |
| 19157_s_at |
| 19158_at |
| 19177_at |
| 19192_at |
| 19198_at |
| 19222_at |
| 19226_g_at |
| 19227_at |
| 19230_at |
| 19232_s_at |
| 19263_at |
| 19285_at |
| 19332_at |
| 19346_at |
| 19347_at |
| 19361_s_at |
| 19362_at |
| 19363_at |
| 19364_at |
| 19365_s_at |
| 19373_at |
| 19379_at |
| 19381_at |
| 19382_at |
| 19401_at |
| 19402_at |
| 19406_at |
| 19413_at |
| 19416_at |
| 19429_at |
| 19432_s_at |
| 19439_at |
| 19448_s_at |
| 19454_at |
| 19462_s_at |
| 19464_at |
| 19469_at |

TABLE 6-continued

2X DOWN COLD, ONLY

| |
|---|
| 19483_at |
| 19484_s_at |
| 19513_at |
| 19548_at |
| 19563_s_at |
| 19567_at |
| 19581_at |
| 19595_s_at |
| 19606_at |
| 19623_at |
| 19627_s_at |
| 19636_at |
| 19641_at |
| 19652_at |
| 19655_at |
| 19658_at |
| 19660_at |
| 19665_s_at |
| 19667_at |
| 19690_s_at |
| 19695_at |
| 19717_at |
| 19726_s_at |
| 19752_s_at |
| 19759_at |
| 19782_at |
| 19789_s_at |
| 19803_s_at |
| 19828_at |
| 19831_i_at |
| 19833_s_at |
| 19834_at |
| 19835_at |
| 19841_at |
| 19867_at |
| 19870_s_at |
| 19871_at |
| 19872_at |
| 19876_at |
| 19897_s_at |
| 19903_at |
| 19905_at |
| 19906_at |
| 19907_at |
| 19910_at |
| 19920_s_at |
| 19932_at |
| 19951_at |
| 19962_at |
| 19963_at |
| 19969_at |
| 19970_s_at |
| 19972_at |
| 19981_at |
| 19990_at |
| 19996_at |
| 19999_s_at |
| 20009_s_at |
| 20013_at |
| 20017_at |
| 20018_at |
| 20024_s_at |
| 20045_at |
| 20047_at |
| 20048_at |
| 20050_at |
| 20051_at |
| 20058_at |
| 20067_at |
| 20069_at |
| 20099_at |
| 20100_at |
| 20113_s_at |
| 20123_at |
| 20127_s_at |
| 20129_at |
| 20133_i_at |

TABLE 6-continued

2X DOWN COLD, ONLY

20152_at
20154_at
20173_at
20178_s_at
20183_at
20188_at
20189_at
20197_at
20200_at
20210_g_at
20213_at
20229_at
20232_s_at
20255_at
20278_s_at
20284_at
20288_g_at
20294_at
20312_s_at
20331_at
20335_s_at
20350_s_at
20354_s_at
20355_at
20369_s_at
20378_g_at
20383_at
20385_s_at
20387_at
20399_at
20409_g_at
20420_at
20429_s_at
20439_at
20440_at
20444_at
20445_at
20449_at
20474_at
20480_s_at
20495_s_at
20499_at
20501_at
20516_at
20520_s_at
20530_s_at
20538_s_at
20547_at
20558_at
20561_at
20567_at
20571_at
20590_at
20592_at
20594_at
20608_s_at
20612_s_at
20616_at
20620_g_at
20635_s_at
20637_at
20643_at
20654_s_at
20670_at
20674_s_at
20684_at
20685_at
20689_s_at
20693_at
20701_s_at
20704_at
20707_s_at
20719_at

TABLE 7

SALINE STRESS RESPONSIVE SEQUENCES

| SEQ ID NO: | AFFYMETRIX ID NO: |
|---|---|
| 2227 | 12011_S_AT |
| 2228 | 12153_AT |
| 2229 | 12180_AT |
| 2230 | 12186_AT |
| 2231 | 12216_AT |
| 2232 | 12265_AT |
| 2233 | 12335_AT |
| 2234 | 12449_S_AT |
| 2235 | 12470_AT |
| 2236 | 12479_AT |
| 2237 | 12487_AT |
| 2238 | 12493_G_AT |
| 2239 | 12562_AT |
| 2240 | 12685_AT |
| 2241 | 12704_F_AT |
| 2242 | 12709_F_AT |
| 2243 | 12734_F_AT |
| 2244 | 12739_S_AT |
| 2245 | 12750_S_AT |
| 2246 | 12761_S_AT |
| 2247 | 12813_AT |
| 2248 | 12845_S_AT |
| 2249 | 12946_AT |
| 2250 | 13003_S_AT |
| 2251 | 13052_S_AT |
| 2252 | 13094_AT |
| 2253 | 13142_AT |
| 2254 | 13172_S_AT |
| | 17880_S_AT |
| 2255 | 13198_I_AT |
| 2256 | 13209_S_AT |
| | 16165_S_AT |
| 2257 | 13229_S_AT |
| 2258 | 13253_F_AT |
| 2259 | 13344_S_AT |
| 2260 | 13370_AT |
| 2261 | 13387_AT |
| 2262 | 13408_S_AT |
| 2263 | 13429_AT |
| 2264 | 13472_AT |
| 2265 | 13526_AT |
| 2266 | 13569_AT |
| 2267 | 13614_AT |
| 2268 | 13686_S_AT |
| 2269 | 13718_AT |
| 2270 | 13719_AT |
| 2271 | 13902_AT |
| 2272 | 13918_AT |
| 2273 | 13944_AT |
| 2274 | 13964_AT |
| 2275 | 13993_S_AT |
| 2276 | 14000_AT |
| 2277 | 14003_AT |
| 2278 | 14032_AT |
| 2279 | 14043_AT |
| 2280 | 14070_AT |
| 2281 | 14267_AT |
| 2282 | 14269_AT |
| 2283 | 14418_AT |
| 2284 | 14427_AT |
| 2285 | 14501_AT |
| 2286 | 14544_AT |
| 2287 | 14546_S_AT |
| 2288 | 14570_AT |
| 2289 | 14596_AT |
| 2290 | 14729_S_AT |
| 2291 | 14874_AT |
| 2292 | 14888_AT |
| 2293 | 14951_AT |
| 2294 | 14952_AT |
| 2295 | 14959_AT |
| 2296 | 14979_AT |
| 2297 | 15006_AT |
| 2298 | 15042_AT |

TABLE 7-continued

SALINE STRESS RESPONSIVE SEQUENCES

| SEQ ID NO: | AFFYMETRIX ID NO: |
|---|---|
| 2299 | 15049_AT |
| 2300 | 15062_AT |
| 2301 | 15108_S_AT |
| 2302 | 15147_S_AT |
| 2303 | 15175_S_AT |
| 2304 | 15176_S_AT |
| 2305 | 15186_S_AT |
|  | 18696_S_AT |
| 2306 | 15192_S_AT |
| 2307 | 15208_S_AT |
| 2308 | 15324_AT |
| 2309 | 15371_AT |
| 2310 | 15424_AT |
| 2311 | 15463_AT |
| 2312 | 15465_AT |
| 2313 | 15497_S_AT |
| 2314 | 15589_S_AT |
| 2315 | 15636_S_AT |
| 2316 | 15663_S_AT |
| 2317 | 15770_AT |
| 2318 | 15792_AT |
| 2319 | 15855_AT |
| 2320 | 15860_AT |
| 2321 | 15891_AT |
| 2322 | 15898_AT |
| 2323 | 15909_AT |
| 2324 | 15965_AT |
| 2325 | 15969_S_AT |
| 2326 | 15975_S_AT |
| 2327 | 15995_S_AT |
| 2328 | 15998_S_AT |
|  | 18090_S_AT |
| 2329 | 16028_AT |
| 2330 | 16050_AT |
| 2331 | 16060_S_AT |
| 2332 | 16067_S_AT |
| 2333 | 16072_S_AT |
| 2334 | 16088_F_AT |
| 2335 | 16273_AT |
| 2336 | 16314_AT |
| 2337 | 16413_S_AT |
| 2338 | 16414_AT |
| 2339 | 16426_AT |
| 2340 | 16436_AT |
| 2341 | 16455_AT |
| 2342 | 16502_AT |
| 2343 | 16548_S_AT |
| 2344 | 16568_S_AT |
| 2345 | 16582_S_AT |
| 2346 | 16589_S_AT |
| 2347 | 16594_S_AT |
| 2348 | 16613_S_AT |
| 2349 | 16651_S_AT |
| 2350 | 16668_AT |
| 2351 | 16820_AT |
| 2352 | 16987_S_AT |
| 2353 | 16995_AT |
| 2354 | 17039_S_AT |
| 2355 | 17273_AT |
| 2356 | 17278_AT |
| 2357 | 17433_AT |
| 2358 | 17467_AT |
| 2359 | 17566_AT |
| 2360 | 17595_S_AT |
| 2361 | 17744_S_AT |
| 2362 | 17758_AT |
| 2363 | 17864_AT |
| 2364 | 17868_AT |
| 2365 | 17876_AT |
| 2366 | 17894_AT |
| 2367 | 17942_S_AT |
| 2368 | 18008_R_AT |
| 2369 | 18027_AT |
| 2370 | 18053_S_AT |

TABLE 7-continued

SALINE STRESS RESPONSIVE SEQUENCES

| SEQ ID NO: | AFFYMETRIX ID NO: |
|---|---|
| 2371 | 18062_AT |
| 2372 | 18082_AT |
| 2373 | 18121_S_AT |
| 2374 | 18240_S_AT |
| 2375 | 18248_S_AT |
| 2376 | 18264_AT |
| 2377 | 18276_AT |
| 2378 | 18287_AT |
| 2379 | 18310_AT |
| 2380 | 18367_S_AT |
| 2381 | 18506_AT |
| 2382 | 18605_S_AT |
| 2383 | 18618_S_AT |
| 2384 | 18626_AT |
| 2385 | 18666_S_AT |
| 2386 | 18834_AT |
| 2387 | 18847_AT |
| 2388 | 18896_AT |
| 2389 | 18899_S_AT |
| 2390 | 18973_AT |
| 2391 | 18983_S_AT |
| 2392 | 18988_AT |
| 2393 | 18998_S_AT |
| 2394 | 19065_AT |
| 2395 | 19119_I_AT |
|  | 19121_AT |
| 2396 | 19207_AT |
| 2397 | 19220_AT |
| 2398 | 19284_AT |
| 2399 | 19315_AT |
| 2400 | 19348_AT |
| 2401 | 19403_S_AT |
| 2402 | 19437_S_AT |
| 2403 | 19502_AT |
| 2404 | 19609_AT |
| 2405 | 19645_AT |
| 2406 | 19742_AT |
| 2407 | 19863_AT |
| 2408 | 19873_AT |
| 2409 | 19891_AT |
| 2410 | 20004_S_AT |
| 2411 | 20053_AT |
| 2412 | 20138_AT |
| 2413 | 20193_AT |
| 2414 | 20199_AT |
| 2415 | 20220_AT |
| 2416 | 20239_G_AT |
| 2417 | 20297_AT |
| 2418 | 20324_S_AT |
| 2419 | 20353_AT |
| 2420 | 20362_AT |
| 2421 | 20389_AT |
| 2422 | 20546_AT |
| 2423 | 20600_AT |
| 2424 | 20623_AT |
| 2425 | 20629_AT |
| 2426 | 20648_S_AT |
| 2427 | 20668_AT |

TABLE 8

2X UP IN SALT, ONLY

12037_at
12137_at
12153_at
12186_at
12216_at
12268_at
12449_s_at
12470_at

TABLE 8-continued

2X UP IN SALT, ONLY

| | |
|---|---|
| 12476_at | 15623_f_at |
| 12487_at | 15636_s_at |
| 12493_g_at | 15646_s_at |
| 12609_at | 15670_s_at |
| 12685_at | 15770_at |
| 12704_f_at | 15775_at |
| 12709_f_at | 15778_at |
| 12734_f_at | 15792_at |
| 12739_s_at | 15855_at |
| 12750_s_at | 15891_at |
| 12761_s_at | 15909_at |
| 12819_at | 15923_at |
| 12845_s_at | 15969_s_at |
| 12946_at | 15975_s_at |
| 13142_at | 15995_s_at |
| 13198_i_at | 15998_s_at |
| 13229_s_at | 16017_at |
| 13275_f_at | 16050_at |
| 13344_s_at | 16067_s_at |
| 13370_at | 16072_s_at |
| 13408_s_at | 16165_s_at |
| 13464_at | 16190_at |
| 13472_at | 16196_at |
| 13526_at | 16273_at |
| 13614_at | 16314_at |
| 13652_at | 16413_s_at |
| 13679_s_at | 16414_at |
| 13751_at | 16417_s_at |
| 13918_at | 16455_at |
| 13919_at | 16548_s_at |
| 13944_at | 16582_s_at |
| 13964_at | 16589_s_at |
| 13987_s_at | 16594_s_at |
| 13993_s_at | 16613_s_at |
| 14000_at | 16651_s_at |
| 14032_at | 16668_at |
| 14043_at | 16690_g_at |
| 14052_at | 16762_at |
| 14067_at | 16820_at |
| 14070_at | 16873_i_at |
| 14269_at | 16987_s_at |
| 14285_at | 16989_at |
| 14427_at | 16995_at |
| 14501_at | 17039_s_at |
| 14540_at | 17040_s_at |
| 14570_at | 17400_s_at |
| 14578_s_at | 17425_s_at |
| 14596_at | 17433_at |
| 14646_s_at | 17467_at |
| 14662_f_at | 17490_s_at |
| 14668_s_at | 17529_s_at |
| 14729_s_at | 17543_s_at |
| 14874_at | 17566_at |
| 14888_at | 17595_s_at |
| 14918_at | 17744_s_at |
| 14952_at | 17758_at |
| 14959_at | 17855_at |
| 14986_at | 17864_at |
| 15006_at | 17876_at |
| 15042_at | 18008_r_at |
| 15047_at | 18013_r_at |
| 15062_at | 18024_s_at |
| 15063_at | 18027_at |
| 15108_s_at | 18053_s_at |
| 15133_s_at | 18078_at |
| 15147_s_at | 18082_at |
| 15170_s_at | 18090_s_at |
| 15175_s_at | 18091_at |
| 15182_s_at | 18121_s_at |
| 15190_s_at | 18264_at |
| 15192_s_at | 18276_at |
| 15324_at | 18300_at |
| 15392_at | 18367_s_at |
| 15424_at | 18471_at |
| 15467_at | 18506_at |
| 15497_s_at | 18605_s_at |
| 15581_s_at | 18626_at |

TABLE 8-continued

2X UP IN SALT, ONLY

18666_s_at
18747_f_at
18782_at
18834_at
18847_at
18913_s_at
18973_at
18988_at
18998_s_at
19065_at
19068_i_at
19123_at
19177_at
19220_at
19284_at
19288_at
19315_at
19437_s_at
19484_s_at
19502_at
19503_at
19592_at
19645_at
19742_at
19835_at
19873_at
19891_at
19992_at
20004_s_at
20053_at
20133_i_at
20138_at
20190_at
20199_at
20200_at
20297_at
20324_s_at
20335_s_at
20353_at
20362_at
20385_s_at
20389_at
20402_s_at
20450_at
20468_at
20489_at
20546_at
20569_s_at
20600_at
20623_at
20648_s_at
20678_at
20686_at
20707_s_at

TABLE 9

2X UP SALT, 3 HR ONLY

12037_at
12137_at
12153_at
12186_at
12216_at
12268_at
12470_at
12476_at
12487_at
12493_g_at
12609_at
12685_at
12704_f_at
12709_f_at
12734_f_at

TABLE 9-continued

2X UP SALT, 3 HR ONLY

12739_s_at
12750_s_at
12819_at
12946_at
13142_at
13229_s_at
13275_f_at
13370_at
13408_s_at
13464_at
13472_at
13614_at
13652_at
13679_s_at
13918_at
13919_at
13944_at
13987_s_at
13993_s_at
14000_at
14032_at
14043_at
14052_at
14067_at
14269_at
14285_at
14501_at
14540_at
14570_at
14596_at
14668_s_at
14729_s_at
14888_at
14918_at
14952_at
14959_at
14986_at
15006_at
15042_at
15047_at
15062_at
15063_at
15108_s_at
15133_s_at
15147_s_at
15170_s_at
15175_s_at
15182_s_at
15190_s_at
15192_s_at
15324_at
15424_at
15467_at
15497_s_at
15623_f_at
15636_s_at
15646_s_at
15670_s_at
15770_at
15775_at
15778_at
15792_at
15855_at
15891_at
15909_at
15923_at
15969_s_at
15975_s_at
15995_s_at
15998_s_at
16017_at
16050_at
16067_s_at
16072_s_at
16165_s_at
16196_at
16273_at

TABLE 9-continued

2X UP SALT, 3 HR ONLY

16314_at
16414_at
16417_s_at
16455_at
16548_s_at
16582_s_at
16589_s_at
16594_s_at
16613_s_at
16651_s_at
16668_at
16762_at
16820_at
16873_i_at
16987_s_at
16989_at
17039_s_at
17040_s_at
17425_s_at
17433_at
17490_s_at
17543_s_at
17744_s_at
17864_at
17876_at
18008_r_at
18013_r_at
18024_s_at
18027_at
18053_s_at
18078_at
18082_at
18090_s_at
18091_at
18121_s_at
18264_at
18276_at
18367_s_at
18471_at
18506_at
18605_s_at
18626_at
18666_s_at
18747_f_at
18782_at
18834_at
18847_at
18913_s_at
18973_at
18988_at
19065_at
19068_i_at
19123_at
19177_at
19220_at
19288_at
19315_at
19437_s_at
19484_s_at
19502_at
19503_at
19592_at
19645_at
19742_at
19835_at
19873_at
19891_at
20004_s_at
20053_at
20133_i_at
20138_at
20190_at
20199_at
20200_at
20220_at
20362_at
20385_s_at

TABLE 9-continued

2X UP SALT, 3 HR ONLY

20389_at
20489_at
20546_at
20623_at
20648_s_at
20678_at
20707_s_at

TABLE 10

2X DOWN SALT, ONLY

12011_s_at
12180_at
12265_at
12335_at
12479_at
12562_at
12656_at
12813_at
13003_s_at
13052_s_at
13094_at
13178_at
13253_f_at
13387_at
13429_at
13472_at
13569_at
13686_s_at
13718_at
13719_at
13902_at
14003_at
14144_at
14267_at
14418_at
14544_at
14546_s_at
14636_s_at
14951_at
14956_s_at
14979_at
14990_at
15040_g_at
15049_at
15115_f_at
15137_s_at
15148_s_at
15176_s_at
15208_s_at
15371_at
15453_s_at
15463_at
15465_at
15589_s_at
15663_s_at
15860_at
15898_at
15931_at
15965_at
15970_s_at
15972_s_at
16005_s_at
16028_at
16046_s_at
16060_s_at
16088_f_at
16150_s_at
16166_s_at
16316_at
16340_at
16367_i_at
16426_at

TABLE 10-continued

2X DOWN SALT, ONLY

16427_at
16436_at
16489_at
16502_at
16568_s_at
16638_s_at
16646_s_at
17273_at
17278_at
17567_at
17868_at
17880_s_at
17894_at
17901_at
17942_s_at
17960_at
17999_at
18062_at
18240_s_at
18248_s_at
18267_at
18279_s_at
18287_at
18310_at
18351_s_at
18455_at
18560_at
18571_at
18618_s_at
18896_at
18899_s_at
18967_s_at
18983_s_at
19119_i_at
19121_at
19207_at
19348_at
19403_s_at
19609_at
19742_at
19826_at
19863_at
19883_at
20193_at
20239_g_at
20433_at
20629_at
20668_at

TABLE 11

OSMOTIC STRESS RESPONSIVE SEQUENCES

| SEQ ID NO: | AFFYMETRIX ID NO: |
|---|---|
| 2428 | 11994_AT |
| 2429 | 12028_AT |
| 2430 | 12033_AT |
| 2431 | 12039_AT |
| 2432 | 12068_AT |
| 2433 | 12096_AT |
| 2434 | 12110_AT |
| 2435 | 12114_AT |
| 2436 | 12135_AT |
| 2437 | 12139_AT |
| 2438 | 12189_AT |
| 2439 | 12191_AT |
| 2440 | 12211_AT |
| 2441 | 12223_S_AT |
| 2442 | 12366_S_AT |
|  | 12869_S_AT |
| 2443 | 12381_AT |
| 2444 | 12406_S_AT |

TABLE 11-continued

OSMOTIC STRESS RESPONSIVE SEQUENCES

| SEQ ID NO: | AFFYMETRIX ID NO: |
|---|---|
| 2445 | 12412_AT |
| 2446 | 12453_AT |
| 2447 | 12571_S_AT |
| 2448 | 12662_AT |
| 2449 | 12746_I_AT |
| 2450 | 12774_AT |
| 2451 | 12787_AT |
| 2452 | 12847_AT |
| 2453 | 12848_AT |
| 2454 | 12895_AT |
| 2455 | 12911_S_AT |
| 2456 | 12920_AT |
|  | 12921_S_AT |
| 2457 | 13027_AT |
| 2458 | 13059_AT |
| 2459 | 13075_I_AT |
| 2460 | 13180_S_AT |
| 2461 | 13255_I_AT |
| 2462 | 13270_AT |
|  | 18167_S_AT |
| 2463 | 13283_S_AT |
| 2464 | 13382_AT |
| 2465 | 13386_S_AT |
| 2466 | 13433_AT |
| 2467 | 13482_AT |
| 2468 | 13732_AT |
| 2469 | 13733_I_AT |
| 2470 | 13842_AT |
| 2471 | 13860_S_AT |
| 2472 | 13868_AT |
| 2473 | 13901_AT |
| 2474 | 13933_AT |
| 2475 | 13995_AT |
| 2476 | 14062_AT |
| 2477 | 14118_I_AT |
| 2478 | 14141_AT |
| 2479 | 14310_AT |
| 2480 | 14354_AT |
| 2481 | 14476_AT |
| 2482 | 14513_S_AT |
| 2483 | 14568_S_AT |
| 2484 | 14604_AT |
| 2485 | 14634_S_AT |
| 2486 | 14660_S_AT |
| 2487 | 14666_S_AT |
| 2488 | 14686_S_AT |
|  | 17464_AT |
| 2489 | 14726_S_AT |
| 2490 | 14848_S_AT |
| 2491 | 14873_AT |
| 2492 | 14883_AT |
| 2493 | 15082_AT |
| 2494 | 15121_S_AT |
|  | 16014_S_AT |
| 2495 | 15168_S_AT |
| 2496 | 15271_AT |
| 2497 | 15338_AT |
| 2498 | 15418_AT |
| 2499 | 15429_AT |
| 2500 | 15548_AT |
| 2501 | 15666_S_AT |
| 2502 | 15672_S_AT |
| 2503 | 15680_S_AT |
| 2504 | 15867_AT |
| 2505 | 15918_AT |
| 2506 | 15999_S_AT |
| 2507 | 16303_AT |
| 2508 | 16363_AT |
| 2509 | 16440_S_AT |
| 2510 | 16458_S_AT |
| 2511 | 16475_AT |
| 2512 | 16513_S_AT |
| 2513 | 16529_AT |
| 2514 | 16547_S_AT |

TABLE 11-continued

OSMOTIC STRESS RESPONSIVE SEQUENCES

| SEQ ID NO: | AFFYMETRIX ID NO: |
|---|---|
| 2515 | 16553_F_AT |
| 2516 | 16563_S_AT |
| 2517 | 16629_S_AT |
| 2518 | 16797_AT |
| 2519 | 16814_AT |
| 2520 | 16832_AT |
| 2521 | 16976_S_AT |
| 2522 | 17007_AT |
| 2523 | 17037_S_AT |
| 2524 | 17054_S_AT |
| 2525 | 17257_S_AT |
|  | 18725_S_AT |
| 2526 | 17270_AT |
| 2527 | 17275_I_AT |
| 2528 | 17376_AT |
| 2529 | 17378_AT |
| 2530 | 17468_AT |
| 2531 | 17481_AT |
| 2532 | 17511_S_AT |
| 2533 | 17519_S_AT |
| 2534 | 17815_S_AT |
| 2535 | 17897_AT |
| 2536 | 17923_S_AT |
| 2537 | 17934_AT |
| 2538 | 17937_S_AT |
| 2539 | 17944_AT |
| 2540 | 17958_AT |
| 2541 | 18216_AT |
| 2542 | 18227_AT |
| 2543 | 18284_AT |
| 2544 | 18301_S_AT |
| 2545 | 18312_S_AT |
| 2546 | 18326_S_AT |
| 2547 | 18369_AT |
| 2548 | 18411_AT |
| 2549 | 18533_AT |
| 2550 | 18576_S_AT |
| 2551 | 18599_AT |
| 2552 | 18640_AT |
| 2553 | 18672_S_AT |
| 2554 | 18720_S_AT |
| 2555 | 18768_AT |
| 2556 | 18877_AT |
| 2557 | 18942_AT |
| 2558 | 18945_AT |
| 2559 | 18960_AT |
| 2560 | 18965_AT |
| 2561 | 19060_AT |
| 2562 | 19164_G_AT |
| 2563 | 19266_AT |
| 2564 | 19366_S_AT |
| 2565 | 19369_AT |
| 2566 | 19371_AT |
| 2567 | 19386_AT |
| 2568 | 19412_AT |
| 2569 | 19427_S_AT |
| 2570 | 19622_G_AT |
| 2571 | 19681_AT |
| 2572 | 19819_S_AT |
| 2573 | 19961_S_AT |
| 2574 | 20002_AT |
| 2575 | 20034_I_AT |
| 2576 | 20062_AT |
| 2577 | 20136_AT |
| 2578 | 20223_AT |
| 2579 | 20235_I_AT |
| 2580 | 20401_AT |
| 2581 | 20407_AT |
| 2582 | 20470_AT |
| 2583 | 20626_AT |
| 2584 | 20631_S_AT |
| 2585 | 20647_AT |

TABLE 12

2X UP IN MANNITOL, ONLY

12039_at
12068_at
12139_at
12212_at
12278_at
12366_s_at
12453_at
12556_at
12575_s_at
12746_i_at
12848_at
12869_s_at
12920_at
12921_s_at
13041_s_at
13059_at
13241_s_at
13255_i_at
13270_at
13382_at
13406_at
13433_at
13550_at
13672_s_at
13716_at
13842_at
13933_at
13995_at
14062_at
14075_at
14162_at
14208_at
14217_at
14235_at
14310_at
14431_at
14513_s_at
14584_at
14604_at
14673_s_at
14856_s_at
15207_s_at
15338_at
15406_at
15418_at
15591_s_at
15666_s_at
15680_s_at
15866_s_at
15918_at
16340_at
16553_f_at
16797_at
16832_at
16993_at
17037_s_at
17054_s_at
17083_s_at
17097_s_at
17119_s_at
17270_at
17305_at
17376_at
17378_at
17449_s_at
17481_at
17533_s_at
17832_s_at
17923_s_at
17944_at
18059_i_at
18216_at
18230_at
18255_at
18284_at
18301_s_at
18312_s_at

TABLE 12-continued

2X UP IN MANNITOL, ONLY

18326_s_at
18599_at
18672_s_at
18720_s_at
18768_at
18814_at
18877_at
18921_g_at
18960_at
19060_at
19182_at
19192_at
19266_at
19369_at
19386_at
19402_at
19412_at
19432_s_at
19469_at
19622_g_at
19819_s_at
19826_at
20152_at
20223_at
20235_i_at
20365_s_at
20470_at
20537_at
20547_at

TABLE 13

2X UP IN MANNITOL, 3 HR ONLY

12039_at
12068_at
12139_at
12212_at
12278_at
12366_s_at
12453_at
12556_at
12575_s_at
12746_i_at
12848_at
12869_s_at
12920_at
12921_s_at
13041_s_at
13059_at
13241_s_at
13382_at
13406_at
13433_at
13550_at
13672_s_at
13933_at
13995_at
14062_at
14075_at
14162_at
14217_at
14310_at
14431_at
14513_s_at
14584_at
14604_at
14673_s_at
14856_s_at
15207_s_at
15338_at
15418_at
15591_s_at
15866_s_at

TABLE 13-continued

2X UP IN MANNITOL, 3 HR ONLY

15918_at
16340_at
16553_f_at
16797_at
16832_at
17037_s_at
17054_s_at
17083_s_at
17097_s_at
17270_at
17305_at
17376_at
17378_at
17449_s_at
17481_at
17533_s_at
17923_s_at
17944_at
18059_i_at
18216_at
18230_at
18255_at
18301_s_at
18312_s_at
18326_s_at
18599_at
18720_s_at
18768_at
18814_at
18877_at
18921_g_at
18960_at
19060_at
19192_at
19266_at
19369_at
19386_at
19402_at
19412_at
19432_s_at
19469_at
19622_g_at
19819_s_at
20152_at
20223_at
20235_i_at
20365_s_at
20470_at
20537_at

TABLE 14

2X DOWN IN MANNITOL, ONLY

12028_at
12033_at
12110_at
12114_at
12189_at
12191_at
12211_at
12223_s_at
12268_at
12345_at
12381_at
12406_s_at
12412_at
12522_at
12571_s_at
12662_at
12787_at
12847_at
12895_at
12911_s_at

TABLE 14-continued

2X DOWN IN MANNITOL, ONLY

13027_at
13075_i_at
13221_at
13262_s_at
13283_s_at
13386_s_at
13447_s_at
13482_at
13634_s_at
13709_s_at
13732_at
13733_i_at
13812_s_at
13825_s_at
13860_s_at
13868_at
13901_at
14052_at
14224_at
14244_s_at
14254_s_at
14256_f_at
14354_at
14476_at
14568_s_at
14634_s_at
14646_at
14660_s_at
14686_s_at
14726_s_at
14848_s_at
14873_at
14883_at
14897_at
14918_at
15082_at
15084_at
15098_s_at
15105_s_at
15121_s_at
15126_s_at
15168_s_at
15271_at
15429_at
15548_at
15672_s_at
15753_at
15867_at
15999_s_at
16001_at
16021_s_at
16190_at
16260_at
16303_at
16363_at
16458_at
16468_at
16475_at
16513_s_at
16529_at
16563_s_at
16690_g_at
16814_at
16847_at
16927_s_at
16976_s_at
17007_at
17014_s_at
17016_s_at
17071_s_at
17090_s_at
17257_s_at
17275_i_at
17424_at
17464_at
17468_at
17511_s_at
17519_s_at
17525_s_at
17645_s_at
17741_at
17815_s_at
17897_at
17899_at
17934_at
17937_s_at
17958_at
18012_s_at
18227_at
18272_at
18331_s_at
18369_at
18411_at
18533_at
18576_s_at
18640_at
18696_s_at
18945_at
18949_at
18953_at
18965_at
19164_g_at
19322_at
19366_s_at
19371_at
19397_at
19427_s_at
19681_at
19707_s_at
19839_at
19961_s_at
19976_at
19998_at
20002_at
20034_i_at
20136_at
20382_s_at
20407_at
20529_at
20626_at
20631_s_at
20647_at
20699_at

TABLE 15

COLD & OSOMOTIC STRESS RESPONSIVE SEQUENCES

| SEQ ID NO: | AFFYMETRIX ID NO: |
|---|---|
| 1699 | 12040_AT |
| 1700 | 12048_AT |
| 1701 | 12054_S_AT |
| 1702 | 12077_AT |
| 1703 | 12107_I_AT |
| 1704 | 12113_AT |
| 1705 | 12154_AT |
| 1706 | 12171_AT |
| 1707 | 12212_AT |
| 1708 | 12278_AT |
| 1709 | 12317_AT |
| 1710 | 12325_AT |
| 1711 | 12333_AT |
| 1712 | 12345_AT |
| 1713 | 12349_S_AT |
|  | 14254_S_AT |
|  | 14256_F_AT |
| 1714 | 12356_AT |
| 1715 | 12380_AT |
| 1716 | 12392_AT |

TABLE 15-continued

COLD & OSOMOTIC STRESS RESPONSIVE SEQUENCES

| SEQ ID NO: | AFFYMETRIX ID NO: |
|---|---|
| 1717 | 12460_S_AT |
| 1718 | 12556_AT |
| 1719 | 12575_S_AT |
| 1720 | 12686_S_AT |
| 1721 | 12701_I_AT |
| 1722 | 12754_G_AT |
| 1723 | 12782_R_AT |
| 1724 | 12784_AT |
| 1725 | 12879_S_AT |
| 1726 | 12891_AT |
|  | 16817_S_AT |
| 1727 | 12898_G_AT |
| 1728 | 12974_AT |
| 1729 | 12998_AT |
| 1730 | 13041_S_AT |
| 1731 | 13124_AT |
| 1732 | 13134_S_AT |
| 1733 | 13144_AT |
| 1734 | 13147_AT |
| 1735 | 13152_S_AT |
| 1736 | 13187_I_AT |
|  | 16981_S_AT |
| 1737 | 13192_S_AT |
|  | 17525_S_AT |
| 1738 | 13212_S_AT |
| 1739 | 13215_S_AT |
|  | 16649_S_AT |
| 1740 | 13241_S_AT |
| 1741 | 13246_AT |
| 1742 | 13262_S_AT |
| 1743 | 13286_S_AT |
| 1744 | 13324_AT |
| 1745 | 13340_S_AT |
| 1746 | 13361_AT |
| 1747 | 13406_AT |
| 1748 | 13441_S_AT |
| 1749 | 13513_AT |
| 1750 | 13550_AT |
| 1751 | 13573_AT |
| 1752 | 13577_S_AT |
| 1753 | 13606_AT |
| 1754 | 13609_AT |
| 1755 | 13625_S_AT |
| 1756 | 13626_AT |
| 1757 | 13634_S_AT |
| 1758 | 13672_S_AT |
|  | 18916_S_AT |
| 1759 | 13709_S_AT |
| 1760 | 13736_AT |
| 1761 | 13775_AT |
| 1762 | 13810_AT |
| 1763 | 13812_S_AT |
| 1764 | 13825_S_AT |
| 1765 | 14015_S_AT |
|  | 14016_S_AT |
| 1766 | 14029_AT |
| 1767 | 14036_AT |
| 1768 | 14051_AT |
| 1769 | 14060_AT |
| 1770 | 14064_AT |
| 1771 | 14066_AT |
| 1772 | 14075_AT |
| 1773 | 14094_S_AT |
|  | 19999_S_AT |
| 1774 | 14096_AT |
| 1775 | 14104_AT |
| 1776 | 14123_S_AT |
| 1777 | 14126_S_AT |
| 1778 | 14131_AT |
| 1779 | 14136_AT |
| 1780 | 14139_AT |
|  | 14140_AT |
| 1781 | 14162_AT |
|  | 14217_AT |
| 1782 | 14178_AT |
| 1783 | 14201_AT |
| 1784 | 14208_AT |
| 1785 | 14235_AT |
| 1786 | 14242_S_AT |
| 1787 | 14431_AT |
| 1788 | 14480_AT |
| 1789 | 14497_AT |
| 1790 | 14553_AT |
| 1791 | 14584_AT |
| 1792 | 14600_AT |
| 1793 | 14673_S_AT |
|  | 19432_S_AT |
| 1794 | 14681_G_AT |
| 1795 | 14699_AT |
| 1796 | 14751_AT |
| 1797 | 14762_AT |
| 1798 | 14828_S_AT |
| 1799 | 14856_S_AT |
| 1800 | 14882_AT |
| 1801 | 14897_AT |
| 1802 | 14978_AT |
| 1803 | 14985_S_AT |
| 1804 | 15031_AT |
| 1805 | 15084_AT |
| 1806 | 15096_AT |
| 1807 | 15105_S_AT |
| 1808 | 15110_S_AT |
| 1809 | 15111_S_AT |
| 1810 | 15120_S_AT |
| 1811 | 15126_S_AT |
| 1812 | 15142_S_AT |
| 1813 | 15144_S_AT |
| 1814 | 15184_S_AT |
| 1815 | 15198_S_AT |
| 1816 | 15203_S_AT |
| 1817 | 15207_S_AT |
| 1818 | 15240_AT |
| 1819 | 15366_AT |
| 1820 | 15398_AT |
| 1821 | 15406_AT |
| 1822 | 15448_AT |
| 1823 | 15466_AT |
| 1824 | 15481_AT |
| 1825 | 15484_AT |
| 1826 | 15549_AT |
| 1827 | 15591_S_AT |
| 1828 | 15606_S_AT |
| 1829 | 15614_S_AT |
|  | 16927_S_AT |
| 1830 | 15629_S_AT |
| 1831 | 15633_S_AT |
| 1832 | 15641_S_AT |
|  | 18012_S_AT |
| 1833 | 15720_AT |
| 1834 | 15815_S_AT |
| 1835 | 15817_AT |
| 1836 | 15837_AT |
| 1837 | 15841_AT |
| 1838 | 15866_S_AT |
|  | 18255_AT |
| 1839 | 15872_AT |
|  | 18331_S_AT |
| 1840 | 15892_AT |
| 1841 | 15933_AT |
| 1842 | 15947_AT |
| 1843 | 15959_S_AT |
| 1844 | 16001_AT |
| 1845 | 16052_AT |
| 1846 | 16161_S_AT |
| 1847 | 16204_AT |
| 1848 | 16232_S_AT |
| 1849 | 16252_AT |
| 1850 | 16260_AT |

TABLE 15-continued

COLD & OSOMOTIC STRESS RESPONSIVE SEQUENCES

| SEQ ID NO: | AFFYMETRIX ID NO: |
|---|---|
| 1851 | 16266_AT |
| 1852 | 16299_AT |
| 1853 | 16365_AT |
| 1854 | 16468_AT |
| 1855 | 16477_AT |
| 1856 | 16491_AT |
| 1857 | 16523_S_AT |
| 1858 | 16566_S_AT |
| 1859 | 16570_S_AT |
| 1860 | 16688_AT |
| 1861 | 16840_AT |
| 1862 | 16847_AT |
| 1863 | 16893_AT |
| 1864 | 16896_S_AT |
| 1865 | 16898_S_AT |
| 1866 | 16912_S_AT |
| 1867 | 16980_AT |
| 1868 | 16993_AT |
| 1869 | 17008_AT |
| 1870 | 17012_S_AT |
| 1871 | 17014_S_AT |
| 1872 | 17016_S_AT |
| 1873 | 17032_S_AT |
| 1874 | 17050_S_AT |
|  | 17051_S_AT |
| 1875 | 17071_S_AT |
| 1876 | 17090_S_AT |
|  | 18690_S_AT |
| 1877 | 17097_S_AT |
| 1878 | 17104_S_AT |
| 1879 | 17119_S_AT |
| 1880 | 17160_AT |
| 1881 | 17305_AT |
| 1882 | 17424_AT |
| 1883 | 17449_S_AT |
| 1884 | 17452_G_AT |
| 1885 | 17540_S_AT |
| 1886 | 17552_S_AT |
| 1887 | 17571_AT |
| 1888 | 17589_AT |
| 1889 | 17641_G_AT |
| 1890 | 17741_AT |
|  | 18098_AT |
| 1891 | 17766_AT |
| 1892 | 17873_S_AT |
| 1893 | 17904_AT |
| 1894 | 17920_S_AT |
| 1895 | 17925_AT |
| 1896 | 17943_AT |
| 1897 | 18059_I_AT |
| 1898 | 18230_AT |
| 1899 | 18263_AT |
| 1900 | 18272_AT |
| 1901 | 18540_AT |
| 1902 | 18608_AT |
| 1903 | 18647_AT |
| 1904 | 18662_S_AT |
| 1905 | 18664_AT |
| 1906 | 18695_S_AT |
| 1907 | 18704_AT |
| 1908 | 18814_AT |
| 1909 | 18907_S_AT |
| 1910 | 18921_G_AT |
| 1911 | 18924_AT |
| 1912 | 18949_AT |
|  | 19707_S_AT |
| 1913 | 18995_AT |
| 1914 | 19017_AT |
| 1915 | 19034_AT |
| 1916 | 19063_AT |
| 1917 | 19142_AT |
| 1918 | 19158_AT |
| 1919 | 19180_AT |
| 1920 | 19187_AT |
| 1921 | 19192_AT |
| 1922 | 19195_AT |
| 1923 | 19199_AT |
| 1924 | 19231_AT |
| 1925 | 19263_AT |
| 1926 | 19308_AT |
| 1927 | 19322_AT |
| 1928 | 19365_S_AT |
| 1929 | 19372_AT |
| 1930 | 19389_AT |
| 1931 | 19392_AT |
| 1932 | 19397_AT |
| 1933 | 19400_AT |
| 1934 | 19402_AT |
| 1935 | 19458_AT |
| 1936 | 19469_AT |
| 1937 | 19473_AT |
| 1938 | 19597_S_AT |
| 1939 | 19710_S_AT |
| 1940 | 19830_AT |
| 1941 | 19839_AT |
| 1942 | 19840_S_AT |
| 1943 | 19853_AT |
| 1944 | 19860_AT |
| 1945 | 19880_AT |
| 1946 | 19889_AT |
| 1947 | 19898_AT |
| 1948 | 19914_AT |
| 1949 | 19924_AT |
| 1950 | 19949_AT |
| 1951 | 19976_AT |
| 1952 | 19998_AT |
| 1953 | 20030_AT |
| 1954 | 20151_AT |
| 1955 | 20152_AT |
| 1956 | 20187_AT |
| 1957 | 20214_I_AT |
| 1958 | 20269_AT |
| 1959 | 20271_AT |
| 1960 | 20273_AT |
| 1961 | 20299_AT |
| 1962 | 20323_AT |
| 1963 | 20429_S_AT |
| 1964 | 20457_AT |
| 1965 | 20480_S_AT |
| 1966 | 20529_AT |
| 1967 | 20547_AT |
| 1968 | 20555_S_AT |
| 1969 | 20699_AT |

TABLE 16

2X UP IN MANNITOL & COLD, ONLY

12345_at
12784_at
13153_r_at
13212_s_at
13215_s_at
13246_at
13262_s_at
13361_at
13625_s_at
13764_at
13810_at
14015_s_at
14016_s_at
14060_at
14096_at
14123_s_at
14139_at

TABLE 16-continued

2X UP IN MANNITOL & COLD, ONLY

14219_at
14248_at
14254_s_at
14256_f_at
14609_at
14636_s_at
14681_g_at
14699_at
14704_s_at
14828_s_at
14882_at
15110_s_at
15184_s_at
15448_at
15629_s_at
15720_at
15846_at
15947_at
16161_s_at
16365_at
16427_at
16566_s_at
16570_at
16649_s_at
16688_at
16712_at
16817_s_at
16840_at
16893_at
16912_s_at
16916_s_at
16927_s_at
16981_s_at
17012_s_at
17014_s_at
17051_s_at
17066_s_at
17540_s_at
17567_at
17766_at
17904_at
17920_s_at
17943_at
18263_at
18351_s_at
18662_s_at
18670_g_at
18695_s_at
18704_at
18729_at
18995_at
19158_at
19473_at
19710_s_at
19883_at
19889_at
20030_at
20269_at
20271_at
20299_at
20429_s_at
20438_at
20480_s_at

TABLE 17

2X DOWN COLD & MANNITOL, ONLY

12040_at
12048_at
12054_s_at
12077_at
12107_i_at
12113_at

TABLE 17-continued

2X DOWN COLD & MANNITOL, ONLY

12154_at
12171_at
12317_at
12325_at
12333_at
12356_at
12380_at
12392_at
12460_s_at
12686_s_at
12701_i_at
12782_r_at
12879_s_at
12898_g_at
12974_at
12998_at
13144_at
13147_at
13152_s_at
13192_s_at
13286_s_at
13324_at
13340_s_at
13441_s_at
13513_at
13573_at
13606_at
13609_at
13626_at
13736_at
13775_at
14029_at
14036_at
14051_at
14064_at
14066_at
14094_s_at
14104_at
14126_s_at
14131_at
14136_at
14178_at
14192_at
14201_at
14242_s_at
14480_at
14497_at
14553_at
14612_at
14751_at
14762_at
14978_at
14985_s_at
15031_at
15096_at
15111_s_at
15120_s_at
15142_s_at
15198_s_at
15203_s_at
15240_at
15366_at
15392_at
15398_at
15466_at
15481_at
15484_at
15549_at
15623_f_at
15815_s_at
15817_at
15841_at
15892_at
15933_at
15959_s_at
16052_at
16204_at

TABLE 17-continued

2X DOWN COLD & MANNITOL, ONLY

16252_at
16266_at
16299_at
16477_at
16491_at
16561_s_at
16645_s_at
16898_s_at
16980_at
17008_at
17104_s_at
17160_at
17317_at
17400_s_at
17452_g_at
17477_s_at
17500_s_at
17552_s_at
17571_at
17572_s_at
17589_at
17641_g_at
17855_at
17873_s_at
17925_at
18098_at
18540_at
18608_at
18647_at
18664_at
18690_s_at
18725_s_at
18924_at
19017_at
19034_at
19063_at
19141_at
19142_at
19180_at
19187_at
19195_at
19199_at
19231_at
19308_at
19372_at
19392_at
19400_at
19458_at
19597_s_at
19762_at
19830_at
19853_at
19869_at
19880_at
19898_at
19914_at
19924_at
19949_at
20151_at
20187_at
20214_i_at
20273_at
20323_at
20457_at
20555_s_at

TABLE 18

COLD & SALINE STRESS RESPONSIVE SEQUENCES

| SEQ ID NO: | AFFYMETRIX ID NO: |
|---|---|
| 1970 | 12021_AT |
| 1971 | 12037_AT |
| 1972 | 12094_AT |

TABLE 18-continued

COLD & SALINE STRESS RESPONSIVE SEQUENCES

| SEQ ID NO: | AFFYMETRIX ID NO: |
|---|---|
| 1973 | 12098_AT |
| 1974 | 12128_AT |
| 1975 | 12148_AT |
| 1976 | 12151_AT |
| 1977 | 12357_S_AT |
| 1978 | 12394_AT |
| 1979 | 12472_S_AT |
| 1980 | 12475_AT |
| 1981 | 12482_S_AT |
| 1982 | 12490_AT |
| 1983 | 12505_S_AT |
| 1984 | 12531_AT |
| 1985 | 12540_S_AT |
| 1986 | 12541_AT |
| 1987 | 12577_AT |
| 1988 | 12594_AT |
| 1989 | 12629_AT |
| 1990 | 12642_AT |
| 1991 | 12656_AT |
| 1992 | 12660_AT |
| 1993 | 12712_F_AT |
| 1994 | 12725_R_AT |
| 1995 | 12745_AT |
| 1996 | 12777_I_AT |
| 1997 | 12790_S_AT |
| 1998 | 12798_AT |
| 1999 | 12801_AT |
| 2000 | 12855_F_AT |
| 2001 | 12887_S_AT |
| 2002 | 12933_R_AT |
| 2003 | 12951_AT |
| 2004 | 13005_AT |
| 2005 | 13015_S_AT |
| 2006 | 13115_AT |
| 2007 | 13178_AT |
| 2008 | 13228_AT |
| 2009 | 13236_S_AT |
|  | 16646_S_AT |
| 2010 | 13266_S_AT |
|  | 15211_S_AT |
| 2011 | 13275_F_AT |
| 2012 | 13335_AT |
| 2013 | 13362_S_AT |
| 2014 | 13428_AT |
| 2015 | 13464_AT |
| 2016 | 13480_AT |
| 2017 | 13538_AT |
| 2018 | 13544_AT |
| 2019 | 13549_AT |
| 2020 | 13565_AT |
| 2021 | 13580_AT |
| 2022 | 13588_AT |
| 2023 | 13649_AT |
| 2024 | 13652_AT |
| 2025 | 13679_S_AT |
| 2026 | 13696_AT |
| 2027 | 13702_S_AT |
| 2028 | 13751_AT |
| 2029 | 13919_AT |
| 2030 | 13943_AT |
| 2031 | 13950_S_AT |
| 2032 | 14050_AT |
| 2033 | 14055_S_AT |
|  | 16166_S_AT |
| 2034 | 14067_AT |
| 2035 | 14078_AT |
| 2036 | 14110_I_AT |
| 2037 | 14144_AT |
| 2038 | 14232_AT |
| 2039 | 14285_AT |
| 2040 | 14346_AT |
| 2041 | 14432_AT |

TABLE 18-continued

COLD & SALINE STRESS RESPONSIVE SEQUENCES

| SEQ ID NO: | AFFYMETRIX ID NO: |
|---|---|
| 2042 | 14468_AT |
| 2043 | 14479_AT |
| 2044 | 14524_S_AT |
| 2045 | 14608_AT |
| 2046 | 14621_AT |
| 2047 | 14635_S_AT |
|  | 17128_S_AT |
| 2048 | 14640_S_AT |
| 2049 | 14643_S_AT |
| 2050 | 14663_S_AT |
| 2051 | 14668_S_AT |
| 2052 | 14688_S_AT |
|  | 18279_S_AT |
| 2053 | 14737_S_AT |
| 2054 | 14768_AT |
| 2055 | 14875_AT |
| 2056 | 14911_S_AT |
|  | 17056_S_AT |
| 2057 | 14924_AT |
| 2058 | 14956_S_AT |
|  | 15148_S_AT |
|  | 18673_AT |
| 2059 | 14964_AT |
| 2060 | 15022_AT |
| 2061 | 15040_G_AT |
| 2062 | 15047_AT |
| 2063 | 15063_AT |
| 2064 | 15085_S_AT |
| 2065 | 15123_S_AT |
| 2066 | 15133_S_AT |
| 2067 | 15137_S_AT |
| 2068 | 15153_S_AT |
| 2069 | 15170_S_AT |
| 2070 | 15172_S_AT |
| 2071 | 15182_S_AT |
| 2072 | 15190_S_AT |
| 2073 | 15241_S_AT |
| 2074 | 15389_AT |
| 2075 | 15453_S_AT |
| 2076 | 15495_AT |
| 2077 | 15496_AT |
| 2078 | 15519_S_AT |
| 2079 | 15562_AT |
| 2080 | 15580_S_AT |
| 2081 | 15582_S_AT |
| 2082 | 15638_S_AT |
|  | 18751_F_AT |
| 2083 | 15646_S_AT |
| 2084 | 15647_S_AT |
| 2085 | 15654_S_AT |
| 2086 | 15655_S_AT |
| 2087 | 15658_S_AT |
| 2088 | 15670_S_AT |
| 2089 | 15775_AT |
| 2090 | 15798_AT |
| 2091 | 15930_AT |
| 2092 | 15931_AT |
| 2093 | 15949_S_AT |
| 2094 | 16017_AT |
| 2095 | 16053_I_AT |
| 2096 | 16078_S_AT |
| 2097 | 16086_S_AT |
| 2098 | 16120_S_AT |
| 2099 | 16126_S_AT |
| 2100 | 16150_S_AT |
| 2101 | 16159_S_AT |
| 2102 | 16230_AT |
| 2103 | 16306_AT |
| 2104 | 16367_I_AT |
| 2105 | 16417_S_AT |
|  | 18083_R_AT |
| 2106 | 16418_S_AT |
| 2107 | 16423_AT |
| 2108 | 16449_S_AT |

TABLE 18-continued

COLD & SALINE STRESS RESPONSIVE SEQUENCES

| SEQ ID NO: | AFFYMETRIX ID NO: |
|---|---|
| 2109 | 16484_S_AT |
| 2110 | 16489_AT |
| 2111 | 16565_S_AT |
| 2112 | 16596_S_AT |
| 2113 | 16600_S_AT |
| 2114 | 16603_S_AT |
| 2115 | 16638_S_AT |
| 2116 | 16642_S_AT |
| 2117 | 16763_AT |
| 2118 | 16914_S_AT |
| 2119 | 16968_AT |
| 2120 | 16983_AT |
| 2121 | 16989_AT |
| 2122 | 17002_AT |
| 2123 | 17015_S_AT |
| 2124 | 17040_S_AT |
|  | 18913_S_AT |
| 2125 | 17232_AT |
| 2126 | 17380_AT |
| 2127 | 17394_S_AT |
|  | 20640_S_AT |
| 2128 | 17398_AT |
| 2129 | 17448_AT |
| 2130 | 17485_S_AT |
| 2131 | 17490_S_AT |
| 2132 | 17499_S_AT |
| 2133 | 17505_S_AT |
| 2134 | 17516_S_AT |
| 2135 | 17529_S_AT |
| 2136 | 17543_S_AT |
| 2137 | 17593_R_AT |
|  | 19858_S_AT |
| 2138 | 17609_AT |
| 2139 | 17698_AT |
| 2140 | 17836_AT |
| 2141 | 17886_AT |
| 2142 | 17896_AT |
| 2143 | 17901_AT |
| 2144 | 17902_S_AT |
| 2145 | 17913_S_AT |
| 2146 | 17924_AT |
| 2147 | 17954_S_AT |
| 2148 | 17960_AT |
| 2149 | 17991_G_AT |
|  | 18967_S_AT |
| 2150 | 17999_AT |
| 2151 | 18057_I_AT |
| 2152 | 18078_AT |
| 2153 | 18091_AT |
| 2154 | 18168_S_AT |
| 2155 | 18252_AT |
| 2156 | 18267_AT |
| 2157 | 18300_AT |
| 2158 | 18308_I_AT |
| 2159 | 18328_AT |
| 2160 | 18354_AT |
| 2161 | 18402_AT |
| 2162 | 18416_AT |
| 2163 | 18455_AT |
| 2164 | 18459_AT |
| 2165 | 18571_AT |
| 2166 | 18604_AT |
|  | 19181_S_AT |
| 2167 | 18644_AT |
| 2168 | 18745_F_AT |
|  | 19611_S_AT |
| 2169 | 18782_AT |
| 2170 | 18881_AT |
| 2171 | 18904_AT |
| 2172 | 18914_S_AT |
| 2173 | 18963_AT |
| 2174 | 19068_I_AT |
| 2175 | 19078_AT |
| 2176 | 19171_AT |

TABLE 18-continued

COLD & SALINE STRESS RESPONSIVE SEQUENCES

| SEQ ID NO: | AFFYMETRIX ID NO: |
|---|---|
| 2177 | 19177_AT |
| 2178 | 19394_AT |
| 2179 | 19411_AT |
| 2180 | 19415_AT |
| 2181 | 19466_S_AT |
| 2182 | 19484_S_AT |
| 2183 | 19549_S_AT |
| 2184 | 19592_AT |
| 2185 | 19633_AT |
| 2186 | 19641_AT |
| 2187 | 19669_AT |
| 2188 | 19672_AT |
| 2189 | 19684_AT |
| 2190 | 19692_AT |
| 2191 | 19746_AT |
| 2192 | 19835_AT |
| 2193 | 19848_S_AT |
| 2194 | 19892_AT |
| 2195 | 19904_AT |
| 2196 | 19936_AT |
| 2197 | 19974_S_AT |
| 2198 | 19994_AT |
| 2199 | 20005_S_AT |
| 2200 | 20022_AT |
| 2201 | 20032_AT |
| 2202 | 20044_AT |
| 2203 | 20049_AT |
| 2204 | 20081_AT |
| 2205 | 20133_I_AT |
| 2206 | 20155_S_AT |
| 2207 | 20163_S_AT |
| 2208 | 20200_AT |
| 2209 | 20296_S_AT |
| 2210 | 20336_AT |
| 2211 | 20341_AT |
| 2212 | 20372_AT |
| 2213 | 20385_S_AT |
| 2214 | 20433_AT |
| 2215 | 20489_AT |
| 2216 | 20525_AT |
| 2217 | 20543_AT |
| 2218 | 20565_AT |
| 2219 | 20570_AT |
| 2220 | 20576_AT |
| 2221 | 20577_AT |
| 2222 | 20609_AT |
| 2223 | 20646_AT |
| 2224 | 20672_AT |
| 2225 | 20707_S_AT |
| 2226 | 20720_AT |

TABLE 19

2X UP IN SALT & COLD, ONLY

12004_at
12098_at
12148_at
12251_at
12357_s_at
12394_at
12457_at
12505_s_at
12522_at
12541_at
12594_at
12606_at
12697_at
12745_at
12781_at
12798_at

TABLE 19-continued

2X UP IN SALT & COLD, ONLY

12855_f_at
12945_at
12951_at
13005_at
13015_s_at
13115_at
13146_s_at
13335_at
13447_s_at
13480_at
13544_at
13549_at
13580_at
13649_at
13943_at
13950_s_at
14110_i_at
14144_at
14224_at
14432_at
14468_at
14479_at
14524_s_at
14640_s_at
14643_s_at
14735_s_at
14737_s_at
14768_at
14784_at
14924_at
15064_at
15127_s_at
15186_s_at
15189_s_at
15255_at
15389_at
15482_at
15495_at
15496_at
15519_s_at
15580_s_at
15582_s_at
15776_at
15798_at
15910_at
15931_at
15937_at
15949_s_at
15972_s_at
16048_at
16086_s_at
16120_s_at
16126_s_at
16150_s_at
16159_s_at
16230_at
16306_at
16418_s_at
16423_at
16449_s_at
16565_s_at
16603_s_at
16763_at
16968_at
16983_at
17002_at
17015_s_at
17019_s_at
17078_s_at
17232_at
17317_at
17394_s_at
17516_s_at
17585_s_at
17609_at
17698_at
17836_at

TABLE 19-continued

2X UP IN SALT & COLD, ONLY

17896_at
17899_at
17902_s_at
17960_at
17963_at
18168_s_at
18252_at
18267_at
18308_i_at
18354_at
18402_at
18459_at
18484_at
18745_f_at
18904_s_at
18914_s_at
18929_s_at
18946_at
18963_at
19078_at
19137_at
19141_at
19411_at
19641_at
19672_at
19684_at
19692_at
19746_at
19762_at
19869_at
19894_at
19904_at
19936_at
19994_at
20005_s_at
20031_at
20044_at
20382_s_at
20406_g_at
20421_at
20525_at
20543_at
20565_at
20570_at
20640_s_at
20646_at
20720_at

TABLE 20

2X DOWN IN COLD & SALT, ONLY

12021_at
12094_at
12128_at
12151_at
12332_s_at
12472_s_at
12475_at
12482_s_at
12490_at
12531_at
12540_s_at
12577_at
12629_at
12642_at
12660_at
12676_s_at
12712_f_at
12725_r_at
12777_i_at
12790_s_at
12801_at
12887_s_at

TABLE 20-continued

2X DOWN IN COLD & SALT, ONLY

12933_r_at
13153_r_at
13228_at
13362_s_at
13428_at
13538_at
13565_at
13588_at
13696_at
13702_s_at
13716_at
13764_at
14050_at
14055_s_at
14069_at
14078_at
14232_at
14346_at
14608_at
14609_at
14621_at
14635_s_at
14663_s_at
14688_s_at
14691_at
14704_s_at
14875_at
14911_s_at
14964_at
15022_at
15085_s_at
15123_s_at
15153_s_at
15172_s_at
15190_s_at
15211_s_at
15241_s_at
15437_at
15562_at
15638_s_at
15647_s_at
15654_s_at
15655_s_at
15658_s_at
15695_s_at
15846_at
15930_at
16053_i_at
16078_s_at
16229_at
16465_at
16484_s_at
16596_s_at
16600_s_at
16642_s_at
16914_s_at
17027_s_at
17066_s_at
17083_s_at
17128_s_at
17380_at
17398_at
17448_at
17485_s_at
17490_s_at
17499_s_at
17505_s_at
17514_s_at
17593_r_at
17886_at
17913_s_at
17924_at
17954_s_at
17991_g_at
18057_i_at
18069_at
18328_at

TABLE 20-continued

2X DOWN IN COLD & SALT, ONLY

18416_at
18604_at
18644_at
18881_at
19171_at
19181_s_at
19182_at
19394_at
19415_at
19466_s_at
19549_s_at
19592_at
19633_at
19669_at
19848_s_at
19858_s_at
19878_at
19892_at
19974_s_at
20022_at
20032_at
20049_at
20081_at
20155_s_at
20163_s_at
20296_s_at
20336_at
20341_at
20365_s_at
20372_at
20489_at
20491_at
20576_at
20577_at
20609_at
20672_at

TABLE 21

OSMOTIC & SALINE STRESS RESPONSIVE SEQUENCES

| SEQ ID NO: | AFFYMETRIX ID NO: |
|---|---|
| 2586 | 12126_S_AT |
| 2587 | 12137_AT |
| 2588 | 12227_AT |
| 2589 | 12239_AT |
| 2590 | 12268_AT |
| 2591 | 12369_AT |
| 2592 | 12476_AT |
| 2593 | 12484_G_AT |
| 2594 | 12494_AT |
| 2595 | 12644_AT |
| 2596 | 12645_AT |
| 2597 | 12796_S_AT |
| 2598 | 12819_AT |
| 2599 | 12841_AT |
| 2600 | 12852_S_AT |
|  | 19455_S_AT |
| 2601 | 13084_AT |
| 2602 | 13171_AT |
| 2603 | 13174_R_AT |
| 2604 | 13596_AT |
| 2605 | 13807_AT |
| 2606 | 13977_AT |
| 2607 | 13999_AT |
| 2608 | 14052_AT |
| 2609 | 14293_AT |
| 2610 | 14335_AT |
| 2611 | 14486_AT |
| 2612 | 14506_AT |
| 2613 | 14518_AT |
| 2614 | 14540_AT |

TABLE 21-continued

OSMOTIC & SALINE STRESS RESPONSIVE SEQUENCES

| SEQ ID NO: | AFFYMETRIX ID NO: |
|---|---|
| 2615 | 14578_S_AT |
| 2616 | 14646_S_AT |
| 2617 | 14662_F_AT |
|  | 15962_S_AT |
| 2618 | 14901_AT |
| 2619 | 14918_AT |
| 2620 | 14986_AT |
| 2621 | 15053_S_AT |
| 2622 | 15179_S_AT |
| 2623 | 15252_G_AT |
| 2624 | 15280_AT |
| 2625 | 15467_AT |
| 2626 | 15607_S_AT |
| 2627 | 15625_S_AT |
| 2628 | 15703_I_AT |
| 2629 | 15827_AT |
| 2630 | 15863_AT |
| 2631 | 15923_AT |
| 2632 | 15946_S_AT |
| 2633 | 16005_S_AT |
| 2634 | 16073_F_AT |
| 2635 | 16114_S_AT |
| 2636 | 16127_S_AT |
|  | 18744_F_AT |
| 2637 | 16190_AT |
| 2638 | 16196_AT |
| 2639 | 16236_G_AT |
|  | 19531_AT |
| 2640 | 16310_AT |
| 2641 | 16316_AT |
| 2642 | 16334_S_AT |
| 2643 | 16335_AT |
| 2644 | 16340_AT |
| 2645 | 16450_S_AT |
| 2646 | 16500_AT |
| 2647 | 16524_AT |
| 2648 | 16533_AT |
| 2649 | 16690_G_AT |
| 2650 | 16762_AT |
| 2651 | 16819_AT |
| 2652 | 16873_I_AT |
| 2653 | 16972_AT |
| 2654 | 16991_AT |
| 2655 | 17099_S_AT |
| 2656 | 17339_AT |
| 2657 | 17397_S_AT |
| 2658 | 17419_AT |
| 2659 | 17460_AT |
| 2660 | 17554_S_AT |
| 2661 | 17939_AT |
| 2662 | 18013_R_AT |
|  | 18178_S_AT |
| 2663 | 18024_S_AT |
| 2664 | 18032_I_AT |
| 2665 | 18054_AT |
| 2666 | 18151_AT |
| 2667 | 18281_AT |
| 2668 | 18445_AT |
| 2669 | 18520_AT |
| 2670 | 18583_AT |
| 2671 | 18663_S_AT |
| 2672 | 18753_S_AT |
| 2673 | 18876_AT |
| 2674 | 18938_G_AT |
| 2675 | 18971_AT |
| 2676 | 18977_AT |
| 2677 | 18981_AT |
| 2678 | 19099_AT |
| 2679 | 19196_AT |
| 2680 | 19376_AT |
| 2681 | 19409_AT |
| 2682 | 19503_AT |
| 2683 | 19826_AT |
| 2684 | 19847_S_AT |

TABLE 21-continued

OSMOTIC & SALINE STRESS RESPONSIVE SEQUENCES

| SEQ ID NO: | AFFYMETRIX ID NO: |
|---|---|
| 2685 | 19930_AT |
| 2686 | 19992_AT |
| 2687 | 20096_AT |
| 2688 | 20108_AT |
| 2689 | 20256_S_AT |
| 2690 | 20290_S_AT |
| 2691 | 20298_AT |
| 2692 | 20305_AT |
| 2693 | 20322_AT |
| 2694 | 20333_AT |
| 2695 | 20402_S_AT |
| 2696 | 20424_AT |
| 2697 | 20446_S_AT |
| 2698 | 20450_AT |
| 2699 | 20468_AT |
| 2700 | 20569_S_AT |
| 2701 | 20639_AT |
| 2702 | 20678_AT |
| 2703 | 20686_AT |

TABLE 22

2X UP IN SALT & MANNITOL, ONLY

12126_s_at
12227_at
12369_at
12521_at
12644_at
12645_at
12724_f_at
12795_at
12796_s_at
12841_at
12852_s_at
12958_at
13014_at
13174_r_at
13211_s_at
13596_at
13640_at
13789_at
13977_at
13999_at
14069_at
14083_at
14089_at
14293_at
14675_s_at
15053_s_at
15058_s_at
15252_g_at
15280_at
15437_at
15607_s_at
15625_s_at
15827_at
15863_at
15880_at
16005_s_at
16031_at
16073_f_at
16316_at
16334_s_at
16335_at
16450_s_at
16500_at
16524_at
16533_at
16597_s_at
16819_at

TABLE 22-continued

2X UP IN SALT & MANNITOL, ONLY

17085_s_at
17099_s_at
17339_at
17419_at
17442_i_at
17514_s_at
17548_s_at
17554_s_at
17961_at
18032_i_at
18054_at
18151_at
18167_s_at
18281_at
18520_at
18663_s_at
18744_f_at
18753_s_at
18789_at
18876_at
18909_s_at
18938_g_at
18977_at
19099_at
19108_at
19135_at
19227_at
19376_at
19429_at
19455_s_at
19531_at
19789_s_at
19878_at
20017_at
20096_at
20256_s_at
20290_s_at
20305_at
20322_at
20333_at
20420_at
20424_at
20689_s_at

TABLE 23

2X DOWN IN MANNITOL & SALT, ONLY

12239_at
12251_at
12476_at
12484_g_at
12494_at
12561_at
12647_s_at
12719_f_at
12819_at
12841_at
13084_at
13171_at
13172_s_at
13435_at
13807_at
14250_r_at
14335_at
14486_at
14506_at
14518_at
14901_at
15046_s_at
15179_s_at
15451_at
15703_i_at
15946_s_at

TABLE 23-continued

2X DOWN IN MANNITOL & SALT, ONLY

16014_s_at
16114_s_at
16310_at
16342_at
16712_at
16762_at
16972_at
16991_at
17397_s_at
17408_at
17460_at
17775_at
17939_at
18445_at
18583_at
18751_f_at
18971_at
18981_at
19156_s_at
19196_at
19359_s_at
19409_at
19503_at
19713_at
19718_at
19847_s_at
19930_at
20108_at
20298_at
20421_at
20432_at
20446_s_at
20639_at

TABLE 24

COLD, OSMOTIC & SALINE RESPONSIVE SEQUENCES

| SEQ ID NO: | AFFYMETRIX ID NO: |
|---|---|
| 1262 | 12004_AT |
| 1263 | 12023_S_AT |
| 1264 | 12078_AT |
| 1265 | 12115_AT |
| 1266 | 12118_AT |
| 1267 | 12150_AT |
| 1268 | 12251_AT |
| 1269 | 12271_S_AT |
| 1270 | 12276_AT |
| 1271 | 12332_S_AT |
|  | 13211_S_AT |
| 1272 | 12338_AT |
| 1273 | 12400_AT |
| 1274 | 12430_AT |
| 1275 | 12457_AT |
| 1276 | 12521_AT |
| 1277 | 12522_AT |
| 1278 | 12530_AT |
| 1279 | 12536_S_AT |
| 1280 | 12538_AT |
| 1281 | 12561_AT |
| 1282 | 12574_AT |
|  | 19019_I_AT |
| 1283 | 12595_AT |
| 1284 | 12606_AT |
| 1285 | 12609_AT |
| 1286 | 12622_AT |
| 1287 | 12630_AT |
| 1288 | 12647_S_AT |
| 1289 | 12676_S_AT |
| 1290 | 12697_AT |
| 1291 | 12698_AT |
| 1292 | 12719_F_AT |

TABLE 24-continued

COLD, OSMOTIC & SALINE RESPONSIVE SEQUENCES

| SEQ ID NO: | AFFYMETRIX ID NO: |
|---|---|
| 1293 | 12724_F_AT |
|  | 15871_S_AT |
|  | 16597_S_AT |
| 1294 | 12749_AT |
| 1295 | 12765_AT |
| 1296 | 12769_AT |
| 1297 | 12781_AT |
| 1298 | 12785_AT |
| 1299 | 12792_S_AT |
| 1300 | 12795_AT |
| 1301 | 12805_S_AT |
| 1302 | 12857_AT |
| 1303 | 12883_S_AT |
| 1304 | 12909_S_AT |
|  | 16539_S_AT |
| 1305 | 12932_S_AT |
|  | 15605_S_AT |
| 1306 | 12945_AT |
| 1307 | 12958_AT |
| 1308 | 12964_AT |
| 1309 | 12968_AT |
| 1310 | 12972_AT |
| 1311 | 12989_S_AT |
| 1312 | 13004_AT |
| 1313 | 13014_AT |
| 1314 | 13025_AT |
| 1315 | 13036_AT |
| 1316 | 13099_S_AT |
| 1317 | 13136_AT |
| 1318 | 13146_S_AT |
|  | 13239_S_AT |
| 1319 | 13153_R_AT |
| 1320 | 13159_AT |
| 1321 | 13176_AT |
| 1322 | 13217_S_AT |
|  | 17500_S_AT |
| 1323 | 13225_S_AT |
|  | 15997_S_AT |
| 1324 | 13230_S_AT |
|  | 15972_S_AT |
| 1325 | 13279_S_AT |
|  | 17477_S_AT |
| 1326 | 13280_S_AT |
|  | 20301_S_AT |
| 1327 | 13282_S_AT |
|  | 17027_S_AT |
| 1328 | 13426_AT |
| 1329 | 13432_AT |
| 1330 | 13435_AT |
| 1331 | 13447_S_AT |
| 1332 | 13474_AT |
| 1333 | 13511_AT |
| 1334 | 13546_AT |
| 1335 | 13547_S_AT |
| 1336 | 13548_AT |
| 1337 | 13555_AT |
| 1338 | 13587_AT |
| 1339 | 13595_AT |
| 1340 | 13610_S_AT |
| 1341 | 13627_AT |
| 1342 | 13640_AT |
| 1343 | 13645_AT |
| 1344 | 13647_AT |
| 1345 | 13706_S_AT |
|  | 19701_S_AT |
| 1346 | 13716_AT |
|  | 18228_AT |
| 1347 | 13725_AT |
| 1348 | 13764_AT |
| 1349 | 13771_AT |
| 1350 | 13789_AT |
| 1351 | 13916_AT |
| 1352 | 13965_S_AT |
| 1353 | 13967_AT |

TABLE 24-continued

COLD, OSMOTIC & SALINE RESPONSIVE SEQUENCES

| SEQ ID NO: | AFFYMETRIX ID NO: |
|---|---|
| 1354 | 14028_AT |
| 1355 | 14039_AT |
| 1356 | 14046_AT |
| 1357 | 14049_AT |
| 1358 | 14069_AT |
| 1359 | 14077_AT |
| 1360 | 14080_AT |
| 1361 | 14083_AT |
| 1362 | 14089_AT |
| 1363 | 14090_I_AT |
| 1364 | 14097_AT |
| 1365 | 14116_AT |
| 1366 | 14151_AT |
|  | 14219_AT |
| 1367 | 14170_AT |
| 1368 | 14172_AT |
| 1369 | 14192_AT |
| 1370 | 14224_AT |
| 1371 | 14227_AT |
| 1372 | 14244_S_AT |
|  | 14245_AT |
|  | 14645_S_AT |
|  | 15974_G_AT |
| 1373 | 14248_AT |
| 1374 | 14250_R_AT |
| 1375 | 14367_AT |
| 1376 | 14381_AT |
| 1377 | 14384_AT |
| 1378 | 14398_S_AT |
| 1379 | 14487_AT |
| 1380 | 14582_AT |
| 1381 | 14597_AT |
| 1382 | 14609_AT |
| 1383 | 14612_AT |
|  | 19267_S_AT |
| 1384 | 14614_AT |
| 1385 | 14636_S_AT |
| 1386 | 14644_S_AT |
|  | 14658_S_AT |
|  | 14659_S_AT |
|  | 15964_S_AT |
| 1387 | 14675_S_AT |
| 1388 | 14691_AT |
|  | 14709_AT |
| 1389 | 14704_S_AT |
|  | 15846_AT |
| 1390 | 14705_I_AT |
| 1391 | 14733_S_AT |
| 1392 | 14735_S_AT |
| 1393 | 14779_AT |
| 1394 | 14784_AT |
| 1395 | 14923_AT |
| 1396 | 14947_AT |
| 1397 | 14950_AT |
| 1398 | 14990_AT |
| 1399 | 14998_AT |
| 1400 | 15005_S_AT |
| 1401 | 15018_AT |
| 1402 | 15045_AT |
| 1403 | 15046_S_AT |
| 1404 | 15052_AT |
| 1405 | 15058_S_AT |
| 1406 | 15064_AT |
| 1407 | 15088_S_AT |
| 1408 | 15098_S_AT |
| 1409 | 15103_S_AT |
| 1410 | 15109_S_AT |
| 1411 | 15124_S_AT |
| 1412 | 15127_S_AT |
| 1413 | 15145_S_AT |
| 1414 | 15154_S_AT |
| 1415 | 15161_S_AT |
| 1416 | 15189_S_AT |
| 1417 | 15214_S_AT |
| 1418 | 15255_AT |
| 1419 | 15356_AT |
| 1420 | 15357_AT |
| 1421 | 15364_AT |
| 1422 | 15392_AT |
| 1423 | 15403_S_AT |
| 1424 | 15437_AT |
| 1425 | 15451_AT |
| 1426 | 15476_AT |
| 1427 | 15482_AT |
| 1428 | 15483_S_AT |
| 1429 | 15521_S_AT |
| 1430 | 15522_I_AT |
| 1431 | 15531_I_AT |
| 1432 | 15573_AT |
| 1433 | 15581_S_AT |
| 1434 | 15586_S_AT |
| 1435 | 15594_S_AT |
| 1436 | 15609_S_AT |
| 1437 | 15611_S_AT |
| 1438 | 15621_F_AT |
| 1439 | 15623_F_AT |
| 1440 | 15669_S_AT |
| 1441 | 15695_S_AT |
| 1442 | 15702_S_AT |
| 1443 | 15753_AT |
| 1444 | 15761_AT |
| 1445 | 15776_AT |
| 1446 | 15778_AT |
| 1447 | 15839_AT |
| 1448 | 15842_AT |
| 1449 | 15857_S_AT |
| 1450 | 15859_AT |
| 1451 | 15880_AT |
| 1452 | 15886_AT |
| 1453 | 15906_S_AT |
| 1454 | 15910_AT |
| 1455 | 15937_AT |
| 1456 | 15957_AT |
| 1457 | 15970_S_AT |
| 1458 | 15985_AT |
| 1459 | 16010_S_AT |
|  | 16011_S_AT |
|  | 17078_S_AT |
| 1460 | 16021_S_AT |
| 1461 | 16031_AT |
| 1462 | 16038_S_AT |
| 1463 | 16045_S_AT |
| 1464 | 16046_S_AT |
| 1465 | 16048_AT |
| 1466 | 16061_S_AT |
| 1467 | 16082_S_AT |
| 1468 | 16111_F_AT |
| 1469 | 16115_S_AT |
| 1470 | 16141_S_AT |
| 1471 | 16144_S_AT |
| 1472 | 16163_S_AT |
| 1473 | 16173_S_AT |
| 1474 | 16229_AT |
| 1475 | 16298_AT |
| 1476 | 16301_S_AT |
| 1477 | 16322_AT |
| 1478 | 16342_AT |
| 1479 | 16351_AT |
| 1480 | 16412_S_AT |
| 1481 | 16422_AT |
| 1482 | 16427_AT |
| 1483 | 16438_AT |
| 1484 | 16474_S_AT |
| 1485 | 16482_S_AT |
| 1486 | 16485_S_AT |
|  | 18052_S_AT |
| 1487 | 16493_AT |
| 1488 | 16534_S_AT |

TABLE 24-continued

COLD, OSMOTIC & SALINE RESPONSIVE SEQUENCES

| SEQ ID NO: | AFFYMETRIX ID NO: |
|---|---|
| 1489 | 16555_S_AT |
| 1490 | 16561_S_AT |
|  | 17572_S_AT |
| 1491 | 16592_S_AT |
| 1492 | 16615_S_AT |
| 1493 | 16637_S_AT |
| 1494 | 16692_AT |
| 1495 | 16712_AT |
| 1496 | 16789_AT |
| 1497 | 16818_S_AT |
| 1498 | 16971_S_AT |
| 1499 | 17018_S_AT |
| 1500 | 17019_S_AT |
| 1501 | 17029_S_AT |
| 1502 | 17041_S_AT |
| 1503 | 17047_S_AT |
| 1504 | 17066_S_AT |
| 1505 | 17085_S_AT |
| 1506 | 17089_S_AT |
| 1507 | 17179_AT |
| 1508 | 17180_AT |
| 1509 | 17228_AT |
| 1510 | 17252_AT |
| 1511 | 17317_AT |
| 1512 | 17338_AT |
| 1513 | 17384_AT |
| 1514 | 17387_S_AT |
| 1515 | 17400_S_AT |
| 1516 | 17407_S_AT |
| 1517 | 17408_AT |
| 1518 | 17413_S_AT |
| 1519 | 17416_AT |
| 1520 | 17425_S_AT |
| 1521 | 17440_I_AT |
| 1522 | 17442_I_AT |
| 1523 | 17473_AT |
| 1524 | 17484_AT |
| 1525 | 17514_S_AT |
| 1526 | 17520_S_AT |
| 1527 | 17533_S_AT |
| 1528 | 17548_S_AT |
|  | 19614_AT |
| 1529 | 17549_S_AT |
| 1530 | 17555_S_AT |
| 1531 | 17567_AT |
| 1532 | 17654_AT |
| 1533 | 17693_AT |
| 1534 | 17697_AT |
| 1535 | 17722_AT |
| 1536 | 17752_AT |
| 1537 | 17755_AT |
| 1538 | 17775_AT |
| 1539 | 17832_S_AT |
| 1540 | 17840_S_AT |
| 1541 | 17843_S_AT |
| 1542 | 17855_AT |
| 1543 | 17860_AT |
| 1544 | 17869_AT |
| 1545 | 17888_AT |
| 1546 | 17899_AT |
| 1547 | 17929_S_AT |
| 1548 | 17930_S_AT |
| 1549 | 17932_S_AT |
| 1550 | 17936_S_AT |
|  | 18670_G_AT |
| 1551 | 17957_AT |
| 1552 | 17961_AT |
| 1553 | 17962_AT |
| 1554 | 17963_AT |
| 1555 | 17971_S_AT |
| 1556 | 17975_AT |
|  | 18742_F_AT |
| 1557 | 18016_R_AT |
| 1558 | 18069_AT |
| 1559 | 18122_AT |
| 1560 | 18140_AT |
| 1561 | 18199_AT |
| 1562 | 18224_S_AT |
| 1563 | 18225_AT |
| 1564 | 18235_AT |
| 1565 | 18259_S_AT |
| 1566 | 18265_AT |
| 1567 | 18270_AT |
| 1568 | 18280_AT |
| 1569 | 18289_AT |
| 1570 | 18296_AT |
| 1571 | 18298_AT |
| 1572 | 18314_I_AT |
| 1573 | 18318_AT |
| 1574 | 18325_AT |
| 1575 | 18351_S_AT |
| 1576 | 18471_AT |
| 1577 | 18482_S_AT |
| 1578 | 18484_AT |
| 1579 | 18560_AT |
| 1580 | 18564_AT |
| 1581 | 18590_AT |
| 1582 | 18594_AT |
| 1583 | 18595_AT |
| 1584 | 18596_AT |
| 1585 | 18629_S_AT |
| 1586 | 18637_AT |
| 1587 | 18661_AT |
| 1588 | 18668_AT |
| 1589 | 18699_I_AT |
| 1590 | 18747_F_AT |
|  | 18789_AT |
| 1591 | 18761_AT |
| 1592 | 18833_AT |
| 1593 | 18875_S_AT |
| 1594 | 18894_AT |
| 1595 | 18936_AT |
| 1596 | 18946_AT |
| 1597 | 18953_AT |
| 1598 | 18955_AT |
| 1599 | 18972_AT |
| 1600 | 19008_S_AT |
| 1601 | 19108_AT |
| 1602 | 19123_AT |
| 1603 | 19135_AT |
| 1604 | 19137_AT |
| 1605 | 19141_AT |
| 1606 | 19152_AT |
| 1607 | 19156_S_AT |
| 1608 | 19182_AT |
| 1609 | 19186_S_AT |
| 1610 | 19214_AT |
| 1611 | 19216_AT |
| 1612 | 19227_AT |
| 1613 | 19243_AT |
| 1614 | 19288_AT |
| 1615 | 19359_S_AT |
| 1616 | 19368_AT |
| 1617 | 19379_AT |
| 1618 | 19380_S_AT |
| 1619 | 19398_AT |
| 1620 | 19421_AT |
| 1621 | 19424_AT |
| 1622 | 19429_AT |
| 1623 | 19430_AT |
| 1624 | 19450_AT |
| 1625 | 19457_AT |
| 1626 | 19467_AT |
| 1627 | 19516_AT |
| 1628 | 19545_AT |
| 1629 | 19564_AT |
| 1630 | 19577_AT |
| 1631 | 19593_AT |

TABLE 24-continued

COLD, OSMOTIC & SALINE RESPONSIVE SEQUENCES

| SEQ ID NO: | AFFYMETRIX ID NO: |
|---|---|
| 1632 | 19602_AT |
| 1633 | 19618_AT |
| 1634 | 19638_AT |
| 1635 | 19640_AT |
| 1636 | 19646_S_AT |
| 1637 | 19656_S_AT |
| 1638 | 19670_AT |
| 1639 | 19696_AT |
| 1640 | 19713_AT |
| 1641 | 19718_AT |
| 1642 | 19722_S_AT |
| 1643 | 19749_AT |
| 1644 | 19755_AT |
| 1645 | 19762_AT |
| 1646 | 19789_S_AT |
| 1647 | 19815_AT |
| 1648 | 19843_AT |
| 1649 | 19869_AT |
| 1650 | 19878_AT |
| 1651 | 19883_AT |
| 1652 | 19894_AT |
| 1653 | 19926_AT |
| 1654 | 19944_AT |
| 1655 | 19968_AT |
| 1656 | 19977_AT |
| 1657 | 19982_AT |
| 1658 | 19987_AT |
| 1659 | 19991_AT |
| 1660 | 20015_AT |
| 1661 | 20017_AT |
| 1662 | 20031_AT |
| 1663 | 20040_AT |
| 1664 | 20042_S_AT |
| 1665 | 20060_AT |
|  | 20438_AT |
| 1666 | 20089_AT |
| 1667 | 20118_AT |
| 1668 | 20144_AT |
| 1669 | 20149_AT |
| 1670 | 20179_AT |
| 1671 | 20190_AT |
| 1672 | 20194_AT |
| 1673 | 20219_AT |
| 1674 | 20245_S_AT |
| 1675 | 20263_AT |
| 1676 | 20308_S_AT |
| 1677 | 20335_S_AT |
| 1678 | 20338_AT |
| 1679 | 20345_AT |
| 1680 | 20365_S_AT |
| 1681 | 20382_S_AT |
| 1682 | 20390_S_AT |
| 1683 | 20395_AT |
| 1684 | 20420_AT |
| 1685 | 20421_AT |
| 1686 | 20432_AT |
| 1687 | 20437_AT |
| 1688 | 20442_I_AT |
| 1689 | 20463_S_AT |
| 1690 | 20491_AT |
| 1691 | 20537_AT |
| 1692 | 20573_AT |
| 1693 | 20636_AT |
| 1694 | 20638_AT |
| 1695 | 20641_AT |
| 1696 | 20658_S_AT |
| 1697 | 20689_S_AT |
| 1698 | 20698_S_AT |

TABLE 25

2X UP IN COLD, SALT & MANNITOL

12023_s_at
12332_s_at
12530_at
12536_s_at
12574_at
12595_at
12698_at
12749_at
12765_at
12769_at
12785_at
12857_at
12964_at
12972_at
12989_s_at
13004_at
13025_at
13036_at
13099_s_at
13136_at
13176_at
13220_s_at
13225_s_at
13230_s_at
13239_s_at
13426_at
13474_at
13548_at
13555_at
13595_at
13627_at
13645_at
13647_at
13706_s_at
13965_s_at
13967_at
14080_at
14090_i_at
14097_at
14116_at
14151_at
14172_at
14192_at
14244_s_at
14245_at
14367_at
14398_s_at
14582_at
14614_at
14644_s_at
14645_s_at
14658_s_at
14659_s_at
14733_s_at
14923_at
14990_at
15005_s_at
15018_at
15052_at
15088_s_at
15098_s_at
15103_s_at
15145_s_at
15154_s_at
15161_s_at
15214_s_at
15356_at
15521_s_at
15573_at
15586_s_at
15609_s_at
15611_s_at
15621_f_at
15669_s_at
15695_s_at
15753_at
15761_at

TABLE 25-continued

2X UP IN COLD, SALT & MANNITOL

15857_s_at
15871_s_at
15964_s_at
15970_s_at
15974_g_at
15997_s_at
16011_s_at
16021_s_at
16038_s_at
16046_s_at
16082_s_at
16111_f_at
16115_s_at
16127_s_at
16141_s_at
16144_s_at
16163_s_at
16236_g_at
16301_s_at
16322_at
16422_at
16474_s_at
16482_s_at
16485_s_at
16555_s_at
16561_s_at
16592_s_at
16637_s_at
17041_s_at
17047_s_at
17179_at
17180_at
17252_at
17384_at
17407_s_at
17484_at
17520_s_at
17555_s_at
17572_s_at
17722_at
17752_at
17840_s_at
17843_s_at
17860_at
17929_s_at
17936_s_at
17962_at
18052_s_at
18069_at
18122_at
18199_at
18259_at
18280_at
18289_at
18314_i_at
18318_at
18325_at
18482_s_at
18590_at
18594_at
18595_at
18596_at
18629_s_at
18661_at
18668_at
18699_i_at
18722_s_at
18936_at
18953_at
18955_at
18972_at
19008_at
19152_at
19186_s_at
19214_at
19368_at
19379_at

TABLE 25-continued

2X UP IN COLD, SALT & MANNITOL

19380_s_at
19421_at
19545_at
19614_at
19638_at
19640_at
19646_s_at
19656_s_at
19701_s_at
19843_at
19944_at
19982_at
19987_at
19991_at
20042_s_at
20060_at
20118_at
20144_at
20149_at
20179_at
20194_at
20245_s_at
20390_s_at
20437_at
20463_s_at
20491_at
20641_at
20658_s_at

TABLE 26

2X DOWN IN COLD, MANNITOL & SALT, ONLY

12078_at
12115_at
12118_at
12150_at
12271_s_at
12276_at
12338_at
12400_at
12430_at
12538_at
12622_at
12630_at
12792_s_at
12805_s_at
12883_s_at
12909_s_at
12932_s_at
12968_at
13159_at
13217_s_at
13279_s_at
13282_s_at
13432_at
13511_at
13546_at
13547_s_at
13587_at
13610_s_at
13640_at
13725_at
13771_at
13916_at
14028_at
14039_at
14046_at
14049_at
14077_at
14170_at
14227_at
14248_at
14381_at

TABLE 26-continued

2X DOWN IN COLD, MANNITOL & SALT, ONLY

14384_at
14487_at
14597_at
14705_i_at
14709_at
14779_at
14947_at
14950_at
14998_at
15045_at
15109_s_at
15124_s_at
15189_s_at
15357_at
15364_at
15403_s_at
15476_at
15483_s_at
15522_i_at
15531_i_at
15594_s_at
15702_s_at
15778_at
15839_at
15842_at
15859_at
15872_at
15880_at
15886_at
15906_s_at
15957_at
15985_at
16045_s_at
16061_s_at
16173_s_at
16298_at
16351_at
16412_s_at
16438_at
16493_at
16534_s_at
16539_s_at
16615_s_at
16692_at
16789_at
16818_s_at
16971_s_at
17018_s_at
17029_s_at
17089_s_at
17228_at
17338_at
17387_s_at
17413_s_at
17416_at
17425_s_at
17440_i_at
17473_at
17533_s_at
17549_s_at
17654_at
17693_at
17697_at
17755_at
17832_s_at
17869_at
17888_at
17930_s_at
17932_s_at
17957_at
17963_at
17971_s_at
17975_at
18016_r_at
18140_at
18224_s_at
18225_at

TABLE 26-continued

2X DOWN IN COLD, MANNITOL & SALT, ONLY

18228_at
18235_at
18265_at
18270_at
18296_at
18298_at
18471_at
18564_at
18637_at
18742_f_at
18761_at
18833_at
18875_s_at
18894_at
18946_at
19123_at
19216_at
19243_at
19267_s_at
19288_at
19398_at
19424_at
19430_at
19450_at
19457_at
19467_at
19516_at
19564_at
19577_at
19593_at
19602_at
19618_at
19670_at
19696_at
19722_s_at
19749_at
19755_at
19815_at
19926_at
19968_at
19977_at
20015_at
20040_at
20089_at
20190_at
20219_at
20263_at
20301_s_at
20308_s_at
20338_at
20345_at
20395_at
20442_i_at
20537_at
20573_at
20636_at
20638_at
20698_s_at

TABLE 27

2X ROOT SPECIFIC (COLD, SALINE & OSMOTIC STRESSES)

11997_at
12004_at
12051_at
12072_at
12150_at
12151_at
12166_i_at
12219_at
12315_at
12332_s_at
12374_i_at

TABLE 27-continued

2X ROOT SPECIFIC (COLD, SALINE & OSMOTIC STRESSES)

12482_s_at
12515_at
12522_at
12538_at
12571_s_at
12574_at
12609_at
12678_i_at
12698_at
12749_at
12760_g_at
12765_at
12768_at
12769_at
12772_at
12777_i_at
12958_at
12989_s_at
13015_s_at
13134_s_at
13146_s_at
13172_s_at
13178_at
13179_at
13187_i_at
13211_s_at
13239_s_at
13273_s_at
13297_s_at
13549_at
13604_at
13629_s_at
13706_s_at
13714_at
13751_at
13895_at
13933_at
13967_at
13985_s_at
14028_at
14030_at
14058_at
14069_at
14072_at
14073_at
14097_at
14139_at
14235_at
14250_r_at
14578_s_at
14582_at
14640_s_at
14643_s_at
14644_s_at
14658_s_at
14659_s_at
14711_s_at
14900_at
14924_at
14990_at
15018_at
15022_at
15107_s_at
15116_f_at
15120_s_at
15124_s_at
15131_s_at
15132_s_at
15137_s_at
15184_s_at
15188_s_at
15208_s_at
15252_g_at
15343_at
15389_at
15392_at
15448_at
15503_at
15531_i_at
15594_s_at
15609_s_at
15623_f_at
15639_s_at
15670_s_at
15680_s_at
15859_at
15900_at
15923_at
15962_s_at
15964_s_at
15965_at
15975_s_at
15985_at
16001_at
16048_at
16052_at
16053_i_at
16105_s_at
16161_s_at
16165_s_at
16298_at
16334_s_at
16422_at
16427_at
16440_s_at
16442_s_at
16468_at
16488_at
16511_at
16529_at
16553_f_at
16568_s_at
16914_s_at
16965_s_at
16981_s_at
16989_at
17033_s_at
17066_s_at
17085_s_at
17252_at
17376_at
17378_at
17388_at
17415_at
17429_s_at
17463_at
17485_s_at
17490_s_at
17567_at
17585_s_at
17595_s_at
17840_s_at
17860_at
17880_s_at
17894_at
17896_at
17899_at
17911_at
17935_at
17961_at
18024_s_at
18122_at
18222_at
18224_s_at
18252_at
18255_at
18269_s_at
18270_at
18327_s_at
18597_at
18607_s_at
18636_at
18663_s_at
18782_at

TABLE 27-continued

2X ROOT SPECIFIC (COLD, SALINE & OSMOTIC STRESSES)

18885_at
18888_at
18942_at
18955_at
19060_at
19108_at
19135_at
19137_at
19195_at
19263_at
19376_at
19406_at
19432_s_at
19835_at
19836_at
19840_s_at
19841_at
19843_at
19926_at
19972_at
19977_at
19991_at
20034_i_at
20042_s_at
20189_at
20194_at
20200_at
20214_i_at
20239_g_at
20262_at
20269_at
20294_at
20312_s_at
20382_s_at
20396_at
20432_at
20444_at
20446_s_at
20480_s_at
20586_i_at
20612_s_at
20672_at
20686_at
20689_s_at

TABLE 28

2X LEAF SPECIFIC (COLD, SALINE & OSMOTIC STRESSES)

12169_i_at
12186_at
12187_at
12211_at
12212_at
12214_g_at
12270_at
12645_at
12754_g_at
12774_at
12793_at
12796_s_at
12910_s_at
12916_s_at
12953_at
13090_at
13124_at
13335_at
13550_at
13567_at
13568_at
13596_at
13614_at
13678_s_at
13719_at
14014_at
14096_at

TABLE 28-continued

2X LEAF SPECIFIC (COLD, SALINE & OSMOTIC STRESSES)

14118_i_at
14369_at
14478_at
14513_s_at
14540_at
14596_at
14733_s_at
14986_at
15045_at
15097_s_at
15098_s_at
15145_s_at
15153_s_at
15154_s_at
15182_s_at
15203_s_at
15372_at
15521_s_at
15581_s_at
15621_f_at
15642_s_at
15776_at
15910_at
16017_at
16046_s_at
16115_s_at
16136_s_at
16172_s_at
16316_at
16385_s_at
16455_at
16485_s_at
16512_s_at
16547_s_at
16548_s_at
16629_s_at
16673_at
16899_at
17010_s_at
17018_s_at
17054_s_at
17095_s_at
17097_s_at
17273_at
17394_s_at
17420_at
17449_s_at
17600_s_at
17843_s_at
17913_s_at
17966_at
18003_at
18081_at
18560_at
18588_at
18626_at
18644_at
18666_s_at
18742_f_at
18977_at
18994_at
19227_at
19373_at
19834_at
19867_at
19998_at
20062_at
20199_at
20256_s_at
20284_at
20437_at
20442_i_at
20450_at
20468_at
20547_at
20635_s_at

TABLE 29

2X TRANSCRIPTION (COLD, SALINE & OSMOTIC STRESSES)

12068_at
12166_i_at
12374_i_at
12392_at
12431_at
12450_s_at
12503_at
12536_s_at
12540_s_at
12541_at
12587_at
12594_at
12595_at
12704_f_at
12705_f_at
12709_f_at
12712_f_at
12719_f_at
12724_f_at
12725_r_at
12726_f_at
12734_f_at
12736_f_at
12737_f_at
12812_at
12949_at
12951_at
12966_s_at
13023_at
13034_s_at
13087_at
13270_at
13273_s_at
13432_at
13555_at
13688_s_at
13714_at
13965_s_at
13987_s_at
14003_at
14144_at
14178_at
14223_at
14235_at
14303_s_at
14393_at
14553_at
14781_at
15046_s_at
15053_s_at
15214_s_at
15510_r_at
15638_s_at
15665_s_at
15679_s_at
15720_at
15871_s_at
16072_s_at
16073_f_at
16105_s_at
16111_f_at
16127_s_at
16534_s_at
16582_s_at
16589_s_at
16747_at
17019_s_at
17129_s_at
17160_at
17520_s_at
17538_s_at
17555_s_at
17609_at
17896_at
17971_s_at

TABLE 29-continued

2X TRANSCRIPTION (COLD, SALINE & OSMOTIC STRESSES)

17975_at
17978_s_at
18121_s_at
18167_s_at
18197_at
18222_at
18318_at
18576_s_at
18629_s_at
18738_f_at
18742_f_at
18744_f_at
18745_f_at
18747_f_at
18750_f_at
18751_f_at
18789_at
18834_at
18942_at
19083_at
19202_at
19209_s_at
19232_s_at
19315_at
19489_s_at
19611_s_at
19646_s_at
19707_s_at
19722_s_at
19744_at
19755_at
19836_at
19860_at
19866_at
19898_at
20262_at
20335_s_at
20362_at
20424_at
20437_at
20456_at
20515_s_at
20635_s_at

TABLE 30

2X PHOSPHATES (COLD, SALINE & OSMOTIC STRESSES)

12470_at
12556_at
13128_at
13135_s_at
13180_s_at
13192_s_at
13193_s_at
13587_at
13995_at
14335_at
15073_at
15171_s_at
15240_at
15586_s_at
15641_s_at
15651_f_at
15990_at
16232_s_at
16576_f_at
16753_at
17423_s_at
17525_s_at
17537_s_at
17929_s_at

TABLE 30-continued

2X PHOSPHATES (COLD, SALINE & OSMOTIC STRESSES)

17954_s_at
18012_s_at
18308_i_at
18616_at
18847_at
18936_at
18980_at
19243_at
19263_at
19638_at
19883_at
19932_at
20333_at
20393_at
20570_at

TABLE 31

2X KINASES (COLD, SALINE & OSMOTIC STRESSES)

12253_g_at
12270_at
12271_s_at
12276_at
12278_at
12284_at
12300_at
12307_at
12353_at
12357_s_at
12390_at
12394_at
12395_s_at
12408_at
12452_at
12477_at
12490_at
12497_at
12532_at
12697_at
12901_s_at
12902_at
12958_at
12959_at
13068_at
13246_at
13324_at
13332_at
13362_s_at
13370_at
13550_at
14030_at
14048_at
14194_at
14196_at
14217_at
14459_at
14603_at
14637_s_at
14686_s_at
15005_s_at
15175_s_at
15270_at
15475_s_at
15497_s_at
15577_s_at
15616_s_at
15633_s_at
15634_s_at
15668_s_at
15680_s_at
15798_at
16034_at
16059_s_at

TABLE 31-continued

2X KINASES (COLD, SALINE & OSMOTIC STRESSES)

16087_s_at
16088_f_at
16125_s_at
16137_s_at
16140_s_at
16143_s_at
16144_s_at
16160_f_at
16171_s_at
16357_at
16412_s_at
16568_s_at
16570_s_at
16571_s_at
16584_s_at
16651_s_at
16652_s_at
16672_at
16818_s_at
16840_at
17068_s_at
17122_s_at
17252_at
17323_at
17475_at
17752_at
17921_s_at
17933_at
17935_at
18013_r_at
18046_s_at
18122_at
18176_at
18316_at
18455_at
18459_at
18482_s_at
18543_at
18706_s_at
18782_at
18924_at
19117_s_at
19437_s_at
19442_at
19458_at
19464_at
19469_at
19562_at
19655_at
19749_at
19854_at
19904_at
20144_at
20219_at
20223_at
20232_s_at
20235_i_at
20282_s_at
20298_at
20396_at
20439_at
20462_at

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07692065B2). An electronic copy of the "Sequence Listing" will also be available from the USPTO upon request and payment of the fee set forth in 37 CFR 1.19(b)(3).

What is claimed is:

1. A transgenic plant, which contains a transgene comprising a regulatory element of a plant stress-regulated gene, wherein the regulatory element comprises the nucleotide sequence as set forth in SEQ ID NO:3729.

2. The transgenic plant of claim 1, wherein the transgenic plant exhibits altered responsiveness to a stress condition as compared to a corresponding wild-type plant.

3. The transgenic plant of claim 2, wherein the transgene disrupts an endogenous stress-regulated gene in the plant, thereby reducing or inhibiting expression of the gene in response to a stress condition.

4. The transgenic plant of claim 1, wherein the transgene comprises a coding sequence of a plant stress-regulated gene.

5. The transgenic plant of claim 4, wherein the coding sequence is operatively linked to said regulatory element.

6. The transgenic plant of claim 1, wherein the transgene comprises said regulatory element operatively linked to a heterologous nucleotide sequence.

7. The transgenic plant of claim 6, wherein the transgenic plant expresses a polypeptide encoded by the heterologous nucleotide sequence.

8. The transgenic plant of claim 1, wherein the plant comprises multiple transgenes.

9. The transgenic plant of claim 1, wherein the transgene comprises an osmotic stress-regulated gene.

10. The transgenic plant of claim 9, wherein the osmotic stress resistance gene is operatively linked to the regulatory element.

11. The transgenic plant of claim 9 which has improved osmotic stress resistance.

12. The transgenic plant of claim 1, wherein the transgene comprises a heat stress-regulated gene.

13. The transgenic plant of claim 12, wherein the heat stress resistance gene is operatively linked to the regulatory element.

14. The transgenic plant of claim 12 which has improved heat stress resistance.

15. The transgenic plant of claim 1, wherein the transgene comprises an anaerobic stress-regulated gene.

16. The transgenic plant of claim 15, wherein the anaerobic stress resistance gene is operatively linked to the regulatory element.

17. The transgenic plant of claim 15 which has improved anaerobic stress resistance.

18. A regulatory element of a plant stress-regulated gene which has at least 90% sequence identity to the nucleotide sequence as set forth in SEQ ID NO:3729.

19. The regulatory element of claim 18, comprising the nucleotide sequence as set forth in SEQ ID NO:3729.

20. The regulatory element of claim 18, comprising a nucleotide sequence that is at least 95% identical to the sequence shown in SEQ ID NO:3729.

21. The regulatory element of claim 18, comprising a nucleotide sequence that is at least 99% identical to the sequence shown in SEQ ID NO:3729.

* * * * *